United States Patent
Brooks et al.

(10) Patent No.: US 11,104,718 B2
(45) Date of Patent: Aug. 31, 2021

(54) RED BLOOD CELL TARGETED FACTOR VIII AND METHOD OF USING THE SAME

(71) Applicant: Bayer HealthCare LLC, Indianola, PA (US)

(72) Inventors: Alan Brooks, Clayton, CA (US); Richard Feldman, El Cerrito, CA (US); Jian-Ming Gu, Lafayette, CA (US); Shaun Lippow, San Carlos, CA (US); Shujun Yuan, Daly City, CA (US); Peter Bringmann, Concord, CA (US)

(73) Assignee: Bayer HealthCare LLC, Whippany, NJ (US)

( * ) Notice: Subject to any disclaimer, the term of this patent is extended or adjusted under 35 U.S.C. 154(b) by 150 days.

(21) Appl. No.: 16/349,794

(22) PCT Filed: Nov. 14, 2017

(86) PCT No.: PCT/US2017/061509
§ 371 (c)(1),
(2) Date: May 14, 2019

(87) PCT Pub. No.: WO2018/093766
PCT Pub. Date: May 24, 2018

(65) Prior Publication Data
US 2019/0359687 A1 Nov. 28, 2019

Related U.S. Application Data

(60) Provisional application No. 62/422,600, filed on Nov. 16, 2016.

(51) Int. Cl.
| | |
|---|---|
| *C07K 16/28* | (2006.01) |
| *C07K 14/755* | (2006.01) |
| *A61P 7/04* | (2006.01) |
| *A61K 39/00* | (2006.01) |

(52) U.S. Cl.
CPC .............. *C07K 14/755* (2013.01); *A61P 7/04* (2018.01); *C07K 16/2896* (2013.01); *A61K 2039/505* (2013.01); *C07K 2317/24* (2013.01); *C07K 2317/33* (2013.01); *C07K 2317/34* (2013.01); *C07K 2317/55* (2013.01); *C07K 2317/565* (2013.01); *C07K 2317/567* (2013.01); *C07K 2317/622* (2013.01); *C07K 2317/64* (2013.01); *C07K 2317/76* (2013.01); *C07K 2317/92* (2013.01); *C07K 2317/94* (2013.01); *C07K 2319/30* (2013.01); *C07K 2319/33* (2013.01); *C07K 2319/50* (2013.01)

(58) Field of Classification Search
None
See application file for complete search history.

(56) References Cited

U.S. PATENT DOCUMENTS

| | | | | |
|---|---|---|---|---|
| 4,752,582 A | * | 6/1988 | Vanderlaan | C07K 16/34 435/343 |
| 6,180,370 B1 | * | 1/2001 | Queen | C07K 16/2866 435/69.6 |
| 8,333,973 B2 | * | 12/2012 | Muzykantov | A61P 11/00 424/185.1 |
| 2012/0178139 A1 | * | 7/2012 | Hubbell | A61K 39/001 435/188 |
| 2016/0263230 A1 | | 9/2016 | Hilden et al. | |

FOREIGN PATENT DOCUMENTS

| | | | |
|---|---|---|---|
| WO | 9409034 A1 | 4/1994 | |
| WO | 2006053299 A2 | 5/2006 | |
| WO | 2009140598 A1 | 11/2009 | |
| WO | WO-2009140598 A1 * | 11/2009 | ............... A61P 7/04 |

OTHER PUBLICATIONS

Villa, Carlos H., et al. "Delivery of drugs bound to erythrocytes: new avenues for an old intravascular carrier." Therapeutic delivery 6.7 (2015): 795-826 (Year: 2015).*
Janeway, Charles A. "Immunobiology: The Immune System in Health and Disease." 2005 (Year: 2005).*
Kipriyanov, Sergey M., and Fabrice Le Gall. "Generation and production of engineered antibodies." Molecular biotechnology 26.1 (2004): 39-60. (Year: 2004).*
Janeway, A. C., et al. "Immunobiology: the immune system in health and disease. London." Current Biology (1997): 3:1-3:11. (Year: 1997).*
Backes Bradley J.; Et. Al., "Synthesis of positional-scanning libraries of fluorogenic peptide substrates to define the extended substrate specificity of plasmin and thrombin", Nature Biotechnology, Feb. 2000, 18, 187-193.
Bird; et al, "Single-Chain Antigen-Binding Proteins", Science, Oct. 21, 1988, vol. 242 No. 4877, 423-426.
Chen; et al, "Fusion Proteins Comprising Annexin V and Kunitz Protease Inhibitors are Highly Potent Thrombogenic Site-Directed Anticoagulants", Blood, May 15, 2005, vol. 105 No. 10, 3902-3909.
Dong; et al, "P-seiectin-targeting of the Fibrin Selective Thrombolytic Des modus Rotund us Salivary Plasminogen Activator a1", Thromb Haemost, 2004, vol. 92, pp. 956-965.
Fay; Philip J., "Factor VIII Structure and Function", International Journal of Hematology, © 2006, 83, 103-108.

(Continued)

*Primary Examiner* — Michael Szperka
*Assistant Examiner* — Lia E Taylor

(57) ABSTRACT

Targeted Factor VIII molecules comprising a Factor VIII linked with at least one domain that specifically binds to a membrane protein on a red blood cell is provided. The disclosed targeted coagulation factors prolong their duration of action and thus, are an improvement for the treatment of hematological diseases such as hemophilia A.

1 Claim, 21 Drawing Sheets

Specification includes a Sequence Listing.

(56) References Cited

OTHER PUBLICATIONS

Gallwitz Maike; Et. Al., "The Extended Cleavage Specificity of Human Thrombin", Plos One, Feb. 27, 2012, 7 /2.

Gruppo; et al, "Comparative Effectiveness of Full-Length and 8-Domain Deleted Factor VIII for Prophylaxis—A Meta-Analysis", Haemophilia, 2003, vol. 9, 251-260.

Habib Ibrahim; Et. Al., "VHH (nanobody) directed against human glycophorin A: A tool for autologous red cell agglutination assays", Analytical Biochemistry, © 2013, 82-89.

Higgins; et al, "Clustal V: Improved Software for Multiple Sequence Alignment", Computer Applications in the Biosciences, 1992, vol. 8 No. 2, 189-191.

Huston; et al, "Protein Engineering of Antibody Binding Sites: Recovery of Specific Activity in an Anti-Digoxin Single-chain Fv Analogue Produced in *Escherichia coli*", Proceedings of the National Academy of Sciences of the United States of America, Aug. 1988, vol. 85 No. 16, 5879-5883.

International Preliminary Report & Written Opinion for International Application PCT/US2017/061509 dated May 31, 2019.

International Search Report & Written Opinion for International Application PCT/US2017/061509 dated Dec. 22, 2017.

Jenny Richard J.; Et. Al., "A critical review of the methods for cleavage of fusion proteins with thrombin and factor Xa", Protein Expression and Purification, © 2003, 1-11.

Leyte Anja; Et. Al., "Sulfation of Tyr of Human Blood Coagulation Factor VIII Is Essential for the Interaction of Factor VIII with von Willebrand Factor", The Journal of Biological Chemistry, © 1991, 266 / 2, 740-746.

Mei Baisong; Et. Al., "Expression of Human Coagulation Factor VIII in a Human Hybrid Cell Line, HKB11", Molecular Biotechnology, © 2006, 34, 165-178.

Pittman Debra D.; Et. Al., "Post-Translational Requirements for Functional factor V and factor VIII Secretion in Mammalian Cells", The Journal of Biological Chemistry, Jun. 24, 1994, 269 / 25, 17329-17337.

Saenko; et al, "Haemophilia A effects of inhibitory Antibodies on factor VIII functional interactions and approaches to prevent their action", Haemophilia, 2002, vol. 8, pp. 1-11.

Shi; et al, "Factor VIII Ectopically Targetted to Platelets is Therapeutic in Hemophilia A with High-Titer Inhibitory Antibodies", J. Clin.Invest., 2006, vol. 116 No. 7, 1974-1982.

Stoll Patrick; Et. Al., "Targeting Ligand-Induced Binding Sites on GPIIb/IIIa via Single-Chain Antibody Allows Effective Anticoagulation Without Bleeding Time Prolongation", Arterioscler Thromb Vasc Biol., © 2007, 1206-1212.

Tang L.; Et. Al., "von Willebrand factor contributes to longer half-life of PEGylated factor VIII in vivo", The Official Journal of the World Federation of Hemophilia, © 2013, 19, 539-545.

Thompson; et al, "Clustal W: Improving the Sensitivity of Progressive Multiple Sequence Alignment Through Sequence Weighting, Position-Specific Gap Penalties and Weight Matrix Choice", Nucleic Acids Research, 1994, vol. 22 No. 22, 4673-4680.

Thompson; Arthur R., "Structure and Function of the Factor VIII Gene and Protein", Seminars in Thrombosis and Hemostasis, 2003, vol. 29 No. 1, 11-22.

Ward; et al, "Binding activities of a repertoire of single immunoglobulin variable domains secreted from *Escherichia coli*", Letters to Nature, Oct. 12, 1989, vol. 341, 544-546.

* cited by examiner

Figure 2

25 bind human and monkey RBC in FACS
1 clone specific to human RBC only 20 positive on GPA ELISA 16 negative on PBMC FACS 12 measurable EC50 in GPA ELISA
(incl 3 x-react to dog)

All 12 sequenced and converted to scFv-Fc
fusions and expressed in mammalian cells 10 clones with intact VH and VL sequences Re-test scFv-Fc binding to RBC in FACS
Test absence of binding to PBMC and endothelial cells 10 clones, align sequences and compare
1 class of CDR in human/monkey cross reactive clones
Distinct CDR sequence in human specific anti-GPA clone Figure 4
A
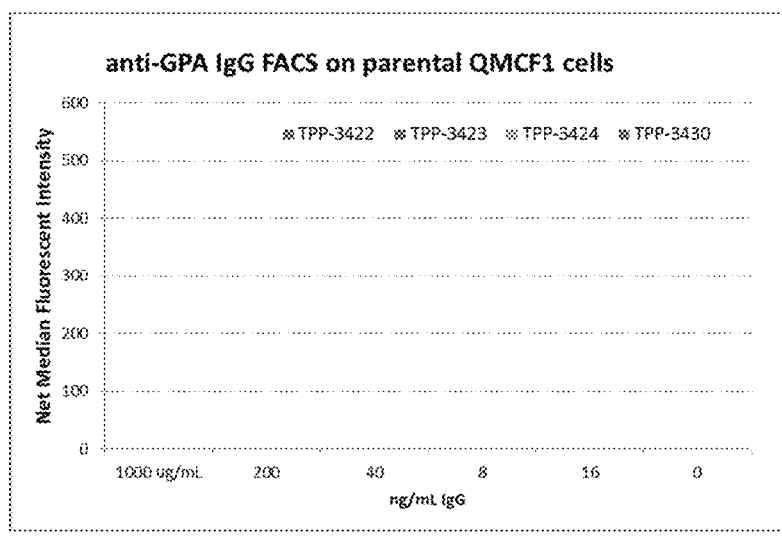
B
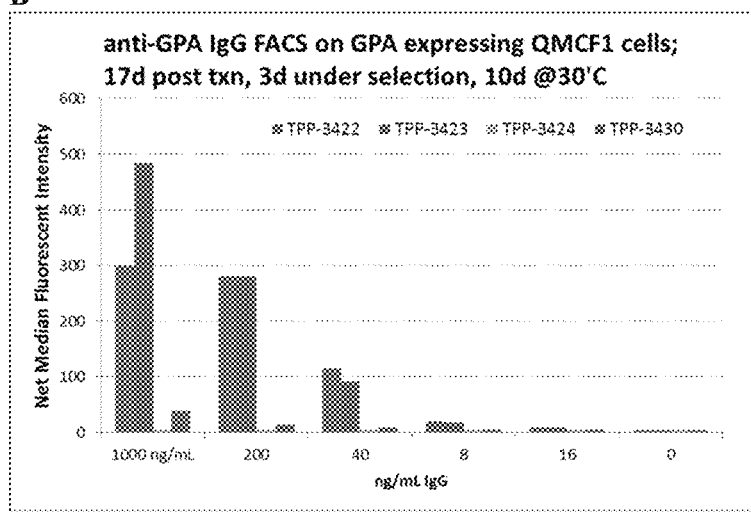

Figure 5

Figure 7
A
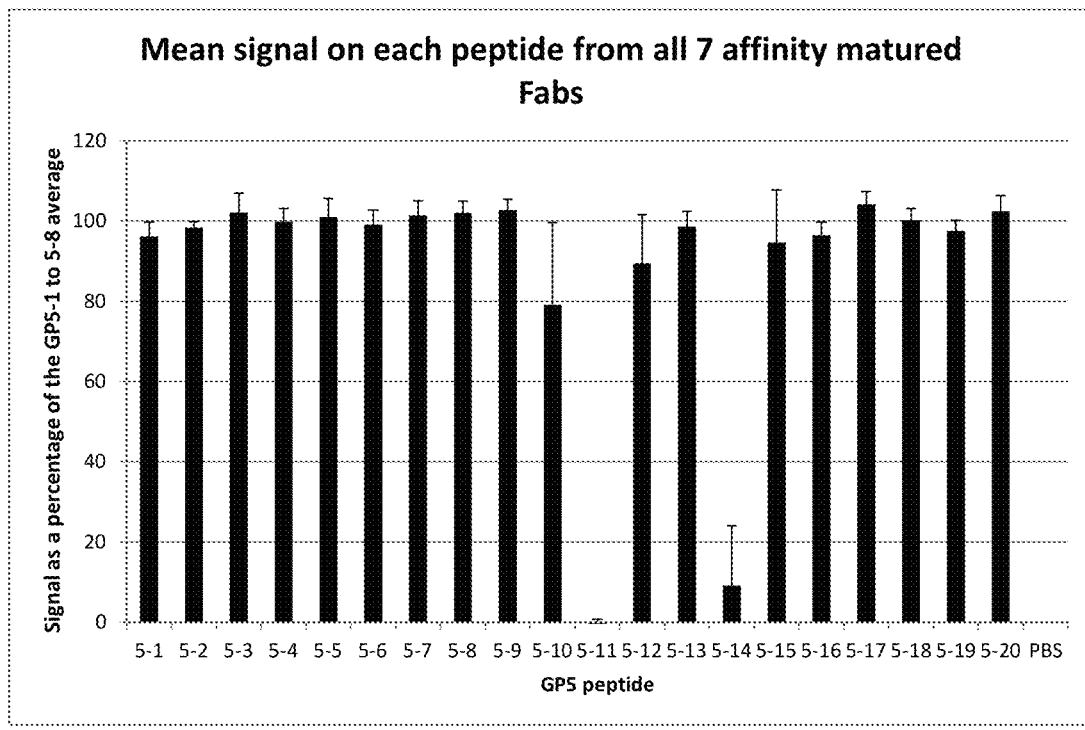
B
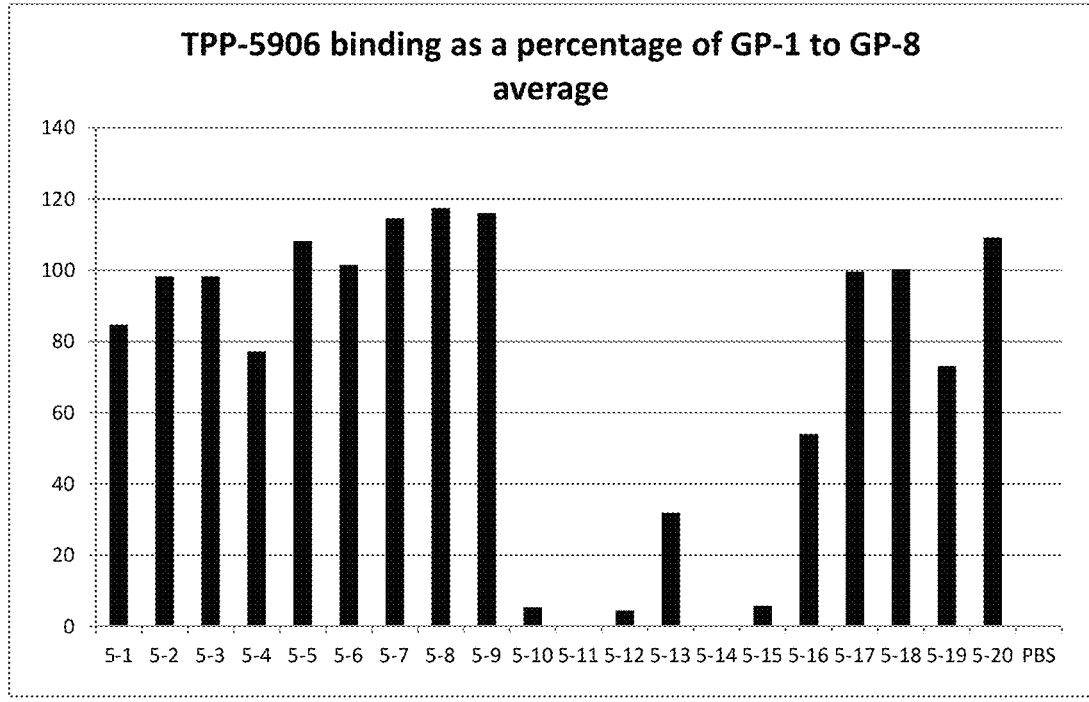

SEQUENCE LISTING

```
<160> NUMBER OF SEQ ID NOS: 133

<210> SEQ ID NO 1
<211> LENGTH: 2351
<212> TYPE: PRT
<213> ORGANISM: Homo Sapiens

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255
```

```
Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
            290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
```

-continued

```
               675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
                740                 745                 750
Asn Asn Ala Ile Glu Pro Arg Ser Phe Ser Gln Asn Ser Arg His Pro
            755                 760                 765
Ser Thr Arg Gln Lys Gln Phe Asn Ala Thr Thr Ile Pro Glu Asn Asp
770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
                805                 810                 815
Pro Thr Pro His Gly Leu Ser Leu Ser Asp Leu Gln Glu Ala Lys Tyr
                820                 825                 830
Glu Thr Phe Ser Asp Asp Pro Ser Pro Gly Ala Ile Asp Ser Asn Asn
                835                 840                 845
Ser Leu Ser Glu Met Thr His Phe Arg Pro Gln Leu His His Ser Gly
            850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
                900                 905                 910
Leu Ala Ala Gly Thr Asp Asn Thr Ser Ser Leu Gly Pro Pro Ser Met
            915                 920                 925
Pro Val His Tyr Asp Ser Gln Leu Asp Thr Thr Leu Phe Gly Lys Lys
        930                 935                 940
Ser Ser Pro Leu Thr Glu Ser Gly Gly Pro Leu Ser Leu Ser Glu Glu
945                 950                 955                 960
Asn Asn Asp Ser Lys Leu Leu Glu Ser Gly Leu Met Asn Ser Gln Glu
                965                 970                 975
Ser Ser Trp Gly Lys Asn Val Ser Ser Thr Glu Ser Gly Arg Leu Phe
            980                 985                 990
Lys Gly Lys Arg Ala His Gly Pro Ala Leu Leu Thr Lys Asp Asn Ala
        995                 1000                1005
Leu Phe Lys Val Ser Ile Ser Leu Leu Lys Thr Asn Lys Thr Ser
    1010                1015                1020
Asn Asn Ser Ala Thr Asn Arg Lys Thr His Ile Asp Gly Pro Ser
        1025                1030                1035
Leu Leu Ile Glu Asn Ser Pro Ser Val Trp Gln Asn Ile Leu Glu
        1040                1045                1050
Ser Asp Thr Glu Phe Lys Lys Val Thr Pro Leu Ile His Asp Arg
        1055                1060                1065
Met Leu Met Asp Lys Asn Ala Thr Ala Leu Arg Leu Asn His Met
        1070                1075                1080
Ser Asn Lys Thr Thr Ser Ser Lys Asn Met Glu Met Val Gln Gln
        1085                1090                1095
```

```
Lys Lys Glu Gly Pro Ile Pro Pro Asp Ala Gln Asn Pro Asp Met
    1100            1105            1110

Ser Phe Phe Lys Met Leu Phe Leu Pro Glu Ser Ala Arg Trp Ile
    1115            1120            1125

Gln Arg Thr His Gly Lys Asn Ser Leu Asn Ser Gly Gln Gly Pro
    1130            1135            1140

Ser Pro Lys Gln Leu Val Ser Leu Gly Pro Glu Lys Ser Val Glu
    1145            1150            1155

Gly Gln Asn Phe Leu Ser Glu Lys Asn Lys Val Val Val Gly Lys
    1160            1165            1170

Gly Glu Phe Thr Lys Asp Val Gly Leu Lys Glu Met Val Phe Pro
    1175            1180            1185

Ser Ser Arg Asn Leu Phe Leu Thr Asn Leu Asp Asn Leu His Glu
    1190            1195            1200

Asn Asn Thr His Asn Gln Glu Lys Lys Ile Gln Glu Glu Ile Glu
    1205            1210            1215

Lys Lys Glu Thr Leu Ile Gln Glu Asn Val Val Leu Pro Gln Ile
    1220            1225            1230

His Thr Val Thr Gly Thr Lys Asn Phe Met Lys Asn Leu Phe Leu
    1235            1240            1245

Leu Ser Thr Arg Gln Asn Val Glu Gly Ser Tyr Glu Gly Ala Tyr
    1250            1255            1260

Ala Pro Val Leu Gln Asp Phe Arg Ser Leu Asn Asp Ser Thr Asn
    1265            1270            1275

Arg Thr Lys Lys His Thr Ala His Phe Ser Lys Lys Gly Glu Glu
    1280            1285            1290

Glu Asn Leu Glu Gly Leu Gly Asn Gln Thr Lys Gln Ile Val Glu
    1295            1300            1305

Lys Tyr Ala Cys Thr Thr Arg Ile Ser Pro Asn Thr Ser Gln Gln
    1310            1315            1320

Asn Phe Val Thr Gln Arg Ser Lys Arg Ala Leu Lys Gln Phe Arg
    1325            1330            1335

Leu Pro Leu Glu Glu Thr Glu Leu Glu Lys Arg Ile Ile Val Asp
    1340            1345            1350

Asp Thr Ser Thr Gln Trp Ser Lys Asn Met Lys His Leu Thr Pro
    1355            1360            1365

Ser Thr Leu Thr Gln Ile Asp Tyr Asn Glu Lys Glu Lys Gly Ala
    1370            1375            1380

Ile Thr Gln Ser Pro Leu Ser Asp Cys Leu Thr Arg Ser His Ser
    1385            1390            1395

Ile Pro Gln Ala Asn Arg Ser Pro Leu Pro Ile Ala Lys Val Ser
    1400            1405            1410

Ser Phe Pro Ser Ile Arg Pro Ile Tyr Leu Thr Arg Val Leu Phe
    1415            1420            1425

Gln Asp Asn Ser Ser His Leu Pro Ala Ala Ser Tyr Arg Lys Lys
    1430            1435            1440

Asp Ser Gly Val Gln Glu Ser Ser His Phe Leu Gln Gly Ala Lys
    1445            1450            1455

Lys Asn Asn Leu Ser Leu Ala Ile Leu Thr Leu Glu Met Thr Gly
    1460            1465            1470

Asp Gln Arg Glu Val Gly Ser Leu Gly Thr Ser Ala Thr Asn Ser
    1475            1480            1485
```

```
Val  Thr  Tyr  Lys  Lys  Val  Glu  Asn  Thr  Val  Leu  Pro  Lys  Pro  Asp
     1490                     1495                1500

Leu  Pro  Lys  Thr  Ser  Gly  Lys  Val  Glu  Leu  Leu  Pro  Lys  Val  His
     1505                     1510                1515

Ile  Tyr  Gln  Lys  Asp  Leu  Phe  Pro  Thr  Glu  Thr  Ser  Asn  Gly  Ser
     1520                     1525                1530

Pro  Gly  His  Leu  Asp  Leu  Val  Glu  Gly  Ser  Leu  Leu  Gln  Gly  Thr
     1535                     1540                1545

Glu  Gly  Ala  Ile  Lys  Trp  Asn  Glu  Ala  Asn  Arg  Pro  Gly  Lys  Val
     1550                     1555                1560

Pro  Phe  Leu  Arg  Val  Ala  Thr  Glu  Ser  Ser  Ala  Lys  Thr  Pro  Ser
     1565                     1570                1575

Lys  Leu  Leu  Asp  Pro  Leu  Ala  Trp  Asp  Asn  His  Tyr  Gly  Thr  Gln
     1580                     1585                1590

Ile  Pro  Lys  Glu  Glu  Trp  Lys  Ser  Gln  Glu  Lys  Ser  Pro  Glu  Lys
     1595                     1600                1605

Thr  Ala  Phe  Lys  Lys  Lys  Asp  Thr  Ile  Leu  Ser  Leu  Asn  Ala  Cys
     1610                     1615                1620

Glu  Ser  Asn  His  Ala  Ile  Ala  Ala  Ile  Asn  Glu  Gly  Gln  Asn  Lys
     1625                     1630                1635

Pro  Glu  Ile  Glu  Val  Thr  Trp  Ala  Lys  Gln  Gly  Arg  Thr  Glu  Arg
     1640                     1645                1650

Leu  Cys  Ser  Gln  Asn  Pro  Pro  Val  Leu  Lys  Arg  His  Gln  Arg  Glu
     1655                     1660                1665

Ile  Thr  Arg  Thr  Thr  Leu  Gln  Ser  Asp  Gln  Glu  Glu  Ile  Asp  Tyr
     1670                     1675                1680

Asp  Asp  Thr  Ile  Ser  Val  Glu  Met  Lys  Lys  Glu  Asp  Phe  Asp  Ile
     1685                     1690                1695

Tyr  Asp  Glu  Asp  Glu  Asn  Gln  Ser  Pro  Arg  Ser  Phe  Gln  Lys  Lys
     1700                     1705                1710

Thr  Arg  His  Tyr  Phe  Ile  Ala  Ala  Val  Glu  Arg  Leu  Trp  Asp  Tyr
     1715                     1720                1725

Gly  Met  Ser  Ser  Ser  Pro  His  Val  Leu  Arg  Asn  Arg  Ala  Gln  Ser
     1730                     1735                1740

Gly  Ser  Val  Pro  Gln  Phe  Lys  Lys  Val  Val  Phe  Gln  Glu  Phe  Thr
     1745                     1750                1755

Asp  Gly  Ser  Phe  Thr  Gln  Pro  Leu  Tyr  Arg  Gly  Glu  Leu  Asn  Glu
     1760                     1765                1770

His  Leu  Gly  Leu  Leu  Gly  Pro  Tyr  Ile  Arg  Ala  Glu  Val  Glu  Asp
     1775                     1780                1785

Asn  Ile  Met  Val  Thr  Phe  Arg  Asn  Gln  Ala  Ser  Arg  Pro  Tyr  Ser
     1790                     1795                1800

Phe  Tyr  Ser  Ser  Leu  Ile  Ser  Tyr  Glu  Glu  Asp  Gln  Arg  Gln  Gly
     1805                     1810                1815

Ala  Glu  Pro  Arg  Lys  Asn  Phe  Val  Lys  Pro  Asn  Glu  Thr  Lys  Thr
     1820                     1825                1830

Tyr  Phe  Trp  Lys  Val  Gln  His  His  Met  Ala  Pro  Thr  Lys  Asp  Glu
     1835                     1840                1845

Phe  Asp  Cys  Lys  Ala  Trp  Ala  Tyr  Phe  Ser  Asp  Val  Asp  Leu  Glu
     1850                     1855                1860

Lys  Asp  Val  His  Ser  Gly  Leu  Ile  Gly  Pro  Leu  Leu  Val  Cys  His
     1865                     1870                1875

Thr  Asn  Thr  Leu  Asn  Pro  Ala  His  Gly  Arg  Gln  Val  Thr  Val  Gln
```

```
                1880               1885               1890
Glu Phe Ala Leu Phe Phe Thr Ile Phe Asp Thr Lys Ser Trp
    1895               1900               1905
Tyr Phe Thr Glu Asn Met Glu Arg Asn Cys Arg Ala Pro Cys Asn
    1910               1915               1920
Ile Gln Met Glu Asp Pro Thr Phe Lys Glu Asn Tyr Arg Phe His
    1925               1930               1935
Ala Ile Asn Gly Tyr Ile Met Asp Thr Leu Pro Gly Leu Val Met
    1940               1945               1950
Ala Gln Asp Gln Arg Ile Arg Trp Tyr Leu Leu Ser Met Gly Ser
    1955               1960               1965
Asn Glu Asn Ile His Ser Ile His Phe Ser Gly His Val Phe Thr
    1970               1975               1980
Val Arg Lys Lys Glu Glu Tyr Lys Met Ala Leu Tyr Asn Leu Tyr
    1985               1990               1995
Pro Gly Val Phe Glu Thr Val Glu Met Leu Pro Ser Lys Ala Gly
    2000               2005               2010
Ile Trp Arg Val Glu Cys Leu Ile Gly Glu His Leu His Ala Gly
    2015               2020               2025
Met Ser Thr Leu Phe Leu Val Tyr Ser Asn Lys Cys Gln Thr Pro
    2030               2035               2040
Leu Gly Met Ala Ser Gly His Ile Arg Asp Phe Gln Ile Thr Ala
    2045               2050               2055
Ser Gly Gln Tyr Gly Gln Trp Ala Pro Lys Leu Ala Arg Leu His
    2060               2065               2070
Tyr Ser Gly Ser Ile Asn Ala Trp Ser Thr Lys Glu Pro Phe Ser
    2075               2080               2085
Trp Ile Lys Val Asp Leu Leu Ala Pro Met Ile Ile His Gly Ile
    2090               2095               2100
Lys Thr Gln Gly Ala Arg Gln Lys Phe Ser Ser Leu Tyr Ile Ser
    2105               2110               2115
Gln Phe Ile Ile Met Tyr Ser Leu Asp Gly Lys Lys Trp Gln Thr
    2120               2125               2130
Tyr Arg Gly Asn Ser Thr Gly Thr Leu Met Val Phe Phe Gly Asn
    2135               2140               2145
Val Asp Ser Ser Gly Ile Lys His Asn Ile Phe Asn Pro Pro Ile
    2150               2155               2160
Ile Ala Arg Tyr Ile Arg Leu His Pro Thr His Tyr Ser Ile Arg
    2165               2170               2175
Ser Thr Leu Arg Met Glu Leu Met Gly Cys Asp Leu Asn Ser Cys
    2180               2185               2190
Ser Met Pro Leu Gly Met Glu Ser Lys Ala Ile Ser Asp Ala Gln
    2195               2200               2205
Ile Thr Ala Ser Ser Tyr Phe Thr Asn Met Phe Ala Thr Trp Ser
    2210               2215               2220
Pro Ser Lys Ala Arg Leu His Leu Gln Gly Arg Ser Asn Ala Trp
    2225               2230               2235
Arg Pro Gln Val Asn Asn Pro Lys Glu Trp Leu Gln Val Asp Phe
    2240               2245               2250
Gln Lys Thr Met Lys Val Thr Gly Val Thr Thr Gln Gly Val Lys
    2255               2260               2265
Ser Leu Leu Thr Ser Met Tyr Val Lys Glu Phe Leu Ile Ser Ser
    2270               2275               2280
```

```
Ser Gln Asp Gly His Gln Trp Thr Leu Phe Phe Gln Asn Gly Lys
    2285            2290                2295

Val Lys Val Phe Gln Gly Asn Gln Asp Ser Phe Thr Pro Val Val
    2300            2305                2310

Asn Ser Leu Asp Pro Pro Leu Leu Thr Arg Tyr Leu Arg Ile His
    2315            2320                2325

Pro Gln Ser Trp Val His Gln Ile Ala Leu Arg Met Glu Val Leu
    2330            2335                2340

Gly Cys Glu Ala Gln Asp Leu Tyr
    2345            2350

<210> SEQ ID NO 2
<211> LENGTH: 2332
<212> TYPE: PRT
<213> ORGANISM: Homo Sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
```

```
                290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Pro Gln Leu Arg
                325                 330                 335
Met Lys Asn Asn Glu Glu Ala Glu Asp Tyr Asp Asp Leu Thr Asp
                340                 345                 350
Ser Glu Met Asp Val Val Arg Phe Asp Asp Asn Ser Pro Ser Phe
            355                 360                 365
Ile Gln Ile Arg Ser Val Ala Lys Lys His Pro Lys Thr Trp Val His
        370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
            450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
```

```
Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125
```

| | | | | | | | | | | | |
|---|---|---|---|---|---|---|---|---|---|---|---|
|Leu|Val|Ser|Leu|Gly|Pro|Glu|Lys|Ser|Val|Glu|Gly|Gln|Asn|Phe|
| |1130| | | | |1135| | | |1140| |
|Leu|Ser|Glu|Lys|Asn|Lys|Val|Val|Val|Gly|Lys|Gly|Glu|Phe|Thr|
| |1145| | | | |1150| | | |1155| |
|Lys|Asp|Val|Gly|Leu|Lys|Glu|Met|Val|Phe|Pro|Ser|Ser|Arg|Asn|
| |1160| | | | |1165| | | |1170| |
|Leu|Phe|Leu|Thr|Asn|Leu|Asp|Asn|Leu|His|Glu|Asn|Asn|Thr|His|
| |1175| | | | |1180| | | |1185| |
|Asn|Gln|Glu|Lys|Lys|Ile|Gln|Glu|Glu|Ile|Glu|Lys|Lys|Glu|Thr|
| |1190| | | | |1195| | | |1200| |
|Leu|Ile|Gln|Glu|Asn|Val|Val|Leu|Pro|Gln|Ile|His|Thr|Val|Thr|
| |1205| | | | |1210| | | |1215| |
|Gly|Thr|Lys|Asn|Phe|Met|Lys|Asn|Leu|Phe|Leu|Leu|Ser|Thr|Arg|
| |1220| | | | |1225| | | |1230| |
|Gln|Asn|Val|Glu|Gly|Ser|Tyr|Glu|Gly|Ala|Tyr|Ala|Pro|Val|Leu|
| |1235| | | | |1240| | | |1245| |
|Gln|Asp|Phe|Arg|Ser|Leu|Asn|Asp|Ser|Thr|Asn|Arg|Thr|Lys|Lys|
| |1250| | | | |1255| | | |1260| |
|His|Thr|Ala|His|Phe|Ser|Lys|Lys|Gly|Glu|Glu|Glu|Asn|Leu|Glu|
| |1265| | | | |1270| | | |1275| |
|Gly|Leu|Gly|Asn|Gln|Thr|Lys|Gln|Ile|Val|Glu|Lys|Tyr|Ala|Cys|
| |1280| | | | |1285| | | |1290| |
|Thr|Thr|Arg|Ile|Ser|Pro|Asn|Thr|Ser|Gln|Gln|Asn|Phe|Val|Thr|
| |1295| | | | |1300| | | |1305| |
|Gln|Arg|Ser|Lys|Arg|Ala|Leu|Lys|Gln|Phe|Arg|Leu|Pro|Leu|Glu|
| |1310| | | | |1315| | | |1320| |
|Glu|Thr|Glu|Leu|Glu|Lys|Arg|Ile|Ile|Val|Asp|Asp|Thr|Ser|Thr|
| |1325| | | | |1330| | | |1335| |
|Gln|Trp|Ser|Lys|Asn|Met|Lys|His|Leu|Thr|Pro|Ser|Thr|Leu|Thr|
| |1340| | | | |1345| | | |1350| |
|Gln|Ile|Asp|Tyr|Asn|Glu|Lys|Glu|Lys|Gly|Ala|Ile|Thr|Gln|Ser|
| |1355| | | | |1360| | | |1365| |
|Pro|Leu|Ser|Asp|Cys|Leu|Thr|Arg|Ser|His|Ser|Ile|Pro|Gln|Ala|
| |1370| | | | |1375| | | |1380| |
|Asn|Arg|Ser|Pro|Leu|Pro|Ile|Ala|Lys|Val|Ser|Ser|Phe|Pro|Ser|
| |1385| | | | |1390| | | |1395| |
|Ile|Arg|Pro|Ile|Tyr|Leu|Thr|Arg|Val|Leu|Phe|Gln|Asp|Asn|Ser|
| |1400| | | | |1405| | | |1410| |
|Ser|His|Leu|Pro|Ala|Ala|Ser|Tyr|Arg|Lys|Lys|Asp|Ser|Gly|Val|
| |1415| | | | |1420| | | |1425| |
|Gln|Glu|Ser|Ser|His|Phe|Leu|Gln|Gly|Ala|Lys|Lys|Asn|Asn|Leu|
| |1430| | | | |1435| | | |1440| |
|Ser|Leu|Ala|Ile|Leu|Thr|Leu|Glu|Met|Thr|Gly|Asp|Gln|Arg|Glu|
| |1445| | | | |1450| | | |1455| |
|Val|Gly|Ser|Leu|Gly|Thr|Ser|Ala|Thr|Asn|Ser|Val|Thr|Tyr|Lys|
| |1460| | | | |1465| | | |1470| |
|Lys|Val|Glu|Asn|Thr|Val|Leu|Pro|Lys|Pro|Asp|Leu|Pro|Lys|Thr|
| |1475| | | | |1480| | | |1485| |
|Ser|Gly|Lys|Val|Glu|Leu|Leu|Pro|Lys|Val|His|Ile|Tyr|Gln|Lys|
| |1490| | | | |1495| | | |1500| |
|Asp|Leu|Phe|Pro|Thr|Glu|Thr|Ser|Asn|Gly|Ser|Pro|Gly|His|Leu|
| |1505| | | | |1510| | | |1515| |
|Asp|Leu|Val|Glu|Gly|Ser|Leu|Leu|Gln|Gly|Thr|Glu|Gly|Ala|Ile|

-continued

```
              1520                1525                1530

Lys  Trp  Asn  Glu  Ala  Asn  Arg  Pro  Gly  Lys  Val  Pro  Phe  Leu  Arg
    1535                1540                1545

Val  Ala  Thr  Glu  Ser  Ser  Ala  Lys  Thr  Pro  Ser  Lys  Leu  Leu  Asp
    1550                1555                1560

Pro  Leu  Ala  Trp  Asp  Asn  His  Tyr  Gly  Thr  Gln  Ile  Pro  Lys  Glu
    1565                1570                1575

Glu  Trp  Lys  Ser  Gln  Glu  Lys  Ser  Pro  Glu  Lys  Thr  Ala  Phe  Lys
    1580                1585                1590

Lys  Lys  Asp  Thr  Ile  Leu  Ser  Leu  Asn  Ala  Cys  Glu  Ser  Asn  His
    1595                1600                1605

Ala  Ile  Ala  Ala  Ile  Asn  Glu  Gly  Gln  Asn  Lys  Pro  Glu  Ile  Glu
    1610                1615                1620

Val  Thr  Trp  Ala  Lys  Gln  Gly  Arg  Thr  Glu  Arg  Leu  Cys  Ser  Gln
    1625                1630                1635

Asn  Pro  Pro  Val  Leu  Lys  Arg  His  Gln  Arg  Glu  Ile  Thr  Arg  Thr
    1640                1645                1650

Thr  Leu  Gln  Ser  Asp  Gln  Glu  Glu  Ile  Asp  Tyr  Asp  Asp  Thr  Ile
    1655                1660                1665

Ser  Val  Glu  Met  Lys  Lys  Glu  Asp  Phe  Asp  Ile  Tyr  Asp  Glu  Asp
    1670                1675                1680

Glu  Asn  Gln  Ser  Pro  Arg  Ser  Phe  Gln  Lys  Lys  Thr  Arg  His  Tyr
    1685                1690                1695

Phe  Ile  Ala  Ala  Val  Glu  Arg  Leu  Trp  Asp  Tyr  Gly  Met  Ser  Ser
    1700                1705                1710

Ser  Pro  His  Val  Leu  Arg  Asn  Arg  Ala  Gln  Ser  Gly  Ser  Val  Pro
    1715                1720                1725

Gln  Phe  Lys  Lys  Val  Val  Phe  Gln  Glu  Phe  Thr  Asp  Gly  Ser  Phe
    1730                1735                1740

Thr  Gln  Pro  Leu  Tyr  Arg  Gly  Glu  Leu  Asn  Glu  His  Leu  Gly  Leu
    1745                1750                1755

Leu  Gly  Pro  Tyr  Ile  Arg  Ala  Glu  Val  Glu  Asp  Asn  Ile  Met  Val
    1760                1765                1770

Thr  Phe  Arg  Asn  Gln  Ala  Ser  Arg  Pro  Tyr  Ser  Phe  Tyr  Ser  Ser
    1775                1780                1785

Leu  Ile  Ser  Tyr  Glu  Glu  Asp  Gln  Arg  Gln  Gly  Ala  Glu  Pro  Arg
    1790                1795                1800

Lys  Asn  Phe  Val  Lys  Pro  Asn  Glu  Thr  Lys  Thr  Tyr  Phe  Trp  Lys
    1805                1810                1815

Val  Gln  His  His  Met  Ala  Pro  Thr  Lys  Asp  Glu  Phe  Asp  Cys  Lys
    1820                1825                1830

Ala  Trp  Ala  Tyr  Phe  Ser  Asp  Val  Asp  Leu  Glu  Lys  Asp  Val  His
    1835                1840                1845

Ser  Gly  Leu  Ile  Gly  Pro  Leu  Leu  Val  Cys  His  Thr  Asn  Thr  Leu
    1850                1855                1860

Asn  Pro  Ala  His  Gly  Arg  Gln  Val  Thr  Val  Gln  Glu  Phe  Ala  Leu
    1865                1870                1875

Phe  Phe  Thr  Ile  Phe  Asp  Glu  Thr  Lys  Ser  Trp  Tyr  Phe  Thr  Glu
    1880                1885                1890

Asn  Met  Glu  Arg  Asn  Cys  Arg  Ala  Pro  Cys  Asn  Ile  Gln  Met  Glu
    1895                1900                1905

Asp  Pro  Thr  Phe  Lys  Glu  Asn  Tyr  Arg  Phe  His  Ala  Ile  Asn  Gly
    1910                1915                1920
```

-continued

```
Tyr Ile Met Asp Thr Leu Pro Gly Leu Val Met Ala Gln Asp Gln
1925                 1930                1935

Arg Ile Arg Trp Tyr Leu Leu Ser Met Gly Ser Asn Glu Asn Ile
1940                 1945                1950

His Ser Ile His Phe Ser Gly His Val Phe Thr Val Arg Lys Lys
1955                 1960                1965

Glu Glu Tyr Lys Met Ala Leu Tyr Asn Leu Tyr Pro Gly Val Phe
1970                 1975                1980

Glu Thr Val Glu Met Leu Pro Ser Lys Ala Gly Ile Trp Arg Val
1985                 1990                1995

Glu Cys Leu Ile Gly Glu His Leu His Ala Gly Met Ser Thr Leu
2000                 2005                2010

Phe Leu Val Tyr Ser Asn Lys Cys Gln Thr Pro Leu Gly Met Ala
2015                 2020                2025

Ser Gly His Ile Arg Asp Phe Gln Ile Thr Ala Ser Gly Gln Tyr
2030                 2035                2040

Gly Gln Trp Ala Pro Lys Leu Ala Arg Leu His Tyr Ser Gly Ser
2045                 2050                2055

Ile Asn Ala Trp Ser Thr Lys Glu Pro Phe Ser Trp Ile Lys Val
2060                 2065                2070

Asp Leu Leu Ala Pro Met Ile Ile His Gly Ile Lys Thr Gln Gly
2075                 2080                2085

Ala Arg Gln Lys Phe Ser Ser Leu Tyr Ile Ser Gln Phe Ile Ile
2090                 2095                2100

Met Tyr Ser Leu Asp Gly Lys Lys Trp Gln Thr Tyr Arg Gly Asn
2105                 2110                2115

Ser Thr Gly Thr Leu Met Val Phe Phe Gly Asn Val Asp Ser Ser
2120                 2125                2130

Gly Ile Lys His Asn Ile Phe Asn Pro Pro Ile Ile Ala Arg Tyr
2135                 2140                2145

Ile Arg Leu His Pro Thr His Tyr Ser Ile Arg Ser Thr Leu Arg
2150                 2155                2160

Met Glu Leu Met Gly Cys Asp Leu Asn Ser Cys Ser Met Pro Leu
2165                 2170                2175

Gly Met Glu Ser Lys Ala Ile Ser Asp Ala Gln Ile Thr Ala Ser
2180                 2185                2190

Ser Tyr Phe Thr Asn Met Phe Ala Thr Trp Ser Pro Ser Lys Ala
2195                 2200                2205

Arg Leu His Leu Gln Gly Arg Ser Asn Ala Trp Arg Pro Gln Val
2210                 2215                2220

Asn Asn Pro Lys Glu Trp Leu Gln Val Asp Phe Gln Lys Thr Met
2225                 2230                2235

Lys Val Thr Gly Val Thr Thr Gln Gly Val Lys Ser Leu Leu Thr
2240                 2245                2250

Ser Met Tyr Val Lys Glu Phe Leu Ile Ser Ser Ser Gln Asp Gly
2255                 2260                2265

His Gln Trp Thr Leu Phe Phe Gln Asn Gly Lys Val Lys Val Phe
2270                 2275                2280

Gln Gly Asn Gln Asp Ser Phe Thr Pro Val Val Asn Ser Leu Asp
2285                 2290                2295

Pro Pro Leu Leu Thr Arg Tyr Leu Arg Ile His Pro Gln Ser Trp
2300                 2305                2310
```

-continued

Val His Gln Ile Ala Leu Arg Met Glu Val Leu Gly Cys Glu Ala
    2315                2320                2325

Gln Asp Leu Tyr
    2330

<210> SEQ ID NO 3
<211> LENGTH: 1457
<212> TYPE: PRT
<213> ORGANISM: Artificial Sequence
<220> FEATURE:
<223> OTHER INFORMATION: Synthetic Sequence

<400> SEQUENCE: 3

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

```
Asp Gly Met Glu Ala Tyr Val Lys Val Asp Ser Cys Pro Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
```

-continued

```
                755                 760                 765
Lys Arg His Gln Arg Glu Ile Thr Arg Thr Thr Leu Gln Ser Asp Gln
770                 775                 780
Glu Glu Ile Asp Tyr Asp Asp Thr Ile Ser Val Glu Met Lys Lys Glu
785                 790                 795                 800
Asp Phe Asp Ile Tyr Asp Glu Asp Glu Asn Gln Ser Pro Arg Ser Phe
                805                 810                 815
Gln Lys Lys Thr Arg His Tyr Phe Ile Ala Ala Val Glu Arg Leu Trp
                820                 825                 830
Asp Tyr Gly Met Ser Ser Ser Pro His Val Leu Arg Asn Arg Ala Gln
                835                 840                 845
Ser Gly Ser Val Pro Gln Phe Lys Lys Val Val Phe Gln Glu Phe Thr
850                 855                 860
Asp Gly Ser Phe Thr Gln Pro Leu Tyr Arg Gly Glu Leu Asn Glu His
865                 870                 875                 880
Leu Gly Leu Leu Gly Pro Tyr Ile Arg Ala Glu Val Glu Asp Asn Ile
                885                 890                 895
Met Val Thr Phe Arg Asn Gln Ala Ser Arg Pro Tyr Ser Phe Tyr Ser
                900                 905                 910
Ser Leu Ile Ser Tyr Glu Glu Asp Gln Arg Gln Gly Ala Glu Pro Arg
                915                 920                 925
Lys Asn Phe Val Lys Pro Asn Glu Thr Lys Thr Tyr Phe Trp Lys Val
930                 935                 940
Gln His His Met Ala Pro Thr Lys Asp Glu Phe Asp Cys Lys Ala Trp
945                 950                 955                 960
Ala Tyr Phe Ser Asp Val Asp Leu Glu Lys Asp Val His Ser Gly Leu
                965                 970                 975
Ile Gly Pro Leu Leu Val Cys His Thr Asn Thr Leu Asn Pro Ala His
                980                 985                 990
Gly Arg Gln Val Thr Val Gln Glu Phe Ala Leu Phe Phe Thr Ile Phe
                995                 1000                1005
Asp Glu Thr Lys Ser Trp Tyr Phe Thr Glu Asn Met Glu Arg Asn
        1010                1015                1020
Cys Arg Ala Pro Cys Asn Ile Gln Met Glu Asp Pro Thr Phe Lys
        1025                1030                1035
Glu Asn Tyr Arg Phe His Ala Ile Asn Gly Tyr Ile Met Asp Thr
        1040                1045                1050
Leu Pro Gly Leu Val Met Ala Gln Asp Gln Arg Ile Arg Trp Tyr
        1055                1060                1065
Leu Leu Ser Met Gly Ser Asn Glu Asn Ile His Ser Ile His Phe
        1070                1075                1080
Ser Gly His Val Phe Thr Val Arg Lys Lys Glu Glu Tyr Lys Met
        1085                1090                1095
Ala Leu Tyr Asn Leu Tyr Pro Gly Val Phe Glu Thr Val Glu Met
        1100                1105                1110
Leu Pro Ser Lys Ala Gly Ile Trp Arg Val Glu Cys Leu Ile Gly
        1115                1120                1125
Glu His Leu His Ala Gly Met Ser Thr Leu Phe Leu Val Tyr Ser
        1130                1135                1140
Asn Lys Cys Gln Thr Pro Leu Gly Met Ala Ser Gly His Ile Arg
        1145                1150                1155
Asp Phe Gln Ile Thr Ala Ser Gly Gln Tyr Gly Gln Trp Ala Pro
        1160                1165                1170
```

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr
    1445                1450                1455

<210> SEQ ID NO 4
<211> LENGTH: 1438
<212> TYPE: PRT
<213> ORGANISM: Artificial Sequence
<220> FEATURE:
<223> OTHER INFORMATION: BDD Factor VIII

<400> SEQUENCE: 4

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

-continued

```
Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
                115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
                195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
                275                 280                 285

Ser Pro Ile Thr Phe Leu Thr Ala Gln Thr Leu Leu Met Asp Leu Gly
                290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
                355                 360                 365

Ile Gln Ile Arg Ser Val Ala Lys Lys His Pro Lys Thr Trp Val His
                370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
                450                 455                 460

Phe Lys Asn Gln Ala Ser Arg Pro Tyr Asn Ile Tyr Pro His Gly Ile
465                 470                 475                 480
```

-continued

```
Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
```

-continued

```
                900              905              910
Val Lys Pro Asn Glu Thr Lys Thr Tyr Phe Trp Lys Val Gln His His
            915              920              925

Met Ala Pro Thr Lys Asp Glu Phe Asp Cys Lys Ala Trp Ala Tyr Phe
            930              935              940

Ser Asp Val Asp Leu Glu Lys Asp Val His Ser Gly Leu Ile Gly Pro
945              950              955              960

Leu Leu Val Cys His Thr Asn Thr Leu Asn Pro Ala His Gly Arg Gln
            965              970              975

Val Thr Val Gln Glu Phe Ala Leu Phe Phe Thr Ile Phe Asp Glu Thr
            980              985              990

Lys Ser Trp Tyr Phe Thr Glu Asn Met Glu Arg Asn Cys Arg Ala Pro
            995             1000             1005

Cys Asn Ile Gln Met Glu Asp Pro Thr Phe Lys Glu Asn Tyr Arg
        1010             1015             1020

Phe His Ala Ile Asn Gly Tyr Ile Met Asp Thr Leu Pro Gly Leu
        1025             1030             1035

Val Met Ala Gln Asp Gln Arg Ile Arg Trp Tyr Leu Leu Ser Met
        1040             1045             1050

Gly Ser Asn Glu Asn Ile His Ser Ile His Phe Ser Gly His Val
        1055             1060             1065

Phe Thr Val Arg Lys Lys Glu Glu Tyr Lys Met Ala Leu Tyr Asn
        1070             1075             1080

Leu Tyr Pro Gly Val Phe Glu Thr Val Glu Met Leu Pro Ser Lys
        1085             1090             1095

Ala Gly Ile Trp Arg Val Glu Cys Leu Ile Gly Glu His Leu His
        1100             1105             1110

Ala Gly Met Ser Thr Leu Phe Leu Val Tyr Ser Asn Lys Cys Gln
        1115             1120             1125

Thr Pro Leu Gly Met Ala Ser Gly His Ile Arg Asp Phe Gln Ile
        1130             1135             1140

Thr Ala Ser Gly Gln Tyr Gly Gln Trp Ala Pro Lys Leu Ala Arg
        1145             1150             1155

Leu His Tyr Ser Gly Ser Ile Asn Ala Trp Ser Thr Lys Glu Pro
        1160             1165             1170

Phe Ser Trp Ile Lys Val Asp Leu Leu Ala Pro Met Ile Ile His
        1175             1180             1185

Gly Ile Lys Thr Gln Gly Ala Arg Gln Lys Phe Ser Ser Leu Tyr
        1190             1195             1200

Ile Ser Gln Phe Ile Ile Met Tyr Ser Leu Asp Gly Lys Lys Trp
        1205             1210             1215

Gln Thr Tyr Arg Gly Asn Ser Thr Gly Thr Leu Met Val Phe Phe
        1220             1225             1230

Gly Asn Val Asp Ser Ser Gly Ile Lys His Asn Ile Phe Asn Pro
        1235             1240             1245

Pro Ile Ile Ala Arg Tyr Ile Arg Leu His Pro Thr His Tyr Ser
        1250             1255             1260

Ile Arg Ser Thr Leu Arg Met Glu Leu Met Gly Cys Asp Leu Asn
        1265             1270             1275

Ser Cys Ser Met Pro Leu Gly Met Glu Ser Lys Ala Ile Ser Asp
        1280             1285             1290

Ala Gln Ile Thr Ala Ser Ser Tyr Phe Thr Asn Met Phe Ala Thr
        1295             1300             1305
```

-continued

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 5
<211> LENGTH: 72
<212> TYPE: PRT
<213> ORGANISM: Artificial Sequence
<220> FEATURE:
<223> OTHER INFORMATION: Extracellular Region of GPA

<400> SEQUENCE: 5

Leu Ser Thr Thr Glu Val Ala Met His Thr Ser Thr Ser Ser Ser Val
1               5                   10                  15

Thr Lys Ser Tyr Ile Ser Ser Gln Thr Asn Asp Thr His Lys Arg Asp
            20                  25                  30

Thr Tyr Ala Ala Thr Pro Arg Ala His Glu Val Ser Glu Ile Ser Val
        35                  40                  45

Arg Thr Val Tyr Pro Pro Glu Glu Glu Thr Gly Glu Arg Val Gln Leu
    50                  55                  60

Ala His His Phe Ser Glu Pro Glu
65                  70

<210> SEQ ID NO 6
<211> LENGTH: 484
<212> TYPE: PRT
<213> ORGANISM: Artificial Sequence
<220> FEATURE:
<223> OTHER INFORMATION: Synthetic Sequence

<400> SEQUENCE: 6

Met Glu Trp Ser Trp Val Phe Leu Phe Phe Leu Ser Val Thr Thr Gly
1               5                   10                  15

Val His Ser Arg Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Thr Tyr Thr Ile His Trp Val Lys Gln Lys Thr Gly Gln Gly Leu
    50                  55                  60

Glu Trp Ile Gly Tyr Ile Asn Pro Ser Ser Asp Tyr Thr Arg Tyr Asn
65                  70                  75                  80

Pro Lys Phe Lys Asp Lys Ala Thr Leu Thr Thr Asp Lys Ser Ser Ser

```
                85                  90                  95
Thr Ala Tyr Met Lys Leu Asn Ser Leu Ala Ser Asp Asp Ser Ala Val
            100                 105                 110

Tyr Tyr Cys Gln Thr Gly Thr Arg Asp Tyr Trp Gly Gln Gly Thr Thr
            115                 120                 125

Leu Thr Val Ser Ser Gly Gly Gly Gly Ser Gly Gly Gly Gly Ser Gly
            130                 135                 140

Gly Gly Ser Gln Ile Val Leu Thr Gln Ser Pro Pro Ile Met Ser
145                 150                 155                 160

Ala Ser Pro Gly Glu Lys Val Thr Met Thr Cys Ser Ala Ala Ser Ser
                165                 170                 175

Val Ser Tyr Ile Tyr Trp Phe Gln Gln Lys Pro Gly Thr Ser Pro Lys
                180                 185                 190

Leu Trp Ile Tyr Ser Thr Ser Thr Leu Pro Ser Gly Val Pro Thr Arg
                195                 200                 205

Phe Ser Gly Ser Gly Ser Gly Thr Ser Tyr Ser Leu Thr Ile Ser Arg
                210                 215                 220

Met Glu Ala Glu Asp Ala Ala Thr Tyr Tyr Cys His Gln Arg Asn Ser
225                 230                 235                 240

Phe Pro Phe Thr Phe Gly Ser Gly Thr Lys Leu Glu Ile Arg Gly Gly
                245                 250                 255

Gly Gly Ala Gly Gly Gly Cys Lys Pro Cys Ile Cys Thr Val Pro
                260                 265                 270

Glu Val Ser Ser Val Phe Ile Phe Pro Pro Lys Pro Lys Asp Val Leu
                275                 280                 285

Thr Ile Thr Leu Thr Pro Lys Val Thr Cys Val Val Val Asp Ile Ser
                290                 295                 300

Lys Asp Asp Pro Glu Val Gln Phe Ser Trp Phe Val Asp Val Glu
305                 310                 315                 320

Val His Thr Ala Gln Thr Gln Pro Arg Glu Glu Gln Phe Asn Ser Thr
                325                 330                 335

Phe Arg Ser Val Ser Glu Leu Pro Ile Met His Gln Asp Trp Leu Asn
                340                 345                 350

Gly Lys Glu Phe Lys Cys Arg Val Asn Ser Ala Ala Phe Pro Ala Pro
                355                 360                 365

Ile Glu Lys Thr Ile Ser Lys Thr Lys Gly Arg Pro Lys Ala Pro Gln
                370                 375                 380

Val Tyr Thr Ile Pro Pro Lys Glu Gln Met Ala Lys Asp Lys Val
385                 390                 395                 400

Ser Leu Thr Cys Met Ile Thr Asp Phe Phe Pro Glu Asp Ile Thr Val
                405                 410                 415

Glu Trp Gln Trp Asn Gly Gln Pro Ala Glu Asn Tyr Lys Asn Thr Gln
                420                 425                 430

Pro Ile Met Asp Thr Asp Gly Ser Tyr Phe Val Tyr Ser Lys Leu Asn
                435                 440                 445

Val Gln Lys Ser Asn Trp Glu Ala Gly Asn Thr Phe Thr Cys Ser Val
                450                 455                 460

Leu His Glu Gly Leu His Asn His His Thr Glu Lys Ser Leu Ser His
465                 470                 475                 480

Ser Pro Gly Lys

<210> SEQ ID NO 7
<211> LENGTH: 484
```

<212> TYPE: PRT
<213> ORGANISM: Artificial Sequence
<220> FEATURE:
<223> OTHER INFORMATION: Synthetic Sequence

<400> SEQUENCE: 7

```
Met Glu Trp Ser Trp Val Phe Leu Phe Phe Leu Ser Val Thr Thr Gly
1               5                   10                  15

Val His Ser Arg Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Asn Tyr Ala Met His Trp Val Lys Gln Arg Pro Gly Gln Gly Leu
    50                  55                  60

Glu Trp Ile Gly Tyr Ile Asn Pro Lys Ser Asp Asn Thr Asn Tyr Asn
65                  70                  75                  80

Gln Lys Phe Lys Asp Lys Ala Thr Leu Thr Thr Asp Lys Ser Ser Ala
                85                  90                  95

Thr Ala Tyr Met Gln Leu Ser Ser Leu Thr Ser Asp Asp Ser Ala Val
            100                 105                 110

Tyr Tyr Cys Gln Thr Gly Thr Arg Asp Tyr Trp Gly Gln Gly Thr Thr
        115                 120                 125

Leu Thr Val Ser Ser Gly Gly Gly Gly Ser Gly Gly Gly Gly Ser Gly
    130                 135                 140

Gly Gly Ser His Ile Val Leu Thr Gln Ser Pro Ala Ile Met Ser
145                 150                 155                 160

Ala Ser Pro Gly Glu Lys Val Thr Ile Phe Cys Ser Ala Ser Ser Ser
                165                 170                 175

Ile Thr Tyr Val Tyr Trp Phe Gln Gln Lys Pro Gly Thr Ser Pro Lys
            180                 185                 190

Leu Trp Ile Tyr Ser Thr Ser Ser Leu Pro Ser Gly Val Pro Ala Arg
        195                 200                 205

Phe Ser Gly Ser Gly Ser Gly Thr Ser Tyr Ser Leu Thr Ile Ser Arg
    210                 215                 220

Met Glu Ala Glu Asp Ala Ala Thr Tyr Tyr Cys His Gln Arg Asn Ser
225                 230                 235                 240

Tyr Pro Phe Thr Phe Gly Ser Gly Thr Lys Leu Glu Ile Lys Gly Gly
                245                 250                 255

Gly Gly Ala Gly Gly Gly Gly Cys Lys Pro Cys Ile Cys Thr Val Pro
            260                 265                 270

Glu Val Ser Ser Val Phe Ile Phe Pro Pro Lys Pro Lys Asp Val Leu
        275                 280                 285

Thr Ile Thr Leu Thr Pro Lys Val Thr Cys Val Val Val Asp Ile Ser
    290                 295                 300

Lys Asp Asp Pro Glu Val Gln Phe Ser Trp Phe Val Asp Asp Val Glu
305                 310                 315                 320

Val His Thr Ala Gln Thr Gln Pro Arg Glu Glu Gln Phe Asn Ser Thr
                325                 330                 335

Phe Arg Ser Val Ser Glu Leu Pro Ile Met His Gln Asp Trp Leu Asn
            340                 345                 350

Gly Lys Glu Phe Lys Cys Arg Val Asn Ser Ala Ala Phe Pro Ala Pro
        355                 360                 365

Ile Glu Lys Thr Ile Ser Lys Thr Lys Gly Arg Pro Lys Ala Pro Gln
    370                 375                 380
```

```
Val Tyr Thr Ile Pro Pro Lys Glu Gln Met Ala Lys Asp Lys Val
385                 390                 395                 400

Ser Leu Thr Cys Met Ile Thr Asp Phe Phe Pro Glu Asp Ile Thr Val
        405                 410                 415

Glu Trp Gln Trp Asn Gly Gln Pro Ala Glu Asn Tyr Lys Asn Thr Gln
            420                 425                 430

Pro Ile Met Asp Thr Asp Gly Ser Tyr Phe Val Tyr Ser Lys Leu Asn
                435                 440                 445

Val Gln Lys Ser Asn Trp Glu Ala Gly Asn Thr Phe Thr Cys Ser Val
        450                 455                 460

Leu His Glu Gly Leu His Asn His His Thr Glu Lys Ser Leu Ser His
465                 470                 475                 480

Ser Pro Gly Lys
```

<210> SEQ ID NO 8
<211> LENGTH: 489
<212> TYPE: PRT
<213> ORGANISM: Artificial Sequence
<220> FEATURE:
<223> OTHER INFORMATION: Synthetic Sequence

<400> SEQUENCE: 8

```
Met Glu Trp Ser Trp Val Phe Leu Phe Phe Leu Ser Val Thr Thr Gly
1               5                   10                  15

Val His Ser Arg Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Thr Tyr Thr Ile His Trp Val Lys Gln Lys Thr Gly Gln Gly Leu
    50                  55                  60

Glu Trp Ile Gly Tyr Ile Asn Pro Ser Ser Asp Tyr Thr Arg Tyr Asn
65                  70                  75                  80

Pro Lys Phe Lys Asp Lys Ala Thr Leu Thr Thr Asp Lys Ser Ser Ser
                85                  90                  95

Thr Ala Tyr Met Lys Leu Asn Ser Leu Ala Ser Asp Asp Ser Ala Val
            100                 105                 110

Tyr Tyr Cys Gln Thr Gly Thr Arg Asp Tyr Trp Gly Gln Gly Thr Thr
        115                 120                 125

Leu Thr Val Ser Ser Gly Gly Gly Gly Ser Gly Gly Gly Gly Ser Gly
    130                 135                 140

Gly Gly Gly Ser Asp Ile Val Leu Thr Gln Ser Pro Ala Ser Leu Ala
145                 150                 155                 160

Val Ser Leu Gly Gln Arg Ala Thr Ile Ser Tyr Arg Ala Ser Lys Ser
                165                 170                 175

Val Ser Thr Ser Gly Tyr Ser Tyr Met His Trp Asn Gln Gln Lys Pro
            180                 185                 190

Gly Gln Pro Pro Arg Leu Leu Ile Tyr Leu Val Ser Asn Leu Glu Ser
        195                 200                 205

Gly Val Pro Thr Arg Phe Ser Gly Ser Gly Ser Gly Thr Ser Tyr Ser
    210                 215                 220

Leu Thr Ile Ser Arg Met Glu Ala Glu Asp Ala Ala Thr Tyr Tyr Cys
225                 230                 235                 240

His Gln Arg Asn Ser Phe Pro Phe Thr Phe Gly Ser Gly Thr Lys Leu
                245                 250                 255

Glu Ile Arg Gly Gly Gly Gly Ala Gly Gly Gly Gly Cys Lys Pro Cys
```

```
            260                 265                 270
Ile Cys Thr Val Pro Glu Val Ser Ser Val Phe Ile Phe Pro Pro Lys
                275                 280                 285

Pro Lys Asp Val Leu Thr Ile Thr Leu Thr Pro Lys Val Thr Cys Val
            290                 295                 300

Val Val Asp Ile Ser Lys Asp Asp Pro Glu Val Gln Phe Ser Trp Phe
305                 310                 315                 320

Val Asp Asp Val Glu Val His Thr Ala Gln Thr Gln Pro Arg Glu Glu
                325                 330                 335

Gln Phe Asn Ser Thr Phe Arg Ser Val Ser Glu Leu Pro Ile Met His
            340                 345                 350

Gln Asp Trp Leu Asn Gly Lys Glu Phe Lys Cys Arg Val Asn Ser Ala
            355                 360                 365

Ala Phe Pro Ala Pro Ile Glu Lys Thr Ile Ser Lys Thr Lys Gly Arg
            370                 375                 380

Pro Lys Ala Pro Gln Val Tyr Thr Ile Pro Pro Lys Glu Gln Met
385                 390                 395                 400

Ala Lys Asp Lys Val Ser Leu Thr Cys Met Ile Thr Asp Phe Phe Pro
                405                 410                 415

Glu Asp Ile Thr Val Glu Trp Gln Trp Asn Gly Gln Pro Ala Glu Asn
            420                 425                 430

Tyr Lys Asn Thr Gln Pro Ile Met Asp Thr Asp Gly Ser Tyr Phe Val
            435                 440                 445

Tyr Ser Lys Leu Asn Val Gln Lys Ser Asn Trp Glu Ala Gly Asn Thr
            450                 455                 460

Phe Thr Cys Ser Val Leu His Glu Gly Leu His Asn His His Thr Glu
465                 470                 475                 480

Lys Ser Leu Ser His Ser Pro Gly Lys
                485

<210> SEQ ID NO 9
<211> LENGTH: 484
<212> TYPE: PRT
<213> ORGANISM: Artificial Sequence
<220> FEATURE:
<223> OTHER INFORMATION: Synthetic Sequence

<400> SEQUENCE: 9

Met Glu Trp Ser Trp Val Phe Leu Phe Phe Leu Ser Val Thr Thr Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Ser Met His Trp Val Lys Gln Arg Pro Gly Gln Gly Leu
    50                  55                  60

Glu Trp Ile Gly Tyr Ile Asn Pro Gly Thr Tyr Tyr Thr Asn Tyr Asn
65                  70                  75                  80

Gln Lys Phe Lys Asp Arg Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Gln Thr Gly Thr Arg Asp Tyr Trp Gly Gln Gly Thr Thr
        115                 120                 125

Leu Thr Val Ser Ser Gly Gly Gly Gly Ser Gly Gly Gly Gly Ser Gly
```

```
Gly Gly Gly Ser Gln Ile Val Leu Thr Gln Ser Pro Ile Met Ser
145                 150                 155                 160

Ala Ser Pro Gly Glu Lys Val Thr Ile Thr Cys Ser Ala Ala Ser Ser
                165                 170                 175

Val Ser Tyr Ile Tyr Trp Phe Gln Gln Lys Pro Gly Thr Ser Pro Lys
            180                 185                 190

Leu Trp Ile Tyr Ser Thr Ser Ser Leu Pro Ser Gly Val Pro Thr Arg
        195                 200                 205

Phe Ser Gly Ser Gly Ser Gly Thr Ser Tyr Ser Leu Thr Ile Ser Arg
    210                 215                 220

Met Glu Ala Glu Asp Ala Ala Thr Tyr Tyr Cys His Gln Arg Ser Ser
225                 230                 235                 240

Tyr Pro Phe Thr Phe Gly Ser Gly Thr Lys Leu Glu Ile Arg Gly Gly
                245                 250                 255

Gly Gly Ala Gly Gly Gly Gly Cys Lys Pro Cys Ile Cys Thr Val Pro
            260                 265                 270

Glu Val Ser Ser Val Phe Ile Phe Pro Pro Lys Pro Lys Asp Val Leu
        275                 280                 285

Thr Ile Thr Leu Thr Pro Lys Val Thr Cys Val Val Val Asp Ile Ser
    290                 295                 300

Lys Asp Asp Pro Glu Val Gln Phe Ser Trp Phe Val Asp Asp Val Glu
305                 310                 315                 320

Val His Thr Ala Gln Thr Gln Pro Arg Glu Glu Gln Phe Asn Ser Thr
                325                 330                 335

Phe Arg Ser Val Ser Glu Leu Pro Ile Met His Gln Asp Trp Leu Asn
            340                 345                 350

Gly Lys Glu Phe Lys Cys Arg Val Asn Ser Ala Ala Phe Pro Ala Pro
        355                 360                 365

Ile Glu Lys Thr Ile Ser Lys Thr Lys Gly Arg Pro Lys Ala Pro Gln
    370                 375                 380

Val Tyr Thr Ile Pro Pro Lys Glu Gln Met Ala Lys Asp Lys Val
385                 390                 395                 400

Ser Leu Thr Cys Met Ile Thr Asp Phe Phe Pro Glu Asp Ile Thr Val
                405                 410                 415

Glu Trp Gln Trp Asn Gly Gln Pro Ala Glu Asn Tyr Lys Asn Thr Gln
            420                 425                 430

Pro Ile Met Asp Thr Asp Gly Ser Tyr Phe Val Tyr Ser Lys Leu Asn
        435                 440                 445

Val Gln Lys Ser Asn Trp Glu Ala Gly Asn Thr Phe Thr Cys Ser Val
    450                 455                 460

Leu His Glu Gly Leu His Asn His His Thr Glu Lys Ser Leu Ser His
465                 470                 475                 480

Ser Pro Gly Lys

<210> SEQ ID NO 10
<211> LENGTH: 484
<212> TYPE: PRT
<213> ORGANISM: Artificial Sequence
<220> FEATURE:
<223> OTHER INFORMATION: Synthetic Sequence

<400> SEQUENCE: 10

Met Glu Trp Ser Trp Val Phe Leu Phe Phe Leu Ser Val Thr Thr Gly
1               5                   10                  15
```

```
Val His Ser Gln Val Gln Leu Leu Gln Ser Gly Ala Glu Leu Ala Arg
            20                  25                  30

Pro Gly Ala Ser Val Arg Ile Ser Cys Lys Ala Ser Gly Tyr Thr Phe
        35                  40                  45

Thr Arg Tyr Ala Met His Trp Val Lys Gln Arg Pro Gly Gln Gly Leu
 50                  55                  60

Glu Trp Ile Gly Tyr Ile Asn Pro Gly Thr Phe Ser Thr Asn Tyr Asn
 65                  70                  75                  80

Gln Lys Phe Lys Asp Arg Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Gln Thr Gly Thr Arg Asp Tyr Trp Gly Gln Gly Thr Thr
            115                 120                 125

Leu Thr Val Ser Ser Gly Gly Gly Ser Gly Gly Gly Ser Gly
130                 135                 140

Gly Gly Gly Ser Gln Ile Val Leu Thr Gln Ser Pro Pro Ile Met Ser
145                 150                 155                 160

Ala Ser Pro Gly Glu Lys Val Thr Ile Thr Cys Ser Ala Ala Ser Ser
                165                 170                 175

Val Ser Tyr Ile Tyr Trp Phe Gln Gln Lys Pro Gly Thr Ser Pro Lys
            180                 185                 190

Leu Trp Ile Tyr Ser Thr Ser Ser Leu Pro Ser Gly Val Pro Thr Arg
            195                 200                 205

Phe Ser Gly Ser Gly Ser Gly Thr Ser Tyr Ser Leu Thr Ile Ser Arg
            210                 215                 220

Met Glu Ala Glu Asp Ala Ala Thr Tyr Tyr Cys His Gln Arg Ser Ser
225                 230                 235                 240

Tyr Pro Phe Thr Phe Gly Ser Gly Thr Lys Leu Glu Ile Arg Gly Gly
                245                 250                 255

Gly Gly Ala Gly Gly Gly Cys Lys Pro Cys Ile Cys Thr Val Pro
            260                 265                 270

Glu Val Ser Ser Val Phe Ile Phe Pro Pro Lys Pro Lys Asp Val Leu
            275                 280                 285

Thr Ile Thr Leu Thr Pro Lys Val Thr Cys Val Val Val Asp Ile Ser
290                 295                 300

Lys Asp Asp Pro Glu Val Gln Phe Ser Trp Phe Val Asp Asp Val Glu
305                 310                 315                 320

Val His Thr Ala Gln Thr Gln Pro Arg Glu Glu Gln Phe Asn Ser Thr
                325                 330                 335

Phe Arg Ser Val Ser Glu Leu Pro Ile Met His Gln Asp Trp Leu Asn
            340                 345                 350

Gly Lys Glu Phe Lys Cys Arg Val Asn Ser Ala Ala Phe Pro Ala Pro
            355                 360                 365

Ile Glu Lys Thr Ile Ser Lys Thr Lys Gly Arg Pro Lys Ala Pro Gln
            370                 375                 380

Val Tyr Thr Ile Pro Pro Pro Lys Glu Gln Met Ala Lys Asp Lys Val
385                 390                 395                 400

Ser Leu Thr Cys Met Ile Thr Asp Phe Phe Pro Glu Asp Ile Thr Val
                405                 410                 415

Glu Trp Gln Trp Asn Gly Gln Pro Ala Glu Asn Tyr Lys Asn Thr Gln
            420                 425                 430
```

Pro Ile Met Asp Thr Asp Gly Ser Tyr Phe Val Tyr Ser Lys Leu Asn
            435                 440                 445

Val Gln Lys Ser Asn Trp Glu Ala Gly Asn Thr Phe Thr Cys Ser Val
        450                 455                 460

Leu His Glu Gly Leu His Asn His His Thr Glu Lys Ser Leu Ser His
465                 470                 475                 480

Ser Pro Gly Lys

<210> SEQ ID NO 11
<211> LENGTH: 484
<212> TYPE: PRT
<213> ORGANISM: Artificial Sequence
<220> FEATURE:
<223> OTHER INFORMATION: Synthetic Sequence

<400> SEQUENCE: 11

Met Glu Trp Ser Trp Val Phe Leu Phe Phe Leu Ser Val Thr Thr Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Ser Tyr Ser Ile His Trp Ile Lys Gln Arg Pro Gly Gln Ser Leu
    50                  55                  60

Glu Trp Ile Gly Tyr Ile Asn Pro Asn Ser Asp Tyr Ala Asn Tyr Asn
65                  70                  75                  80

Gln Lys Phe Lys Asp Lys Ala Thr Leu Thr Thr Asp Lys Ser Ser Thr
                85                  90                  95

Thr Ala Tyr Met Gln Leu Ser Ser Leu Thr Thr Asp Asp Ser Ala Val
            100                 105                 110

Tyr Tyr Cys Gln Thr Gly Thr Arg Asp Tyr Trp Gly Gln Gly Thr Thr
        115                 120                 125

Leu Thr Val Ser Ser Gly Gly Gly Gly Ser Gly Gly Gly Gly Ser Gly
    130                 135                 140

Gly Gly Gly Ser His Ile Val Leu Thr Gln Ser Pro Ala Ile Met Ser
145                 150                 155                 160

Ala Ser Pro Gly Glu Lys Val Thr Ile Ile Cys Ser Ala Arg Ser Ser
                165                 170                 175

Val Ser Tyr Met Tyr Trp Phe Gln Gln Lys Pro Gly Thr Ser Pro Lys
            180                 185                 190

Leu Trp Ile Tyr Ala Thr Ser Ser Leu Pro Ser Gly Val Pro Ala Arg
        195                 200                 205

Phe Ser Gly Ser Gly Ser Gly Thr Ser Tyr Ser Leu Thr Ile Ser Arg
    210                 215                 220

Met Glu Ala Glu Asp Ala Ala Thr Tyr Tyr Cys His Gln Arg Ser Ser
225                 230                 235                 240

Tyr Pro Tyr Thr Phe Gly Ser Gly Thr Lys Leu Glu Ile Lys Gly Gly
                245                 250                 255

Gly Gly Ala Gly Gly Gly Gly Cys Lys Pro Cys Ile Cys Thr Val Pro
            260                 265                 270

Glu Val Ser Ser Val Phe Ile Phe Pro Pro Lys Pro Lys Asp Val Leu
        275                 280                 285

Thr Ile Thr Leu Thr Pro Lys Val Thr Cys Val Val Val Asp Ile Ser
    290                 295                 300

Lys Asp Asp Pro Glu Val Gln Phe Ser Trp Phe Val Asp Asp Val Glu

```
            305                 310                 315                 320
Val His Thr Ala Gln Thr Gln Pro Arg Glu Glu Gln Phe Asn Ser Thr
                325                 330                 335

Phe Arg Ser Val Ser Glu Leu Pro Ile Met His Gln Asp Trp Leu Asn
                340                 345                 350

Gly Lys Glu Phe Lys Cys Arg Val Asn Ser Ala Ala Phe Pro Ala Pro
                355                 360                 365

Ile Glu Lys Thr Ile Ser Lys Thr Lys Gly Arg Pro Lys Ala Pro Gln
                370                 375                 380

Val Tyr Thr Ile Pro Pro Lys Glu Gln Met Ala Lys Asp Lys Val
385                 390                 395                 400

Ser Leu Thr Cys Met Ile Thr Asp Phe Phe Pro Glu Asp Ile Thr Val
                405                 410                 415

Glu Trp Gln Trp Asn Gly Gln Pro Ala Glu Asn Tyr Lys Asn Thr Gln
                420                 425                 430

Pro Ile Met Asp Thr Asp Gly Ser Tyr Phe Val Tyr Ser Lys Leu Asn
                435                 440                 445

Val Gln Lys Ser Asn Trp Glu Ala Gly Asn Thr Phe Thr Cys Ser Val
                450                 455                 460

Leu His Glu Gly Leu His Asn His Thr Glu Lys Ser Leu Ser His
465                 470                 475                 480

Ser Pro Gly Lys

<210> SEQ ID NO 12
<211> LENGTH: 491
<212> TYPE: PRT
<213> ORGANISM: Artificial Sequence
<220> FEATURE:
<223> OTHER INFORMATION: Synthetic Sequence

<400> SEQUENCE: 12

Met Glu Trp Ser Trp Val Phe Leu Phe Leu Ser Val Thr Thr Gly
1               5                   10                  15

Val His Ser Gln Val Gln Leu Gln Gln Ser Gly Ala Glu Leu Ala Arg
                20                  25                  30

Pro Gly Ala Ser Val Lys Met Ser Cys Lys Ala Ser Gly Tyr Thr Phe
                35                  40                  45

Thr Ser Tyr Ser Ile His Trp Ile Lys Gln Arg Pro Gly Gln Ser Leu
                50                  55                  60

Glu Trp Ile Gly Tyr Ile Asn Pro Asn Ser Asp Tyr Ala Asn Tyr Asn
65                  70                  75                  80

Gln Lys Phe Lys Asp Lys Ala Thr Leu Thr Thr Asp Lys Ser Ser Thr
                85                  90                  95

Thr Ala Tyr Met Gln Leu Ser Ser Leu Thr Thr Asp Asp Ser Ala Val
                100                 105                 110

Tyr Tyr Cys Gln Thr Gly Thr Arg Asp Tyr Trp Gly Gln Gly Thr Thr
                115                 120                 125

Leu Thr Val Ser Ser Gly Gly Gly Gly Ser Gly Gly Gly Gly Ser Gly
                130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Asn Ser Gly Asn Gln Lys Asn Tyr Leu Ala Trp Tyr Gln Gln
                180                 185                 190
```

```
Lys Pro Gly Gln Pro Pro Lys Leu Leu Ile Tyr Gly Ala Ser Thr Arg
            195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Gly Gly Gly Ala Gly Gly Gly Cys Lys
            260                 265                 270

Pro Cys Ile Cys Thr Val Pro Glu Val Ser Ser Val Phe Ile Phe Pro
            275                 280                 285

Pro Lys Pro Lys Asp Val Leu Thr Ile Thr Leu Thr Pro Lys Val Thr
    290                 295                 300

Cys Val Val Asp Ile Ser Lys Asp Asp Pro Glu Val Gln Phe Ser
305                 310                 315                 320

Trp Phe Val Asp Asp Val Glu Val His Thr Ala Gln Thr Gln Pro Arg
                325                 330                 335

Glu Glu Gln Phe Asn Ser Thr Phe Arg Ser Val Ser Glu Leu Pro Ile
            340                 345                 350

Met His Gln Asp Trp Leu Asn Gly Lys Glu Phe Lys Cys Arg Val Asn
            355                 360                 365

Ser Ala Ala Phe Pro Ala Pro Ile Glu Lys Thr Ile Ser Lys Thr Lys
    370                 375                 380

Gly Arg Pro Lys Ala Pro Gln Val Tyr Thr Ile Pro Pro Lys Glu
385                 390                 395                 400

Gln Met Ala Lys Asp Lys Val Ser Leu Thr Cys Met Ile Thr Asp Phe
                405                 410                 415

Phe Pro Glu Asp Ile Thr Val Glu Trp Gln Trp Asn Gly Gln Pro Ala
            420                 425                 430

Glu Asn Tyr Lys Asn Thr Gln Pro Ile Met Asp Thr Asp Gly Ser Tyr
        435                 440                 445

Phe Val Tyr Ser Lys Leu Asn Val Gln Lys Ser Asn Trp Glu Ala Gly
    450                 455                 460

Asn Thr Phe Thr Cys Ser Val Leu His Glu Gly Leu His Asn His His
465                 470                 475                 480

Thr Glu Lys Ser Leu Ser His Ser Pro Gly Lys
                485                 490

<210> SEQ ID NO 13
<211> LENGTH: 484
<212> TYPE: PRT
<213> ORGANISM: Artificial Sequence
<220> FEATURE:
<223> OTHER INFORMATION: Synthetic Sequence

<400> SEQUENCE: 13

Met Glu Trp Ser Trp Val Phe Leu Phe Phe Leu Ser Val Thr Thr Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Ser Met His Trp Val Lys Gln Arg Pro Gly Gln Gly Leu
    50                  55                  60
```

-continued

```
Glu Trp Ile Gly Tyr Ile Asn Pro Gly Thr Tyr Ser Thr Asn Tyr Asn
 65                  70                  75                  80

Gln Lys Phe Lys Asp Arg Ala Thr Leu Thr Ala Asp Lys Ser Ser Ser
             85                  90                  95

Thr Ala Tyr Met Gln Leu Asn Ser Leu Thr Ser Glu Asp Ser Ala Val
            100                 105                 110

Tyr Tyr Cys Gln Thr Gly Thr Arg Asp Tyr Trp Gly Gln Gly Thr Thr
            115                 120                 125

Leu Thr Val Ser Ser Gly Gly Gly Ser Gly Gly Gly Ser Gly
130                 135                 140

Gly Gly Gly Ser Gln Ile Val Leu Thr Gln Ser Pro Pro Ile Met Ser
145                 150                 155                 160

Ala Ser Pro Gly Glu Lys Val Thr Ile Thr Cys Ser Ala Ala Ser Ser
                165                 170                 175

Val Ser Tyr Ile Tyr Trp Phe Gln Gln Lys Pro Gly Thr Ser Pro Lys
            180                 185                 190

Leu Trp Ile Tyr Ser Thr Ser Ser Leu Pro Ser Gly Val Pro Thr Arg
            195                 200                 205

Phe Ser Gly Ser Gly Ser Gly Thr Ser Tyr Ser Leu Thr Ile Ser Arg
210                 215                 220

Met Glu Ala Glu Asp Ala Ala Thr Tyr Tyr Cys His Gln Arg Ser Ser
225                 230                 235                 240

Tyr Pro Phe Thr Phe Gly Ser Gly Thr Lys Leu Glu Ile Arg Gly Gly
                245                 250                 255

Gly Gly Ala Gly Gly Gly Cys Lys Pro Cys Ile Cys Thr Val Pro
                260                 265                 270

Glu Val Ser Ser Val Phe Ile Phe Pro Pro Lys Pro Lys Asp Val Leu
            275                 280                 285

Thr Ile Thr Leu Thr Pro Lys Val Thr Cys Val Val Val Asp Ile Ser
            290                 295                 300

Lys Asp Asp Pro Glu Val Gln Phe Ser Trp Phe Val Asp Asp Val Glu
305                 310                 315                 320

Val His Thr Ala Gln Thr Gln Pro Arg Glu Glu Gln Phe Asn Ser Thr
                325                 330                 335

Phe Arg Ser Val Ser Glu Leu Pro Ile Met His Gln Asp Trp Leu Asn
            340                 345                 350

Gly Lys Glu Phe Lys Cys Arg Val Asn Ser Ala Ala Phe Pro Ala Pro
            355                 360                 365

Ile Glu Lys Thr Ile Ser Lys Thr Lys Gly Arg Pro Lys Ala Pro Gln
            370                 375                 380

Val Tyr Thr Ile Pro Pro Pro Lys Glu Gln Met Ala Lys Asp Lys Val
385                 390                 395                 400

Ser Leu Thr Cys Met Ile Thr Asp Phe Phe Pro Glu Asp Ile Thr Val
                405                 410                 415

Glu Trp Gln Trp Asn Gly Gln Pro Ala Glu Asn Tyr Lys Asn Thr Gln
            420                 425                 430

Pro Ile Met Asp Thr Asp Gly Ser Tyr Phe Val Tyr Ser Lys Leu Asn
            435                 440                 445

Val Gln Lys Ser Asn Trp Glu Ala Gly Asn Thr Phe Thr Cys Ser Val
            450                 455                 460

Leu His Glu Gly Leu His Asn His His Thr Glu Lys Ser Leu Ser His
465                 470                 475                 480
```

Ser Pro Gly Lys

<210> SEQ ID NO 14
<211> LENGTH: 490
<212> TYPE: PRT
<213> ORGANISM: Artificial Sequence
<220> FEATURE:
<223> OTHER INFORMATION: Synthetic Sequence

<400> SEQUENCE: 14

```
Met Glu Trp Ser Trp Val Phe Leu Phe Phe Leu Ser Val Thr Thr Gly
1               5                   10                  15

Val His Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Arg Phe Gly Ile Ser Trp Val Arg Gln Pro Pro Gly Lys Gly Leu
    50                  55                  60

Glu Trp Met Gly Val Ile Trp Gly Asp Gly Ser Thr Asp Tyr His Ser
65                  70                  75                  80

Ala Leu Ile Ser Arg Leu Ser Ile Thr Lys Asp Asn Ser Lys Ser Gln
                85                  90                  95

Val Phe Phe Arg Leu Asn Ser Leu Gln Ser Asp Asp Ser Ala Thr Tyr
            100                 105                 110

Tyr Cys Ala Arg Ser Phe Gly Met Asp Tyr Trp Gly Gln Gly Thr Ser
        115                 120                 125

Val Thr Val Ser Ser Gly Gly Gly Ser Gly Gly Gly Ser Gly
    130                 135                 140

Gly Gly Ser Asn Ile Met Met Thr Gln Ser Pro Ser Ser Leu Ala
145                 150                 155                 160

Val Ser Ala Gly Glu Lys Val Thr Met Ser Cys Lys Ser Ser Gln Ser
                165                 170                 175

Ile Leu Asn Ser Ser Asn Gln Lys Asn Tyr Leu Ala Trp Tyr Gln Gln
            180                 185                 190

Lys Pro Gly Gln Ser Pro Lys Leu Leu Ile Tyr Trp Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys His Gln Tyr Phe Ser Ser Arg Thr Phe Gly Gly Gly Thr Lys
                245                 250                 255

Leu Glu Ile Lys Gly Gly Gly Gly Ala Gly Gly Gly Cys Lys Pro
            260                 265                 270

Cys Ile Cys Thr Val Pro Glu Val Ser Ser Val Phe Ile Phe Pro Pro
        275                 280                 285

Lys Pro Lys Asp Val Leu Thr Ile Thr Leu Thr Pro Lys Val Thr Cys
    290                 295                 300

Val Val Val Asp Ile Ser Lys Asp Asp Pro Glu Val Gln Phe Ser Trp
305                 310                 315                 320

Phe Val Asp Asp Val Glu Val His Thr Ala Gln Thr Gln Pro Arg Glu
                325                 330                 335

Glu Gln Phe Asn Ser Thr Phe Arg Ser Val Ser Glu Leu Pro Ile Met
            340                 345                 350

His Gln Asp Trp Leu Asn Gly Lys Glu Phe Lys Cys Arg Val Asn Ser
```

```
                    355                 360                 365
Ala Ala Phe Pro Ala Pro Ile Glu Lys Thr Ile Ser Lys Thr Lys Gly
    370                 375                 380

Arg Pro Lys Ala Pro Gln Val Tyr Thr Ile Pro Pro Lys Glu Gln
385                 390                 395                 400

Met Ala Lys Asp Lys Val Ser Leu Thr Cys Met Ile Thr Asp Phe Phe
                405                 410                 415

Pro Glu Asp Ile Thr Val Glu Trp Gln Trp Asn Gly Gln Pro Ala Glu
                420                 425                 430

Asn Tyr Lys Asn Thr Gln Pro Ile Met Asp Thr Asp Gly Ser Tyr Phe
            435                 440                 445

Val Tyr Ser Lys Leu Asn Val Gln Lys Ser Asn Trp Glu Ala Gly Asn
        450                 455                 460

Thr Phe Thr Cys Ser Val Leu His Glu Gly Leu His Asn His His Thr
465                 470                 475                 480

Glu Lys Ser Leu Ser His Ser Pro Gly Lys
                485                 490

<210> SEQ ID NO 15
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 16

Asp Ile Gln Leu Thr Gln Ser Pro Ser Phe Leu Ser Ala Ser Val Gly
1               5                   10                  15

Asp Arg Val Thr Ile Thr Cys Ser Ala Ala Ser Ser Val Ser Tyr Ile
                20                  25                  30

Tyr Trp Tyr Gln Gln Lys Pro Gly Lys Ala Pro Lys Leu Leu Ile Tyr
            35                  40                  45

Ser Thr Ser Thr Leu Pro Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Arg Asn Ser Phe Pro Phe Thr
                85                  90                  95

Phe Gly Gln Gly Thr Lys Leu Glu Ile Lys
            100                 105

<210> SEQ ID NO 17
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 17
```

Asp Ile Gln Leu Thr Gln Ser Pro Ser Phe Leu Ser Ala Ser Val Gly
1               5                   10                  15

Asp Arg Val Thr Ile Thr Cys Ser Ala Ala Ser Ser Val Ser Tyr Ile
            20                  25                  30

Tyr Trp Tyr Gln Gln Lys Pro Gly Lys Ala Pro Lys Leu Leu Ile Tyr
            35                  40                  45

Ser Thr Ser Thr Leu Pro Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Phe Thr
                85                  90                  95

Phe Gly Gln Gly Thr Lys Leu Glu Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 18

Asp Ile Gln Leu Thr Gln Ser Pro Ser Phe Leu Ser Ala Ser Val Gly
1               5                   10                  15

Asp Arg Val Thr Ile Thr Cys Ser Ala Ala Ser Ser Val Ser Tyr Ile
            20                  25                  30

Tyr Trp Phe Gln Gln Lys Pro Gly Lys Ala Pro Lys Leu Leu Ile Tyr
            35                  40                  45

Ser Thr Ser Thr Leu Pro Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Phe Thr
                85                  90                  95

Phe Gly Gln Gly Thr Lys Leu Glu Ile Lys
            100                 105

<210> SEQ ID NO 19
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Met
        35                  40                  45

Gly Tyr Ile Asn Pro Ser Ser Asp Tyr Thr Arg Tyr Asn Pro Lys Phe
        50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys 85                  90                  95

Ala Arg Gly Thr Arg Asp Tyr Trp Gly Gln Gly Thr Thr Val Thr Val
                100                 105                 110

Ser Ser

<210> SEQ ID NO 20
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 20

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Thr Ile His Trp Val Arg Gln Ala Pro Gly Gln Gly Leu Glu Trp Met
            35                  40                  45

Gly Tyr Ile Asn Pro Ser Ser Asp Tyr Thr Arg Tyr Asn Pro Lys Phe
50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Arg Gly Thr Arg Asp Tyr Trp Gly Gln Gly Thr Thr Val Thr Val
                100                 105                 110

Ser Ser

<210> SEQ ID NO 21
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Thr Ile His Trp Val Arg Gln Ala Pro Gly Gln Gly Leu Glu Trp Met
            35                  40                  45

Gly Tyr Ile Asn Pro Ser Ser Asp Tyr Thr Arg Tyr Asn Pro Lys Phe
50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Thr Gly Thr Arg Asp Tyr Trp Gly Gln Gly Thr Thr Val Thr Val
                100                 105                 110

Ser Ser

<210> SEQ ID NO 22
<211> LENGTH: 114
<212> TYPE: PRT
<213> ORGANISM: Artificial Sequence
<220> FEATURE:

-continued

<223> OTHER INFORMATION: Synthetic Sequence

<400> SEQUENCE: 22

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Thr Ile His Trp Val Arg Gln Ala Pro Gly Gln Gly Leu Glu Trp Met
            35                  40                  45

Gly Tyr Ile Asn Pro Ser Ser Asp Tyr Thr Arg Tyr Asn Pro Lys Phe
        50                  55                  60

Lys Asp Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Arg Gly Thr Arg Asp Tyr Trp Gly Gln Gly Thr Thr Val Thr Val
                100                 105                 110

Ser Ser

<210> SEQ ID NO 23
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 23

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Thr Ile His Trp Val Arg Gln Ala Pro Gly Gln Gly Leu Glu Trp Met
            35                  40                  45

Gly Tyr Ile Asn Pro Ser Ser Asp Tyr Thr Arg Tyr Asn Pro Lys Phe
        50                  55                  60

Lys Asp Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Gly Thr Arg Asp Tyr Trp Gly Gln Gly Thr Thr Val Thr Val
                100                 105                 110

Ser Ser

<210> SEQ ID NO 24
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Thr Ile His Trp Val Arg Gln Ala Pro Gly Gln Gly Leu Glu Trp Met
            35                  40                  45

```
Gly Tyr Ile Asn Pro Ser Ser Asp Tyr Thr Arg Tyr Asn Pro Lys Phe
            50                  55                  60

Lys Asp Arg Val Thr Leu Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Gln Thr Gly Thr Arg Asp Tyr Trp Gly Gln Gly Thr Thr Val Thr Val
                100                 105                 110

Ser Ser

<210> SEQ ID NO 25
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 25

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                20                  25                  30

Thr Ile His Trp Val Arg Gln Ala Pro Gly Gln Gly Leu Glu Trp Ile
            35                  40                  45

Gly Tyr Ile Asn Pro Ser Ser Asp Tyr Thr Arg Tyr Asn Pro Lys Phe
        50                  55                  60

Lys Asp Arg Val Thr Leu Thr Thr Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Gln Thr Gly Thr Arg Asp Tyr Trp Gly Gln Gly Thr Thr Val Thr Val
                100                 105                 110

Ser Ser

<210> SEQ ID NO 26
<211> LENGTH: 221
<212> TYPE: PRT
<213> ORGANISM: Artificial Sequence
<220> FEATURE:
<223> OTHER INFORMATION: Synthetic Sequence

<400> SEQUENCE: 26

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                20                  25                  30

Thr Ile His Trp Val Arg Gln Ala Pro Gly Gln Gly Leu Glu Trp Ile
            35                  40                  45

Gly Tyr Ile Asn Pro Ser Ser Asp Tyr Thr Arg Tyr Asn Pro Lys Phe
        50                  55                  60

Lys Asp Arg Val Thr Leu Thr Thr Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Gln Thr Gly Thr Arg Asp Tyr Trp Gly Gln Gly Thr Thr Val Thr Val
                100                 105                 110

Ser Ser Ala Ser Thr Lys Gly Pro Ser Val Phe Pro Leu Ala Pro Ser
```

115                 120                 125
Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Ala Ala Gly Ser
    210                 215                 220

<210> SEQ ID NO 27
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 27

Asp Ile Gln Leu Thr Gln Ser Pro Ser Phe Leu Ser Ala Ser Val Gly
1               5                   10                  15

Asp Arg Val Thr Ile Thr Cys Ser Ala Ala Ser Ser Val Ser Tyr Ile
                20                  25                  30

Tyr Trp Phe Gln Gln Lys Pro Gly Lys Ala Pro Lys Leu Leu Ile Tyr
            35                  40                  45

Ser Thr Ser Thr Leu Pro Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 28
<211> LENGTH: 221
<212> TYPE: PRT
<213> ORGANISM: Artificial Sequence
<220> FEATURE:
<223> OTHER INFORMATION: Synthetic Sequence

<400> SEQUENCE: 28

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
    50                  55                  60

Lys Gly Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Thr Gly Thr Arg Asp Tyr Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Ala Ala Gly Ser
    210                 215                 220

<210> SEQ ID NO 29
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 29

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Tyr Ile
            20                  25                  30

Tyr Trp Phe Gln Gln Lys Pro Gly Lys Ala Pro Lys Leu Leu Ile Tyr
        35                  40                  45

Ala Thr Ser Thr Leu Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Leu Tyr Ala
            180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 30
<211> LENGTH: 221
<212> TYPE: PRT
<213> ORGANISM: Artificial Sequence
<220> FEATURE:
<223> OTHER INFORMATION: Synthetic Sequence

<400> SEQUENCE: 30

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Met
        35                  40                  45

Gly Tyr Ile Asn Pro Gly Ser Gly Tyr Thr Arg Tyr Asn Pro Lys Phe
    50                  55                  60

Lys Gly Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Thr Gly Thr Arg Asp Tyr Trp Gly Gln Gly Thr Thr Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Ala Ala Gly Ser
    210                 215                 220

<210> SEQ ID NO 31
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 31
```

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Ser Tyr Ile
            20                  25                  30

Tyr Trp Phe Gln Gln Lys Pro Gly Lys Ala Pro Lys Leu Leu Ile Tyr
            35                  40                  45

Ala Thr Ser Thr Leu Gln Ser Gly Val Pro Ser Arg Phe Ser Gly Ser
50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Leu Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 32
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 32

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Arg Tyr Ile
            20                  25                  30

Tyr Trp Phe Gln Gln Lys Pro Gly Lys Ala Pro Lys Leu Leu Ile Tyr
            35                  40                  45

Ala Thr Ser Thr Leu Arg Ser Gly Val Pro Ser Arg Phe Ser Gly Ser
50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

<210> SEQ ID NO 33
<211> LENGTH: 114
<212> TYPE: PRT
<213> ORGANISM: Artificial Sequence
```

-continued

```
<220> FEATURE:
<223> OTHER INFORMATION: Synthetic Sequence

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Ala Ile His Trp Val Arg Gln Ala Pro Gly Gln Gly Leu Glu Trp Met
            35                  40                  45

Gly Tyr Ile Asn Pro Ser Ser Gly Tyr Thr Arg Tyr Asn Pro Lys Phe
        50                  55                  60

Lys Gly Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Thr Gly Thr Arg Asp Tyr Trp Gly Gln Gly Thr Thr Val Thr Val
            100                 105                 110

Ser Ser

<210> SEQ ID NO 34
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 34

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Tyr Ile
                20                  25                  30

Tyr Trp Phe Gln Gln Lys Pro Gly Lys Ala Pro Lys Leu Leu Ile Tyr
            35                  40                  45

Ala Thr Ser Thr Arg Gln Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

<210> SEQ ID NO 35
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Thr Ile His Trp Val Arg Gln Ala Pro Gly Gln Gly Leu Glu Trp Met
            35                  40                  45

Gly Tyr Ile Asn Pro Ser Ser Gly Trp Thr Arg Tyr Asn Pro Lys Phe
```

```
                    50                  55                  60
Lys Gly Arg Val Thr Met Thr Arg Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Trp Thr Gly Arg Arg Asp Tyr Trp Gly Gln Gly Thr Thr Val Thr Val
                100                 105                 110

Ser Ser

<210> SEQ ID NO 36
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 36

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Ser Ser Val Arg Tyr Ile
                20                  25                  30

Tyr Trp Phe Gln Gln Lys Pro Gly Lys Ala Pro Lys Leu Leu Ile Tyr
             35                  40                  45

Ala Thr Ser Thr Leu Gln Ser Gly Val Pro Ser Arg Phe Ser Gly Ser
 50                  55                  60

Gly Ser Gly Thr Glu Tyr Thr Leu Thr Ile Ser Ser Leu Gln Pro Glu
 65                  70                  75                  80

Asp Phe Ala Thr Tyr Tyr Cys His Gln Arg Asn Ser Phe Pro Tyr Thr
                 85                  90                  95

Phe Gly Gln Gly Thr Lys Leu Glu Ile Lys
                100                 105

<210> SEQ ID NO 37
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 37

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                20                  25                  30

Ala Ile His Trp Val Arg Gln Ala Pro Gly Gln Gly Leu Glu Trp Met
             35                  40                  45

Gly Tyr Ile Asn Pro Ser Ser Gly Tyr Thr Arg Tyr Asn Pro Lys Phe
 50                  55                  60

Lys His Arg Val Thr Met Thr Arg Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Gln Thr Gly Thr Arg Asp Tyr Trp Gly Gln Gly Thr Thr Val Thr Val
                100                 105                 110

Ser Ser

<210> SEQ ID NO 38
```

-continued

```
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 38

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Thr Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

<210> SEQ ID NO 39
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 39

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Ala Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
    50                  55                  60

Lys His Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Trp Thr Gly Thr Arg Asp Tyr Trp Gly Gln Gly Thr Thr Val Thr Val
            100                 105                 110

Ser Ser

<210> SEQ ID NO 40
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 40

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Arg Tyr Ile
            20                  25                  30

Tyr Trp Phe Gln Gln Lys Pro Gly Lys Ala Pro Lys Leu Leu Ile Tyr
```

```
              35                  40                  45
Ala Thr Ser Thr Leu Gln Ser Gly Val Pro Ser Arg Phe Ser Gly Ser
         50                  55                  60

Gly Ser Gly Thr Glu Tyr Thr Leu Thr Ile Ser Ser Leu Gln Pro Glu
 65                  70                  75                  80

Asp Phe Ala Thr Tyr Tyr Cys His Gln Arg Asn Ser Phe Pro Tyr Thr
                 85                  90                  95

Phe Gly Gln Gly Thr Lys Leu Glu Ile Lys
            100                 105

<210> SEQ ID NO 41
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 41

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
             20                  25                  30

Thr Ile His Trp Val Arg Gln Ala Pro Gly Gln Gly Leu Glu Trp Met
         35                  40                  45

Gly Tyr Ile Asn Pro Lys Ser Gly Trp Thr Arg Tyr Asn Pro Lys Phe
     50                  55                  60

Lys Gly Arg Val Thr Met Thr Arg Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Gln Thr Gly Thr Arg Asp Tyr Trp Gly Gln Gly Thr Thr Val Thr Val
            100                 105                 110

Ser Ser

<210> SEQ ID NO 42
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 42

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Ser Ser Val Arg Tyr Ile
             20                  25                  30

Tyr Trp Phe Gln Gln Lys Pro Gly Lys Ala Pro Lys Leu Leu Ile Tyr
         35                  40                  45

Ala Thr Ser Phe Arg Gln Ser Gly Val Pro Ser Arg Phe Ser Gly Ser
     50                  55                  60

Gly Ser Gly Thr Glu Tyr Thr Leu Thr Ile Ser Ser Leu Gln Pro Glu
 65                  70                  75                  80

Asp Phe Ala Thr Tyr Tyr Cys His Gln Arg Asn Ser Phe Pro Tyr Thr
                 85                  90                  95

Phe Gly Gln Gly Thr Lys Leu Glu Ile Lys
            100                 105
```

-continued

```
<210> SEQ ID NO 43
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 43
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
    50                  55                  60

Lys Gly Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Thr Gly Thr Arg Asp Tyr Trp Gly Gln Gly Thr Thr Val Thr Val
            100                 105                 110

Ser Ser

```
<210> SEQ ID NO 44
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 44
```

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Arg Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

```
<210> SEQ ID NO 45
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 45
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

```
Ala Ile His Trp Val Arg Gln Ala Pro Gly Gln Gly Leu Glu Trp Met
         35                  40                  45

Gly Tyr Ile Asn Pro Ser Ser Gly Tyr Thr Arg Tyr Asn Pro Lys Phe
 50                      55                  60

Lys His Arg Val Thr Met Thr Arg Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Trp Thr Gly Thr Arg Asp Tyr Trp Gly Gln Gly Thr Thr Val Thr Val
            100                 105                 110

Ser Ser
```

<210> SEQ ID NO 46
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 46

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Ser Ser Val Ser Tyr Ile
             20                  25                  30

Tyr Trp Phe Gln Gln Lys Pro Gly Lys Ala Pro Lys Leu Leu Ile Tyr
         35                  40                  45

Ala Thr Ser Thr Arg Gln Ser Gly Val Pro Ser Arg Phe Ser Gly Ser
 50                      55                  60

Gly Ser Gly Thr Glu Tyr Thr Leu Thr Ile Ser Ser Leu Gln Pro Glu
 65                  70                  75                  80

Asp Phe Ala Thr Tyr Tyr Cys His Gln Arg Asn Ser Phe Pro Tyr Thr
                 85                  90                  95

Phe Gly Gln Gly Thr Lys Leu Glu Ile Lys
            100                 105
```

<210> SEQ ID NO 47
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 47

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
             20                  25                  30

Ala Ile His Trp Val Arg Gln Ala Pro Gly Gln Gly Leu Glu Trp Met
         35                  40                  45

Gly Tyr Ile Asn Pro Ser Ser Gly Tyr Thr Arg Tyr Asn Pro Lys Phe
 50                      55                  60

Lys Gly Arg Val Thr Met Thr Arg Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Trp Thr Gly Thr Arg Asp Tyr Trp Gly Gln Gly Thr Thr Val Thr Val
            100                 105                 110
```

Ser Ser

<210> SEQ ID NO 48
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 48

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Ser Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

<210> SEQ ID NO 49
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Met
        35                  40                  45

Gly Tyr Ile Asn Pro Lys Ser Gly Trp Thr Arg Tyr Asn Pro Lys Phe
    50                  55                  60

Lys Gly Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Thr Gly Thr Arg Asp Tyr Trp Gly Gln Gly Thr Thr Val Thr Val
            100                 105                 110

Ser Ser

<210> SEQ ID NO 50
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 50

Asp Ile Gln Leu Thr Gln Ser Pro Ser Phe Leu Ser Ala Ser Val Gly
1               5                   10                  15

```
Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Thr Leu Gln Ser Gly Val Pro Ser Arg Phe Ser Gly Ser
50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

<210> SEQ ID NO 51
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
50                  55                  60

Lys His Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Trp Thr Gly Thr Arg Asp Tyr Trp Gly Gln Gly Thr Thr Val Thr Val
            100                 105                 110

Ser Ser

<210> SEQ ID NO 52
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 52

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Leu Gln Ser Gly Val Pro Ser Arg Phe Ser Gly Ser
50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95
```

```
Phe Gly Gln Gly Thr Lys Leu Glu Ile Lys
            100                 105

<210> SEQ ID NO 53
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 53

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ala Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
    50                  55                  60

Lys His Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Trp Thr Gly Thr Arg Asp Tyr Trp Gly Gln Gly Thr Thr Val Thr Val
            100                 105                 110

Ser Ser

<210> SEQ ID NO 54
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 54

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Thr Leu Arg Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

<210> SEQ ID NO 55
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 55

Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Thr Tyr
            20                  25                  30

Ala Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
 50                  55                  60

Lys His Arg Val Thr Met Thr Arg Asp Lys Ser Thr Ser Thr Ala Tyr
 65                  70                  75                  80

Met Glu Leu Arg Ser Leu Arg Ser Asp Asp Thr Ala Val Tyr Tyr Cys
            85                  90                  95

Trp Thr Gly Thr Arg Asp Tyr Trp Gly Gln Gly Thr Thr Val Thr Val
            100                 105                 110

Ser Ser

<210> SEQ ID NO 56
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 56

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Gln Ser Gly Val Pro Ser Arg Phe Ser Gly Ser
 50                  55                  60

Gly Ser Gly Thr Glu Tyr Thr Leu Thr Ile Ser Ser Leu Gln Pro Glu
 65                  70                  75                  80

Asp Phe Ala Thr Tyr Tyr Cys His Gln Arg Asn Ser Phe Pro Tyr Thr
            85                  90                  95

Phe Gly Gln Gly Thr Lys Leu Glu Ile Lys
            100                 105

<210> SEQ ID NO 57
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 57

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
            20                  25                  30

Ala Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
 50                  55                  60

Lys Gly Arg Val Thr Met Thr Arg Asp Lys Ser Thr Ser Thr Ala Tyr
 65                  70                  75                  80

Met Glu Leu Arg Ser Leu Arg Ser Asp Asp Thr Ala Val Tyr Tyr Cys
            85                  90                  95
```

Trp Thr Gly Thr Arg Asp Tyr Trp Gly Gln Gly Thr Val Thr Val
            100                 105                 110
Ser Ser

<210> SEQ ID NO 58
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 58

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Tyr Ile
            20                  25                  30

Tyr Trp Phe Gln Gln Lys Pro Gly Lys Ala Pro Lys Leu Leu Ile Tyr
        35                  40                  45

Ala Thr Ser Thr Leu Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

<210> SEQ ID NO 59
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 59

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
    50                  55                  60

Lys Gly Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Trp Thr Gly Thr Arg Asp Tyr Trp Gly Gln Gly Thr Val Thr Val
            100                 105                 110

Ser Ser

<210> SEQ ID NO 60
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 60

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Arg Tyr Ile
            20                  25                  30

Tyr Trp Phe Gln Gln Lys Pro Gly Lys Ala Pro Lys Leu Leu Ile Tyr
                35                  40                  45

Ala Thr Ser Phe Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Pro Tyr Thr
                85                  90                  95

Phe Gly Gln Gly Thr Lys Leu Glu Ile Lys
                100                 105
```

<210> SEQ ID NO 61
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 61

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ala Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
    50                  55                  60

Lys His Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Trp Thr Gly Thr Arg Asp Tyr Trp Gly Gln Gly Thr Thr Val Thr Val
                100                 105                 110

Ser Ser
```

<210> SEQ ID NO 62
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 62

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Ser Tyr Ile
            20                  25                  30

Tyr Trp Phe Gln Gln Lys Pro Gly Lys Ala Pro Lys Leu Leu Ile Tyr
                35                  40                  45

Ala Thr Ser Phe Leu Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80
```

Asp Phe Ala Thr Tyr Tyr Cys His Gln Arg Asn Ser Phe Pro Tyr Thr
            85                  90                  95

Phe Gly Gln Gly Thr Lys Leu Glu Ile Lys
            100                 105

<210> SEQ ID NO 63
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Thr Ile His Trp Val Arg Gln Ala Pro Gly Gln Gly Leu Glu Trp Met
            35                  40                  45

Gly Tyr Ile Asn Pro Lys Ser Gly Trp Thr Arg Tyr Asn Pro Lys Phe
        50                  55                  60

Lys Gly Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Thr Gly Thr Arg Asp Tyr Trp Gly Gln Gly Thr Thr Val Thr Val
            100                 105                 110

Ser Ser

<210> SEQ ID NO 64
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 64

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Tyr Ile
                20                  25                  30

Tyr Trp Phe Gln Gln Lys Pro Gly Lys Ala Pro Lys Leu Leu Ile Tyr
            35                  40                  45

Ala Thr Ser Thr Leu Gln Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

<210> SEQ ID NO 65
<211> LENGTH: 114
<212> TYPE: PRT
<213> ORGANISM: Artificial Sequence
<220> FEATURE:
<223> OTHER INFORMATION: Synthetic Sequence -continued

<400> SEQUENCE: 65

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Met
        35                  40                  45

Gly Tyr Ile Asn Pro Lys Ser Gly Trp Thr Arg Tyr Asn Pro Lys Phe
    50                  55                  60

Lys Gly Arg Val Thr Met Thr Arg Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Gln Thr Gly Thr Arg Asp Tyr Trp Gly Gln Gly Thr Thr Val Thr Val
            100                 105                 110

Ser Ser

<210> SEQ ID NO 66
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 66

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys
            100                 105

<210> SEQ ID NO 67
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 67

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Met
        35                  40                  45

Gly Tyr Ile Asn Pro Ser Ser Gly Tyr Thr Arg Tyr Asn Pro Lys Phe
    50                  55                  60

Lys Gly Arg Val Thr Met Thr Arg Asp Lys Ser Thr Ser Thr Ala Tyr

```
                 65                  70                  75                  80
Met Glu Leu Arg Ser Leu Arg Ser Asp Asp Thr Ala Val Tyr Tyr Cys
                     85                  90                  95

Trp Thr Gly Arg Arg Asp Tyr Trp Gly Gln Gly Thr Thr Val Thr Val
                100                 105                 110

Ser Ser

<210> SEQ ID NO 68
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 68

Glu Val Ser Glu Ile Ser Val Arg Thr Val Tyr Pro Pro Glu Glu Glu
1               5                   10                  15

Thr Gly Glu Arg
            20

<210> SEQ ID NO 69
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 69

Ser Val Arg Thr Val Tyr Pro Pro
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 70

Val Arg Thr Val Tyr Pro Pro Glu
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 71

Arg Thr Val Tyr Pro Pro Glu Glu
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 72

Thr Val Tyr Pro Pro Glu Glu Glu
1               5
```

```
<210> SEQ ID NO 73
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 73

Val Tyr Pro Pro Glu Glu Glu Thr
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 74

Tyr Pro Pro Glu Glu Glu Thr Gly
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 75

Pro Pro Glu Glu Glu Thr Gly Glu
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 76

Pro Glu Glu Glu Thr Gly Glu Arg
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 77

Glu Glu Glu Thr Gly Glu Arg Val
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 78

Glu Glu Thr Gly Glu Arg Val Gln
1               5

<210> SEQ ID NO 79
```

```
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 79

Ala Val Ser Glu Ile Ser Val Arg Thr Val Tyr Pro Pro Glu Glu Glu
1               5                   10                  15

Thr Gly Glu Arg
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 80

Glu Ala Ser Glu Ile Ser Val Arg Thr Val Tyr Pro Pro Glu Glu Glu
1               5                   10                  15

Thr Gly Glu Arg
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 81

Glu Val Ala Glu Ile Ser Val Arg Thr Val Tyr Pro Pro Glu Glu Glu
1               5                   10                  15

Thr Gly Glu Arg
            20

<210> SEQ ID NO 82
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 82

Glu Val Ser Ala Ile Ser Val Arg Thr Val Tyr Pro Pro Glu Glu Glu
1               5                   10                  15

Thr Gly Glu Arg
            20

<210> SEQ ID NO 83
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 83

Glu Val Ser Glu Ala Ser Val Arg Thr Val Tyr Pro Pro Glu Glu Glu
1               5                   10                  15

Thr Gly Glu Arg
            20
```

```
<210> SEQ ID NO 84
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 84

Glu Val Ser Glu Ile Ala Val Arg Thr Val Tyr Pro Pro Glu Glu Glu
1               5                   10                  15

Thr Gly Glu Arg
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 85

Glu Val Ser Glu Ile Ser Ala Arg Thr Val Tyr Pro Pro Glu Glu Glu
1               5                   10                  15

Thr Gly Glu Arg
            20

<210> SEQ ID NO 86
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 86

Glu Val Ser Glu Ile Ser Val Ala Thr Val Tyr Pro Pro Glu Glu Glu
1               5                   10                  15

Thr Gly Glu Arg
            20

<210> SEQ ID NO 87
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 87

Glu Val Ser Glu Ile Ser Val Arg Ala Val Tyr Pro Pro Glu Glu Glu
1               5                   10                  15

Thr Gly Glu Arg
            20

<210> SEQ ID NO 88
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 88

Glu Val Ser Glu Ile Ser Val Arg Thr Ala Tyr Pro Pro Glu Glu Glu
1               5                   10                  15

Thr Gly Glu Arg
            20
```

```
<210> SEQ ID NO 89
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 89

Glu Val Ser Glu Ile Ser Val Arg Thr Val Ala Pro Pro Glu Glu Glu
1               5                   10                  15

Thr Gly Glu Arg
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 90

Glu Val Ser Glu Ile Ser Val Arg Thr Val Tyr Ala Pro Glu Glu Glu
1               5                   10                  15

Thr Gly Glu Arg
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 91

Glu Val Ser Glu Ile Ser Val Arg Thr Val Tyr Pro Ala Glu Glu Glu
1               5                   10                  15

Thr Gly Glu Arg
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 92

Glu Val Ser Glu Ile Ser Val Arg Thr Val Tyr Pro Pro Ala Glu Glu
1               5                   10                  15

Thr Gly Glu Arg
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 93

Glu Val Ser Glu Ile Ser Val Arg Thr Val Tyr Pro Pro Glu Ala Glu
1               5                   10                  15

Thr Gly Glu Arg
            20
```

```
<210> SEQ ID NO 94
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 94

Glu Val Ser Glu Ile Ser Val Arg Thr Val Tyr Pro Pro Glu Glu Ala
1               5                   10                  15

Thr Gly Glu Arg
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 95

Glu Val Ser Glu Ile Ser Val Arg Thr Val Tyr Pro Pro Glu Glu Glu
1               5                   10                  15

Ala Gly Glu Arg
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 96

Glu Val Ser Glu Ile Ser Val Arg Thr Val Tyr Pro Pro Glu Glu Glu
1               5                   10                  15

Thr Ala Glu Arg
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 97

Glu Val Ser Glu Ile Ser Val Arg Thr Val Tyr Pro Pro Glu Glu Glu
1               5                   10                  15

Thr Gly Ala Arg
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 98

Glu Val Ser Glu Ile Ser Val Arg Thr Val Tyr Pro Pro Glu Glu Glu
1               5                   10                  15

Thr Gly Glu Ala
```

```
<210> SEQ ID NO 99
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 99

Ser Val Arg Thr Val Tyr Pro Pro
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 100

Val Arg Thr Val Tyr Pro Pro Glu
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 101

Arg Thr Val Tyr Pro Pro Glu Glu
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 102

Thr Val Tyr Pro Pro Glu Glu Glu
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 103

Val Tyr Pro Pro Glu Glu Glu Thr
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 104

Tyr Pro Pro Glu Glu Glu Thr Gly
1               5
```

<210> SEQ ID NO 105
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 105

Pro Pro Glu Glu Glu Thr Gly Glu
1               5

<210> SEQ ID NO 106
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 106

Gly Gly Gly Gly Ser Gly Gly Gly Gly Ser Gly Gly Gly Gly Ser
1               5                   10                  15

<210> SEQ ID NO 107
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 107

Gly Gly Gly Gly Ser Gly Gly Gly Gly Ser Gly Gly Gly Gly Ser Gly
1               5                   10                  15

Gly Gly Gly Ser
            20

<210> SEQ ID NO 108
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 108

Leu Val Pro Arg Gly Ser
1               5

<210> SEQ ID NO 109
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 109

Gly Gly Gly Ser Gly Gly Gly Gly Ser Gly Leu Val Pro Arg Gly Ser
1               5                   10                  15

Gly Gly Gly Ser Gly Gly Gly Gly Ser Gly
            20                  25

<210> SEQ ID NO 110
<211> LENGTH: 29
<212> TYPE: PRT
<213> ORGANISM: Artificial Sequence
<220> FEATURE:
<223> OTHER INFORMATION: Synthetic Sequence -continued

<400> SEQUENCE: 110

Gly Gly Glu Gly Arg Thr Ala Thr Gly Gly Ser Gly Leu Val Pro
1               5                   10                  15

Arg Gly Ser Gly Gly Gly Ser Gly Gly Gly Ser Gly
            20                  25

<210> SEQ ID NO 111
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 111

Gly Glu Gly Arg Thr Ala Thr
1               5

<210> SEQ ID NO 112
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 112

Gly Gly Gly Gly Ser Gly Gly Gly Ser Gly Leu Val Pro Arg
1               5                   10                  15

Gly Ser Gly Gly Gly Gly
            20

<210> SEQ ID NO 113
<211> LENGTH: 1715
<212> TYPE: PRT
<213> ORGANISM: Artificial Sequence
<220> FEATURE:
<223> OTHER INFORMATION: Synthetic Sequence

<400> SEQUENCE: 113

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu

-continued

```
                165                 170                 175
Leu Val Cys Arg Glu Gly Ser Leu Ala Lys Glu Lys Thr Gln Thr Leu
                180                 185                 190
His Lys Phe Ile Leu Leu Phe Ala Val Phe Asp Glu Gly Lys Ser Trp
                195                 200                 205
His Ser Glu Thr Lys Asn Ser Leu Met Gln Asp Arg Asp Ala Ala Ser
                210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
                275                 280                 285
Ser Pro Ile Thr Phe Leu Thr Ala Gln Thr Leu Leu Met Asp Leu Gly
                290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Pro Gln Leu Arg
                325                 330                 335
Met Lys Asn Asn Glu Glu Ala Glu Asp Tyr Asp Asp Asp Leu Thr Asp
                340                 345                 350
Ser Glu Met Asp Val Val Arg Phe Asp Asp Asn Ser Pro Ser Phe
                355                 360                 365
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
                450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
                515                 520                 525
Leu Thr Arg Tyr Tyr Ser Ser Phe Val Asn Met Glu Arg Asp Leu Ala
                530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
```

```
Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Gly Gly Gly Ser Thr Gly
        740                 745                 750

Gly Thr Gly Gly Ser Ser Gly Gly Thr Gly Ser Gly Gly Gly
        755                 760                 765

Thr Gly Gly Ser Gly Gly Thr Asp Ile Gln Leu Thr Gln Ser Pro Ser
        770                 775                 780

Phe Leu Ser Ala Ser Val Gly Asp Arg Val Thr Ile Thr Cys Arg Ala
785                 790                 795                 800

Ser Ser Ser Val Ser Tyr Ile Tyr Trp Phe Gln Gln Lys Pro Gly Lys
                805                 810                 815

Ala Pro Lys Leu Leu Ile Tyr Ala Thr Ser Thr Leu Gln Ser Gly Val
                820                 825                 830

Pro Ser Arg Phe Ser Gly Ser Gly Ser Gly Thr Glu Tyr Thr Leu Thr
        835                 840                 845

Ile Ser Ser Leu Gln Pro Glu Asp Phe Ala Thr Tyr Tyr Cys His Gln
        850                 855                 860

Arg Asn Ser Phe Pro Tyr Thr Phe Gly Gln Gly Thr Lys Leu Glu Ile
865                 870                 875                 880

Lys Gly Gly Gly Gly Ser Gly Gly Gly Gly Ser Gly Gly Gly Gly Ser
                885                 890                 895

Gly Gly Gly Gly Ser Glu Val Gln Leu Val Gln Ser Gly Ala Glu Val
                900                 905                 910

Lys Lys Pro Gly Ala Ser Val Lys Val Ser Cys Lys Ala Ser Gly Tyr
        915                 920                 925

Thr Phe Thr Thr Tyr Thr Ile His Trp Val Arg Gln Ala Pro Gly Gln
        930                 935                 940

Gly Leu Glu Trp Met Gly Tyr Ile Asn Pro Ser Ser Gly Tyr Thr Arg
945                 950                 955                 960

Tyr Asn Pro Lys Phe Lys Gly Arg Val Thr Met Thr Arg Asp Lys Ser
                965                 970                 975

Thr Ser Thr Ala Tyr Met Glu Leu Arg Ser Leu Arg Ser Asp Asp Thr
                980                 985                 990

Ala Val Tyr Tyr Cys Gln Thr Gly  Thr Arg Asp Tyr Trp  Gly Gln Gly
        995                 1000                1005
```

```
Thr Thr Val Thr Val Ser Ser Gly Gly Gly Gly Ser Gln Asn Pro
1010                1015                1020

Pro Val Leu Lys Arg His Gln Arg Glu Ile Thr Arg Thr Thr Leu
1025                1030                1035

Gln Ser Asp Gln Glu Glu Ile Asp Tyr Asp Asp Thr Ile Ser Val
1040                1045                1050

Glu Met Lys Lys Glu Asp Phe Asp Ile Phe Asp Glu Asp Glu Asn
1055                1060                1065

Gln Ser Pro Arg Ser Phe Gln Lys Lys Thr Arg His Tyr Phe Ile
1070                1075                1080

Ala Ala Val Glu Arg Leu Trp Asp Tyr Gly Met Ser Ser Ser Pro
1085                1090                1095

His Val Leu Arg Asn Arg Ala Gln Ser Gly Ser Val Pro Gln Phe
1100                1105                1110

Lys Lys Val Val Phe Gln Glu Phe Thr Asp Gly Ser Phe Thr Gln
1115                1120                1125

Pro Leu Tyr Arg Gly Glu Leu Asn Glu His Leu Gly Leu Leu Gly
1130                1135                1140

Pro Tyr Ile Arg Ala Glu Val Glu Asp Asn Ile Met Val Thr Phe
1145                1150                1155

Arg Asn Gln Ala Ser Arg Pro Tyr Ser Phe Tyr Ser Ser Leu Ile
1160                1165                1170

Ser Tyr Glu Glu Asp Gln Arg Gln Gly Ala Glu Pro Arg Lys Asn
1175                1180                1185

Phe Val Lys Pro Asn Glu Thr Lys Thr Tyr Phe Trp Lys Val Gln
1190                1195                1200

His His Met Ala Pro Thr Lys Asp Glu Phe Asp Cys Lys Ala Trp
1205                1210                1215

Ala Tyr Phe Ser Asp Val Asp Leu Glu Lys Asp Val His Ser Gly
1220                1225                1230

Leu Ile Gly Pro Leu Leu Val Cys His Thr Asn Thr Leu Asn Pro
1235                1240                1245

Ala His Gly Arg Gln Val Thr Val Gln Glu Phe Ala Leu Phe Phe
1250                1255                1260

Thr Ile Phe Asp Glu Thr Lys Ser Trp Tyr Phe Thr Glu Asn Met
1265                1270                1275

Glu Arg Asn Cys Arg Ala Pro Cys Asn Ile Gln Met Glu Asp Pro
1280                1285                1290

Thr Phe Lys Glu Asn Tyr Arg Phe His Ala Ile Asn Gly Tyr Ile
1295                1300                1305

Met Asp Thr Leu Pro Gly Leu Val Met Ala Gln Asp Gln Arg Ile
1310                1315                1320

Arg Trp Tyr Leu Leu Ser Met Gly Ser Asn Glu Asn Ile His Ser
1325                1330                1335

Ile His Phe Ser Gly His Val Phe Thr Val Arg Lys Lys Glu Glu
1340                1345                1350

Tyr Lys Met Ala Leu Tyr Asn Leu Tyr Pro Gly Val Phe Glu Thr
1355                1360                1365

Val Glu Met Leu Pro Ser Lys Ala Gly Ile Trp Arg Val Glu Cys
1370                1375                1380

Leu Ile Gly Glu His Leu His Ala Gly Met Ser Thr Leu Phe Leu
1385                1390                1395

Val Tyr Ser Asn Lys Cys Gln Thr Pro Leu Gly Met Ala Ser Gly
```

```
                1400                1405                1410

His Ile Arg Asp Phe Gln Ile Thr Ala Ser Gly Gln Tyr Gly Gln
    1415                1420                1425

Trp Ala Pro Lys Leu Ala Arg Leu His Tyr Ser Gly Ser Ile Asn
    1430                1435                1440

Ala Trp Ser Thr Lys Glu Pro Phe Ser Trp Ile Lys Val Asp Leu
    1445                1450                1455

Leu Ala Pro Met Ile Ile His Gly Ile Lys Thr Gln Gly Ala Arg
    1460                1465                1470

Gln Lys Phe Ser Ser Leu Tyr Ile Ser Gln Phe Ile Ile Met Tyr
    1475                1480                1485

Ser Leu Asp Gly Lys Lys Trp Gln Thr Tyr Arg Gly Asn Ser Thr
    1490                1495                1500

Gly Thr Leu Met Val Phe Phe Gly Asn Val Asp Ser Ser Gly Ile
    1505                1510                1515

Lys His Asn Ile Phe Asn Pro Pro Ile Ile Ala Arg Tyr Ile Arg
    1520                1525                1530

Leu His Pro Thr His Tyr Ser Ile Arg Ser Thr Leu Arg Met Glu
    1535                1540                1545

Leu Met Gly Cys Asp Leu Asn Ser Cys Ser Met Pro Leu Gly Met
    1550                1555                1560

Glu Ser Lys Ala Ile Ser Asp Ala Gln Ile Thr Ala Ser Ser Tyr
    1565                1570                1575

Phe Thr Asn Met Phe Ala Thr Trp Ser Pro Ser Lys Ala Arg Leu
    1580                1585                1590

His Leu Gln Gly Arg Ser Asn Ala Trp Arg Pro Gln Val Asn Asn
    1595                1600                1605

Pro Lys Glu Trp Leu Gln Val Asp Phe Gln Lys Thr Met Lys Val
    1610                1615                1620

Thr Gly Val Thr Thr Gln Gly Val Lys Ser Leu Leu Thr Ser Met
    1625                1630                1635

Tyr Val Lys Glu Phe Leu Ile Ser Ser Ser Gln Asp Gly His Gln
    1640                1645                1650

Trp Thr Leu Phe Phe Gln Asn Gly Lys Val Lys Val Phe Gln Gly
    1655                1660                1665

Asn Gln Asp Ser Phe Thr Pro Val Val Asn Ser Leu Asp Pro Pro
    1670                1675                1680

Leu Leu Thr Arg Tyr Leu Arg Ile His Pro Gln Ser Trp Val His
    1685                1690                1695

Gln Ile Ala Leu Arg Met Glu Val Leu Gly Cys Glu Ala Gln Asp
    1700                1705                1710

Leu Tyr
    1715

<210> SEQ ID NO 114
<211> LENGTH: 1680
<212> TYPE: PRT
<213> ORGANISM: Artificial Sequence
<220> FEATURE:
<223> OTHER INFORMATION: Synthetic Sequence

<400> SEQUENCE: 114

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
```

-continued

```
            20               25                30
Arg Val Pro Lys Ser Phe Pro Phe Asn Thr Ser Val Val Tyr Lys Lys
                 35                  40                  45
Thr Leu Phe Val Glu Phe Thr Asp His Leu Phe Asn Ile Ala Lys Pro
 50                  55                  60
Arg Pro Pro Trp Met Gly Leu Leu Gly Pro Thr Ile Gln Ala Glu Val
 65                  70                  75                  80
Tyr Asp Thr Val Ile Thr Leu Lys Asn Met Ala Ser His Pro Val
                 85                  90                  95
Ser Leu His Ala Val Gly Val Ser Tyr Trp Lys Ala Ser Glu Gly Ala
                100                 105                 110
Glu Tyr Asp Asp Gln Thr Ser Gln Arg Glu Lys Glu Asp Asp Lys Val
                115                 120                 125
Phe Pro Gly Gly Ser His Thr Tyr Val Trp Gln Val Leu Lys Glu Asn
                130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
                180                 185                 190
His Lys Phe Ile Leu Leu Phe Ala Val Phe Asp Glu Gly Lys Ser Trp
                195                 200                 205
His Ser Glu Thr Lys Asn Ser Leu Met Gln Asp Arg Asp Ala Ala Ser
                210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
                275                 280                 285
Ser Pro Ile Thr Phe Leu Thr Ala Gln Thr Leu Leu Met Asp Leu Gly
                290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
                340                 345                 350
Ser Glu Met Asp Val Val Arg Phe Asp Asp Asp Asn Ser Pro Ser Phe
                355                 360                 365
Ile Gln Ile Arg Ser Val Ala Lys Lys His Pro Lys Thr Trp Val His
                370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
                435                 440                 445
```

```
Leu Gly Pro Leu Leu Tyr Gly Glu Val Gly Asp Thr Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
                675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Gly Gly Gly Ser Thr Gly
                740                 745                 750

Gly Thr Gly Gly Ser Ser Gly Gly Thr Gly Ser Gly Gly Gly
        755                 760                 765

Thr Gly Gly Ser Gly Gly Thr Asp Ile Gln Leu Thr Gln Ser Pro Ser
    770                 775                 780

Phe Leu Ser Ala Ser Val Gly Asp Arg Val Thr Ile Thr Cys Arg Ala
785                 790                 795                 800

Ser Ser Ser Val Ser Tyr Ile Tyr Trp Phe Gln Gln Lys Pro Gly Lys
                805                 810                 815

Ala Pro Lys Leu Leu Ile Tyr Ala Thr Ser Thr Leu Gln Ser Gly Val
                820                 825                 830

Pro Ser Arg Phe Ser Gly Ser Gly Ser Gly Thr Glu Tyr Thr Leu Thr
            835                 840                 845

Ile Ser Ser Leu Gln Pro Glu Asp Phe Ala Thr Tyr Tyr Cys His Gln
    850                 855                 860
```

```
Arg Asn Ser Phe Pro Tyr Thr Phe Gly Gln Gly Thr Lys Leu Glu Ile
865                 870                 875                 880

Lys Gly Gly Gly Gly Ser Gly Gly Gly Ser Gly Gly Gly Ser
            885                 890                 895

Gly Gly Gly Gly Ser Glu Val Gln Leu Val Gln Ser Gly Ala Glu Val
            900                 905                 910

Lys Lys Pro Gly Ala Ser Val Lys Val Ser Cys Lys Ala Ser Gly Tyr
            915                 920                 925

Thr Phe Thr Thr Tyr Thr Ile His Trp Val Arg Gln Ala Pro Gly Gln
            930                 935                 940

Gly Leu Glu Trp Met Gly Tyr Ile Asn Pro Ser Ser Gly Tyr Thr Arg
945                 950                 955                 960

Tyr Asn Pro Lys Phe Lys Gly Arg Val Thr Met Thr Arg Asp Lys Ser
                965                 970                 975

Thr Ser Thr Ala Tyr Met Glu Leu Arg Ser Leu Arg Ser Asp Asp Thr
            980                 985                 990

Ala Val Tyr Tyr Cys Gln Thr Gly  Thr Arg Asp Tyr Trp  Gly Gln Gly
            995                 1000                1005

Thr Thr Val Thr Val Ser Ser  Gly Gly Gly Gly Ser  Gly Gly Gly
1010                1015                1020

Gly Ser  Gly Gly Gly Gly Ser  Asp Glu Asn Gln Ser  Pro Arg Ser
1025                1030                1035

Phe Gln Lys Lys Thr Arg His  Tyr Phe Ile Ala Ala  Val Glu Arg
1040                1045                1050

Leu Trp Asp Tyr Gly Met Ser  Ser Ser Pro His Val  Leu Arg Asn
1055                1060                1065

Arg Ala Gln Ser Gly Ser Val  Pro Gln Phe Lys Lys  Val Val Phe
1070                1075                1080

Gln Glu Phe Thr Asp Gly Ser  Phe Thr Gln Pro Leu  Tyr Arg Gly
1085                1090                1095

Glu Leu Asn Glu His Leu Gly  Leu Leu Gly Pro Tyr  Ile Arg Ala
1100                1105                1110

Glu Val Glu Asp Asn Ile Met  Val Thr Phe Arg Asn  Gln Ala Ser
1115                1120                1125

Arg Pro Tyr Ser Phe Tyr Ser  Ser Leu Ile Ser Tyr  Glu Glu Asp
1130                1135                1140

Gln Arg Gln Gly Ala Glu Pro  Arg Lys Asn Phe Val  Lys Pro Asn
1145                1150                1155

Glu Thr Lys Thr Tyr Phe Trp  Lys Val Gln His His  Met Ala Pro
1160                1165                1170

Thr Lys Asp Glu Phe Asp Cys  Lys Ala Trp Ala Tyr  Phe Ser Asp
1175                1180                1185

Val Asp Leu Glu Lys Asp Val  His Ser Gly Leu Ile  Gly Pro Leu
1190                1195                1200

Leu Val Cys His Thr Asn Thr  Leu Asn Pro Ala His  Gly Arg Gln
1205                1210                1215

Val Thr Val Gln Glu Phe Ala  Leu Phe Phe Thr Ile  Phe Asp Glu
1220                1225                1230

Thr Lys Ser Trp Tyr Phe Thr  Glu Asn Met Glu Arg  Asn Cys Arg
1235                1240                1245

Ala Pro Cys Asn Ile Gln Met  Glu Asp Pro Thr Phe  Lys Glu Asn
1250                1255                1260

Tyr Arg Phe His Ala Ile Asn  Gly Tyr Ile Met Asp  Thr Leu Pro
```

```
       1265                1270                1275

Gly Leu Val Met Ala Gln Asp Gln Arg Ile Arg Trp Tyr Leu Leu
        1280                1285                1290

Ser Met Gly Ser Asn Glu Asn Ile His Ser Ile His Phe Ser Gly
        1295                1300                1305

His Val Phe Thr Val Arg Lys Lys Glu Glu Tyr Lys Met Ala Leu
        1310                1315                1320

Tyr Asn Leu Tyr Pro Gly Val Phe Glu Thr Val Glu Met Leu Pro
        1325                1330                1335

Ser Lys Ala Gly Ile Trp Arg Val Glu Cys Leu Ile Gly Glu His
        1340                1345                1350

Leu His Ala Gly Met Ser Thr Leu Phe Leu Val Tyr Ser Asn Lys
        1355                1360                1365

Cys Gln Thr Pro Leu Gly Met Ala Ser Gly His Ile Arg Asp Phe
        1370                1375                1380

Gln Ile Thr Ala Ser Gly Gln Tyr Gly Gln Trp Ala Pro Lys Leu
        1385                1390                1395

Ala Arg Leu His Tyr Ser Gly Ser Ile Asn Ala Trp Ser Thr Lys
        1400                1405                1410

Glu Pro Phe Ser Trp Ile Lys Val Asp Leu Leu Ala Pro Met Ile
        1415                1420                1425

Ile His Gly Ile Lys Thr Gln Gly Ala Arg Gln Lys Phe Ser Ser
        1430                1435                1440

Leu Tyr Ile Ser Gln Phe Ile Ile Met Tyr Ser Leu Asp Gly Lys
        1445                1450                1455

Lys Trp Gln Thr Tyr Arg Gly Asn Ser Thr Gly Thr Leu Met Val
        1460                1465                1470

Phe Phe Gly Asn Val Asp Ser Ser Gly Ile Lys His Asn Ile Phe
        1475                1480                1485

Asn Pro Pro Ile Ile Ala Arg Tyr Ile Arg Leu His Pro Thr His
        1490                1495                1500

Tyr Ser Ile Arg Ser Thr Leu Arg Met Glu Leu Met Gly Cys Asp
        1505                1510                1515

Leu Asn Ser Cys Ser Met Pro Leu Gly Met Glu Ser Lys Ala Ile
        1520                1525                1530

Ser Asp Ala Gln Ile Thr Ala Ser Ser Tyr Phe Thr Asn Met Phe
        1535                1540                1545

Ala Thr Trp Ser Pro Ser Lys Ala Arg Leu His Leu Gln Gly Arg
        1550                1555                1560

Ser Asn Ala Trp Arg Pro Gln Val Asn Asn Pro Lys Glu Trp Leu
        1565                1570                1575

Gln Val Asp Phe Gln Lys Thr Met Lys Val Thr Gly Val Thr Thr
        1580                1585                1590

Gln Gly Val Lys Ser Leu Leu Thr Ser Met Tyr Val Lys Glu Phe
        1595                1600                1605

Leu Ile Ser Ser Ser Gln Asp Gly His Gln Trp Thr Leu Phe Phe
        1610                1615                1620

Gln Asn Gly Lys Val Lys Val Phe Gln Gly Asn Gln Asp Ser Phe
        1625                1630                1635

Thr Pro Val Val Asn Ser Leu Asp Pro Pro Leu Leu Thr Arg Tyr
        1640                1645                1650

Leu Arg Ile His Pro Gln Ser Trp Val His Gln Ile Ala Leu Arg
        1655                1660                1665
```

Met Glu Val Leu Gly Cys Glu Ala Gln Asp Leu Tyr
        1670                1675                1680

<210> SEQ ID NO 115
<211> LENGTH: 1684
<212> TYPE: PRT
<213> ORGANISM: Artificial Sequence
<220> FEATURE:
<223> OTHER INFORMATION: Synthetic Sequence

<400> SEQUENCE: 115

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

```
Ser Glu Met Asp Val Val Arg Phe Asp Asp Asn Ser Pro Ser Phe
        355                 360                 365
Ile Gln Ile Arg Ser Val Ala Lys Lys His Pro Lys Thr Trp Val His
    370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Val Arg Phe Met Ala Tyr Thr
            420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
    515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
    595                 600                 605
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
    690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Gly Gly Gly Ser Thr Gly
            740                 745                 750
Gly Thr Gly Gly Ser Ser Gly Gly Gly Thr Gly Ser Gly Gly Gly
    755                 760                 765
```

```
Thr Gly Gly Ser Gly Gly Thr Asp Ile Gln Leu Thr Gln Ser Pro Ser
770                 775                 780
Phe Leu Ser Ala Ser Val Gly Asp Arg Val Thr Ile Thr Cys Arg Ala
785                 790                 795                 800
Ser Ser Ser Val Arg Tyr Ile Tyr Trp Phe Gln Gln Lys Pro Gly Lys
                805                 810                 815
Ala Pro Lys Leu Leu Ile Tyr Ala Thr Ser Phe Arg Gln Ser Gly Val
            820                 825                 830
Pro Ser Arg Phe Ser Gly Ser Gly Ser Gly Thr Glu Tyr Thr Leu Thr
            835                 840                 845
Ile Ser Ser Leu Gln Pro Glu Asp Phe Ala Thr Tyr Tyr Cys His Gln
    850                 855                 860
Arg Asn Ser Phe Pro Tyr Thr Phe Gly Gln Gly Thr Lys Leu Glu Ile
865                 870                 875                 880
Lys Gly Gly Gly Gly Ser Gly Gly Gly Gly Ser Gly Gly Gly Gly Ser
                885                 890                 895
Gly Gly Gly Gly Ser Glu Val Gln Leu Val Gln Ser Gly Ala Glu Val
                900                 905                 910
Lys Lys Pro Gly Ala Ser Val Lys Val Ser Cys Lys Ala Ser Gly Tyr
            915                 920                 925
Thr Phe Thr Thr Tyr Ala Ile His Trp Val Arg Gln Ala Pro Gly Gln
            930                 935                 940
Gly Leu Glu Trp Met Gly Tyr Ile Asn Pro Ser Ser Gly Tyr Thr Arg
945                 950                 955                 960
Tyr Asn Pro Lys Phe Lys Gly Arg Val Thr Met Thr Arg Asp Lys Ser
                965                 970                 975
Thr Ser Thr Ala Tyr Met Glu Leu Arg Ser Leu Arg Ser Asp Asp Thr
            980                 985                 990
Ala Val Tyr Tyr Cys Trp Thr Gly Thr Arg Asp Tyr Trp Gly Gln Gly
            995                 1000                1005
Thr Thr Val Thr Val Ser Ser Gly Gly Gly Gly Ser Gln Asn Pro
    1010                1015                1020
Pro Val Leu Lys Arg His Gln Arg Glu Ile Thr Asp Glu Asn Gln
    1025                1030                1035
Ser Pro Arg Ser Phe Gln Lys Lys Thr Arg His Tyr Phe Ile Ala
    1040                1045                1050
Ala Val Glu Arg Leu Trp Asp Tyr Gly Met Ser Ser Ser Pro His
    1055                1060                1065
Val Leu Arg Asn Arg Ala Gln Ser Gly Ser Val Pro Gln Phe Lys
    1070                1075                1080
Lys Val Val Phe Gln Glu Phe Thr Asp Gly Ser Phe Thr Gln Pro
    1085                1090                1095
Leu Tyr Arg Gly Glu Leu Asn Glu His Leu Gly Leu Leu Gly Pro
    1100                1105                1110
Tyr Ile Arg Ala Glu Val Glu Asp Asn Ile Met Val Thr Phe Arg
    1115                1120                1125
Asn Gln Ala Ser Arg Pro Tyr Ser Phe Tyr Ser Ser Leu Ile Ser
    1130                1135                1140
Tyr Glu Glu Asp Gln Arg Gln Gly Ala Glu Pro Arg Lys Asn Phe
    1145                1150                1155
Val Lys Pro Asn Glu Thr Lys Thr Tyr Phe Trp Lys Val Gln His
    1160                1165                1170
His Met Ala Pro Thr Lys Asp Glu Phe Asp Cys Lys Ala Trp Ala
```

-continued

```
            1175                1180                1185

Tyr Phe Ser Asp Val Asp Leu Glu Lys Asp Val His Ser Gly Leu
        1190                1195                1200

Ile Gly Pro Leu Leu Val Cys His Thr Asn Thr Leu Asn Pro Ala
        1205                1210                1215

His Gly Arg Gln Val Thr Val Gln Glu Phe Ala Leu Phe Phe Thr
        1220                1225                1230

Ile Phe Asp Glu Thr Lys Ser Trp Tyr Phe Thr Glu Asn Met Glu
        1235                1240                1245

Arg Asn Cys Arg Ala Pro Cys Asn Ile Gln Met Glu Asp Pro Thr
        1250                1255                1260

Phe Lys Glu Asn Tyr Arg Phe His Ala Ile Asn Gly Tyr Ile Met
        1265                1270                1275

Asp Thr Leu Pro Gly Leu Val Met Ala Gln Asp Gln Arg Ile Arg
        1280                1285                1290

Trp Tyr Leu Leu Ser Met Gly Ser Asn Glu Asn Ile His Ser Ile
        1295                1300                1305

His Phe Ser Gly His Val Phe Thr Val Arg Lys Lys Glu Glu Tyr
        1310                1315                1320

Lys Met Ala Leu Tyr Asn Leu Tyr Pro Gly Val Phe Glu Thr Val
        1325                1330                1335

Glu Met Leu Pro Ser Lys Ala Gly Ile Trp Arg Val Glu Cys Leu
        1340                1345                1350

Ile Gly Glu His Leu His Ala Gly Met Ser Thr Leu Phe Leu Val
        1355                1360                1365

Tyr Ser Asn Lys Cys Gln Thr Pro Leu Gly Met Ala Ser Gly His
        1370                1375                1380

Ile Arg Asp Phe Gln Ile Thr Ala Ser Gly Gln Tyr Gly Gln Trp
        1385                1390                1395

Ala Pro Lys Leu Ala Arg Leu His Tyr Ser Gly Ser Ile Asn Ala
        1400                1405                1410

Trp Ser Thr Lys Glu Pro Phe Ser Trp Ile Lys Val Asp Leu Leu
        1415                1420                1425

Ala Pro Met Ile Ile His Gly Ile Lys Thr Gln Gly Ala Arg Gln
        1430                1435                1440

Lys Phe Ser Ser Leu Tyr Ile Ser Gln Phe Ile Ile Met Tyr Ser
        1445                1450                1455

Leu Asp Gly Lys Lys Trp Gln Thr Tyr Arg Gly Asn Ser Thr Gly
        1460                1465                1470

Thr Leu Met Val Phe Phe Gly Asn Val Asp Ser Ser Gly Ile Lys
        1475                1480                1485

His Asn Ile Phe Asn Pro Pro Ile Ile Ala Arg Tyr Ile Arg Leu
        1490                1495                1500

His Pro Thr His Tyr Ser Ile Arg Ser Thr Leu Arg Met Glu Leu
        1505                1510                1515

Met Gly Cys Asp Leu Asn Ser Cys Ser Met Pro Leu Gly Met Glu
        1520                1525                1530

Ser Lys Ala Ile Ser Asp Ala Gln Ile Thr Ala Ser Ser Tyr Phe
        1535                1540                1545

Thr Asn Met Phe Ala Thr Trp Ser Pro Ser Lys Ala Arg Leu His
        1550                1555                1560

Leu Gln Gly Arg Ser Asn Ala Trp Arg Pro Gln Val Asn Asn Pro
        1565                1570                1575
```

```
Lys Glu Trp Leu Gln Val Asp Phe Gln Lys Thr Met Lys Val Thr
    1580                1585                1590

Gly Val Thr Thr Gln Gly Val Lys Ser Leu Leu Thr Ser Met Tyr
    1595                1600                1605

Val Lys Glu Phe Leu Ile Ser Ser Ser Gln Asp Gly His Gln Trp
    1610                1615                1620

Thr Leu Phe Phe Gln Asn Gly Lys Val Lys Val Phe Gln Gly Asn
    1625                1630                1635

Gln Asp Ser Phe Thr Pro Val Val Asn Ser Leu Asp Pro Pro Leu
    1640                1645                1650

Leu Thr Arg Tyr Leu Arg Ile His Pro Gln Ser Trp Val His Gln
    1655                1660                1665

Ile Ala Leu Arg Met Glu Val Leu Gly Cys Glu Ala Gln Asp Leu
    1670                1675                1680

Tyr

<210> SEQ ID NO 116
<211> LENGTH: 1684
<212> TYPE: PRT
<213> ORGANISM: Artificial Sequence
<220> FEATURE:
<223> OTHER INFORMATION: Synthetic Sequence

<400> SEQUENCE: 116

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240
```

```
Ser Leu Pro Gly Leu Ile Gly Cys His Arg Lys Ser Val Tyr Trp His
            245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
            355                 360                 365
Ile Gln Ile Arg Ser Val Ala Lys Lys His Pro Lys Thr Trp Val His
            370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
            450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
            530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
            610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
```

```
                  660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
            690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Gly Gly Gly Ser Thr Gly
            740                 745                 750
Gly Thr Gly Gly Ser Ser Gly Gly Thr Gly Ser Gly Gly Gly
            755                 760                 765
Thr Gly Gly Ser Gly Gly Thr Asp Ile Gln Leu Thr Gln Ser Pro Ser
            770                 775                 780
Phe Leu Ser Ala Ser Val Gly Asp Arg Val Thr Ile Thr Cys Arg Ala
785                 790                 795                 800
Ser Ser Ser Val Arg Tyr Ile Tyr Trp Phe Gln Gln Lys Pro Gly Lys
                805                 810                 815
Ala Pro Lys Leu Leu Ile Tyr Ala Thr Ser Phe Leu Gln Ser Gly Val
            820                 825                 830
Pro Ser Arg Phe Ser Gly Ser Gly Ser Gly Thr Glu Tyr Thr Leu Thr
            835                 840                 845
Ile Ser Ser Leu Gln Pro Glu Asp Phe Ala Thr Tyr Tyr Cys His Gln
            850                 855                 860
Arg Asn Ser Phe Pro Tyr Thr Phe Gly Gln Gly Thr Lys Leu Glu Ile
865                 870                 875                 880
Lys Gly Gly Gly Gly Ser Gly Gly Gly Gly Ser Gly Gly Gly Gly Ser
                885                 890                 895
Gly Gly Gly Gly Ser Glu Val Gln Leu Val Gln Ser Gly Ala Glu Val
            900                 905                 910
Lys Lys Pro Gly Ala Ser Val Lys Val Ser Cys Lys Ala Ser Gly Tyr
            915                 920                 925
Thr Phe Thr Thr Tyr Ala Ile His Trp Val Arg Gln Ala Pro Gly Gln
            930                 935                 940
Gly Leu Glu Trp Met Gly Tyr Ile Asn Pro Ser Ser Gly Tyr Thr Arg
945                 950                 955                 960
Tyr Asn Pro Lys Phe Lys His Arg Val Thr Met Thr Arg Asp Lys Ser
                965                 970                 975
Thr Ser Thr Ala Tyr Met Glu Leu Arg Ser Leu Arg Ser Asp Asp Thr
            980                 985                 990
Ala Val Tyr Tyr Cys Trp Thr Gly  Thr Arg Asp Tyr Trp  Gly Gln Gly
            995                 1000                1005
Thr Thr  Val Thr Val Ser Ser  Gly Gly Gly Gly Ser  Gln Asn Pro
    1010                1015                1020
Pro Val  Leu Lys Arg His Gln  Arg Glu Ile Thr Asp  Glu Asn Gln
    1025                1030                1035
Ser Pro Arg Ser Phe Gln Lys  Lys Thr Arg His Tyr  Phe Ile Ala
    1040                1045                1050
Ala Val  Glu Arg Leu Trp Asp  Tyr Gly Met Ser Ser  Ser Pro His
    1055                1060                1065
Val Leu  Arg Asn Arg Ala Gln  Ser Gly Ser Val Pro  Gln Phe Lys
    1070                1075                1080
```

```
Lys Val Val Phe Gln Glu Phe Thr Asp Gly Ser Phe Thr Gln Pro
    1085            1090                1095

Leu Tyr Arg Gly Glu Leu Asn Glu His Leu Gly Leu Leu Gly Pro
    1100            1105                1110

Tyr Ile Arg Ala Glu Val Glu Asp Asn Ile Met Val Thr Phe Arg
    1115            1120                1125

Asn Gln Ala Ser Arg Pro Tyr Ser Phe Tyr Ser Leu Ile Ser
    1130            1135                1140

Tyr Glu Glu Asp Gln Arg Gln Gly Ala Glu Pro Arg Lys Asn Phe
    1145            1150                1155

Val Lys Pro Asn Glu Thr Lys Thr Tyr Phe Trp Lys Val Gln His
    1160            1165                1170

His Met Ala Pro Thr Lys Asp Glu Phe Asp Cys Lys Ala Trp Ala
    1175            1180                1185

Tyr Phe Ser Asp Val Asp Leu Glu Lys Asp Val His Ser Gly Leu
    1190            1195                1200

Ile Gly Pro Leu Leu Val Cys His Thr Asn Thr Leu Asn Pro Ala
    1205            1210                1215

His Gly Arg Gln Val Thr Val Gln Glu Phe Ala Leu Phe Phe Thr
    1220            1225                1230

Ile Phe Asp Glu Thr Lys Ser Trp Tyr Phe Thr Glu Asn Met Glu
    1235            1240                1245

Arg Asn Cys Arg Ala Pro Cys Asn Ile Gln Met Glu Asp Pro Thr
    1250            1255                1260

Phe Lys Glu Asn Tyr Arg Phe His Ala Ile Asn Gly Tyr Ile Met
    1265            1270                1275

Asp Thr Leu Pro Gly Leu Val Met Ala Gln Asp Gln Arg Ile Arg
    1280            1285                1290

Trp Tyr Leu Leu Ser Met Gly Ser Asn Glu Asn Ile His Ser Ile
    1295            1300                1305

His Phe Ser Gly His Val Phe Thr Val Arg Lys Lys Glu Glu Tyr
    1310            1315                1320

Lys Met Ala Leu Tyr Asn Leu Tyr Pro Gly Val Phe Glu Thr Val
    1325            1330                1335

Glu Met Leu Pro Ser Lys Ala Gly Ile Trp Arg Val Glu Cys Leu
    1340            1345                1350

Ile Gly Glu His Leu His Ala Gly Met Ser Thr Leu Phe Leu Val
    1355            1360                1365

Tyr Ser Asn Lys Cys Gln Thr Pro Leu Gly Met Ala Ser Gly His
    1370            1375                1380

Ile Arg Asp Phe Gln Ile Thr Ala Ser Gly Gln Tyr Gly Gln Trp
    1385            1390                1395

Ala Pro Lys Leu Ala Arg Leu His Tyr Ser Gly Ser Ile Asn Ala
    1400            1405                1410

Trp Ser Thr Lys Glu Pro Phe Ser Trp Ile Lys Val Asp Leu Leu
    1415            1420                1425

Ala Pro Met Ile Ile His Gly Ile Lys Thr Gln Gly Ala Arg Gln
    1430            1435                1440

Lys Phe Ser Ser Leu Tyr Ile Ser Gln Phe Ile Ile Met Tyr Ser
    1445            1450                1455

Leu Asp Gly Lys Lys Trp Gln Thr Tyr Arg Gly Asn Ser Thr Gly
    1460            1465                1470
```

```
Thr Leu Met Val Phe Phe Gly Asn Val Asp Ser Ser Gly Ile Lys
    1475                1480                1485

His Asn Ile Phe Asn Pro Pro Ile Ile Ala Arg Tyr Ile Arg Leu
    1490                1495                1500

His Pro Thr His Tyr Ser Ile Arg Ser Thr Leu Arg Met Glu Leu
    1505                1510                1515

Met Gly Cys Asp Leu Asn Ser Cys Ser Met Pro Leu Gly Met Glu
    1520                1525                1530

Ser Lys Ala Ile Ser Asp Ala Gln Ile Thr Ala Ser Ser Tyr Phe
    1535                1540                1545

Thr Asn Met Phe Ala Thr Trp Ser Pro Ser Lys Ala Arg Leu His
    1550                1555                1560

Leu Gln Gly Arg Ser Asn Ala Trp Arg Pro Gln Val Asn Asn Pro
    1565                1570                1575

Lys Glu Trp Leu Gln Val Asp Phe Gln Lys Thr Met Lys Val Thr
    1580                1585                1590

Gly Val Thr Thr Gln Gly Val Lys Ser Leu Leu Thr Ser Met Tyr
    1595                1600                1605

Val Lys Glu Phe Leu Ile Ser Ser Ser Gln Asp Gly His Gln Trp
    1610                1615                1620

Thr Leu Phe Phe Gln Asn Gly Lys Val Lys Val Phe Gln Gly Asn
    1625                1630                1635

Gln Asp Ser Phe Thr Pro Val Val Asn Ser Leu Asp Pro Pro Leu
    1640                1645                1650

Leu Thr Arg Tyr Leu Arg Ile His Pro Gln Ser Trp Val His Gln
    1655                1660                1665

Ile Ala Leu Arg Met Glu Val Leu Gly Cys Glu Ala Gln Asp Leu
    1670                1675                1680

Tyr

<210> SEQ ID NO 117
<211> LENGTH: 1684
<212> TYPE: PRT
<213> ORGANISM: Artificial Sequence
<220> FEATURE:
<223> OTHER INFORMATION: Synthetic Sequence

<400> SEQUENCE: 117

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
```

```
            130                 135                 140
Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560
```

```
Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Gly Gly Gly Ser Thr Gly
            740                 745                 750

Gly Thr Gly Gly Ser Gly Gly Thr Gly Ser Gly Gly Gly
        755                 760                 765

Thr Gly Gly Ser Gly Gly Thr Asp Ile Gln Leu Thr Gln Ser Pro Ser
    770                 775                 780

Phe Leu Ser Ala Ser Val Gly Asp Arg Val Thr Ile Thr Cys Arg Ala
785                 790                 795                 800

Ser Ser Ser Val Ser Tyr Ile Tyr Trp Phe Gln Gln Lys Pro Gly Lys
                805                 810                 815

Ala Pro Lys Leu Leu Ile Tyr Ala Thr Ser Thr Leu Gln Ser Gly Val
            820                 825                 830

Pro Ser Arg Phe Ser Gly Ser Gly Ser Gly Thr Glu Tyr Thr Leu Thr
        835                 840                 845

Ile Ser Ser Leu Gln Pro Glu Asp Phe Ala Thr Tyr Tyr Cys His Gln
    850                 855                 860

Arg Asn Ser Phe Pro Tyr Thr Phe Gly Gln Gly Thr Lys Leu Glu Ile
865                 870                 875                 880

Lys Gly Gly Gly Gly Ser Gly Gly Gly Gly Ser Gly Gly Gly Gly Ser
                885                 890                 895

Gly Gly Gly Gly Ser Glu Val Gln Leu Val Gln Ser Gly Ala Glu Val
            900                 905                 910

Lys Lys Pro Gly Ala Ser Val Lys Val Ser Cys Lys Ala Ser Gly Tyr
        915                 920                 925

Thr Phe Thr Arg Tyr Thr Ile His Trp Val Arg Gln Ala Pro Gly Gln
    930                 935                 940

Gly Leu Glu Trp Met Gly Tyr Ile Asn Pro Ser Ser Gly Tyr Thr Arg
945                 950                 955                 960

Tyr Asn Pro Lys Phe Lys Gly Arg Val Thr Met Thr Arg Asp Lys Ser
                965                 970                 975
```

```
Thr Ser Thr Ala Tyr Met Glu Leu Arg Ser Leu Arg Ser Asp Asp Thr
            980                 985                 990

Ala Val Tyr Tyr Cys Trp Thr Gly  Thr Arg Asp Tyr Trp Gly Gln Gly
            995             1000                 1005

Thr Thr Val Thr Val Ser Ser Gly Gly Gly Ser  Gln Asn Pro
    1010             1015                 1020

Pro Val Leu Lys Arg His Gln Arg Glu Ile Thr Asp  Glu Asn Gln
    1025             1030             1035

Ser Pro Arg Ser Phe Gln Lys Lys Thr Arg His Tyr  Phe Ile Ala
    1040             1045             1050

Ala Val Glu Arg Leu Trp Asp Tyr Gly Met Ser Ser  Ser Pro His
    1055             1060             1065

Val Leu Arg Asn Arg Ala Gln Ser Gly Ser Val Pro  Gln Phe Lys
    1070             1075             1080

Lys Val Val Phe Gln Glu Phe Thr Asp Gly Ser Phe  Thr Gln Pro
    1085             1090             1095

Leu Tyr Arg Gly Glu Leu Asn Glu His Leu Gly Leu  Leu Gly Pro
    1100             1105             1110

Tyr Ile Arg Ala Glu Val Glu Asp Asn Ile Met Val  Thr Phe Arg
    1115             1120             1125

Asn Gln Ala Ser Arg Pro Tyr Ser Phe Tyr Ser Ser  Leu Ile Ser
    1130             1135             1140

Tyr Glu Glu Asp Gln Arg Gln Gly Ala Glu Pro Arg  Lys Asn Phe
    1145             1150             1155

Val Lys Pro Asn Glu Thr Lys Thr Tyr Phe Trp Lys  Val Gln His
    1160             1165             1170

His Met Ala Pro Thr Lys Asp Glu Phe Asp Cys Lys  Ala Trp Ala
    1175             1180             1185

Tyr Phe Ser Asp Val Asp Leu Glu Lys Asp Val His  Ser Gly Leu
    1190             1195             1200

Ile Gly Pro Leu Leu Val Cys His Thr Asn Thr Leu  Asn Pro Ala
    1205             1210             1215

His Gly Arg Gln Val Thr Val Gln Glu Phe Ala Leu  Phe Phe Thr
    1220             1225             1230

Ile Phe Asp Glu Thr Lys Ser Trp Tyr Phe Thr Glu  Asn Met Glu
    1235             1240             1245

Arg Asn Cys Arg Ala Pro Cys Asn Ile Gln Met Glu  Asp Pro Thr
    1250             1255             1260

Phe Lys Glu Asn Tyr Arg Phe His Ala Ile Asn Gly  Tyr Ile Met
    1265             1270             1275

Asp Thr Leu Pro Gly Leu Val Met Ala Gln Asp Gln  Arg Ile Arg
    1280             1285             1290

Trp Tyr Leu Leu Ser Met Gly Ser Asn Glu Asn Ile  His Ser Ile
    1295             1300             1305

His Phe Ser Gly His Val Phe Thr Val Arg Lys Lys  Glu Glu Tyr
    1310             1315             1320

Lys Met Ala Leu Tyr Asn Leu Tyr Pro Gly Val Phe  Glu Thr Val
    1325             1330             1335

Glu Met Leu Pro Ser Lys Ala Gly Ile Trp Arg Val  Glu Cys Leu
    1340             1345             1350

Ile Gly Glu His Leu His Ala Gly Met Ser Thr Leu  Phe Leu Val
    1355             1360             1365

Tyr Ser Asn Lys Cys Gln Thr Pro Leu Gly Met Ala  Ser Gly His
```

Ile Arg Asp Phe Gln Ile Thr Ala Ser Gly Gln Tyr Gly Gln Trp
1385                1390                1395

Ala Pro Lys Leu Ala Arg Leu His Tyr Ser Gly Ser Ile Asn Ala
1400                1405                1410

Trp Ser Thr Lys Glu Pro Phe Ser Trp Ile Lys Val Asp Leu Leu
1415                1420                1425

Ala Pro Met Ile Ile His Gly Ile Lys Thr Gln Gly Ala Arg Gln
1430                1435                1440

Lys Phe Ser Ser Leu Tyr Ile Ser Gln Phe Ile Ile Met Tyr Ser
1445                1450                1455

Leu Asp Gly Lys Lys Trp Gln Thr Tyr Arg Gly Asn Ser Thr Gly
1460                1465                1470

Thr Leu Met Val Phe Phe Gly Asn Val Asp Ser Ser Gly Ile Lys
1475                1480                1485

His Asn Ile Phe Asn Pro Pro Ile Ile Ala Arg Tyr Ile Arg Leu
1490                1495                1500

His Pro Thr His Tyr Ser Ile Arg Ser Thr Leu Arg Met Glu Leu
1505                1510                1515

Met Gly Cys Asp Leu Asn Ser Cys Ser Met Pro Leu Gly Met Glu
1520                1525                1530

Ser Lys Ala Ile Ser Asp Ala Gln Ile Thr Ala Ser Ser Tyr Phe
1535                1540                1545

Thr Asn Met Phe Ala Thr Trp Ser Pro Ser Lys Ala Arg Leu His
1550                1555                1560

Leu Gln Gly Arg Ser Asn Ala Trp Arg Pro Gln Val Asn Asn Pro
1565                1570                1575

Lys Glu Trp Leu Gln Val Asp Phe Gln Lys Thr Met Lys Val Thr
1580                1585                1590

Gly Val Thr Thr Gln Gly Val Lys Ser Leu Leu Thr Ser Met Tyr
1595                1600                1605

Val Lys Glu Phe Leu Ile Ser Ser Ser Gln Asp Gly His Gln Trp
1610                1615                1620

Thr Leu Phe Phe Gln Asn Gly Lys Val Lys Val Phe Gln Gly Asn
1625                1630                1635

Gln Asp Ser Phe Thr Pro Val Val Asn Ser Leu Asp Pro Pro Leu
1640                1645                1650

Leu Thr Arg Tyr Leu Arg Ile His Pro Gln Ser Trp Val His Gln
1655                1660                1665

Ile Ala Leu Arg Met Glu Val Leu Gly Cys Glu Ala Gln Asp Leu
1670                1675                1680

Tyr

<210> SEQ ID NO 118
<211> LENGTH: 1715
<212> TYPE: PRT
<213> ORGANISM: Artificial Sequence
<220> FEATURE:
<223> OTHER INFORMATION: Synthetic Sequence

<400> SEQUENCE: 118

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

```
Arg Val Pro Lys Ser Phe Pro Phe Asn Thr Ser Val Val Tyr Lys Lys
         35                  40                  45

Thr Leu Phe Val Glu Phe Thr Asp His Leu Phe Asn Ile Ala Lys Pro
 50                  55                  60

Arg Pro Pro Trp Met Gly Leu Leu Gly Pro Thr Ile Gln Ala Glu Val
 65                  70                  75                  80

Tyr Asp Thr Val Ile Thr Leu Lys Asn Met Ala Ser His Pro Val
                 85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Lys Val
                115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
                195                 200                 205

His Ser Glu Thr Lys Asn Ser Leu Met Gln Asp Arg Asp Ala Ala Ser
                210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
                275                 280                 285

Ser Pro Ile Thr Phe Leu Thr Ala Gln Thr Leu Leu Met Asp Leu Gly
                290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
                340                 345                 350

Ser Glu Met Asp Val Val Arg Phe Asp Asp Asn Ser Pro Ser Phe
                355                 360                 365

Ile Gln Ile Arg Ser Val Ala Lys Lys His Pro Lys Thr Trp Val His
                370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445
```

```
Leu Gly Pro Leu Leu Tyr Gly Glu Val Gly Asp Thr Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Gly Gly Gly Ser Thr Gly
                740                 745                 750

Gly Thr Gly Gly Ser Ser Gly Gly Thr Gly Ser Gly Gly Gly Gly
            755                 760                 765

Thr Gly Gly Ser Gly Gly Thr Asp Ile Gln Leu Thr Gln Ser Pro Ser
    770                 775                 780

Phe Leu Ser Ala Ser Val Gly Asp Arg Val Thr Ile Thr Cys Arg Ala
785                 790                 795                 800

Ser Ser Ser Val Arg Tyr Ile Tyr Trp Phe Gln Gln Lys Pro Gly Lys
                805                 810                 815

Ala Pro Lys Leu Leu Ile Tyr Ala Thr Ser Phe Arg Gln Ser Gly Val
                820                 825                 830

Pro Ser Arg Phe Ser Gly Ser Gly Ser Gly Thr Glu Tyr Thr Leu Thr
            835                 840                 845

Ile Ser Ser Leu Gln Pro Glu Asp Phe Ala Thr Tyr Tyr Cys His Gln
    850                 855                 860

Arg Asn Ser Phe Pro Tyr Thr Phe Gly Gln Gly Thr Lys Leu Glu Ile
```

```
            865                 870                 875                 880
Lys Gly Gly Gly Ser Gly Gly Gly Ser Gly Gly Gly Ser
                885                 890                 895
Gly Gly Gly Gly Ser Glu Val Gln Leu Val Gln Ser Gly Ala Glu Val
                900                 905                 910
Lys Lys Pro Gly Ala Ser Val Lys Val Ser Cys Lys Ala Ser Gly Tyr
                915                 920                 925
Thr Phe Thr Thr Tyr Ala Ile His Trp Val Arg Gln Ala Pro Gly Gln
                930                 935                 940
Gly Leu Glu Trp Met Gly Tyr Ile Asn Pro Ser Ser Gly Tyr Thr Arg
945                 950                 955                 960
Tyr Asn Pro Lys Phe Lys Gly Arg Val Thr Met Thr Arg Asp Lys Ser
                965                 970                 975
Thr Ser Thr Ala Tyr Met Glu Leu Arg Ser Leu Arg Ser Asp Asp Thr
                980                 985                 990
Ala Val Tyr Tyr Cys Trp Thr Gly  Thr Arg Asp Tyr Trp  Gly Gln Gly
                995                 1000                1005
Thr Thr  Val Thr Val Ser Ser  Gly Gly Gly Gly Ser  Gln Asn Pro
    1010                1015                1020
Pro Val  Leu Lys Arg His Gln  Arg Glu Ile Thr Arg  Thr Thr Leu
    1025                1030                1035
Gln Ser  Asp Gln Glu Glu Ile  Asp Tyr Asp Asp Thr  Ile Ser Val
    1040                1045                1050
Glu Met  Lys Lys Glu Asp Phe  Asp Ile Tyr Asp Glu  Asp Glu Asn
    1055                1060                1065
Gln Ser  Pro Arg Ser Phe Gln  Lys Lys Thr Arg His  Tyr Phe Ile
    1070                1075                1080
Ala Ala  Val Glu Arg Leu Trp  Asp Tyr Gly Met Ser  Ser Ser Pro
    1085                1090                1095
His Val  Leu Arg Asn Arg Ala  Gln Ser Gly Ser Val  Pro Gln Phe
    1100                1105                1110
Lys Lys  Val Val Phe Gln Glu  Phe Thr Asp Gly Ser  Phe Thr Gln
    1115                1120                1125
Pro Leu  Tyr Arg Gly Glu Leu  Asn Glu His Leu Gly  Leu Leu Gly
    1130                1135                1140
Pro Tyr  Ile Arg Ala Glu Val  Glu Asp Asn Ile Met  Val Thr Phe
    1145                1150                1155
Arg Asn  Gln Ala Ser Arg Pro  Tyr Ser Phe Tyr Ser  Ser Leu Ile
    1160                1165                1170
Ser Tyr  Glu Glu Asp Gln Arg  Gln Gly Ala Glu Pro  Arg Lys Asn
    1175                1180                1185
Phe Val  Lys Pro Asn Glu Thr  Lys Thr Tyr Phe Trp  Lys Val Gln
    1190                1195                1200
His His  Met Ala Pro Thr Lys  Asp Glu Phe Asp Cys  Lys Ala Trp
    1205                1210                1215
Ala Tyr  Phe Ser Asp Val Asp  Leu Glu Lys Asp Val  His Ser Gly
    1220                1225                1230
Leu Ile  Gly Pro Leu Leu Val  Cys His Thr Asn Thr  Leu Asn Pro
    1235                1240                1245
Ala His  Gly Arg Gln Val Thr  Val Gln Glu Phe Ala  Leu Phe Phe
    1250                1255                1260
Thr Ile  Phe Asp Glu Thr Lys  Ser Trp Tyr Phe Thr  Glu Asn Met
    1265                1270                1275
```

```
Glu Arg Asn Cys Arg Ala Pro Cys Asn Ile Gln Met Glu Asp Pro
    1280            1285                1290
Thr Phe Lys Glu Asn Tyr Arg Phe His Ala Ile Asn Gly Tyr Ile
    1295            1300                1305
Met Asp Thr Leu Pro Gly Leu Val Met Ala Gln Asp Gln Arg Ile
    1310            1315                1320
Arg Trp Tyr Leu Leu Ser Met Gly Ser Asn Glu Asn Ile His Ser
    1325            1330                1335
Ile His Phe Ser Gly His Val Phe Thr Val Arg Lys Lys Glu Glu
    1340            1345                1350
Tyr Lys Met Ala Leu Tyr Asn Leu Tyr Pro Gly Val Phe Glu Thr
    1355            1360                1365
Val Glu Met Leu Pro Ser Lys Ala Gly Ile Trp Arg Val Glu Cys
    1370            1375                1380
Leu Ile Gly Glu His Leu His Ala Gly Met Ser Thr Leu Phe Leu
    1385            1390                1395
Val Tyr Ser Asn Lys Cys Gln Thr Pro Leu Gly Met Ala Ser Gly
    1400            1405                1410
His Ile Arg Asp Phe Gln Ile Thr Ala Ser Gly Gln Tyr Gly Gln
    1415            1420                1425
Trp Ala Pro Lys Leu Ala Arg Leu His Tyr Ser Gly Ser Ile Asn
    1430            1435                1440
Ala Trp Ser Thr Lys Glu Pro Phe Ser Trp Ile Lys Val Asp Leu
    1445            1450                1455
Leu Ala Pro Met Ile Ile His Gly Ile Lys Thr Gln Gly Ala Arg
    1460            1465                1470
Gln Lys Phe Ser Ser Leu Tyr Ile Ser Gln Phe Ile Ile Met Tyr
    1475            1480                1485
Ser Leu Asp Gly Lys Lys Trp Gln Thr Tyr Arg Gly Asn Ser Thr
    1490            1495                1500
Gly Thr Leu Met Val Phe Phe Gly Asn Val Asp Ser Ser Gly Ile
    1505            1510                1515
Lys His Asn Ile Phe Asn Pro Pro Ile Ile Ala Arg Tyr Ile Arg
    1520            1525                1530
Leu His Pro Thr His Tyr Ser Ile Arg Ser Thr Leu Arg Met Glu
    1535            1540                1545
Leu Met Gly Cys Asp Leu Asn Ser Cys Ser Met Pro Leu Gly Met
    1550            1555                1560
Glu Ser Lys Ala Ile Ser Asp Ala Gln Ile Thr Ala Ser Ser Tyr
    1565            1570                1575
Phe Thr Asn Met Phe Ala Thr Trp Ser Pro Ser Lys Ala Arg Leu
    1580            1585                1590
His Leu Gln Gly Arg Ser Asn Ala Trp Arg Pro Gln Val Asn Asn
    1595            1600                1605
Pro Lys Glu Trp Leu Gln Val Asp Phe Gln Lys Thr Met Lys Val
    1610            1615                1620
Thr Gly Val Thr Thr Gln Gly Val Lys Ser Leu Leu Thr Ser Met
    1625            1630                1635
Tyr Val Lys Glu Phe Leu Ile Ser Ser Ser Gln Asp Gly His Gln
    1640            1645                1650
Trp Thr Leu Phe Phe Gln Asn Gly Lys Val Lys Val Phe Gln Gly
    1655            1660                1665
```

```
Asn Gln Asp Ser Phe Thr Pro Val Val Asn Ser Leu Asp Pro Pro
    1670                1675                1680

Leu Leu Thr Arg Tyr Leu Arg Ile His Pro Gln Ser Trp Val His
    1685                1690                1695

Gln Ile Ala Leu Arg Met Glu Val Leu Gly Cys Glu Ala Gln Asp
    1700                1705                1710

Leu Tyr
    1715

<210> SEQ ID NO 119
<211> LENGTH: 1704
<212> TYPE: PRT
<213> ORGANISM: Artificial Sequence
<220> FEATURE:
<223> OTHER INFORMATION: Synthetic Sequence

<400> SEQUENCE: 119

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65              70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys Gly Gly Gly Gly Ser Gly
            100                 105                 110

Gly Gly Gly Ser Gly Gly Gly Ser Gly Gly Gly Ser Glu Val
        115                 120                 125

Gln Leu Val Gln Ser Gly Ala Glu Val Lys Lys Pro Gly Ala Ser Val
130                 135                 140

Lys Val Ser Cys Lys Ala Ser Gly Tyr Thr Phe Thr Tyr Ala Ile
145                 150                 155                 160

His Trp Val Arg Gln Ala Pro Gly Gln Gly Leu Glu Trp Met Gly Tyr
                165                 170                 175

Ile Asn Pro Ser Ser Gly Tyr Thr Arg Tyr Asn Pro Lys Phe Lys Gly
            180                 185                 190

Arg Val Thr Met Thr Arg Asp Lys Ser Thr Ser Thr Ala Tyr Met Glu
        195                 200                 205

Leu Arg Ser Leu Arg Ser Asp Asp Thr Ala Val Tyr Tyr Cys Trp Thr
    210                 215                 220

Gly Thr Arg Asp Tyr Trp Gly Gln Gly Thr Thr Val Thr Val Ser Ser
225                 230                 235                 240

Gly Gly Gly Ser Gly Gly Gly Gly Ser Gly Leu Val Pro Arg Gly Ser
                245                 250                 255

Gly Gly Gly Ser Gly Gly Gly Gly Ser Gly Ala Thr Arg Tyr Tyr
            260                 265                 270

Leu Gly Ala Val Glu Leu Ser Trp Asp Tyr Met Gln Ser Asp Leu Gly
        275                 280                 285

Glu Leu Pro Val Asp Ala Arg Phe Pro Pro Arg Val Pro Lys Ser Phe
    290                 295                 300
```

```
Pro Phe Asn Thr Ser Val Val Tyr Lys Lys Thr Leu Phe Val Glu Phe
305                 310                 315                 320

Thr Asp His Leu Phe Asn Ile Ala Lys Pro Arg Pro Trp Met Gly
            325                 330                 335

Leu Leu Gly Pro Thr Ile Gln Ala Glu Val Tyr Asp Thr Val Val Ile
                340                 345                 350

Thr Leu Lys Asn Met Ala Ser His Pro Val Ser Leu His Ala Val Gly
        355                 360                 365

Val Ser Tyr Trp Lys Ala Ser Glu Gly Ala Glu Tyr Asp Asp Gln Thr
    370                 375                 380

Ser Gln Arg Glu Lys Glu Asp Asp Lys Val Phe Pro Gly Gly Ser His
385                 390                 395                 400

Thr Tyr Val Trp Gln Val Leu Lys Glu Asn Gly Pro Met Ala Ser Asp
        405                 410                 415

Pro Leu Cys Leu Thr Tyr Ser Tyr Leu Ser His Val Asp Leu Val Lys
                420                 425                 430

Asp Leu Asn Ser Gly Leu Ile Gly Ala Leu Leu Val Cys Arg Glu Gly
        435                 440                 445

Ser Leu Ala Lys Glu Lys Thr Gln Thr Leu His Lys Phe Ile Leu Leu
450                 455                 460

Phe Ala Val Phe Asp Glu Gly Lys Ser Trp His Ser Glu Thr Lys Asn
465                 470                 475                 480

Ser Leu Met Gln Asp Arg Asp Ala Ala Ser Ala Arg Ala Trp Pro Lys
                485                 490                 495

Met His Thr Val Asn Gly Tyr Val Asn Arg Ser Leu Pro Gly Leu Ile
                500                 505                 510

Gly Cys His Arg Lys Ser Val Tyr Trp His Val Ile Gly Met Gly Thr
        515                 520                 525

Thr Pro Glu Val His Ser Ile Phe Leu Glu Gly His Thr Phe Leu Val
530                 535                 540

Arg Asn His Arg Gln Ala Ser Leu Glu Ile Ser Pro Ile Thr Phe Leu
545                 550                 555                 560

Thr Ala Gln Thr Leu Leu Met Asp Leu Gly Gln Phe Leu Leu Phe Cys
                565                 570                 575

His Ile Ser Ser His Gln His Asp Gly Met Glu Ala Tyr Val Lys Val
            580                 585                 590

Asp Ser Cys Pro Glu Glu Pro Gln Leu Arg Met Lys Asn Asn Glu Glu
        595                 600                 605

Ala Glu Asp Tyr Asp Asp Asp Leu Thr Asp Ser Glu Met Asp Val Val
    610                 615                 620

Arg Phe Asp Asp Asp Asn Ser Pro Ser Phe Ile Gln Ile Arg Ser Val
625                 630                 635                 640

Ala Lys Lys His Pro Lys Thr Trp Val His Tyr Ile Ala Ala Glu Glu
                645                 650                 655

Glu Asp Trp Asp Tyr Ala Pro Leu Val Leu Ala Pro Asp Asp Arg Ser
            660                 665                 670

Tyr Lys Ser Gln Tyr Leu Asn Asn Gly Pro Gln Arg Ile Gly Arg Lys
        675                 680                 685

Tyr Lys Lys Val Arg Phe Met Ala Tyr Thr Asp Glu Thr Phe Lys Thr
    690                 695                 700

Arg Glu Ala Ile Gln His Glu Ser Gly Ile Leu Gly Pro Leu Leu Tyr
705                 710                 715                 720

Gly Glu Val Gly Asp Thr Leu Leu Ile Ile Phe Lys Asn Gln Ala Ser
```

-continued

```
                725                 730                 735
Arg Pro Tyr Asn Ile Tyr Pro His Gly Ile Thr Asp Val Arg Pro Leu
            740                 745                 750
Tyr Ser Arg Arg Leu Pro Lys Gly Val Lys His Leu Lys Asp Phe Pro
            755                 760                 765
Ile Leu Pro Gly Glu Ile Phe Lys Tyr Lys Trp Thr Val Thr Val Glu
            770                 775                 780
Asp Gly Pro Thr Lys Ser Asp Pro Arg Cys Leu Thr Arg Tyr Tyr Ser
785                 790                 795                 800
Ser Phe Val Asn Met Glu Arg Asp Leu Ala Ser Gly Leu Ile Gly Pro
                805                 810                 815
Leu Leu Ile Cys Tyr Lys Glu Ser Val Asp Gln Arg Gly Asn Gln Ile
                820                 825                 830
Met Ser Asp Lys Arg Asn Val Ile Leu Phe Ser Val Phe Asp Glu Asn
                835                 840                 845
Arg Ser Trp Tyr Leu Thr Glu Asn Ile Gln Arg Phe Leu Pro Asn Pro
            850                 855                 860
Ala Gly Val Gln Leu Glu Asp Pro Glu Phe Gln Ala Ser Asn Ile Met
865                 870                 875                 880
His Ser Ile Asn Gly Tyr Val Phe Asp Ser Leu Gln Leu Ser Val Cys
                885                 890                 895
Leu His Glu Val Ala Tyr Trp Tyr Ile Leu Ser Ile Gly Ala Gln Thr
            900                 905                 910
Asp Phe Leu Ser Val Phe Phe Ser Gly Tyr Thr Phe Lys His Lys Met
            915                 920                 925
Val Tyr Glu Asp Thr Leu Thr Leu Phe Pro Phe Ser Gly Glu Thr Val
            930                 935                 940
Phe Met Ser Met Glu Asn Pro Gly Leu Trp Ile Leu Gly Cys His Asn
945                 950                 955                 960
Ser Asp Phe Arg Asn Arg Gly Met Thr Ala Leu Leu Lys Val Ser Ser
            965                 970                 975
Cys Asp Lys Asn Thr Gly Asp Tyr Tyr Glu Asp Ser Tyr Glu Asp Ile
            980                 985                 990
Ser Ala Tyr Leu Leu Ser Lys Asn  Asn Ala Ile Glu Pro  Arg Ser Phe
            995                  1000                1005
Ser Gln Asn Pro Pro Val Leu  Lys Arg His Gln Arg  Glu Ile Thr
            1010                1015                1020
Arg Thr  Thr Leu Gln Ser Asp  Gln Glu Glu Ile Asp  Tyr Asp Asp
            1025                1030                1035
Thr Ile  Ser Val Glu Met Lys  Lys Glu Asp Phe Asp  Ile Tyr Asp
            1040                1045                1050
Glu Asp  Glu Asn Gln Ser Pro  Arg Ser Phe Gln Lys  Lys Thr Arg
            1055                1060                1065
His Tyr  Phe Ile Ala Ala Val  Glu Arg Leu Trp Asp  Tyr Gly Met
            1070                1075                1080
Ser Ser  Ser Pro His Val Leu  Arg Asn Arg Ala Gln  Ser Gly Ser
            1085                1090                1095
Val Pro  Gln Phe Lys Lys Val  Val Phe Gln Glu Phe  Thr Asp Gly
            1100                1105                1110
Ser Phe  Thr Gln Pro Leu Tyr  Arg Gly Glu Leu Asn  Glu His Leu
            1115                1120                1125
Gly Leu  Leu Gly Pro Tyr Ile  Arg Ala Glu Val Glu  Asp Asn Ile
            1130                1135                1140
```

-continued

Met Val Thr Phe Arg Asn Gln Ala Ser Arg Pro Tyr Ser Phe Tyr
1145            1150                1155

Ser Ser Leu Ile Ser Tyr Glu Glu Asp Gln Arg Gln Gly Ala Glu
1160            1165                1170

Pro Arg Lys Asn Phe Val Lys Pro Asn Glu Thr Lys Thr Tyr Phe
1175            1180                1185

Trp Lys Val Gln His His Met Ala Pro Thr Lys Asp Glu Phe Asp
1190            1195                1200

Cys Lys Ala Trp Ala Tyr Phe Ser Asp Val Asp Leu Glu Lys Asp
1205            1210                1215

Val His Ser Gly Leu Ile Gly Pro Leu Leu Val Cys His Thr Asn
1220            1225                1230

Thr Leu Asn Pro Ala His Gly Arg Gln Val Thr Val Gln Glu Phe
1235            1240                1245

Ala Leu Phe Phe Thr Ile Phe Asp Glu Thr Lys Ser Trp Tyr Phe
1250            1255                1260

Thr Glu Asn Met Glu Arg Asn Cys Arg Ala Pro Cys Asn Ile Gln
1265            1270                1275

Met Glu Asp Pro Thr Phe Lys Glu Asn Tyr Arg Phe His Ala Ile
1280            1285                1290

Asn Gly Tyr Ile Met Asp Thr Leu Pro Gly Leu Val Met Ala Gln
1295            1300                1305

Asp Gln Arg Ile Arg Trp Tyr Leu Leu Ser Met Gly Ser Asn Glu
1310            1315                1320

Asn Ile His Ser Ile His Phe Ser Gly His Val Phe Thr Val Arg
1325            1330                1335

Lys Lys Glu Glu Tyr Lys Met Ala Leu Tyr Asn Leu Tyr Pro Gly
1340            1345                1350

Val Phe Glu Thr Val Glu Met Leu Pro Ser Lys Ala Gly Ile Trp
1355            1360                1365

Arg Val Glu Cys Leu Ile Gly Glu His Leu His Ala Gly Met Ser
1370            1375                1380

Thr Leu Phe Leu Val Tyr Ser Asn Lys Cys Gln Thr Pro Leu Gly
1385            1390                1395

Met Ala Ser Gly His Ile Arg Asp Phe Gln Ile Thr Ala Ser Gly
1400            1405                1410

Gln Tyr Gly Gln Trp Ala Pro Lys Leu Ala Arg Leu His Tyr Ser
1415            1420                1425

Gly Ser Ile Asn Ala Trp Ser Thr Lys Glu Pro Phe Ser Trp Ile
1430            1435                1440

Lys Val Asp Leu Leu Ala Pro Met Ile Ile His Gly Ile Lys Thr
1445            1450                1455

Gln Gly Ala Arg Gln Lys Phe Ser Ser Leu Tyr Ile Ser Gln Phe
1460            1465                1470

Ile Ile Met Tyr Ser Leu Asp Gly Lys Lys Trp Gln Thr Tyr Arg
1475            1480                1485

Gly Asn Ser Thr Gly Thr Leu Met Val Phe Phe Gly Asn Val Asp
1490            1495                1500

Ser Ser Gly Ile Lys His Asn Ile Phe Asn Pro Pro Ile Ile Ala
1505            1510                1515

Arg Tyr Ile Arg Leu His Pro Thr His Tyr Ser Ile Arg Ser Thr
1520            1525                1530

```
Leu Arg Met Glu Leu Met Gly Cys Asp Leu Asn Ser Cys Ser Met
1535                1540                1545

Pro Leu Gly Met Glu Ser Lys Ala Ile Ser Asp Ala Gln Ile Thr
    1550                1555                1560

Ala Ser Ser Tyr Phe Thr Asn Met Phe Ala Thr Trp Ser Pro Ser
    1565                1570                1575

Lys Ala Arg Leu His Leu Gln Gly Arg Ser Asn Ala Trp Arg Pro
    1580                1585                1590

Gln Val Asn Asn Pro Lys Glu Trp Leu Gln Val Asp Phe Gln Lys
    1595                1600                1605

Thr Met Lys Val Thr Gly Val Thr Thr Gln Gly Val Lys Ser Leu
    1610                1615                1620

Leu Thr Ser Met Tyr Val Lys Glu Phe Leu Ile Ser Ser Ser Gln
    1625                1630                1635

Asp Gly His Gln Trp Thr Leu Phe Phe Gln Asn Gly Lys Val Lys
    1640                1645                1650

Val Phe Gln Gly Asn Gln Asp Ser Phe Thr Pro Val Val Asn Ser
    1655                1660                1665

Leu Asp Pro Pro Leu Leu Thr Arg Tyr Leu Arg Ile His Pro Gln
    1670                1675                1680

Ser Trp Val His Gln Ile Ala Leu Arg Met Glu Val Leu Gly Cys
    1685                1690                1695

Glu Ala Gln Asp Leu Tyr
    1700

<210> SEQ ID NO 120
<211> LENGTH: 1704
<212> TYPE: PRT
<213> ORGANISM: Artificial Sequence
<220> FEATURE:
<223> OTHER INFORMATION: Synthetic Sequence

<400> SEQUENCE: 120

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175
```

```
Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
        370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
```

|  | 595 |  |  |  | 600 |  |  |  | 605 |  |  |
|---|---|---|---|---|---|---|---|---|---|---|---|

Gln Ala Ser Asn Ile Met His Ser Ile Asn Gly Tyr Val Phe Asp Ser
      610              615              620

Leu Gln Leu Ser Val Cys Leu His Glu Val Ala Tyr Trp Tyr Ile Leu
625              630              635              640

Ser Ile Gly Ala Gln Thr Asp Phe Leu Ser Val Phe Phe Ser Gly Tyr
              645              650              655

Thr Phe Lys His Lys Met Val Tyr Glu Asp Thr Leu Thr Leu Phe Pro
            660              665              670

Phe Ser Gly Glu Thr Val Phe Met Ser Met Glu Asn Pro Gly Leu Trp
            675              680              685

Ile Leu Gly Cys His Asn Ser Asp Phe Arg Asn Arg Gly Met Thr Ala
690              695              700

Leu Leu Lys Val Ser Ser Cys Asp Lys Asn Thr Gly Asp Tyr Tyr Glu
705              710              715              720

Asp Ser Tyr Glu Asp Ile Ser Ala Tyr Leu Leu Ser Lys Asn Asn Ala
            725              730              735

Ile Glu Pro Arg Ser Phe Ser Gln Asn Pro Pro Val Leu Lys Arg His
            740              745              750

Gln Arg Glu Ile Thr Arg Thr Thr Leu Gln Ser Asp Gln Glu Glu Ile
            755              760              765

Asp Tyr Asp Asp Thr Ile Ser Val Glu Met Lys Lys Glu Asp Phe Asp
770              775              780

Ile Tyr Asp Glu Asp Glu Asn Gln Ser Pro Arg Ser Phe Gln Lys Lys
785              790              795              800

Thr Arg His Tyr Phe Ile Ala Ala Val Glu Arg Leu Trp Asp Tyr Gly
            805              810              815

Met Ser Ser Ser Pro His Val Leu Arg Asn Arg Ala Gln Ser Gly Ser
            820              825              830

Val Pro Gln Phe Lys Lys Val Val Phe Gln Glu Phe Thr Asp Gly Ser
            835              840              845

Phe Thr Gln Pro Leu Tyr Arg Gly Glu Leu Asn Glu His Leu Gly Leu
850              855              860

Leu Gly Pro Tyr Ile Arg Ala Glu Val Glu Asp Asn Ile Met Val Thr
865              870              875              880

Phe Arg Asn Gln Ala Ser Arg Pro Tyr Ser Phe Tyr Ser Ser Leu Ile
            885              890              895

Ser Tyr Glu Glu Asp Gln Arg Gln Gly Ala Glu Pro Arg Lys Asn Phe
            900              905              910

Val Lys Pro Asn Glu Thr Lys Thr Tyr Phe Trp Lys Val Gln His His
            915              920              925

Met Ala Pro Thr Lys Asp Glu Phe Asp Cys Lys Ala Trp Ala Tyr Phe
            930              935              940

Ser Asp Val Asp Leu Glu Lys Asp Val His Ser Gly Leu Ile Gly Pro
945              950              955              960

Leu Leu Val Cys His Thr Asn Thr Leu Asn Pro Ala His Gly Arg Gln
            965              970              975

Val Thr Val Gln Glu Phe Ala Leu Phe Phe Thr Ile Phe Asp Glu Thr
            980              985              990

Lys Ser Trp Tyr Phe Thr Glu Asn Met Glu Arg Asn Cys Arg Ala Pro
            995              1000              1005

Cys Asn Ile Gln Met Glu Asp Pro Thr Phe Lys Glu Asn Tyr Arg
            1010              1015              1020

```
Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410
```

-continued

```
Ile His Pro Gln Ser Trp Val His Gln Ile Ala Leu Arg Met Glu
    1415                1420                1425

Val Leu Gly Cys Glu Ala Gln Asp Leu Tyr Gly Gly Gly Ser Gly
    1430                1435                1440

Gly Gly Gly Ser Gly Leu Val Pro Arg Gly Ser Gly Gly Gly Ser
    1445                1450                1455

Gly Gly Gly Gly Ser Gly Asp Ile Gln Leu Thr Gln Ser Pro Ser
    1460                1465                1470

Phe Leu Ser Ala Ser Val Gly Asp Arg Val Thr Ile Thr Cys Arg
    1475                1480                1485

Ala Ser Ser Val Arg Tyr Ile Tyr Trp Phe Gln Gln Lys Pro
    1490                1495                1500

Gly Lys Ala Pro Lys Leu Leu Ile Tyr Ala Thr Ser Phe Arg Gln
    1505                1510                1515

Ser Gly Val Pro Ser Arg Phe Ser Gly Ser Gly Ser Gly Thr Glu
    1520                1525                1530

Tyr Thr Leu Thr Ile Ser Ser Leu Gln Pro Glu Asp Phe Ala Thr
    1535                1540                1545

Tyr Tyr Cys His Gln Arg Asn Ser Phe Pro Tyr Thr Phe Gly Gln
    1550                1555                1560

Gly Thr Lys Leu Glu Ile Lys Gly Gly Gly Gly Ser Gly Gly Gly
    1565                1570                1575

Gly Ser Gly Gly Gly Gly Ser Gly Gly Gly Gly Ser Glu Val Gln
    1580                1585                1590

Leu Val Gln Ser Gly Ala Glu Val Lys Lys Pro Gly Ala Ser Val
    1595                1600                1605

Lys Val Ser Cys Lys Ala Ser Gly Tyr Thr Phe Thr Thr Tyr Ala
    1610                1615                1620

Ile His Trp Val Arg Gln Ala Pro Gly Gln Gly Leu Glu Trp Met
    1625                1630                1635

Gly Tyr Ile Asn Pro Ser Ser Gly Tyr Thr Arg Tyr Asn Pro Lys
    1640                1645                1650

Phe Lys Gly Arg Val Thr Met Thr Arg Asp Lys Ser Thr Ser Thr
    1655                1660                1665

Ala Tyr Met Glu Leu Arg Ser Leu Arg Ser Asp Asp Thr Ala Val
    1670                1675                1680

Tyr Tyr Cys Trp Thr Gly Thr Arg Asp Tyr Trp Gly Gln Gly Thr
    1685                1690                1695

Thr Val Thr Val Ser Ser
    1700
```

<210> SEQ ID NO 121
<211> LENGTH: 1661
<212> TYPE: PRT
<213> ORGANISM: Artificial Sequence
<220> FEATURE:
<223> OTHER INFORMATION: Synthetic Sequence

<400> SEQUENCE: 121

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
        35                  40                  45
```

```
Thr Leu Phe Val Glu Phe Thr Asp His Leu Phe Asn Ile Ala Lys Pro
 50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
```

-continued

```
            465                 470                 475                 480
        Thr Asp Val Arg Pro Leu Tyr Ser Arg Arg Leu Pro Lys Gly Val Lys
                            485                 490                 495
        His Leu Lys Asp Phe Pro Ile Leu Pro Gly Glu Ile Phe Lys Tyr Lys
                            500                 505                 510
        Trp Thr Val Thr Val Glu Asp Gly Pro Thr Lys Ser Asp Pro Arg Cys
                            515                 520                 525
        Leu Thr Arg Tyr Tyr Ser Ser Phe Val Asn Met Glu Arg Asp Leu Ala
                            530                 535                 540
        Ser Gly Leu Ile Gly Pro Leu Leu Ile Cys Tyr Lys Glu Ser Val Asp
        545                 550                 555                 560
        Gln Arg Gly Asn Gln Ile Met Ser Asp Lys Arg Asn Val Ile Leu Phe
                            565                 570                 575
        Ser Val Phe Asp Glu Asn Arg Ser Trp Tyr Leu Thr Glu Asn Ile Gln
                            580                 585                 590
        Arg Phe Leu Pro Asn Pro Ala Gly Val Gln Leu Glu Asp Pro Glu Phe
                            595                 600                 605
        Gln Ala Ser Asn Ile Met His Ser Ile Asn Gly Tyr Val Phe Asp Ser
                            610                 615                 620
        Leu Gln Leu Ser Val Cys Leu His Glu Val Ala Tyr Trp Tyr Ile Leu
        625                 630                 635                 640
        Ser Ile Gly Ala Gln Thr Asp Phe Leu Ser Val Phe Phe Ser Gly Tyr
                            645                 650                 655
        Thr Phe Lys His Lys Met Val Tyr Glu Asp Thr Leu Thr Leu Phe Pro
                            660                 665                 670
        Phe Ser Gly Glu Thr Val Phe Met Ser Met Glu Asn Pro Gly Leu Trp
                            675                 680                 685
        Ile Leu Gly Cys His Asn Ser Asp Phe Arg Asn Arg Gly Met Thr Ala
                            690                 695                 700
        Leu Leu Lys Val Ser Ser Cys Asp Lys Asn Thr Gly Asp Tyr Tyr Glu
        705                 710                 715                 720
        Asp Ser Tyr Glu Asp Ile Ser Ala Tyr Leu Leu Ser Lys Asn Asn Ala
                            725                 730                 735
        Ile Glu Pro Arg Ser Phe Ser Gln Asn Asp Glu Asn Gln Ser Pro Arg
                            740                 745                 750
        Ser Phe Gln Lys Lys Thr Arg His Tyr Phe Ile Ala Ala Val Glu Arg
                            755                 760                 765
        Leu Trp Asp Tyr Gly Met Ser Ser Ser Pro His Val Leu Arg Asn Arg
                            770                 775                 780
        Ala Gln Ser Gly Ser Val Pro Gln Phe Lys Lys Val Val Phe Gln Glu
        785                 790                 795                 800
        Phe Thr Asp Gly Ser Phe Thr Gln Pro Leu Tyr Arg Gly Glu Leu Asn
                            805                 810                 815
        Glu His Leu Gly Leu Leu Gly Pro Tyr Ile Arg Ala Glu Val Glu Asp
                            820                 825                 830
        Asn Ile Met Val Thr Phe Arg Asn Gln Ala Ser Arg Pro Tyr Ser Phe
                            835                 840                 845
        Tyr Ser Ser Leu Ile Ser Tyr Glu Glu Asp Gln Arg Gln Gly Ala Glu
                            850                 855                 860
        Pro Arg Lys Asn Phe Val Lys Pro Asn Glu Thr Lys Thr Tyr Phe Trp
        865                 870                 875                 880
        Lys Val Gln His His Met Ala Pro Thr Lys Asp Glu Phe Asp Cys Lys
                            885                 890                 895
```

```
Ala Trp Ala Tyr Phe Ser Asp Val Asp Leu Glu Lys Asp Val His Ser
            900                 905                 910

Gly Leu Ile Gly Pro Leu Leu Val Cys His Thr Asn Thr Leu Asn Pro
            915                 920                 925

Ala His Gly Arg Gln Val Thr Val Gln Glu Phe Ala Leu Phe Phe Thr
        930                 935                 940

Ile Phe Asp Glu Thr Lys Ser Trp Tyr Phe Thr Glu Asn Met Glu Arg
945                 950                 955                 960

Asn Cys Arg Ala Pro Cys Asn Ile Gln Met Glu Asp Pro Thr Phe Lys
                965                 970                 975

Glu Asn Tyr Arg Phe His Ala Ile Asn Gly Tyr Ile Met Asp Thr Leu
            980                 985                 990

Pro Gly Leu Val Met Ala Gln Asp Gln Arg Ile Arg Trp Tyr Leu Leu
            995                 1000                1005

Ser Met Gly Ser Asn Glu Asn Ile His Ser Ile His Phe Ser Gly
      1010                1015                1020

His Val Phe Thr Val Arg Lys Lys Glu Glu Tyr Lys Met Ala Leu
      1025                1030                1035

Tyr Asn Leu Tyr Pro Gly Val Phe Glu Thr Val Glu Met Leu Pro
      1040                1045                1050

Ser Lys Ala Gly Ile Trp Arg Val Glu Cys Leu Ile Gly Glu His
      1055                1060                1065

Leu His Ala Gly Met Ser Thr Leu Phe Leu Val Tyr Ser Asn Lys
      1070                1075                1080

Cys Gln Thr Pro Leu Gly Met Ala Ser Gly His Ile Arg Asp Phe
      1085                1090                1095

Gln Ile Thr Ala Ser Gly Gln Tyr Gly Gln Trp Ala Pro Lys Leu
      1100                1105                1110

Ala Arg Leu His Tyr Ser Gly Ser Ile Asn Ala Trp Ser Thr Lys
      1115                1120                1125

Glu Pro Phe Ser Trp Ile Lys Val Asp Leu Leu Ala Pro Met Ile
      1130                1135                1140

Ile His Gly Ile Lys Thr Gln Gly Ala Arg Gln Lys Phe Ser Ser
      1145                1150                1155

Leu Tyr Ile Ser Gln Phe Ile Ile Met Tyr Ser Leu Asp Gly Lys
      1160                1165                1170

Lys Trp Gln Thr Tyr Arg Gly Asn Ser Thr Gly Thr Leu Met Val
      1175                1180                1185

Phe Phe Gly Asn Val Asp Ser Ser Gly Ile Lys His Asn Ile Phe
      1190                1195                1200

Asn Pro Pro Ile Ile Ala Arg Tyr Ile Arg Leu His Pro Thr His
      1205                1210                1215

Tyr Ser Ile Arg Ser Thr Leu Arg Met Glu Leu Met Gly Cys Asp
      1220                1225                1230

Leu Asn Ser Cys Ser Met Pro Leu Gly Met Glu Ser Lys Ala Ile
      1235                1240                1245

Ser Asp Ala Gln Ile Thr Ala Ser Ser Tyr Phe Thr Asn Met Phe
      1250                1255                1260

Ala Thr Trp Ser Pro Ser Lys Ala Arg Leu His Leu Gln Gly Arg
      1265                1270                1275

Ser Asn Ala Trp Arg Pro Gln Val Asn Asn Pro Lys Glu Trp Leu
      1280                1285                1290
```

-continued

```
Gln Val Asp Phe Gln Lys Thr Met Lys Val Thr Gly Val Thr Thr
    1295                1300                1305

Gln Gly Val Lys Ser Leu Leu Thr Ser Met Tyr Val Lys Glu Phe
    1310                1315                1320

Leu Ile Ser Ser Ser Gln Asp Gly His Gln Trp Thr Leu Phe Phe
    1325                1330                1335

Gln Asn Gly Lys Val Lys Val Phe Gln Gly Asn Gln Asp Ser Phe
    1340                1345                1350

Thr Pro Val Val Asn Ser Leu Asp Pro Leu Leu Thr Arg Tyr
    1355                1360                1365

Leu Arg Ile His Pro Gln Ser Trp Val His Gln Ile Ala Leu Arg
    1370                1375                1380

Met Glu Val Leu Gly Cys Glu Ala Gln Asp Leu Tyr Gly Gly Gly
    1385                1390                1395

Ser Gly Gly Gly Gly Ser Gly Leu Val Pro Arg Gly Ser Gly Gly
    1400                1405                1410

Gly Ser Gly Gly Gly Gly Ser Gly Asp Ile Gln Leu Thr Gln Ser
    1415                1420                1425

Pro Ser Phe Leu Ser Ala Ser Val Gly Asp Arg Val Thr Ile Thr
    1430                1435                1440

Cys Arg Ala Ser Ser Ser Val Arg Tyr Ile Tyr Trp Phe Gln Gln
    1445                1450                1455

Lys Pro Gly Lys Ala Pro Lys Leu Leu Ile Tyr Ala Thr Ser Phe
    1460                1465                1470

Arg Gln Ser Gly Val Pro Ser Arg Phe Ser Gly Ser Gly Ser Gly
    1475                1480                1485

Thr Glu Tyr Thr Leu Thr Ile Ser Ser Leu Gln Pro Glu Asp Phe
    1490                1495                1500

Ala Thr Tyr Tyr Cys His Gln Arg Asn Ser Phe Pro Tyr Thr Phe
    1505                1510                1515

Gly Gln Gly Thr Lys Leu Glu Ile Lys Gly Gly Gly Gly Ser Gly
    1520                1525                1530

Gly Gly Gly Ser Gly Gly Gly Gly Ser Gly Gly Gly Gly Ser Glu
    1535                1540                1545

Val Gln Leu Val Gln Ser Gly Ala Glu Val Lys Lys Pro Gly Ala
    1550                1555                1560

Ser Val Lys Val Ser Cys Lys Ala Ser Gly Tyr Thr Phe Thr Thr
    1565                1570                1575

Tyr Ala Ile His Trp Val Arg Gln Ala Pro Gly Gln Gly Leu Glu
    1580                1585                1590

Trp Met Gly Tyr Ile Asn Pro Ser Ser Gly Tyr Thr Arg Tyr Asn
    1595                1600                1605

Pro Lys Phe Lys Gly Arg Val Thr Met Thr Arg Asp Lys Ser Thr
    1610                1615                1620

Ser Thr Ala Tyr Met Glu Leu Arg Ser Leu Arg Ser Asp Asp Thr
    1625                1630                1635

Ala Val Tyr Tyr Cys Trp Thr Gly Thr Arg Asp Tyr Trp Gly Gln
    1640                1645                1650

Gly Thr Thr Val Thr Val Ser Ser
    1655                1660

<210> SEQ ID NO 122
<211> LENGTH: 1673
<212> TYPE: PRT
```

<213> ORGANISM: Artificial Sequence
<220> FEATURE:
<223> OTHER INFORMATION: Synthetic Sequence

<400> SEQUENCE: 122

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
```

```
            385                 390                 395                 400
Ala Pro Asp Asp Arg Ser Tyr Lys Ser Gln Tyr Leu Asn Asn Gly Pro
                    405                 410                 415

Gln Arg Ile Gly Arg Lys Tyr Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                    485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                    645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                    725                 730                 735

Ile Glu Pro Arg Ser Phe Ser Gln Asn Pro Pro Val Leu Lys Arg His
                740                 745                 750

Gln Arg Glu Ile Thr Asp Glu Asn Gln Ser Pro Arg Ser Phe Gln Lys
            755                 760                 765

Lys Thr Arg His Tyr Phe Ile Ala Ala Val Glu Arg Leu Trp Asp Tyr
    770                 775                 780

Gly Met Ser Ser Pro His Val Leu Arg Asn Arg Ala Gln Ser Gly
785                 790                 795                 800

Ser Val Pro Gln Phe Lys Lys Val Val Phe Gln Glu Phe Thr Asp Gly
                    805                 810                 815
```

```
Ser Phe Thr Gln Pro Leu Tyr Arg Gly Glu Leu Asn Glu His Leu Gly
                820             825                 830

Leu Leu Gly Pro Tyr Ile Arg Ala Glu Val Glu Asp Asn Ile Met Val
        835                 840                 845

Thr Phe Arg Asn Gln Ala Ser Arg Pro Tyr Ser Phe Tyr Ser Ser Leu
850                 855                 860

Ile Ser Tyr Glu Glu Asp Gln Arg Gln Gly Ala Glu Pro Arg Lys Asn
865                 870                 875                 880

Phe Val Lys Pro Asn Glu Thr Lys Thr Tyr Phe Trp Lys Val Gln His
                885                 890                 895

His Met Ala Pro Thr Lys Asp Glu Phe Asp Cys Lys Ala Trp Ala Tyr
                900                 905                 910

Phe Ser Asp Val Asp Leu Glu Lys Asp Val His Ser Gly Leu Ile Gly
        915                 920                 925

Pro Leu Leu Val Cys His Thr Asn Thr Leu Asn Pro Ala His Gly Arg
    930                 935                 940

Gln Val Thr Val Gln Glu Phe Ala Leu Phe Phe Thr Ile Phe Asp Glu
945                 950                 955                 960

Thr Lys Ser Trp Tyr Phe Thr Glu Asn Met Glu Arg Asn Cys Arg Ala
                965                 970                 975

Pro Cys Asn Ile Gln Met Glu Asp Pro Thr Phe Lys Glu Asn Tyr Arg
            980                 985                 990

Phe His Ala Ile Asn Gly Tyr Ile Met Asp Thr Leu Pro Gly Leu Val
        995                 1000                1005

Met Ala Gln Asp Gln Arg Ile Arg Trp Tyr Leu Leu Ser Met Gly
    1010                1015                1020

Ser Asn Glu Asn Ile His Ser Ile His Phe Ser Gly His Val Phe
    1025                1030                1035

Thr Val Arg Lys Lys Glu Glu Tyr Lys Met Ala Leu Tyr Asn Leu
    1040                1045                1050

Tyr Pro Gly Val Phe Glu Thr Val Glu Met Leu Pro Ser Lys Ala
    1055                1060                1065

Gly Ile Trp Arg Val Glu Cys Leu Ile Gly Glu His Leu His Ala
    1070                1075                1080

Gly Met Ser Thr Leu Phe Leu Val Tyr Ser Asn Lys Cys Gln Thr
    1085                1090                1095

Pro Leu Gly Met Ala Ser Gly His Ile Arg Asp Phe Gln Ile Thr
    1100                1105                1110

Ala Ser Gly Gln Tyr Gly Gln Trp Ala Pro Lys Leu Ala Arg Leu
    1115                1120                1125

His Tyr Ser Gly Ser Ile Asn Ala Trp Ser Thr Lys Glu Pro Phe
    1130                1135                1140

Ser Trp Ile Lys Val Asp Leu Leu Ala Pro Met Ile Ile His Gly
    1145                1150                1155

Ile Lys Thr Gln Gly Ala Arg Gln Lys Phe Ser Ser Leu Tyr Ile
    1160                1165                1170

Ser Gln Phe Ile Ile Met Tyr Ser Leu Asp Gly Lys Lys Trp Gln
    1175                1180                1185

Thr Tyr Arg Gly Asn Ser Thr Gly Thr Leu Met Val Phe Phe Gly
    1190                1195                1200

Asn Val Asp Ser Ser Gly Ile Lys His Asn Ile Phe Asn Pro Pro
    1205                1210                1215
```

```
Ile Ile Ala Arg Tyr Ile Arg Leu His Pro Thr His Tyr Ser Ile
    1220                1225                1230

Arg Ser Thr Leu Arg Met Glu Leu Met Gly Cys Asp Leu Asn Ser
    1235                1240                1245

Cys Ser Met Pro Leu Gly Met Glu Ser Lys Ala Ile Ser Asp Ala
    1250                1255                1260

Gln Ile Thr Ala Ser Ser Tyr Phe Thr Asn Met Phe Ala Thr Trp
    1265                1270                1275

Ser Pro Ser Lys Ala Arg Leu His Leu Gln Gly Arg Ser Asn Ala
    1280                1285                1290

Trp Arg Pro Gln Val Asn Asn Pro Lys Glu Trp Leu Gln Val Asp
    1295                1300                1305

Phe Gln Lys Thr Met Lys Val Thr Gly Val Thr Thr Gln Gly Val
    1310                1315                1320

Lys Ser Leu Leu Thr Ser Met Tyr Val Lys Glu Phe Leu Ile Ser
    1325                1330                1335

Ser Ser Gln Asp Gly His Gln Trp Thr Leu Phe Phe Gln Asn Gly
    1340                1345                1350

Lys Val Lys Val Phe Gln Gly Asn Gln Asp Ser Phe Thr Pro Val
    1355                1360                1365

Val Asn Ser Leu Asp Pro Pro Leu Leu Thr Arg Tyr Leu Arg Ile
    1370                1375                1380

His Pro Gln Ser Trp Val His Gln Ile Ala Leu Arg Met Glu Val
    1385                1390                1395

Leu Gly Cys Glu Ala Gln Asp Leu Tyr Gly Gly Gly Ser Gly Gly
    1400                1405                1410

Gly Gly Ser Gly Leu Val Pro Arg Gly Ser Gly Gly Gly Ser Gly
    1415                1420                1425

Gly Gly Gly Ser Gly Asp Ile Gln Leu Thr Gln Ser Pro Ser Phe
    1430                1435                1440

Leu Ser Ala Ser Val Gly Asp Arg Val Thr Ile Thr Cys Arg Ala
    1445                1450                1455

Ser Ser Ser Val Arg Tyr Ile Tyr Trp Phe Gln Gln Lys Pro Gly
    1460                1465                1470

Lys Ala Pro Lys Leu Leu Ile Tyr Ala Thr Ser Phe Arg Gln Ser
    1475                1480                1485

Gly Val Pro Ser Arg Phe Ser Gly Ser Gly Ser Gly Thr Glu Tyr
    1490                1495                1500

Thr Leu Thr Ile Ser Ser Leu Gln Pro Glu Asp Phe Ala Thr Tyr
    1505                1510                1515

Tyr Cys His Gln Arg Asn Ser Phe Pro Tyr Thr Phe Gly Gln Gly
    1520                1525                1530

Thr Lys Leu Glu Ile Lys Gly Gly Gly Gly Ser Gly Gly Gly Gly
    1535                1540                1545

Ser Gly Gly Gly Gly Ser Gly Gly Gly Ser Glu Val Gln Leu
    1550                1555                1560

Val Gln Ser Gly Ala Glu Val Lys Lys Pro Gly Ala Ser Val Lys
    1565                1570                1575

Val Ser Cys Lys Ala Ser Gly Tyr Thr Phe Thr Thr Tyr Ala Ile
    1580                1585                1590

His Trp Val Arg Gln Ala Pro Gly Gln Gly Leu Glu Trp Met Gly
    1595                1600                1605

Tyr Ile Asn Pro Ser Ser Gly Tyr Thr Arg Tyr Asn Pro Lys Phe
```

```
                    1610                1615                1620

Lys Gly Arg Val Thr Met Thr Arg Asp Lys Ser Thr Ser Thr Ala
        1625                1630                1635

Tyr Met Glu Leu Arg Ser Leu Arg Ser Asp Asp Thr Ala Val Tyr
        1640                1645                1650

Tyr Cys Trp Thr Gly Thr Arg Asp Tyr Trp Gly Gln Gly Thr Thr
        1655                1660                1665

Val Thr Val Ser Ser
        1670

<210> SEQ ID NO 123
<211> LENGTH: 1669
<212> TYPE: PRT
<213> ORGANISM: Artificial Sequence
<220> FEATURE:
<223> OTHER INFORMATION: Synthetic Sequence

<400> SEQUENCE: 123

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
```

```
            290                 295                 300
Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Leu Thr Asp
                340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
            370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720
```

```
Asp Ser Tyr Glu Asp Ile Ser Ala Tyr Leu Leu Ser Lys Asn Asn Ala
                725                 730                 735

Ile Glu Pro Arg Ser Phe Ser Gln Asn Gly Gly Gly Ser Thr Gly
            740                 745                 750

Gly Thr Gly Gly Ser Ser Gly Gly Gly Thr Gly Ser Gly Gly Gly Gly
                755                 760                 765

Thr Gly Gly Ser Gly Gly Thr Asp Ile Gln Leu Thr Gln Ser Pro Ser
                770                 775                 780

Phe Leu Ser Ala Ser Val Gly Asp Arg Val Thr Ile Thr Cys Arg Ala
785                 790                 795                 800

Ser Ser Ser Val Arg Tyr Ile Tyr Trp Phe Gln Gln Lys Pro Gly Lys
                805                 810                 815

Ala Pro Lys Leu Leu Ile Tyr Ala Thr Ser Phe Arg Gln Ser Gly Val
                820                 825                 830

Pro Ser Arg Phe Ser Gly Ser Gly Ser Gly Thr Glu Tyr Thr Leu Thr
                835                 840                 845

Ile Ser Ser Leu Gln Pro Glu Asp Phe Ala Thr Tyr Tyr Cys His Gln
    850                 855                 860

Arg Asn Ser Phe Pro Tyr Thr Phe Gly Gln Gly Thr Lys Leu Glu Ile
865                 870                 875                 880

Lys Gly Gly Gly Gly Ser Gly Gly Gly Gly Ser Gly Gly Gly Gly Ser
                885                 890                 895

Gly Gly Gly Gly Ser Glu Val Gln Leu Val Gln Ser Gly Ala Glu Val
                900                 905                 910

Lys Lys Pro Gly Ala Ser Val Lys Val Ser Cys Lys Ala Ser Gly Tyr
                915                 920                 925

Thr Phe Thr Thr Tyr Ala Ile His Trp Val Arg Gln Ala Pro Gly Gln
    930                 935                 940

Gly Leu Glu Trp Met Gly Tyr Ile Asn Pro Ser Ser Gly Tyr Thr Arg
945                 950                 955                 960

Tyr Asn Pro Lys Phe Lys Gly Arg Val Thr Met Thr Arg Asp Lys Ser
                965                 970                 975

Thr Ser Thr Ala Tyr Met Glu Leu Arg Ser Leu Arg Ser Asp Asp Thr
                980                 985                 990

Ala Val Tyr Tyr Cys Trp Thr Gly  Thr Arg Asp Tyr Trp  Gly Gln Gly
                995                 1000                1005

Thr Thr  Val Thr Val Ser Ser  Gly Gly Gly Gly  Asp Glu Asn Gln
    1010                1015                1020

Ser Pro  Arg Ser Phe Gln Lys  Lys Thr Arg His Tyr  Phe Ile Ala
    1025                1030                1035

Ala Val  Glu Arg Leu Trp Asp  Tyr Gly Met Ser  Ser Pro His
    1040                1045                1050

Val Leu  Arg Asn Arg Ala Gln  Ser Gly Ser Val Pro  Gln Phe Lys
    1055                1060                1065

Lys Val  Val Phe Gln Glu Phe  Thr Asp Gly Ser Phe  Thr Gln Pro
    1070                1075                1080

Leu Tyr  Arg Gly Glu Leu Asn  Glu His Leu Gly Leu  Leu Gly Pro
    1085                1090                1095

Tyr Ile  Arg Ala Glu Val Glu  Asp Asn Ile Met Val  Thr Phe Arg
    1100                1105                1110

Asn Gln  Ala Ser Arg Pro Tyr  Ser Phe Tyr Ser Ser  Leu Ile Ser
    1115                1120                1125
```

-continued

Tyr Glu Glu Asp Gln Arg Gln Gly Ala Glu Pro Arg Lys Asn Phe
1130                    1135                    1140

Val Lys Pro Asn Glu Thr Lys Thr Tyr Phe Trp Lys Val Gln His
    1145                    1150                    1155

His Met Ala Pro Thr Lys Asp Glu Phe Asp Cys Lys Ala Trp Ala
    1160                    1165                    1170

Tyr Phe Ser Asp Val Asp Leu Glu Lys Asp Val His Ser Gly Leu
    1175                    1180                    1185

Ile Gly Pro Leu Leu Val Cys His Thr Asn Thr Leu Asn Pro Ala
    1190                    1195                    1200

His Gly Arg Gln Val Thr Val Gln Glu Phe Ala Leu Phe Phe Thr
    1205                    1210                    1215

Ile Phe Asp Glu Thr Lys Ser Trp Tyr Phe Thr Glu Asn Met Glu
    1220                    1225                    1230

Arg Asn Cys Arg Ala Pro Cys Asn Ile Gln Met Glu Asp Pro Thr
    1235                    1240                    1245

Phe Lys Glu Asn Tyr Arg Phe His Ala Ile Asn Gly Tyr Ile Met
    1250                    1255                    1260

Asp Thr Leu Pro Gly Leu Val Met Ala Gln Asp Gln Arg Ile Arg
    1265                    1270                    1275

Trp Tyr Leu Leu Ser Met Gly Ser Asn Glu Asn Ile His Ser Ile
    1280                    1285                    1290

His Phe Ser Gly His Val Phe Thr Val Arg Lys Lys Glu Glu Tyr
    1295                    1300                    1305

Lys Met Ala Leu Tyr Asn Leu Tyr Pro Gly Val Phe Glu Thr Val
    1310                    1315                    1320

Glu Met Leu Pro Ser Lys Ala Gly Ile Trp Arg Val Glu Cys Leu
    1325                    1330                    1335

Ile Gly Glu His Leu His Ala Gly Met Ser Thr Leu Phe Leu Val
    1340                    1345                    1350

Tyr Ser Asn Lys Cys Gln Thr Pro Leu Gly Met Ala Ser Gly His
    1355                    1360                    1365

Ile Arg Asp Phe Gln Ile Thr Ala Ser Gly Gln Tyr Gly Gln Trp
    1370                    1375                    1380

Ala Pro Lys Leu Ala Arg Leu His Tyr Ser Gly Ser Ile Asn Ala
    1385                    1390                    1395

Trp Ser Thr Lys Glu Pro Phe Ser Trp Ile Lys Val Asp Leu Leu
    1400                    1405                    1410

Ala Pro Met Ile Ile His Gly Ile Lys Thr Gln Gly Ala Arg Gln
    1415                    1420                    1425

Lys Phe Ser Ser Leu Tyr Ile Ser Gln Phe Ile Ile Met Tyr Ser
    1430                    1435                    1440

Leu Asp Gly Lys Lys Trp Gln Thr Tyr Arg Gly Asn Ser Thr Gly
    1445                    1450                    1455

Thr Leu Met Val Phe Phe Gly Asn Val Asp Ser Ser Gly Ile Lys
    1460                    1465                    1470

His Asn Ile Phe Asn Pro Pro Ile Ile Ala Arg Tyr Ile Arg Leu
    1475                    1480                    1485

His Pro Thr His Tyr Ser Ile Arg Ser Thr Leu Arg Met Glu Leu
    1490                    1495                    1500

Met Gly Cys Asp Leu Asn Ser Cys Ser Met Pro Leu Gly Met Glu
    1505                    1510                    1515

Ser Lys Ala Ile Ser Asp Ala Gln Ile Thr Ala Ser Ser Tyr Phe

```
                        1520                1525                1530

Thr  Asn  Met  Phe  Ala  Thr  Trp  Ser  Pro  Ser  Lys  Ala  Arg  Leu  His
    1535                1540                1545

Leu  Gln  Gly  Arg  Ser  Asn  Ala  Trp  Arg  Pro  Gln  Val  Asn  Asn  Pro
    1550                1555                1560

Lys  Glu  Trp  Leu  Gln  Val  Asp  Phe  Gln  Lys  Thr  Met  Lys  Val  Thr
    1565                1570                1575

Gly  Val  Thr  Thr  Gln  Gly  Val  Lys  Ser  Leu  Leu  Thr  Ser  Met  Tyr
    1580                1585                1590

Val  Lys  Glu  Phe  Leu  Ile  Ser  Ser  Ser  Gln  Asp  Gly  His  Gln  Trp
    1595                1600                1605

Thr  Leu  Phe  Phe  Gln  Asn  Gly  Lys  Val  Lys  Val  Phe  Gln  Gly  Asn
    1610                1615                1620

Gln  Asp  Ser  Phe  Thr  Pro  Val  Val  Asn  Ser  Leu  Asp  Pro  Pro  Leu
    1625                1630                1635

Leu  Thr  Arg  Tyr  Leu  Arg  Ile  His  Pro  Gln  Ser  Trp  Val  His  Gln
    1640                1645                1650

Ile  Ala  Leu  Arg  Met  Glu  Val  Leu  Gly  Cys  Glu  Ala  Gln  Asp  Leu
    1655                1660                1665

Tyr

<210> SEQ ID NO 124
<211> LENGTH: 1684
<212> TYPE: PRT
<213> ORGANISM: Artificial Sequence
<220> FEATURE:
<223> OTHER INFORMATION: Synthetic Sequence

<400> SEQUENCE: 124

Ala  Thr  Arg  Arg  Tyr  Tyr  Leu  Gly  Ala  Val  Glu  Leu  Ser  Trp  Asp  Tyr
 1                   5                  10                  15

Met  Gln  Ser  Asp  Leu  Gly  Glu  Leu  Pro  Val  Asp  Ala  Arg  Phe  Pro  Pro
                20                  25                  30

Arg  Val  Pro  Lys  Ser  Phe  Pro  Phe  Asn  Thr  Ser  Val  Val  Tyr  Lys  Lys
            35                  40                  45

Thr  Leu  Phe  Val  Glu  Phe  Thr  Asp  His  Leu  Phe  Asn  Ile  Ala  Lys  Pro
        50                  55                  60

Arg  Pro  Pro  Trp  Met  Gly  Leu  Leu  Gly  Pro  Thr  Ile  Gln  Ala  Glu  Val
 65                  70                  75                  80

Tyr  Asp  Thr  Val  Val  Ile  Thr  Leu  Lys  Asn  Met  Ala  Ser  His  Pro  Val
                85                  90                  95

Ser  Leu  His  Ala  Val  Gly  Val  Ser  Tyr  Trp  Lys  Ala  Ser  Glu  Gly  Ala
            100                 105                 110

Glu  Tyr  Asp  Asp  Gln  Thr  Ser  Gln  Arg  Glu  Lys  Glu  Asp  Asp  Lys  Val
        115                 120                 125

Phe  Pro  Gly  Gly  Ser  His  Thr  Tyr  Val  Trp  Gln  Val  Leu  Lys  Glu  Asn
    130                 135                 140

Gly  Pro  Met  Ala  Ser  Asp  Pro  Leu  Cys  Leu  Thr  Tyr  Ser  Tyr  Leu  Ser
145                 150                 155                 160

His  Val  Asp  Leu  Val  Lys  Asp  Leu  Asn  Ser  Gly  Leu  Ile  Gly  Ala  Leu
                165                 170                 175

Leu  Val  Cys  Arg  Glu  Gly  Ser  Leu  Ala  Lys  Glu  Lys  Thr  Gln  Thr  Leu
            180                 185                 190

His  Lys  Phe  Ile  Leu  Leu  Phe  Ala  Val  Phe  Asp  Glu  Gly  Lys  Ser  Trp
        195                 200                 205
```

-continued

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

-continued

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Gly Gly Gly Ser Thr Gly
            740                 745                 750

Gly Thr Gly Gly Ser Gly Gly Thr Gly Ser Gly Gly Gly
    755                 760                 765

Thr Gly Gly Ser Gly Gly Thr Asp Ile Gln Leu Thr Gln Ser Pro Ser
770                 775                 780

Phe Leu Ser Ala Ser Val Gly Asp Arg Val Thr Ile Thr Cys Arg Ala
785                 790                 795                 800

Ser Ser Ser Val Arg Tyr Ile Tyr Trp Phe Gln Gln Lys Pro Gly Lys
            805                 810                 815

Ala Pro Lys Leu Leu Ile Tyr Ala Thr Ser Phe Arg Gln Ser Gly Val
            820                 825                 830

Pro Ser Arg Phe Ser Gly Ser Gly Ser Gly Thr Glu Tyr Thr Leu Thr
            835                 840                 845

Ile Ser Ser Leu Gln Pro Glu Asp Phe Ala Thr Tyr Tyr Cys His Gln
850                 855                 860

Arg Asn Ser Phe Pro Tyr Thr Phe Gly Gln Gly Thr Lys Leu Glu Ile
865                 870                 875                 880

Lys Gly Gly Gly Gly Ser Gly Gly Gly Gly Ser Gly Gly Gly Gly Ser
            885                 890                 895

Gly Gly Gly Gly Ser Glu Val Gln Leu Val Gln Ser Gly Ala Glu Val
            900                 905                 910

Lys Lys Pro Gly Ala Ser Val Lys Val Ser Cys Lys Ala Ser Gly Tyr
            915                 920                 925

Thr Phe Thr Thr Tyr Ala Ile His Trp Val Arg Gln Ala Pro Gly Gln
            930                 935                 940

Gly Leu Glu Trp Met Gly Tyr Ile Asn Pro Ser Ser Gly Tyr Thr Arg
945                 950                 955                 960

Tyr Asn Pro Lys Phe Lys Gly Arg Val Thr Met Thr Arg Asp Lys Ser
            965                 970                 975

Thr Ser Thr Ala Tyr Met Glu Leu Arg Ser Leu Arg Ser Asp Asp Thr
            980                 985                 990

Ala Val Tyr Tyr Cys Trp Thr Gly Thr Arg Asp Tyr Trp Gly Gln Gly
            995                 1000                1005

Thr Thr Val Thr Val Ser Ser Gly Gly Gly Gly Ser Gln Asn Pro
        1010                1015                1020

Pro Val Leu Lys Arg His Gln Arg Glu Ile Thr Asp Glu Asn Gln
        1025                1030                1035

Ser Pro Arg Ser Phe Gln Lys Lys Thr Arg His Tyr Phe Ile Ala

-continued

```
            1040                1045                1050
Ala Val Glu Arg Leu Trp Asp Tyr Gly Met Ser Ser Ser Pro His
        1055                1060                1065
Val Leu Arg Asn Arg Ala Gln Ser Gly Ser Val Pro Gln Phe Lys
        1070                1075                1080
Lys Val Val Phe Gln Glu Phe Thr Asp Gly Ser Phe Thr Gln Pro
        1085                1090                1095
Leu Tyr Arg Gly Glu Leu Asn Glu His Leu Gly Leu Leu Gly Pro
        1100                1105                1110
Tyr Ile Arg Ala Glu Val Glu Asp Asn Ile Met Val Thr Phe Arg
        1115                1120                1125
Asn Gln Ala Ser Arg Pro Tyr Ser Phe Tyr Ser Ser Leu Ile Ser
        1130                1135                1140
Tyr Glu Glu Asp Gln Arg Gln Gly Ala Glu Pro Arg Lys Asn Phe
        1145                1150                1155
Val Lys Pro Asn Glu Thr Lys Thr Tyr Phe Trp Lys Val Gln His
        1160                1165                1170
His Met Ala Pro Thr Lys Asp Glu Phe Asp Cys Lys Ala Trp Ala
        1175                1180                1185
Tyr Phe Ser Asp Val Asp Leu Glu Lys Asp Val His Ser Gly Leu
        1190                1195                1200
Ile Gly Pro Leu Leu Val Cys His Thr Asn Thr Leu Asn Pro Ala
        1205                1210                1215
His Gly Arg Gln Val Thr Val Gln Glu Phe Ala Leu Phe Phe Thr
        1220                1225                1230
Ile Phe Asp Glu Thr Lys Ser Trp Tyr Phe Thr Glu Asn Met Glu
        1235                1240                1245
Arg Asn Cys Arg Ala Pro Cys Asn Ile Gln Met Glu Asp Pro Thr
        1250                1255                1260
Phe Lys Glu Asn Tyr Arg Phe His Ala Ile Asn Gly Tyr Ile Met
        1265                1270                1275
Asp Thr Leu Pro Gly Leu Val Met Ala Gln Asp Gln Arg Ile Arg
        1280                1285                1290
Trp Tyr Leu Leu Ser Met Gly Ser Asn Glu Asn Ile His Ser Ile
        1295                1300                1305
His Phe Ser Gly His Val Phe Thr Val Arg Lys Lys Glu Glu Tyr
        1310                1315                1320
Lys Met Ala Leu Tyr Asn Leu Tyr Pro Gly Val Phe Glu Thr Val
        1325                1330                1335
Glu Met Leu Pro Ser Lys Ala Gly Ile Trp Arg Val Glu Cys Leu
        1340                1345                1350
Ile Gly Glu His Leu His Ala Gly Met Ser Thr Leu Phe Leu Val
        1355                1360                1365
Tyr Ser Asn Lys Cys Gln Thr Pro Leu Gly Met Ala Ser Gly His
        1370                1375                1380
Ile Arg Asp Phe Gln Ile Thr Ala Ser Gly Gln Tyr Gly Gln Trp
        1385                1390                1395
Ala Pro Lys Leu Ala Arg Leu His Tyr Ser Gly Ser Ile Asn Ala
        1400                1405                1410
Trp Ser Thr Lys Glu Pro Phe Ser Trp Ile Lys Val Asp Leu Leu
        1415                1420                1425
Ala Pro Met Ile Ile His Gly Ile Lys Thr Gln Gly Ala Arg Gln
        1430                1435                1440
```

-continued

```
Lys Phe Ser Ser Leu Tyr Ile Ser Gln Phe Ile Ile Met Tyr Ser
    1445                1450                1455

Leu Asp Gly Lys Lys Trp Gln Thr Tyr Arg Gly Asn Ser Thr Gly
    1460                1465                1470

Thr Leu Met Val Phe Phe Gly Asn Val Asp Ser Ser Gly Ile Lys
    1475                1480                1485

His Asn Ile Phe Asn Pro Pro Ile Ile Ala Arg Tyr Ile Arg Leu
    1490                1495                1500

His Pro Thr His Tyr Ser Ile Arg Ser Thr Leu Arg Met Glu Leu
    1505                1510                1515

Met Gly Cys Asp Leu Asn Ser Cys Ser Met Pro Leu Gly Met Glu
    1520                1525                1530

Ser Lys Ala Ile Ser Asp Ala Gln Ile Thr Ala Ser Ser Tyr Phe
    1535                1540                1545

Thr Asn Met Phe Ala Thr Trp Ser Pro Ser Lys Ala Arg Leu His
    1550                1555                1560

Leu Gln Gly Arg Ser Asn Ala Trp Arg Pro Gln Val Asn Asn Pro
    1565                1570                1575

Lys Glu Trp Leu Gln Val Asp Phe Gln Lys Thr Met Lys Val Thr
    1580                1585                1590

Gly Val Thr Thr Gln Gly Val Lys Ser Leu Leu Thr Ser Met Tyr
    1595                1600                1605

Val Lys Glu Phe Leu Ile Ser Ser Ser Gln Asp Gly His Gln Trp
    1610                1615                1620

Thr Leu Phe Phe Gln Asn Gly Lys Val Lys Val Phe Gln Gly Asn
    1625                1630                1635

Gln Asp Ser Phe Thr Pro Val Val Asn Ser Leu Asp Pro Pro Leu
    1640                1645                1650

Leu Thr Arg Tyr Leu Arg Ile His Pro Gln Ser Trp Val His Gln
    1655                1660                1665

Ile Ala Leu Arg Met Glu Val Leu Gly Cys Glu Ala Gln Asp Leu
    1670                1675                1680

Tyr

<210> SEQ ID NO 125
<211> LENGTH: 1661
<212> TYPE: PRT
<213> ORGANISM: Artificial Sequence
<220> FEATURE:
<223> OTHER INFORMATION: Synthetic Sequence

<400> SEQUENCE: 125

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
                20                  25                  30

Tyr Trp Phe Gln Gln Lys Pro Gly Lys Ala Pro Lys Leu Leu Ile Tyr
            35                  40                  45

Ala Thr Ser Phe Arg Gln Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95
```

```
Phe Gly Gln Gly Thr Lys Leu Glu Ile Lys Gly Gly Gly Ser Gly
                100                 105                 110
Gly Gly Gly Ser Gly Gly Gly Ser Gly Gly Gly Ser Glu Val
            115                 120                 125
Gln Leu Val Gln Ser Gly Ala Glu Val Lys Lys Pro Gly Ala Ser Val
130                 135                 140
Lys Val Ser Cys Lys Ala Ser Gly Tyr Thr Phe Thr Thr Tyr Ala Ile
145                 150                 155                 160
His Trp Val Arg Gln Ala Pro Gly Gln Gly Leu Glu Trp Met Gly Tyr
                165                 170                 175
Ile Asn Pro Ser Ser Gly Tyr Thr Arg Tyr Asn Pro Lys Phe Lys Gly
                180                 185                 190
Arg Val Thr Met Thr Arg Asp Lys Ser Thr Ser Thr Ala Tyr Met Glu
                195                 200                 205
Leu Arg Ser Leu Arg Ser Asp Asp Thr Ala Val Tyr Tyr Cys Trp Thr
210                 215                 220
Gly Thr Arg Asp Tyr Trp Gly Gln Gly Thr Thr Val Thr Val Ser Ser
225                 230                 235                 240
Gly Gly Gly Ser Gly Gly Gly Ser Gly Leu Val Pro Arg Gly Ser
            245                 250                 255
Gly Gly Gly Ser Gly Gly Gly Ser Gly Ala Thr Arg Arg Tyr Tyr
            260                 265                 270
Leu Gly Ala Val Glu Leu Ser Trp Asp Tyr Met Gln Ser Asp Leu Gly
                275                 280                 285
Glu Leu Pro Val Asp Ala Arg Phe Pro Pro Arg Val Pro Lys Ser Phe
                290                 295                 300
Pro Phe Asn Thr Ser Val Val Tyr Lys Lys Thr Leu Phe Val Glu Phe
305                 310                 315                 320
Thr Asp His Leu Phe Asn Ile Ala Lys Pro Arg Pro Trp Met Gly
                325                 330                 335
Leu Leu Gly Pro Thr Ile Gln Ala Glu Val Tyr Asp Thr Val Val Ile
                340                 345                 350
Thr Leu Lys Asn Met Ala Ser His Pro Val Ser Leu His Ala Val Gly
                355                 360                 365
Val Ser Tyr Trp Lys Ala Ser Glu Gly Ala Glu Tyr Asp Asp Gln Thr
370                 375                 380
Ser Gln Arg Glu Lys Glu Asp Asp Lys Val Phe Pro Gly Gly Ser His
385                 390                 395                 400
Thr Tyr Val Trp Gln Val Leu Lys Glu Asn Gly Pro Met Ala Ser Asp
                405                 410                 415
Pro Leu Cys Leu Thr Tyr Ser Tyr Leu Ser His Val Asp Leu Val Lys
                420                 425                 430
Asp Leu Asn Ser Gly Leu Ile Gly Ala Leu Leu Val Cys Arg Glu Gly
            435                 440                 445
Ser Leu Ala Lys Glu Lys Thr Gln Thr Leu His Lys Phe Ile Leu Leu
450                 455                 460
Phe Ala Val Phe Asp Glu Gly Lys Ser Trp His Ser Glu Thr Lys Asn
465                 470                 475                 480
Ser Leu Met Gln Asp Arg Asp Ala Ala Ser Ala Arg Ala Trp Pro Lys
                485                 490                 495
Met His Thr Val Asn Gly Tyr Val Asn Arg Ser Leu Pro Gly Leu Ile
                500                 505                 510
Gly Cys His Arg Lys Ser Val Tyr Trp His Val Ile Gly Met Gly Thr
```

```
            515                 520                 525
Thr Pro Glu Val His Ser Ile Phe Leu Glu Gly His Thr Phe Leu Val
    530                 535                 540
Arg Asn His Arg Gln Ala Ser Leu Glu Ile Ser Pro Ile Thr Phe Leu
545                 550                 555                 560
Thr Ala Gln Thr Leu Leu Met Asp Leu Gly Gln Phe Leu Leu Phe Cys
                565                 570                 575
His Ile Ser Ser His Gln His Asp Gly Met Glu Ala Tyr Val Lys Val
            580                 585                 590
Asp Ser Cys Pro Glu Glu Pro Gln Leu Arg Met Lys Asn Asn Glu Glu
            595                 600                 605
Ala Glu Asp Tyr Asp Asp Leu Thr Asp Ser Glu Met Asp Val Val
    610                 615                 620
Arg Phe Asp Asp Asp Asn Ser Pro Ser Phe Ile Gln Ile Arg Ser Val
625                 630                 635                 640
Ala Lys Lys His Pro Lys Thr Trp Val His Tyr Ile Ala Ala Glu Glu
                645                 650                 655
Glu Asp Trp Asp Tyr Ala Pro Leu Val Leu Ala Pro Asp Asp Arg Ser
            660                 665                 670
Tyr Lys Ser Gln Tyr Leu Asn Asn Gly Pro Gln Arg Ile Gly Arg Lys
        675                 680                 685
Tyr Lys Lys Val Arg Phe Met Ala Tyr Thr Asp Glu Thr Phe Lys Thr
    690                 695                 700
Arg Glu Ala Ile Gln His Glu Ser Gly Ile Leu Gly Pro Leu Leu Tyr
705                 710                 715                 720
Gly Glu Val Gly Asp Thr Leu Leu Ile Ile Phe Lys Asn Gln Ala Ser
                725                 730                 735
Arg Pro Tyr Asn Ile Tyr Pro His Gly Ile Thr Asp Val Arg Pro Leu
            740                 745                 750
Tyr Ser Arg Arg Leu Pro Lys Gly Val Lys His Leu Lys Asp Phe Pro
        755                 760                 765
Ile Leu Pro Gly Glu Ile Phe Lys Tyr Lys Trp Thr Val Thr Val Glu
    770                 775                 780
Asp Gly Pro Thr Lys Ser Asp Pro Arg Cys Leu Thr Arg Tyr Tyr Ser
785                 790                 795                 800
Ser Phe Val Asn Met Glu Arg Asp Leu Ala Ser Gly Leu Ile Gly Pro
                805                 810                 815
Leu Leu Ile Cys Tyr Lys Glu Ser Val Asp Gln Arg Gly Asn Gln Ile
            820                 825                 830
Met Ser Asp Lys Arg Asn Val Ile Leu Phe Ser Val Phe Asp Glu Asn
        835                 840                 845
Arg Ser Trp Tyr Leu Thr Glu Asn Ile Gln Arg Phe Leu Pro Asn Pro
    850                 855                 860
Ala Gly Val Gln Leu Glu Asp Pro Glu Phe Gln Ala Ser Asn Ile Met
865                 870                 875                 880
His Ser Ile Asn Gly Tyr Val Phe Asp Ser Leu Gln Leu Ser Val Cys
                885                 890                 895
Leu His Glu Val Ala Tyr Trp Tyr Ile Leu Ser Ile Gly Ala Gln Thr
            900                 905                 910
Asp Phe Leu Ser Val Phe Phe Ser Gly Tyr Thr Phe Lys His Lys Met
        915                 920                 925
Val Tyr Glu Asp Thr Leu Thr Leu Phe Pro Phe Ser Gly Glu Thr Val
    930                 935                 940
```

-continued

```
Phe Met Ser Met Glu Asn Pro Gly Leu Trp Ile Leu Gly Cys His Asn
945                 950                 955                 960

Ser Asp Phe Arg Asn Arg Gly Met Thr Ala Leu Leu Lys Val Ser Ser
                965                 970                 975

Cys Asp Lys Asn Thr Gly Asp Tyr Tyr Glu Asp Ser Tyr Glu Asp Ile
            980                 985                 990

Ser Ala Tyr Leu Leu Ser Lys Asn Asn Ala Ile Glu Pro Arg Ser Phe
        995                 1000                1005

Ser Gln Asn Asp Glu Asn Gln Ser Pro Arg Ser Phe Gln Lys Lys
    1010                1015                1020

Thr Arg His Tyr Phe Ile Ala Ala Val Glu Arg Leu Trp Asp Tyr
    1025                1030                1035

Gly Met Ser Ser Ser Pro His Val Leu Arg Asn Arg Ala Gln Ser
    1040                1045                1050

Gly Ser Val Pro Gln Phe Lys Lys Val Val Phe Gln Glu Phe Thr
    1055                1060                1065

Asp Gly Ser Phe Thr Gln Pro Leu Tyr Arg Gly Glu Leu Asn Glu
    1070                1075                1080

His Leu Gly Leu Leu Gly Pro Tyr Ile Arg Ala Glu Val Glu Asp
    1085                1090                1095

Asn Ile Met Val Thr Phe Arg Asn Gln Ala Ser Arg Pro Tyr Ser
    1100                1105                1110

Phe Tyr Ser Ser Leu Ile Ser Tyr Glu Glu Asp Gln Arg Gln Gly
    1115                1120                1125

Ala Glu Pro Arg Lys Asn Phe Val Lys Pro Asn Glu Thr Lys Thr
    1130                1135                1140

Tyr Phe Trp Lys Val Gln His His Met Ala Pro Thr Lys Asp Glu
    1145                1150                1155

Phe Asp Cys Lys Ala Trp Ala Tyr Phe Ser Asp Val Asp Leu Glu
    1160                1165                1170

Lys Asp Val His Ser Gly Leu Ile Gly Pro Leu Leu Val Cys His
    1175                1180                1185

Thr Asn Thr Leu Asn Pro Ala His Gly Arg Gln Val Thr Val Gln
    1190                1195                1200

Glu Phe Ala Leu Phe Phe Thr Ile Phe Asp Glu Thr Lys Ser Trp
    1205                1210                1215

Tyr Phe Thr Glu Asn Met Glu Arg Asn Cys Arg Ala Pro Cys Asn
    1220                1225                1230

Ile Gln Met Glu Asp Pro Thr Phe Lys Glu Asn Tyr Arg Phe His
    1235                1240                1245

Ala Ile Asn Gly Tyr Ile Met Asp Thr Leu Pro Gly Leu Val Met
    1250                1255                1260

Ala Gln Asp Gln Arg Ile Arg Trp Tyr Leu Leu Ser Met Gly Ser
    1265                1270                1275

Asn Glu Asn Ile His Ser Ile His Phe Ser Gly His Val Phe Thr
    1280                1285                1290

Val Arg Lys Lys Glu Glu Tyr Lys Met Ala Leu Tyr Asn Leu Tyr
    1295                1300                1305

Pro Gly Val Phe Glu Thr Val Glu Met Leu Pro Ser Lys Ala Gly
    1310                1315                1320

Ile Trp Arg Val Glu Cys Leu Ile Gly Glu His Leu His Ala Gly
    1325                1330                1335
```

```
Met Ser Thr Leu Phe Leu Val Tyr Ser Asn Lys Cys Gln Thr Pro
    1340                1345                1350

Leu Gly Met Ala Ser Gly His Ile Arg Asp Phe Gln Ile Thr Ala
    1355                1360                1365

Ser Gly Gln Tyr Gly Gln Trp Ala Pro Lys Leu Ala Arg Leu His
    1370                1375                1380

Tyr Ser Gly Ser Ile Asn Ala Trp Ser Thr Lys Glu Pro Phe Ser
    1385                1390                1395

Trp Ile Lys Val Asp Leu Leu Ala Pro Met Ile Ile His Gly Ile
    1400                1405                1410

Lys Thr Gln Gly Ala Arg Gln Lys Phe Ser Ser Leu Tyr Ile Ser
    1415                1420                1425

Gln Phe Ile Ile Met Tyr Ser Leu Asp Gly Lys Lys Trp Gln Thr
    1430                1435                1440

Tyr Arg Gly Asn Ser Thr Gly Thr Leu Met Val Phe Phe Gly Asn
    1445                1450                1455

Val Asp Ser Ser Gly Ile Lys His Asn Ile Phe Asn Pro Pro Ile
    1460                1465                1470

Ile Ala Arg Tyr Ile Arg Leu His Pro Thr His Tyr Ser Ile Arg
    1475                1480                1485

Ser Thr Leu Arg Met Glu Leu Met Gly Cys Asp Leu Asn Ser Cys
    1490                1495                1500

Ser Met Pro Leu Gly Met Glu Ser Lys Ala Ile Ser Asp Ala Gln
    1505                1510                1515

Ile Thr Ala Ser Ser Tyr Lys Thr Asn Met Phe Ala Thr Trp Ser
    1520                1525                1530

Pro Ser Lys Ala Arg Leu His Leu Gln Gly Arg Ser Asn Ala Trp
    1535                1540                1545

Arg Pro Gln Val Asn Asn Pro Lys Glu Trp Leu Gln Val Asp Phe
    1550                1555                1560

Gln Lys Thr Met Lys Val Thr Gly Val Thr Thr Gln Gly Val Lys
    1565                1570                1575

Ser Leu Leu Thr Ser Met Tyr Val Lys Glu Phe Leu Ile Ser Ser
    1580                1585                1590

Ser Gln Asp Gly His Gln Trp Thr Leu Phe Phe Gln Asn Gly Lys
    1595                1600                1605

Val Lys Val Phe Gln Gly Asn Gln Asp Ser Phe Thr Pro Val Val
    1610                1615                1620

Asn Ser Leu Asp Pro Pro Leu Leu Thr Arg Tyr Leu Arg Ile His
    1625                1630                1635

Pro Gln Ser Trp Val His Gln Ile Ala Leu Arg Met Glu Val Leu
    1640                1645                1650

Gly Cys Glu Ala Gln Asp Leu Tyr
    1655                1660
```

<210> SEQ ID NO 126
<211> LENGTH: 1661
<212> TYPE: PRT
<213> ORGANISM: Artificial Sequence
<220> FEATURE:
<223> OTHER INFORMATION: Synthetic Sequence

<400> SEQUENCE: 126

```
Asp Ile Gln Leu Thr Gln Ser Pro Ser Phe Leu Ser Ala Ser Val Gly
1               5                   10                  15
```

-continued

Asp Arg Val Thr Ile Thr Cys Arg Ala Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys Gly Gly Gly Gly Ser Gly
            100                 105                 110

Gly Gly Gly Ser Gly Gly Gly Gly Ser Gly Gly Gly Gly Ser Glu Val
            115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Thr Tyr Ala Ile
145                 150                 155                 160

His Trp Val Arg Gln Ala Pro Gly Gln Gly Leu Glu Trp Met Gly Tyr
                165                 170                 175

Ile Asn Pro Ser Ser Gly Tyr Thr Arg Tyr Asn Pro Lys Phe Lys Gly
            180                 185                 190

Arg Val Thr Met Thr Arg Asp Lys Ser Thr Ser Thr Ala Tyr Met Glu
        195                 200                 205

Leu Arg Ser Leu Arg Ser Asp Asp Thr Ala Val Tyr Tyr Cys Trp Thr
    210                 215                 220

Gly Thr Arg Asp Tyr Trp Gly Gln Gly Thr Thr Val Thr Val Ser Ser
225                 230                 235                 240

Gly Gly Gly Ser Gly Gly Gly Ser Gly Leu Val Pro Arg Gly Ser
                245                 250                 255

Gly Gly Gly Ser Gly Gly Gly Gly Ser Gly Ala Thr Arg Tyr Tyr
            260                 265                 270

Leu Gly Ala Val Glu Leu Ser Trp Asp Tyr Met Gln Ser Asp Leu Gly
    275                 280                 285

Glu Leu Pro Val Asp Ala Arg Phe Pro Pro Arg Val Pro Lys Ser Phe
    290                 295                 300

Pro Phe Asn Thr Ser Val Val Tyr Lys Lys Thr Leu Phe Val Glu Phe
305                 310                 315                 320

Thr Asp His Leu Phe Asn Ile Ala Lys Pro Arg Pro Pro Trp Met Gly
                325                 330                 335

Leu Leu Gly Pro Thr Ile Gln Ala Glu Val Tyr Asp Thr Val Val Ile
            340                 345                 350

Thr Leu Lys Asn Met Ala Ser His Pro Val Ser Leu His Ala Val Gly
        355                 360                 365

Val Ser Tyr Trp Lys Ala Ser Glu Gly Ala Glu Tyr Asp Asp Gln Thr
    370                 375                 380

Ser Gln Arg Glu Lys Glu Asp Asp Lys Val Phe Pro Gly Gly Ser His
385                 390                 395                 400

Thr Tyr Val Trp Gln Val Leu Lys Glu Asn Gly Pro Met Ala Ser Asp
                405                 410                 415

Pro Leu Cys Leu Thr Tyr Ser Tyr Leu Ser His Val Asp Leu Val Lys
            420                 425                 430

Asp Leu Asn Ser Gly Leu Ile Gly Ala Leu Leu Val Cys Arg Glu Gly

|  | 435 |  |  | 440 |  |  | 445 |  |  |  |  |
|---|---|---|---|---|---|---|---|---|---|---|---|

Ser Leu Ala Lys Glu Lys Thr Gln Thr Leu His Lys Phe Ile Leu Leu
450                 455                 460

Phe Ala Val Phe Asp Glu Gly Lys Ser Trp His Ser Glu Thr Lys Asn
465                 470                 475                 480

Ser Leu Met Gln Asp Arg Asp Ala Ala Ser Ala Arg Ala Trp Pro Lys
                485                 490                 495

Met His Thr Val Asn Gly Tyr Val Asn Arg Ser Leu Pro Gly Leu Ile
                500                 505                 510

Gly Cys His Arg Lys Ser Val Tyr Trp His Val Ile Gly Met Gly Thr
                515                 520                 525

Thr Pro Glu Val His Ser Ile Phe Leu Glu Gly His Thr Phe Leu Val
530                 535                 540

Arg Asn His Arg Gln Ala Ser Leu Glu Ile Ser Pro Ile Thr Phe Leu
545                 550                 555                 560

Thr Ala Gln Thr Leu Leu Met Asp Leu Gly Gln Phe Leu Leu Phe Cys
                565                 570                 575

His Ile Ser Ser His Gln His Asp Gly Met Glu Ala Tyr Val Lys Val
                580                 585                 590

Asp Ser Cys Pro Glu Glu Pro Gln Leu Arg Met Lys Asn Asn Glu Glu
                595                 600                 605

Ala Glu Asp Tyr Asp Asp Asp Leu Thr Asp Ser Glu Met Asp Val Val
                610                 615                 620

Arg Phe Asp Asp Asp Asn Ser Pro Ser Phe Ile Gln Ile Arg Ser Val
625                 630                 635                 640

Ala Lys Lys His Pro Lys Thr Trp Val His Tyr Ile Ala Ala Glu Glu
                645                 650                 655

Glu Asp Trp Asp Tyr Ala Pro Leu Val Leu Ala Pro Asp Asp Arg Ser
                660                 665                 670

Tyr Lys Ser Gln Tyr Leu Asn Asn Gly Pro Gln Arg Ile Gly Arg Lys
                675                 680                 685

Tyr Lys Lys Val Arg Phe Met Ala Tyr Thr Asp Glu Thr Phe Lys Thr
690                 695                 700

Arg Glu Ala Ile Gln His Glu Ser Gly Ile Leu Gly Pro Leu Leu Tyr
705                 710                 715                 720

Gly Glu Val Gly Asp Thr Leu Leu Ile Ile Phe Lys Asn Gln Ala Ser
                725                 730                 735

Arg Pro Tyr Asn Ile Tyr Pro His Gly Ile Thr Asp Val Arg Pro Leu
                740                 745                 750

Tyr Ser Arg Arg Leu Pro Lys Gly Val Lys His Leu Lys Asp Phe Pro
                755                 760                 765

Ile Leu Pro Gly Glu Ile Phe Lys Tyr Lys Trp Thr Val Thr Val Glu
770                 775                 780

Asp Gly Pro Thr Lys Ser Asp Pro Arg Cys Leu Thr Arg Tyr Tyr Ser
785                 790                 795                 800

Ser Phe Val Asn Met Glu Arg Asp Leu Ala Ser Gly Leu Ile Gly Pro
                805                 810                 815

Leu Leu Ile Cys Tyr Lys Glu Ser Val Asp Gln Arg Gly Asn Gln Ile
                820                 825                 830

Met Ser Asp Lys Arg Asn Val Ile Leu Phe Ser Val Phe Asp Glu Asn
                835                 840                 845

Arg Ser Trp Tyr Leu Thr Glu Asn Ile Gln Arg Phe Leu Pro Asn Pro
850                 855                 860

Ala Gly Val Gln Leu Glu Asp Pro Glu Phe Gln Ala Ser Asn Ile Met
865                 870                 875                 880

His Ser Ile Asn Gly Tyr Val Phe Asp Ser Leu Gln Leu Ser Val Cys
                885                 890                 895

Leu His Glu Val Ala Tyr Trp Tyr Ile Leu Ser Ile Gly Ala Gln Thr
            900                 905                 910

Asp Phe Leu Ser Val Phe Phe Ser Gly Tyr Thr Phe Lys His Lys Met
        915                 920                 925

Val Tyr Glu Asp Thr Leu Thr Leu Phe Pro Phe Ser Gly Glu Thr Val
    930                 935                 940

Phe Met Ser Met Glu Asn Pro Gly Leu Trp Ile Leu Gly Cys His Asn
945                 950                 955                 960

Ser Asp Phe Arg Asn Arg Gly Met Thr Ala Leu Leu Lys Val Ser Ser
                965                 970                 975

Cys Asp Lys Asn Thr Gly Asp Tyr Tyr Glu Asp Ser Tyr Glu Asp Ile
            980                 985                 990

Ser Ala Tyr Leu Leu Ser Lys Asn Asn Ala Ile Glu Pro Arg Ser Phe
        995                 1000                1005

Ser Gln Asn Asp Glu Asn Gln Ser Pro Arg Ser Phe Gln Lys Lys
    1010                1015                1020

Thr Arg His Tyr Phe Ile Ala Ala Val Glu Arg Leu Trp Asp Tyr
    1025                1030                1035

Gly Met Ser Ser Ser Pro His Val Leu Arg Asn Arg Ala Gln Ser
    1040                1045                1050

Gly Ser Val Pro Gln Phe Lys Lys Val Val Phe Gln Glu Phe Thr
    1055                1060                1065

Asp Gly Ser Phe Thr Gln Pro Leu Tyr Arg Gly Glu Leu Asn Glu
    1070                1075                1080

His Leu Gly Leu Leu Gly Pro Tyr Ile Arg Ala Glu Val Glu Asp
    1085                1090                1095

Asn Ile Met Val Thr Phe Arg Asn Gln Ala Ser Arg Pro Tyr Ser
    1100                1105                1110

Phe Tyr Ser Ser Leu Ile Ser Tyr Glu Glu Asp Gln Arg Gln Gly
    1115                1120                1125

Ala Glu Pro Arg Lys Asn Phe Val Lys Pro Asn Glu Thr Lys Thr
    1130                1135                1140

Tyr Phe Trp Lys Val Gln His His Met Ala Pro Thr Lys Asp Glu
    1145                1150                1155

Phe Asp Cys Lys Ala Trp Ala Tyr Phe Ser Asp Val Asp Leu Glu
    1160                1165                1170

Lys Asp Val His Ser Gly Leu Ile Gly Pro Leu Leu Val Cys His
    1175                1180                1185

Thr Asn Thr Leu Asn Pro Ala His Gly Arg Gln Val Thr Val Gln
    1190                1195                1200

Glu Phe Ala Leu Phe Phe Thr Ile Phe Asp Glu Thr Lys Ser Trp
    1205                1210                1215

Tyr Phe Thr Glu Asn Met Glu Arg Asn Cys Arg Ala Pro Cys Asn
    1220                1225                1230

Ile Gln Met Glu Asp Pro Thr Phe Lys Glu Asn Tyr Arg Phe His
    1235                1240                1245

Ala Ile Asn Gly Tyr Ile Met Asp Thr Leu Pro Gly Leu Val Met
    1250                1255                1260

```
Ala Gln Asp Gln Arg Ile Arg Trp Tyr Leu Leu Ser Met Gly Ser
    1265                1270                1275

Asn Glu Asn Ile His Ser Ile His Phe Ser Gly His Val Phe Thr
    1280                1285                1290

Val Arg Lys Lys Glu Glu Tyr Lys Met Ala Leu Tyr Asn Leu Tyr
    1295                1300                1305

Pro Gly Val Phe Glu Thr Val Glu Met Leu Pro Ser Lys Ala Gly
    1310                1315                1320

Ile Trp Arg Val Glu Cys Leu Ile Gly Glu His Leu His Ala Gly
    1325                1330                1335

Met Ser Thr Leu Phe Leu Val Tyr Ser Asn Lys Cys Gln Thr Pro
    1340                1345                1350

Leu Gly Met Ala Ser Gly His Ile Arg Asp Phe Gln Ile Thr Ala
    1355                1360                1365

Ser Gly Gln Tyr Gly Gln Trp Ala Pro Lys Leu Ala Arg Leu His
    1370                1375                1380

Tyr Ser Gly Ser Ile Asn Ala Trp Ser Thr Lys Glu Pro Phe Ser
    1385                1390                1395

Trp Ile Lys Val Asp Leu Leu Ala Pro Met Ile Ile His Gly Ile
    1400                1405                1410

Lys Thr Gln Gly Ala Arg Gln Lys Phe Ser Ser Leu Tyr Ile Ser
    1415                1420                1425

Gln Phe Ile Ile Met Tyr Ser Leu Asp Gly Lys Lys Trp Gln Thr
    1430                1435                1440

Tyr Arg Gly Asn Ser Thr Gly Thr Leu Met Val Phe Phe Gly Asn
    1445                1450                1455

Val Asp Ser Ser Gly Ile Lys His Asn Ile Phe Asn Pro Pro Ile
    1460                1465                1470

Ile Ala Arg Tyr Ile Arg Leu His Pro Thr His Tyr Ser Ile Arg
    1475                1480                1485

Ser Thr Leu Arg Met Glu Leu Met Gly Cys Asp Leu Asn Ser Cys
    1490                1495                1500

Ser Met Pro Leu Gly Met Glu Ser Lys Ala Ile Ser Asp Ala Gln
    1505                1510                1515

Ile Thr Ala Ser Ser Tyr Phe Thr Asn Met Phe Ala Thr Trp Ser
    1520                1525                1530

Pro Ser Lys Ala Arg Leu His Leu Gln Gly Arg Ser Asn Ala Trp
    1535                1540                1545

Arg Pro Gln Val Asn Asn Pro Lys Glu Trp Leu Gln Val Asp Phe
    1550                1555                1560

Gln Lys Thr Met Lys Val Thr Gly Val Thr Thr Gln Gly Val Lys
    1565                1570                1575

Ser Leu Leu Thr Ser Met Tyr Val Lys Glu Phe Leu Ile Ser Ser
    1580                1585                1590

Ser Gln Asp Gly His Gln Trp Thr Leu Phe Phe Gln Asn Gly Lys
    1595                1600                1605

Val Lys Val Phe Gln Gly Asn Gln Asp Ser Phe Thr Pro Val Val
    1610                1615                1620

Asn Ser Leu Asp Pro Pro Leu Leu Thr Arg Tyr Leu Arg Ile His
    1625                1630                1635

Pro Gln Ser Trp Val His Gln Ile Ala Leu Arg Met Glu Val Leu
    1640                1645                1650

Gly Cys Glu Ala Gln Asp Leu Tyr
```

-continued

```
                1655                1660
```

<210> SEQ ID NO 127
<211> LENGTH: 1927
<212> TYPE: PRT
<213> ORGANISM: Artificial Sequence
<220> FEATURE:
<223> OTHER INFORMATION: Synthetic Sequence

<400> SEQUENCE: 127

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys Gly Gly Gly Gly Ser Gly
            100                 105                 110

Gly Gly Gly Ser Gly Gly Gly Ser Gly Gly Gly Ser Glu Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Thr Tyr Ala Ile
145                 150                 155                 160

His Trp Val Arg Gln Ala Pro Gly Gln Gly Leu Glu Trp Met Gly Tyr
                165                 170                 175

Ile Asn Pro Ser Ser Gly Tyr Thr Arg Tyr Asn Pro Lys Phe Lys Gly
            180                 185                 190

Arg Val Thr Met Thr Arg Asp Lys Ser Thr Ser Thr Ala Tyr Met Glu
        195                 200                 205

Leu Arg Ser Leu Arg Ser Asp Asp Thr Ala Val Tyr Tyr Cys Trp Thr
    210                 215                 220

Gly Thr Arg Asp Tyr Trp Gly Gln Gly Thr Thr Val Thr Val Ser Ser
225                 230                 235                 240

Gly Gly Gly Ser Gly Gly Gly Ser Gly Leu Val Pro Arg Gly Ser
                245                 250                 255

Gly Gly Gly Ser Gly Gly Gly Ser Gly Ala Thr Arg Arg Tyr Tyr
            260                 265                 270

Leu Gly Ala Val Glu Leu Ser Trp Asp Tyr Met Gln Ser Asp Leu Gly
        275                 280                 285

Glu Leu Pro Val Asp Ala Arg Phe Pro Pro Arg Val Pro Lys Ser Phe
    290                 295                 300

Pro Phe Asn Thr Ser Val Val Tyr Lys Lys Thr Leu Phe Val Glu Phe
305                 310                 315                 320

Thr Asp His Leu Phe Asn Ile Ala Lys Pro Arg Pro Trp Met Gly
                325                 330                 335

Leu Leu Gly Pro Thr Ile Gln Ala Glu Val Tyr Asp Thr Val Val Ile
            340                 345                 350

Thr Leu Lys Asn Met Ala Ser His Pro Val Ser Leu His Ala Val Gly
```

-continued

```
            355                 360                 365
Val Ser Tyr Trp Lys Ala Ser Glu Gly Ala Glu Tyr Asp Asp Gln Thr
370                 375                 380

Ser Gln Arg Glu Lys Glu Asp Asp Lys Val Phe Pro Gly Gly Ser His
385                 390                 395                 400

Thr Tyr Val Trp Gln Val Leu Lys Glu Asn Gly Pro Met Ala Ser Asp
                405                 410                 415

Pro Leu Cys Leu Thr Tyr Ser Tyr Leu Ser His Val Asp Leu Val Lys
                420                 425                 430

Asp Leu Asn Ser Gly Leu Ile Gly Ala Leu Leu Val Cys Arg Glu Gly
                435                 440                 445

Ser Leu Ala Lys Glu Lys Thr Gln Thr Leu His Lys Phe Ile Leu Leu
450                 455                 460

Phe Ala Val Phe Asp Glu Gly Lys Ser Trp His Ser Glu Thr Lys Asn
465                 470                 475                 480

Ser Leu Met Gln Asp Arg Asp Ala Ala Ser Ala Arg Ala Trp Pro Lys
                485                 490                 495

Met His Thr Val Asn Gly Tyr Val Asn Arg Ser Leu Pro Gly Leu Ile
                500                 505                 510

Gly Cys His Arg Lys Ser Val Tyr Trp His Val Ile Gly Met Gly Thr
                515                 520                 525

Thr Pro Glu Val His Ser Ile Phe Leu Glu Gly His Thr Phe Leu Val
530                 535                 540

Arg Asn His Arg Gln Ala Ser Leu Glu Ile Ser Pro Ile Thr Phe Leu
545                 550                 555                 560

Thr Ala Gln Thr Leu Leu Met Asp Leu Gly Gln Phe Leu Leu Phe Cys
                565                 570                 575

His Ile Ser Ser His Gln His Asp Gly Met Glu Ala Tyr Val Lys Val
                580                 585                 590

Asp Ser Cys Pro Glu Glu Pro Gln Leu Arg Met Lys Asn Asn Glu Glu
                595                 600                 605

Ala Glu Asp Tyr Asp Asp Leu Thr Asp Ser Glu Met Asp Val Val
                610                 615                 620

Arg Phe Asp Asp Asp Asn Ser Pro Ser Phe Ile Gln Ile Arg Ser Val
625                 630                 635                 640

Ala Lys Lys His Pro Lys Thr Trp Val His Tyr Ile Ala Ala Glu Glu
                645                 650                 655

Glu Asp Trp Asp Tyr Ala Pro Leu Val Leu Ala Pro Asp Asp Arg Ser
                660                 665                 670

Tyr Lys Ser Gln Tyr Leu Asn Asn Gly Pro Gln Arg Ile Gly Arg Lys
                675                 680                 685

Tyr Lys Lys Val Arg Phe Met Ala Tyr Thr Asp Glu Thr Phe Lys Thr
                690                 695                 700

Arg Glu Ala Ile Gln His Glu Ser Gly Ile Leu Gly Pro Leu Leu Tyr
705                 710                 715                 720

Gly Glu Val Gly Asp Thr Leu Leu Ile Ile Phe Lys Asn Gln Ala Ser
                725                 730                 735

Arg Pro Tyr Asn Ile Tyr Pro His Gly Ile Thr Asp Val Arg Pro Leu
                740                 745                 750

Tyr Ser Arg Arg Leu Pro Lys Gly Val Lys His Leu Lys Asp Phe Pro
                755                 760                 765

Ile Leu Pro Gly Glu Ile Phe Lys Tyr Lys Trp Thr Val Thr Val Glu
770                 775                 780
```

```
Asp Gly Pro Thr Lys Ser Asp Pro Arg Cys Leu Thr Arg Tyr Tyr Ser
785                 790                 795                 800

Ser Phe Val Asn Met Glu Arg Asp Leu Ala Ser Gly Leu Ile Gly Pro
                805                 810                 815

Leu Leu Ile Cys Tyr Lys Glu Ser Val Asp Gln Arg Gly Asn Gln Ile
            820                 825                 830

Met Ser Asp Lys Arg Asn Val Ile Leu Phe Ser Val Phe Asp Glu Asn
        835                 840                 845

Arg Ser Trp Tyr Leu Thr Glu Asn Ile Gln Arg Phe Leu Pro Asn Pro
    850                 855                 860

Ala Gly Val Gln Leu Glu Asp Pro Glu Phe Gln Ala Ser Asn Ile Met
865                 870                 875                 880

His Ser Ile Asn Gly Tyr Val Phe Asp Ser Leu Gln Leu Ser Val Cys
                885                 890                 895

Leu His Glu Val Ala Tyr Trp Tyr Ile Leu Ser Ile Gly Ala Gln Thr
            900                 905                 910

Asp Phe Leu Ser Val Phe Phe Ser Gly Tyr Thr Phe Lys His Lys Met
        915                 920                 925

Val Tyr Glu Asp Thr Leu Thr Leu Phe Pro Phe Ser Gly Glu Thr Val
    930                 935                 940

Phe Met Ser Met Glu Asn Pro Gly Leu Trp Ile Leu Gly Cys His Asn
945                 950                 955                 960

Ser Asp Phe Arg Asn Arg Gly Met Thr Ala Leu Leu Lys Val Ser Ser
                965                 970                 975

Cys Asp Lys Asn Thr Gly Asp Tyr Tyr Glu Asp Ser Tyr Glu Asp Ile
            980                 985                 990

Ser Ala Tyr Leu Leu Ser Lys Asn Asn Ala Ile Glu Pro Arg Ser Phe
        995                 1000                1005

Ser Gln Asn Asp Glu Asn Gln Ser Pro Arg Ser Phe Gln Lys Lys
    1010                1015                1020

Thr Arg His Tyr Phe Ile Ala Ala Val Glu Arg Leu Trp Asp Tyr
    1025                1030                1035

Gly Met Ser Ser Ser Pro His Val Leu Arg Asn Arg Ala Gln Ser
    1040                1045                1050

Gly Ser Val Pro Gln Phe Lys Lys Val Val Phe Gln Glu Phe Thr
    1055                1060                1065

Asp Gly Ser Phe Thr Gln Pro Leu Tyr Arg Gly Glu Leu Asn Glu
    1070                1075                1080

His Leu Gly Leu Leu Gly Pro Tyr Ile Arg Ala Glu Val Glu Asp
    1085                1090                1095

Asn Ile Met Val Thr Phe Arg Asn Gln Ala Ser Arg Pro Tyr Ser
    1100                1105                1110

Phe Tyr Ser Ser Leu Ile Ser Tyr Glu Glu Asp Gln Arg Gln Gly
    1115                1120                1125

Ala Glu Pro Arg Lys Asn Phe Val Lys Pro Asn Glu Thr Lys Thr
    1130                1135                1140

Tyr Phe Trp Lys Val Gln His His Met Ala Pro Thr Lys Asp Glu
    1145                1150                1155

Phe Asp Cys Lys Ala Trp Ala Tyr Phe Ser Asp Val Asp Leu Glu
    1160                1165                1170

Lys Asp Val His Ser Gly Leu Ile Gly Pro Leu Leu Val Cys His
    1175                1180                1185
```

-continued

```
Thr Asn Thr Leu Asn Pro Ala His Gly Arg Gln Val Thr Val Gln
    1190                1195                1200

Glu Phe Ala Leu Phe Phe Thr Ile Phe Asp Glu Thr Lys Ser Trp
    1205                1210                1215

Tyr Phe Thr Glu Asn Met Glu Arg Asn Cys Arg Ala Pro Cys Asn
    1220                1225                1230

Ile Gln Met Glu Asp Pro Thr Phe Lys Glu Asn Tyr Arg Phe His
    1235                1240                1245

Ala Ile Asn Gly Tyr Ile Met Asp Thr Leu Pro Gly Leu Val Met
    1250                1255                1260

Ala Gln Asp Gln Arg Ile Arg Trp Tyr Leu Leu Ser Met Gly Ser
    1265                1270                1275

Asn Glu Asn Ile His Ser Ile His Phe Ser Gly His Val Phe Thr
    1280                1285                1290

Val Arg Lys Lys Glu Glu Tyr Lys Met Ala Leu Tyr Asn Leu Tyr
    1295                1300                1305

Pro Gly Val Phe Glu Thr Val Glu Met Leu Pro Ser Lys Ala Gly
    1310                1315                1320

Ile Trp Arg Val Glu Cys Leu Ile Gly Glu His Leu His Ala Gly
    1325                1330                1335

Met Ser Thr Leu Phe Leu Val Tyr Ser Asn Lys Cys Gln Thr Pro
    1340                1345                1350

Leu Gly Met Ala Ser Gly His Ile Arg Asp Phe Gln Ile Thr Ala
    1355                1360                1365

Ser Gly Gln Tyr Gly Gln Trp Ala Pro Lys Leu Ala Arg Leu His
    1370                1375                1380

Tyr Ser Gly Ser Ile Asn Ala Trp Ser Thr Lys Glu Pro Phe Ser
    1385                1390                1395

Trp Ile Lys Val Asp Leu Leu Ala Pro Met Ile Ile His Gly Ile
    1400                1405                1410

Lys Thr Gln Gly Ala Arg Gln Lys Phe Ser Ser Leu Tyr Ile Ser
    1415                1420                1425

Gln Phe Ile Ile Met Tyr Ser Leu Asp Gly Lys Lys Trp Gln Thr
    1430                1435                1440

Tyr Arg Gly Asn Ser Thr Gly Thr Leu Met Val Phe Phe Gly Asn
    1445                1450                1455

Val Asp Ser Ser Gly Ile Lys His Asn Ile Phe Asn Pro Pro Ile
    1460                1465                1470

Ile Ala Arg Tyr Ile Arg Leu His Pro Thr His Tyr Ser Ile Arg
    1475                1480                1485

Ser Thr Leu Arg Met Glu Leu Met Gly Cys Asp Leu Asn Ser Cys
    1490                1495                1500

Ser Met Pro Leu Gly Met Glu Ser Lys Ala Ile Ser Asp Ala Gln
    1505                1510                1515

Ile Thr Ala Ser Ser Tyr Phe Thr Asn Met Phe Ala Thr Trp Ser
    1520                1525                1530

Pro Ser Lys Ala Arg Leu His Leu Gln Gly Arg Ser Asn Ala Trp
    1535                1540                1545

Arg Pro Gln Val Asn Asn Pro Lys Glu Trp Leu Gln Val Asp Phe
    1550                1555                1560

Gln Lys Thr Met Lys Val Thr Gly Val Thr Thr Gln Gly Val Lys
    1565                1570                1575

Ser Leu Leu Thr Ser Met Tyr Val Lys Glu Phe Leu Ile Ser Ser
```

```
              1580                1585                1590
Ser Gln Asp Gly His Gln Trp Thr Leu Phe Phe Gln Asn Gly Lys
    1595                1600                1605
Val Lys Val Phe Gln Gly Asn Gln Asp Ser Phe Thr Pro Val Val
1610                1615                1620
Asn Ser Leu Asp Pro Pro Leu Leu Thr Arg Tyr Leu Arg Ile His
    1625                1630                1635
Pro Gln Ser Trp Val His Gln Ile Ala Leu Arg Met Glu Val Leu
1640                1645                1650
Gly Cys Glu Ala Gln Asp Leu Tyr Gly Gly Ser Gly Gly Gly
    1655                1660                1665
Gly Ser Gly Leu Val Pro Arg Gly Ser Gly Gly Ser Gly Gly
1670                1675                1680
Gly Gly Ser Gly Asp Ile Gln Leu Thr Gln Ser Pro Ser Phe Leu
    1685                1690                1695
Ser Ala Ser Val Gly Asp Arg Val Thr Ile Thr Cys Arg Ala Ser
1700                1705                1710
Ser Ser Val Arg Tyr Ile Tyr Trp Phe Gln Gln Lys Pro Gly Lys
    1715                1720                1725
Ala Pro Lys Leu Leu Ile Tyr Ala Thr Ser Phe Arg Gln Ser Gly
1730                1735                1740
Val Pro Ser Arg Phe Ser Gly Ser Gly Ser Gly Thr Glu Tyr Thr
    1745                1750                1755
Leu Thr Ile Ser Ser Leu Gln Pro Glu Asp Phe Ala Thr Tyr Tyr
1760                1765                1770
Cys His Gln Arg Asn Ser Phe Pro Tyr Thr Phe Gly Gln Gly Thr
    1775                1780                1785
Lys Leu Glu Ile Lys Gly Gly Gly Gly Ser Gly Gly Gly Gly Ser
1790                1795                1800
Gly Gly Gly Gly Ser Gly Gly Gly Ser Glu Val Gln Leu Val
    1805                1810                1815
Gln Ser Gly Ala Glu Val Lys Lys Pro Gly Ala Ser Val Lys Val
1820                1825                1830
Ser Cys Lys Ala Ser Gly Tyr Thr Phe Thr Thr Tyr Ala Ile His
    1835                1840                1845
Trp Val Arg Gln Ala Pro Gly Gln Gly Leu Glu Trp Met Gly Tyr
1850                1855                1860
Ile Asn Pro Ser Ser Gly Tyr Thr Arg Tyr Asn Pro Lys Phe Lys
    1865                1870                1875
Gly Arg Val Thr Met Thr Arg Asp Lys Ser Thr Ser Thr Ala Tyr
1880                1885                1890
Met Glu Leu Arg Ser Leu Arg Ser Asp Asp Thr Ala Val Tyr Tyr
    1895                1900                1905
Cys Trp Thr Gly Thr Arg Asp Tyr Trp Gly Gln Gly Thr Thr Val
1910                1915                1920
Thr Val Ser Ser
    1925

<210> SEQ ID NO 128
<211> LENGTH: 1935
<212> TYPE: PRT
<213> ORGANISM: Artificial Sequence
<220> FEATURE:
<223> OTHER INFORMATION: Synthetic Sequence
```

<400> SEQUENCE: 128

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Asp His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415
```

```
Gln Arg Ile Gly Arg Lys Tyr Lys Val Arg Phe Met Ala Tyr Thr
            420             425             430

Asp Glu Thr Phe Lys Thr Arg Glu Ala Ile Gln His Glu Ser Gly Ile
            435             440             445

Leu Gly Pro Leu Leu Tyr Gly Glu Val Gly Asp Thr Leu Leu Ile Ile
450             455             460

Phe Lys Asn Gln Ala Ser Arg Pro Tyr Asn Ile Tyr Pro His Gly Ile
465             470             475             480

Thr Asp Val Arg Pro Leu Tyr Ser Arg Arg Leu Pro Lys Gly Val Lys
                485             490             495

His Leu Lys Asp Phe Pro Ile Leu Pro Gly Glu Ile Phe Lys Tyr Lys
                500             505             510

Trp Thr Val Thr Val Glu Asp Gly Pro Thr Lys Ser Asp Pro Arg Cys
                515             520             525

Leu Thr Arg Tyr Tyr Ser Ser Phe Val Asn Met Glu Arg Asp Leu Ala
            530             535             540

Ser Gly Leu Ile Gly Pro Leu Leu Ile Cys Tyr Lys Glu Ser Val Asp
545             550             555             560

Gln Arg Gly Asn Gln Ile Met Ser Asp Lys Arg Asn Val Ile Leu Phe
                565             570             575

Ser Val Phe Asp Glu Asn Arg Ser Trp Tyr Leu Thr Glu Asn Ile Gln
                580             585             590

Arg Phe Leu Pro Asn Pro Ala Gly Val Gln Leu Glu Asp Pro Glu Phe
                595             600             605

Gln Ala Ser Asn Ile Met His Ser Ile Asn Gly Tyr Val Phe Asp Ser
            610             615             620

Leu Gln Leu Ser Val Cys Leu His Glu Val Ala Tyr Trp Tyr Ile Leu
625             630             635             640

Ser Ile Gly Ala Gln Thr Asp Phe Leu Ser Val Phe Phe Ser Gly Tyr
                645             650             655

Thr Phe Lys His Lys Met Val Tyr Glu Asp Thr Leu Thr Leu Phe Pro
                660             665             670

Phe Ser Gly Glu Thr Val Phe Met Ser Met Glu Asn Pro Gly Leu Trp
            675             680             685

Ile Leu Gly Cys His Asn Ser Asp Phe Arg Asn Arg Gly Met Thr Ala
            690             695             700

Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
                725             730             735

Ile Glu Pro Arg Ser Phe Ser Gln Asn Gly Gly Gly Ser Thr Gly
                740             745             750

Gly Thr Gly Gly Ser Ser Gly Gly Gly Thr Gly Ser Gly Gly Gly
            755             760             765

Thr Gly Gly Ser Gly Gly Thr Asp Ile Gln Leu Thr Gln Ser Pro Ser
            770             775             780

Phe Leu Ser Ala Ser Val Gly Asp Arg Val Thr Ile Thr Cys Arg Ala
785             790             795             800

Ser Ser Ser Val Arg Tyr Ile Tyr Trp Phe Gln Gln Lys Pro Gly Lys
                805             810             815

Ala Pro Lys Leu Leu Ile Tyr Ala Thr Ser Phe Arg Gln Ser Gly Val
            820             825             830
```

```
Pro Ser Arg Phe Ser Gly Ser Gly Ser Gly Thr Glu Tyr Thr Leu Thr
        835                 840                 845
Ile Ser Ser Leu Gln Pro Glu Asp Phe Ala Thr Tyr Tyr Cys His Gln
    850                 855                 860
Arg Asn Ser Phe Pro Tyr Thr Phe Gly Gln Gly Thr Lys Leu Glu Ile
865                 870                 875                 880
Lys Gly Gly Gly Gly Ser Gly Gly Gly Gly Ser Gly Gly Gly Gly Ser
                885                 890                 895
Gly Gly Gly Gly Ser Glu Val Gln Leu Val Gln Ser Gly Ala Glu Val
            900                 905                 910
Lys Lys Pro Gly Ala Ser Val Lys Val Ser Cys Lys Ala Ser Gly Tyr
        915                 920                 925
Thr Phe Thr Thr Tyr Ala Ile His Trp Val Arg Gln Ala Pro Gly Gln
    930                 935                 940
Gly Leu Glu Trp Met Gly Tyr Ile Asn Pro Ser Ser Gly Tyr Thr Arg
945                 950                 955                 960
Tyr Asn Pro Lys Phe Lys Gly Arg Val Thr Met Thr Arg Asp Lys Ser
                965                 970                 975
Thr Ser Thr Ala Tyr Met Glu Leu Arg Ser Leu Arg Ser Asp Asp Thr
            980                 985                 990
Ala Val Tyr Tyr Cys Trp Thr Gly  Thr Arg Asp Tyr Trp  Gly Gln Gly
        995                 1000                1005
Thr Thr  Val Thr Val Ser Ser  Gly Gly Gly Gly  Asp Glu Asn Gln
    1010                1015                1020
Ser Pro Arg Ser Phe Gln Lys  Lys Thr Arg His  Tyr Phe Ile Ala
    1025                1030                1035
Ala Val  Glu Arg Leu Trp Asp  Tyr Gly Met Ser  Ser Pro His
    1040                1045                1050
Val Leu  Arg Asn Arg Ala Gln  Ser Gly Ser Val  Pro Gln Phe Lys
    1055                1060                1065
Lys Val  Val Phe Gln Glu Phe  Thr Asp Gly Ser  Phe Thr Gln Pro
    1070                1075                1080
Leu Tyr  Arg Gly Glu Leu Asn  Glu His Leu Gly  Leu Leu Gly Pro
    1085                1090                1095
Tyr Ile  Arg Ala Glu Val Glu  Asp Asn Ile Met  Val Thr Phe Arg
    1100                1105                1110
Asn Gln  Ala Ser Arg Pro Tyr  Ser Phe Tyr Ser  Ser Leu Ile Ser
    1115                1120                1125
Tyr Glu  Glu Asp Gln Arg Gln  Gly Ala Glu Pro  Arg Lys Asn Phe
    1130                1135                1140
Val Lys  Pro Asn Glu Thr Lys  Thr Tyr Phe Trp  Lys Val Gln His
    1145                1150                1155
His Met  Ala Pro Thr Lys Asp  Glu Phe Asp Cys  Lys Ala Trp Ala
    1160                1165                1170
Tyr Phe  Ser Asp Val Asp Leu  Glu Lys Asp Val  His Ser Gly Leu
    1175                1180                1185
Ile Gly  Pro Leu Leu Val Cys  His Thr Asn Thr  Leu Asn Pro Ala
    1190                1195                1200
His Gly  Arg Gln Val Thr Val  Gln Glu Phe Ala  Leu Phe Phe Thr
    1205                1210                1215
Ile Phe  Asp Glu Thr Lys Ser  Trp Tyr Phe Thr  Glu Asn Met Glu
    1220                1225                1230
Arg Asn  Cys Arg Ala Pro Cys  Asn Ile Gln Met  Glu Asp Pro Thr
```

```
                1235                1240                1245
Phe Lys Glu Asn Tyr Arg Phe His Ala Ile Asn Gly Tyr Ile Met
    1250                1255                1260
Asp Thr Leu Pro Gly Leu Val Met Ala Gln Asp Gln Arg Ile Arg
    1265                1270                1275
Trp Tyr Leu Leu Ser Met Gly Ser Asn Glu Asn Ile His Ser Ile
    1280                1285                1290
His Phe Ser Gly His Val Phe Thr Val Arg Lys Lys Glu Glu Tyr
    1295                1300                1305
Lys Met Ala Leu Tyr Asn Leu Tyr Pro Gly Val Phe Glu Thr Val
    1310                1315                1320
Glu Met Leu Pro Ser Lys Ala Gly Ile Trp Arg Val Glu Cys Leu
    1325                1330                1335
Ile Gly Glu His Leu His Ala Gly Met Ser Thr Leu Phe Leu Val
    1340                1345                1350
Tyr Ser Asn Lys Cys Gln Thr Pro Leu Gly Met Ala Ser Gly His
    1355                1360                1365
Ile Arg Asp Phe Gln Ile Thr Ala Ser Gly Gln Tyr Gly Gln Trp
    1370                1375                1380
Ala Pro Lys Leu Ala Arg Leu His Tyr Ser Gly Ser Ile Asn Ala
    1385                1390                1395
Trp Ser Thr Lys Glu Pro Phe Ser Trp Ile Lys Val Asp Leu Leu
    1400                1405                1410
Ala Pro Met Ile Ile His Gly Ile Lys Thr Gln Gly Ala Arg Gln
    1415                1420                1425
Lys Phe Ser Ser Leu Tyr Ile Ser Gln Phe Ile Ile Met Tyr Ser
    1430                1435                1440
Leu Asp Gly Lys Lys Trp Gln Thr Tyr Arg Gly Asn Ser Thr Gly
    1445                1450                1455
Thr Leu Met Val Phe Phe Gly Asn Val Asp Ser Ser Gly Ile Lys
    1460                1465                1470
His Asn Ile Phe Asn Pro Pro Ile Ile Ala Arg Tyr Ile Arg Leu
    1475                1480                1485
His Pro Thr His Tyr Ser Ile Arg Ser Thr Leu Arg Met Glu Leu
    1490                1495                1500
Met Gly Cys Asp Leu Asn Ser Cys Ser Met Pro Leu Gly Met Glu
    1505                1510                1515
Ser Lys Ala Ile Ser Asp Ala Gln Ile Thr Ala Ser Ser Tyr Phe
    1520                1525                1530
Thr Asn Met Phe Ala Thr Trp Ser Pro Ser Lys Ala Arg Leu His
    1535                1540                1545
Leu Gln Gly Arg Ser Asn Ala Trp Arg Pro Gln Val Asn Asn Pro
    1550                1555                1560
Lys Glu Trp Leu Gln Val Asp Phe Gln Lys Thr Met Lys Val Thr
    1565                1570                1575
Gly Val Thr Thr Gln Gly Val Lys Ser Leu Leu Thr Ser Met Tyr
    1580                1585                1590
Val Lys Glu Phe Leu Ile Ser Ser Ser Gln Asp Gly His Gln Trp
    1595                1600                1605
Thr Leu Phe Phe Gln Asn Gly Lys Val Lys Val Phe Gln Gly Asn
    1610                1615                1620
Gln Asp Ser Phe Thr Pro Val Val Asn Ser Leu Asp Pro Pro Leu
    1625                1630                1635
```

Leu Thr Arg Tyr Leu Arg Ile His Pro Gln Ser Trp Val His Gln
        1640                1645                1650

Ile Ala Leu Arg Met Glu Val Leu Gly Cys Glu Ala Gln Asp Leu
        1655                1660                1665

Tyr Gly Gly Gly Ser Gly Gly Gly Ser Gly Leu Val Pro Arg
        1670                1675                1680

Gly Ser Gly Gly Gly Ser Gly Gly Gly Ser Gly Asp Ile Gln
        1685                1690                1695

Leu Thr Gln Ser Pro Ser Phe Leu Ser Ala Ser Val Gly Asp Arg
        1700                1705                1710

Val Thr Ile Thr Cys Arg Ala Ser Ser Ser Val Arg Tyr Ile Tyr
        1715                1720                1725

Trp Phe Gln Gln Lys Pro Gly Lys Ala Pro Lys Leu Leu Ile Tyr
        1730                1735                1740

Ala Thr Ser Phe Arg Gln Ser Gly Val Pro Ser Arg Phe Ser Gly
        1745                1750                1755

Ser Gly Ser Gly Thr Glu Tyr Thr Leu Thr Ile Ser Ser Leu Gln
        1760                1765                1770

Pro Glu Asp Phe Ala Thr Tyr Tyr Cys His Gln Arg Asn Ser Phe
        1775                1780                1785

Pro Tyr Thr Phe Gly Gln Gly Thr Lys Leu Glu Ile Lys Gly Gly
        1790                1795                1800

Gly Gly Ser Gly Gly Gly Gly Ser Gly Gly Gly Gly Ser Gly Gly
        1805                1810                1815

Gly Gly Ser Glu Val Gln Leu Val Gln Ser Gly Ala Glu Val Lys
        1820                1825                1830

Lys Pro Gly Ala Ser Val Lys Val Ser Cys Lys Ala Ser Gly Tyr
        1835                1840                1845

Thr Phe Thr Thr Tyr Ala Ile His Trp Val Arg Gln Ala Pro Gly
        1850                1855                1860

Gln Gly Leu Glu Trp Met Gly Tyr Ile Asn Pro Ser Ser Gly Tyr
        1865                1870                1875

Thr Arg Tyr Asn Pro Lys Phe Lys Gly Arg Val Thr Met Thr Arg
        1880                1885                1890

Asp Lys Ser Thr Ser Thr Ala Tyr Met Glu Leu Arg Ser Leu Arg
        1895                1900                1905

Ser Asp Asp Thr Ala Val Tyr Tyr Cys Trp Thr Gly Thr Arg Asp
        1910                1915                1920

Tyr Trp Gly Gln Gly Thr Thr Val Thr Val Ser Ser
        1925                1930                1935

<210> SEQ ID NO 129
<211> LENGTH: 1913
<212> TYPE: PRT
<213> ORGANISM: Artificial Sequence
<220> FEATURE:
<223> OTHER INFORMATION: Synthetic Sequence

<400> SEQUENCE: 129

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

```
Thr Leu Phe Val Glu Phe Thr Asp His Leu Phe Asn Ile Ala Lys Pro
 50                  55                  60

Arg Pro Pro Trp Met Gly Leu Leu Gly Pro Thr Ile Gln Ala Glu Val
 65                  70                  75                  80

Tyr Asp Thr Val Ile Thr Leu Lys Asn Met Ala Ser His Pro Val
                 85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460
```

```
Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
        500                 505                 510

Trp Thr Val Thr Val Glu Asp Gly Pro Thr Lys Ser Asp Pro Arg Cys
    515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Gly Gly Gly Ser Thr Gly
            740                 745                 750

Gly Thr Gly Gly Ser Ser Gly Gly Thr Gly Ser Gly Gly Gly
        755                 760                 765

Thr Gly Gly Ser Gly Gly Thr Asp Ile Gln Leu Thr Gln Ser Pro Ser
770                 775                 780

Phe Leu Ser Ala Ser Val Gly Asp Arg Val Thr Ile Thr Cys Arg Ala
785                 790                 795                 800

Ser Ser Ser Val Arg Tyr Ile Tyr Trp Phe Gln Gln Lys Pro Gly Lys
                805                 810                 815

Ala Pro Lys Leu Leu Ile Tyr Ala Thr Ser Phe Arg Gln Ser Gly Val
            820                 825                 830

Pro Ser Arg Phe Ser Gly Ser Gly Ser Gly Thr Glu Tyr Thr Leu Thr
        835                 840                 845

Ile Ser Ser Leu Gln Pro Glu Asp Phe Ala Thr Tyr Tyr Cys His Gln
850                 855                 860

Arg Asn Ser Phe Pro Tyr Thr Phe Gly Gln Gly Thr Lys Leu Glu Ile
865                 870                 875                 880

Lys Gly Gly Gly Gly Ser Gly Gly Gly Gly Ser Gly Gly Gly Gly Ser
```

```
                    885                 890                 895
Gly Gly Gly Gly Ser Glu Val Gln Leu Val Gln Ser Gly Ala Glu Val
                900                 905                 910
Lys Lys Pro Gly Ala Ser Val Lys Val Ser Cys Lys Ala Ser Gly Tyr
                915                 920                 925
Thr Phe Thr Thr Tyr Ala Ile His Trp Val Arg Gln Ala Pro Gly Gln
                930                 935                 940
Gly Leu Glu Trp Met Gly Tyr Ile Asn Pro Ser Ser Gly Tyr Thr Arg
945                 950                 955                 960
Tyr Asn Pro Lys Phe Lys Gly Arg Val Thr Met Thr Arg Asp Lys Ser
                965                 970                 975
Thr Ser Thr Ala Tyr Met Glu Leu Arg Ser Leu Arg Ser Asp Asp Thr
                980                 985                 990
Ala Val Tyr Tyr Cys Trp Thr Gly  Thr Arg Asp Tyr Trp  Gly Gln Gly
                995                1000                1005
Thr Thr  Val Thr Val Ser Ser  Gly Gly Gly Gly Asp  Ile Gln Leu
         1010                1015                1020
Thr Gln  Ser Pro Ser Phe Leu  Ser Ala Ser Val Gly  Asp Arg Val
         1025                1030                1035
Thr Ile  Thr Cys Arg Ala Ser  Ser Ser Val Arg Tyr  Ile Tyr Trp
         1040                1045                1050
Phe Gln  Gln Lys Pro Gly Lys  Ala Pro Lys Leu Leu  Ile Tyr Ala
         1055                1060                1065
Thr Ser  Phe Arg Gln Ser Gly  Val Pro Ser Arg Phe  Ser Gly Ser
         1070                1075                1080
Gly Ser  Gly Thr Glu Tyr Thr  Leu Thr Ile Ser Ser  Leu Gln Pro
         1085                1090                1095
Glu Asp  Phe Ala Thr Tyr Tyr  Cys His Gln Arg Asn  Ser Phe Pro
         1100                1105                1110
Tyr Thr  Phe Gly Gln Gly Thr  Lys Leu Glu Ile Lys  Gly Gly Gly
         1115                1120                1125
Gly Ser  Gly Gly Gly Gly Ser  Gly Gly Gly Gly Ser  Gly Gly Gly
         1130                1135                1140
Gly Ser  Glu Val Gln Leu Val  Gln Ser Gly Ala Glu  Val Lys Lys
         1145                1150                1155
Pro Gly  Ala Ser Val Lys Val  Ser Cys Lys Ala Ser  Gly Tyr Thr
         1160                1165                1170
Phe Thr  Thr Tyr Ala Ile His  Trp Val Arg Gln Ala  Pro Gly Gln
         1175                1180                1185
Gly Leu  Glu Trp Met Gly Tyr  Ile Asn Pro Ser Ser  Gly Tyr Thr
         1190                1195                1200
Arg Tyr  Asn Pro Lys Phe Lys  Gly Arg Val Thr Met  Thr Arg Asp
         1205                1210                1215
Lys Ser  Thr Ser Thr Ala Tyr  Met Glu Leu Arg Ser  Leu Arg Ser
         1220                1225                1230
Asp Asp  Thr Ala Val Tyr Tyr  Cys Trp Thr Gly Thr  Arg Asp Tyr
         1235                1240                1245
Trp Gly  Gln Gly Thr Thr Val  Thr Val Ser Ser Gly  Gly Gly Gly
         1250                1255                1260
Asp Glu  Asn Gln Ser Pro Arg  Ser Phe Gln Lys Lys  Thr Arg His
         1265                1270                1275
Tyr Phe  Ile Ala Ala Val Glu  Arg Leu Trp Asp Tyr  Gly Met Ser
         1280                1285                1290
```

```
Ser Ser Pro His Val Leu Arg Asn Arg Ala Gln Ser Gly Ser Val
1295                1300                1305

Pro Gln Phe Lys Lys Val Val Phe Gln Glu Phe Thr Asp Gly Ser
1310                1315                1320

Phe Thr Gln Pro Leu Tyr Arg Gly Glu Leu Asn Glu His Leu Gly
1325                1330                1335

Leu Leu Gly Pro Tyr Ile Arg Ala Glu Val Glu Asp Asn Ile Met
1340                1345                1350

Val Thr Phe Arg Asn Gln Ala Ser Arg Pro Tyr Ser Phe Tyr Ser
1355                1360                1365

Ser Leu Ile Ser Tyr Glu Glu Asp Gln Arg Gln Gly Ala Glu Pro
1370                1375                1380

Arg Lys Asn Phe Val Lys Pro Asn Glu Thr Lys Thr Tyr Phe Trp
1385                1390                1395

Lys Val Gln His His Met Ala Pro Thr Lys Asp Glu Phe Asp Cys
1400                1405                1410

Lys Ala Trp Ala Tyr Phe Ser Asp Val Asp Leu Glu Lys Asp Val
1415                1420                1425

His Ser Gly Leu Ile Gly Pro Leu Leu Val Cys His Thr Asn Thr
1430                1435                1440

Leu Asn Pro Ala His Gly Arg Gln Val Thr Val Gln Glu Phe Ala
1445                1450                1455

Leu Phe Phe Thr Ile Phe Asp Glu Thr Lys Ser Trp Tyr Phe Thr
1460                1465                1470

Glu Asn Met Glu Arg Asn Cys Arg Ala Pro Cys Asn Ile Gln Met
1475                1480                1485

Glu Asp Pro Thr Phe Lys Glu Asn Tyr Arg Phe His Ala Ile Asn
1490                1495                1500

Gly Tyr Ile Met Asp Thr Leu Pro Gly Leu Val Met Ala Gln Asp
1505                1510                1515

Gln Arg Ile Arg Trp Tyr Leu Leu Ser Met Gly Ser Asn Glu Asn
1520                1525                1530

Ile His Ser Ile His Phe Ser Gly His Val Phe Thr Val Arg Lys
1535                1540                1545

Lys Glu Glu Tyr Lys Met Ala Leu Tyr Asn Leu Tyr Pro Gly Val
1550                1555                1560

Phe Glu Thr Val Glu Met Leu Pro Ser Lys Ala Gly Ile Trp Arg
1565                1570                1575

Val Glu Cys Leu Ile Gly Glu His Leu His Ala Gly Met Ser Thr
1580                1585                1590

Leu Phe Leu Val Tyr Ser Asn Lys Cys Gln Thr Pro Leu Gly Met
1595                1600                1605

Ala Ser Gly His Ile Arg Asp Phe Gln Ile Thr Ala Ser Gly Gln
1610                1615                1620

Tyr Gly Gln Trp Ala Pro Lys Leu Ala Arg Leu His Tyr Ser Gly
1625                1630                1635

Ser Ile Asn Ala Trp Ser Thr Lys Glu Pro Phe Ser Trp Ile Lys
1640                1645                1650

Val Asp Leu Leu Ala Pro Met Ile Ile His Gly Ile Lys Thr Gln
1655                1660                1665

Gly Ala Arg Gln Lys Phe Ser Ser Leu Tyr Ile Ser Gln Phe Ile
1670                1675                1680
```

Ile Met Tyr Ser Leu Asp Gly Lys Lys Trp Gln Thr Tyr Arg Gly
    1685                1690                1695

Asn Ser Thr Gly Thr Leu Met Val Phe Phe Gly Asn Val Asp Ser
    1700                1705                1710

Ser Gly Ile Lys His Asn Ile Phe Asn Pro Pro Ile Ile Ala Arg
    1715                1720                1725

Tyr Ile Arg Leu His Pro Thr His Tyr Ser Ile Arg Ser Thr Leu
    1730                1735                1740

Arg Met Glu Leu Met Gly Cys Asp Leu Asn Ser Cys Ser Met Pro
    1745                1750                1755

Leu Gly Met Glu Ser Lys Ala Ile Ser Asp Ala Gln Ile Thr Ala
    1760                1765                1770

Ser Ser Tyr Phe Thr Asn Met Phe Ala Thr Trp Ser Pro Ser Lys
    1775                1780                1785

Ala Arg Leu His Leu Gln Gly Arg Ser Asn Ala Trp Arg Pro Gln
    1790                1795                1800

Val Asn Asn Pro Lys Glu Trp Leu Gln Val Asp Phe Gln Lys Thr
    1805                1810                1815

Met Lys Val Thr Gly Val Thr Thr Gln Gly Val Lys Ser Leu Leu
    1820                1825                1830

Thr Ser Met Tyr Val Lys Glu Phe Leu Ile Ser Ser Ser Gln Asp
    1835                1840                1845

Gly His Gln Trp Thr Leu Phe Phe Gln Asn Gly Lys Val Lys Val
    1850                1855                1860

Phe Gln Gly Asn Gln Asp Ser Phe Thr Pro Val Val Asn Ser Leu
    1865                1870                1875

Asp Pro Pro Leu Leu Thr Arg Tyr Leu Arg Ile His Pro Gln Ser
    1880                1885                1890

Trp Val His Gln Ile Ala Leu Arg Met Glu Val Leu Gly Cys Glu
    1895                1900                1905

Ala Gln Asp Leu Tyr
    1910

<210> SEQ ID NO 130
<211> LENGTH: 1935
<212> TYPE: PRT
<213> ORGANISM: Artificial Sequence
<220> FEATURE:
<223> OTHER INFORMATION: Synthetic Sequence

<400> SEQUENCE: 130

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys Gly Gly Gly Gly Ser Gly
            100                 105                 110

```
Gly Gly Gly Ser Gly Gly Gly Ser Gly Gly Gly Ser Glu Val
            115                 120                 125
Gln Leu Val Gln Ser Gly Ala Glu Val Lys Lys Pro Gly Ala Ser Val
130                 135                 140
Lys Val Ser Cys Lys Ala Ser Gly Tyr Thr Phe Thr Thr Tyr Ala Ile
145                 150                 155                 160
His Trp Val Arg Gln Ala Pro Gly Gln Gly Leu Glu Trp Met Gly Tyr
                165                 170                 175
Ile Asn Pro Ser Ser Gly Tyr Thr Arg Tyr Asn Pro Lys Phe Lys Gly
                180                 185                 190
Arg Val Thr Met Thr Arg Asp Lys Ser Thr Ser Thr Ala Tyr Met Glu
                195                 200                 205
Leu Arg Ser Leu Arg Ser Asp Asp Thr Ala Val Tyr Tyr Cys Trp Thr
210                 215                 220
Gly Thr Arg Asp Tyr Trp Gly Gln Gly Thr Thr Val Thr Val Ser Ser
225                 230                 235                 240
Gly Gly Gly Ser Gly Gly Gly Ser Gly Leu Val Pro Arg Gly Ser
                245                 250                 255
Gly Gly Gly Ser Gly Gly Gly Ser Gly Ala Thr Arg Arg Tyr Tyr
                260                 265                 270
Leu Gly Ala Val Glu Leu Ser Trp Asp Tyr Met Gln Ser Asp Leu Gly
                275                 280                 285
Glu Leu Pro Val Asp Ala Arg Phe Pro Pro Arg Val Pro Lys Ser Phe
        290                 295                 300
Pro Phe Asn Thr Ser Val Val Tyr Lys Lys Thr Leu Phe Val Glu Phe
305                 310                 315                 320
Thr Asp His Leu Phe Asn Ile Ala Lys Pro Arg Pro Pro Trp Met Gly
                325                 330                 335
Leu Leu Gly Pro Thr Ile Gln Ala Glu Val Tyr Asp Thr Val Val Ile
                340                 345                 350
Thr Leu Lys Asn Met Ala Ser His Pro Val Ser Leu His Ala Val Gly
                355                 360                 365
Val Ser Tyr Trp Lys Ala Ser Glu Gly Ala Glu Tyr Asp Asp Gln Thr
                370                 375                 380
Ser Gln Arg Glu Lys Glu Asp Asp Lys Val Phe Pro Gly Gly Ser His
385                 390                 395                 400
Thr Tyr Val Trp Gln Val Leu Lys Glu Asn Gly Pro Met Ala Ser Asp
                405                 410                 415
Pro Leu Cys Leu Thr Tyr Ser Tyr Leu Ser His Val Asp Leu Val Lys
                420                 425                 430
Asp Leu Asn Ser Gly Leu Ile Gly Ala Leu Leu Val Cys Arg Glu Gly
                435                 440                 445
Ser Leu Ala Lys Glu Lys Thr Gln Thr Leu His Lys Phe Ile Leu Leu
        450                 455                 460
Phe Ala Val Phe Asp Glu Gly Lys Ser Trp His Ser Glu Thr Lys Asn
465                 470                 475                 480
Ser Leu Met Gln Asp Arg Asp Ala Ala Ser Ala Arg Ala Trp Pro Lys
                485                 490                 495
Met His Thr Val Asn Gly Tyr Val Asn Arg Ser Leu Pro Gly Leu Ile
                500                 505                 510
Gly Cys His Arg Lys Ser Val Tyr Trp His Val Ile Gly Met Gly Thr
                515                 520                 525
Thr Pro Glu Val His Ser Ile Phe Leu Glu Gly His Thr Phe Leu Val
```

```
            530                 535                 540
Arg Asn His Arg Gln Ala Ser Leu Glu Ile Ser Pro Ile Thr Phe Leu
545                 550                 555                 560

Thr Ala Gln Thr Leu Leu Met Asp Leu Gly Gln Phe Leu Leu Phe Cys
                565                 570                 575

His Ile Ser Ser His Gln His Asp Gly Met Glu Ala Tyr Val Lys Val
                580                 585                 590

Asp Ser Cys Pro Glu Glu Pro Gln Leu Arg Met Lys Asn Asn Glu Glu
                595                 600                 605

Ala Glu Asp Tyr Asp Asp Leu Thr Asp Ser Glu Met Asp Val Val
610                 615                 620

Arg Phe Asp Asp Asp Asn Ser Pro Ser Phe Ile Gln Ile Arg Ser Val
625                 630                 635                 640

Ala Lys Lys His Pro Lys Thr Trp Val His Tyr Ile Ala Ala Glu Glu
                645                 650                 655

Glu Asp Trp Asp Tyr Ala Pro Leu Val Leu Ala Pro Asp Asp Arg Ser
                660                 665                 670

Tyr Lys Ser Gln Tyr Leu Asn Asn Gly Pro Gln Arg Ile Gly Arg Lys
                675                 680                 685

Tyr Lys Lys Val Arg Phe Met Ala Tyr Thr Asp Glu Thr Phe Lys Thr
690                 695                 700

Arg Glu Ala Ile Gln His Glu Ser Gly Ile Leu Gly Pro Leu Leu Tyr
705                 710                 715                 720

Gly Glu Val Gly Asp Thr Leu Leu Ile Ile Phe Lys Asn Gln Ala Ser
                725                 730                 735

Arg Pro Tyr Asn Ile Tyr Pro His Gly Ile Thr Asp Val Arg Pro Leu
                740                 745                 750

Tyr Ser Arg Arg Leu Pro Lys Gly Val Lys His Leu Lys Asp Phe Pro
                755                 760                 765

Ile Leu Pro Gly Glu Ile Phe Lys Tyr Lys Trp Thr Val Thr Val Glu
770                 775                 780

Asp Gly Pro Thr Lys Ser Asp Pro Arg Cys Leu Thr Arg Tyr Tyr Ser
785                 790                 795                 800

Ser Phe Val Asn Met Glu Arg Asp Leu Ala Ser Gly Leu Ile Gly Pro
                805                 810                 815

Leu Leu Ile Cys Tyr Lys Glu Ser Val Asp Gln Arg Gly Asn Gln Ile
                820                 825                 830

Met Ser Asp Lys Arg Asn Val Ile Leu Phe Ser Val Phe Asp Glu Asn
                835                 840                 845

Arg Ser Trp Tyr Leu Thr Glu Asn Ile Gln Arg Phe Leu Pro Asn Pro
850                 855                 860

Ala Gly Val Gln Leu Glu Asp Pro Glu Phe Gln Ala Ser Asn Ile Met
865                 870                 875                 880

His Ser Ile Asn Gly Tyr Val Phe Asp Ser Leu Gln Leu Ser Val Cys
                885                 890                 895

Leu His Glu Val Ala Tyr Trp Tyr Ile Leu Ser Ile Gly Ala Gln Thr
                900                 905                 910

Asp Phe Leu Ser Val Phe Phe Ser Gly Tyr Thr Phe Lys His Lys Met
                915                 920                 925

Val Tyr Glu Asp Thr Leu Thr Leu Phe Pro Phe Ser Gly Glu Thr Val
930                 935                 940

Phe Met Ser Met Glu Asn Pro Gly Leu Trp Ile Leu Gly Cys His Asn
945                 950                 955                 960
```

```
Ser Asp Phe Arg Asn Arg Gly Met Thr Ala Leu Leu Lys Val Ser Ser
            965                 970                 975

Cys Asp Lys Asn Thr Gly Asp Tyr Tyr Glu Asp Ser Tyr Glu Asp Ile
            980                 985                 990

Ser Ala Tyr Leu Leu Ser Lys Asn  Asn Ala Ile Glu Pro  Arg Ser Phe
            995                 1000                1005

Ser Gln Asn Gly Gly Gly  Ser Thr Gly Gly Thr  Gly Gly Ser
        1010                1015                1020

Ser Gly Gly Gly Thr Gly Ser  Gly Gly Gly Gly Thr  Gly Gly Ser
        1025                 1030                1035

Gly Gly  Thr Asp Ile Gln Leu  Thr Gln Ser Pro Ser  Phe Leu Ser
        1040                 1045                1050

Ala Ser Val Gly Asp Arg Val  Thr Ile Thr Cys Arg  Ala Ser Ser
        1055                1060                1065

Ser Val Arg Tyr Ile Tyr Trp  Phe Gln Gln Lys Pro  Gly Lys Ala
        1070                1075                1080

Pro Lys Leu Leu Ile Tyr Ala  Thr Ser Phe Arg Gln  Ser Gly Val
        1085                1090                1095

Pro Ser Arg Phe Ser Gly Ser  Gly Ser Gly Thr Glu  Tyr Thr Leu
        1100                 1105                1110

Thr Ile Ser Ser Leu Gln Pro  Glu Asp Phe Ala Thr  Tyr Tyr Cys
        1115                1120                1125

His Gln Arg Asn Ser Phe Pro  Tyr Thr Phe Gly Gln  Gly Thr Lys
        1130                1135                1140

Leu Glu Ile Lys Gly Gly  Gly Ser Gly Gly Gly  Gly Ser Gly
        1145                 1150                1155

Gly Gly Gly Ser Gly Gly  Gly Ser Glu Val Gln  Leu Val Gln
        1160                1165                1170

Ser Gly Ala Glu Val Lys Lys  Pro Gly Ala Ser Val  Lys Val Ser
        1175                1180                1185

Cys Lys Ala Ser Gly Tyr Thr  Phe Thr Thr Tyr Ala  Ile His Trp
        1190                1195                1200

Val Arg  Gln Ala Pro Gly Gln  Gly Leu Glu Trp Met  Gly Tyr Ile
        1205                 1210                1215

Asn Pro  Ser Ser Gly Tyr Thr  Arg Tyr Asn Pro Lys  Phe Lys Gly
        1220                1225                1230

Arg Val  Thr Met Thr Arg Asp  Lys Ser Thr Ser Thr  Ala Tyr Met
        1235                1240                1245

Glu Leu  Arg Ser Leu Arg Ser  Asp Asp Thr Ala Val  Tyr Tyr Cys
        1250                 1255                1260

Trp Thr  Gly Thr Arg Asp Tyr  Trp Gly Gln Gly Thr  Thr Val Thr
        1265                1270                1275

Val Ser  Ser Gly Gly Gly Gly  Asp Glu Asn Gln Ser  Pro Arg Ser
        1280                1285                1290

Phe Gln Lys Lys Thr Arg His  Tyr Phe Ile Ala Ala  Val Glu Arg
        1295                1300                1305

Leu Trp Asp Tyr Gly Met Ser  Ser Ser Pro His Val  Leu Arg Asn
        1310                1315                1320

Arg Ala  Gln Ser Gly Ser Val  Pro Gln Phe Lys Lys  Val Val Phe
        1325                 1330                1335

Gln Glu  Phe Thr Asp Gly Ser  Phe Thr Gln Pro Leu  Tyr Arg Gly
        1340                1345                1350
```

| | | | | | | | | | | | | |
|---|---|---|---|---|---|---|---|---|---|---|---|---|
| Glu | Leu | Asn | Glu | His | Leu | Gly | Leu | Leu | Gly | Pro | Tyr | Ile | Arg | Ala |
| | 1355 | | | | 1360 | | | | | 1365 | | |
| Glu | Val | Glu | Asp | Asn | Ile | Met | Val | Thr | Phe | Arg | Asn | Gln | Ala | Ser |
| 1370 | | | | | 1375 | | | | | 1380 | | |
| Arg | Pro | Tyr | Ser | Phe | Tyr | Ser | Ser | Leu | Ile | Ser | Tyr | Glu | Glu | Asp |
| 1385 | | | | | 1390 | | | | | 1395 | | |
| Gln | Arg | Gln | Gly | Ala | Glu | Pro | Arg | Lys | Asn | Phe | Val | Lys | Pro | Asn |
| 1400 | | | | | 1405 | | | | | 1410 | | |
| Glu | Thr | Lys | Thr | Tyr | Phe | Trp | Lys | Val | Gln | His | His | Met | Ala | Pro |
| 1415 | | | | | 1420 | | | | | 1425 | | |
| Thr | Lys | Asp | Glu | Phe | Asp | Cys | Lys | Ala | Trp | Ala | Tyr | Phe | Ser | Asp |
| 1430 | | | | | 1435 | | | | | 1440 | | |
| Val | Asp | Leu | Glu | Lys | Asp | Val | His | Ser | Gly | Leu | Ile | Gly | Pro | Leu |
| 1445 | | | | | 1450 | | | | | 1455 | | |
| Leu | Val | Cys | His | Thr | Asn | Thr | Leu | Asn | Pro | Ala | His | Gly | Arg | Gln |
| 1460 | | | | | 1465 | | | | | 1470 | | |
| Val | Thr | Val | Gln | Glu | Phe | Ala | Leu | Phe | Phe | Thr | Ile | Phe | Asp | Glu |
| 1475 | | | | | 1480 | | | | | 1485 | | |
| Thr | Lys | Ser | Trp | Tyr | Phe | Thr | Glu | Asn | Met | Glu | Arg | Asn | Cys | Arg |
| 1490 | | | | | 1495 | | | | | 1500 | | |
| Ala | Pro | Cys | Asn | Ile | Gln | Met | Glu | Asp | Pro | Thr | Phe | Lys | Glu | Asn |
| 1505 | | | | | 1510 | | | | | 1515 | | |
| Tyr | Arg | Phe | His | Ala | Ile | Asn | Gly | Tyr | Ile | Met | Asp | Thr | Leu | Pro |
| 1520 | | | | | 1525 | | | | | 1530 | | |
| Gly | Leu | Val | Met | Ala | Gln | Asp | Gln | Arg | Ile | Arg | Trp | Tyr | Leu | Leu |
| 1535 | | | | | 1540 | | | | | 1545 | | |
| Ser | Met | Gly | Ser | Asn | Glu | Asn | Ile | His | Ser | Ile | His | Phe | Ser | Gly |
| 1550 | | | | | 1555 | | | | | 1560 | | |
| His | Val | Phe | Thr | Val | Arg | Lys | Lys | Glu | Glu | Tyr | Lys | Met | Ala | Leu |
| 1565 | | | | | 1570 | | | | | 1575 | | |
| Tyr | Asn | Leu | Tyr | Pro | Gly | Val | Phe | Glu | Thr | Val | Glu | Met | Leu | Pro |
| 1580 | | | | | 1585 | | | | | 1590 | | |
| Ser | Lys | Ala | Gly | Ile | Trp | Arg | Val | Glu | Cys | Leu | Ile | Gly | Glu | His |
| 1595 | | | | | 1600 | | | | | 1605 | | |
| Leu | His | Ala | Gly | Met | Ser | Thr | Leu | Phe | Leu | Val | Tyr | Ser | Asn | Lys |
| 1610 | | | | | 1615 | | | | | 1620 | | |
| Cys | Gln | Thr | Pro | Leu | Gly | Met | Ala | Ser | Gly | His | Ile | Arg | Asp | Phe |
| 1625 | | | | | 1630 | | | | | 1635 | | |
| Gln | Ile | Thr | Ala | Ser | Gly | Gln | Tyr | Gly | Gln | Trp | Ala | Pro | Lys | Leu |
| 1640 | | | | | 1645 | | | | | 1650 | | |
| Ala | Arg | Leu | His | Tyr | Ser | Gly | Ser | Ile | Asn | Ala | Trp | Ser | Thr | Lys |
| 1655 | | | | | 1660 | | | | | 1665 | | |
| Glu | Pro | Phe | Ser | Trp | Ile | Lys | Val | Asp | Leu | Leu | Ala | Pro | Met | Ile |
| 1670 | | | | | 1675 | | | | | 1680 | | |
| Ile | His | Gly | Ile | Lys | Thr | Gln | Gly | Ala | Arg | Gln | Lys | Phe | Ser | Ser |
| 1685 | | | | | 1690 | | | | | 1695 | | |
| Leu | Tyr | Ile | Ser | Gln | Phe | Ile | Ile | Met | Tyr | Ser | Leu | Asp | Gly | Lys |
| 1700 | | | | | 1705 | | | | | 1710 | | |
| Lys | Trp | Gln | Thr | Tyr | Arg | Gly | Asn | Ser | Thr | Gly | Thr | Leu | Met | Val |
| 1715 | | | | | 1720 | | | | | 1725 | | |
| Phe | Phe | Gly | Asn | Val | Asp | Ser | Ser | Gly | Ile | Lys | His | Asn | Ile | Phe |
| 1730 | | | | | 1735 | | | | | 1740 | | |
| Asn | Pro | Pro | Ile | Ile | Ala | Arg | Tyr | Ile | Arg | Leu | His | Pro | Thr | His |

```
                 1745                1750                1755

Tyr Ser Ile Arg Ser Thr Leu Arg Met Glu Leu Met Gly Cys Asp
         1760                1765                1770

Leu Asn Ser Cys Ser Met Pro Leu Gly Met Glu Ser Lys Ala Ile
    1775                1780                1785

Ser Asp Ala Gln Ile Thr Ala Ser Ser Tyr Phe Thr Asn Met Phe
    1790                1795                1800

Ala Thr Trp Ser Pro Ser Lys Ala Arg Leu His Leu Gln Gly Arg
    1805                1810                1815

Ser Asn Ala Trp Arg Pro Gln Val Asn Asn Pro Lys Glu Trp Leu
    1820                1825                1830

Gln Val Asp Phe Gln Lys Thr Met Lys Val Thr Gly Val Thr Thr
    1835                1840                1845

Gln Gly Val Lys Ser Leu Leu Thr Ser Met Tyr Val Lys Glu Phe
    1850                1855                1860

Leu Ile Ser Ser Ser Gln Asp Gly His Gln Trp Thr Leu Phe Phe
    1865                1870                1875

Gln Asn Gly Lys Val Lys Val Phe Gln Gly Asn Gln Asp Ser Phe
    1880                1885                1890

Thr Pro Val Val Asn Ser Leu Asp Pro Pro Leu Leu Thr Arg Tyr
    1895                1900                1905

Leu Arg Ile His Pro Gln Ser Trp Val His Gln Ile Ala Leu Arg
    1910                1915                1920

Met Glu Val Leu Gly Cys Glu Ala Gln Asp Leu Tyr
    1925                1930                1935

<210> SEQ ID NO 131
<211> LENGTH: 1681
<212> TYPE: PRT
<213> ORGANISM: Artificial Sequence
<220> FEATURE:
<223> OTHER INFORMATION: Synthetic Sequence

<400> SEQUENCE: 131

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys Gly Gly Gly Gly Ser Gly
            100                 105                 110

Gly Gly Gly Ser Gly Gly Gly Gly Ser Gly Gly Gly Gly Ser Glu Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Thr Tyr Ala Ile
145                 150                 155                 160

His Trp Val Arg Gln Ala Pro Gly Gln Gly Leu Glu Trp Met Gly Tyr
```

```
                    165                 170                 175
Ile Asn Pro Ser Ser Gly Tyr Thr Arg Tyr Asn Pro Lys Phe Lys Gly
                180                 185                 190

Arg Val Thr Met Thr Arg Asp Lys Ser Thr Ser Thr Ala Tyr Met Glu
            195                 200                 205

Leu Arg Ser Leu Arg Ser Asp Thr Ala Val Tyr Tyr Cys Trp Thr
        210                 215                 220

Gly Thr Arg Asp Tyr Trp Gly Gln Gly Thr Thr Val Thr Val Ser Ser
225                 230                 235                 240

Gly Gly Gly Ser Gly Gly Gly Ser Gly Leu Val Pro Arg Gly Ser
                245                 250                 255

Gly Gly Gly Ser Gly Gly Gly Ser Gly Ala Thr Arg Arg Tyr Tyr
                260                 265                 270

Leu Gly Ala Val Glu Leu Ser Trp Asp Tyr Met Gln Ser Asp Leu Gly
                275                 280                 285

Glu Leu Pro Val Asp Ala Arg Phe Pro Pro Arg Val Pro Lys Ser Phe
            290                 295                 300

Pro Phe Asn Thr Ser Val Val Tyr Lys Lys Thr Leu Phe Val Glu Phe
305                 310                 315                 320

Thr Asp His Leu Phe Asn Ile Ala Lys Pro Arg Pro Trp Met Gly
                325                 330                 335

Leu Leu Gly Pro Thr Ile Gln Ala Glu Val Tyr Asp Thr Val Val Ile
                340                 345                 350

Thr Leu Lys Asn Met Ala Ser His Pro Val Ser Leu His Ala Val Gly
                355                 360                 365

Val Ser Tyr Trp Lys Ala Ser Glu Gly Ala Glu Tyr Asp Asp Gln Thr
                370                 375                 380

Ser Gln Arg Glu Lys Glu Asp Asp Lys Val Phe Pro Gly Gly Ser His
385                 390                 395                 400

Thr Tyr Val Trp Gln Val Leu Lys Glu Asn Gly Pro Met Ala Ser Asp
                405                 410                 415

Pro Leu Cys Leu Thr Tyr Ser Tyr Leu Ser His Val Asp Leu Val Lys
                420                 425                 430

Asp Leu Asn Ser Gly Leu Ile Gly Ala Leu Leu Val Cys Arg Glu Gly
                435                 440                 445

Ser Leu Ala Lys Glu Lys Thr Gln Thr Leu His Lys Phe Ile Leu Leu
            450                 455                 460

Phe Ala Val Phe Asp Glu Gly Lys Ser Trp His Ser Glu Thr Lys Asn
465                 470                 475                 480

Ser Leu Met Gln Asp Arg Asp Ala Ala Ser Ala Arg Ala Trp Pro Lys
                485                 490                 495

Met His Thr Val Asn Gly Tyr Val Asn Arg Ser Leu Pro Gly Leu Ile
                500                 505                 510

Gly Cys His Arg Lys Ser Val Tyr Trp His Val Ile Gly Met Gly Thr
            515                 520                 525

Thr Pro Glu Val His Ser Ile Phe Leu Glu Gly His Thr Phe Leu Val
530                 535                 540

Arg Asn His Arg Gln Ala Ser Leu Glu Ile Ser Pro Ile Thr Phe Leu
545                 550                 555                 560

Thr Ala Gln Thr Leu Leu Met Asp Leu Gly Gln Phe Leu Leu Phe Cys
                565                 570                 575

His Ile Ser Ser His Gln His Asp Gly Met Glu Ala Tyr Val Lys Val
                580                 585                 590
```

```
Asp Ser Cys Pro Glu Glu Pro Gln Leu Arg Met Lys Asn Asn Glu Glu
        595                 600                 605

Ala Glu Asp Tyr Asp Asp Leu Thr Asp Ser Glu Met Asp Val Val
        610                 615                 620

Arg Phe Asp Asp Asp Asn Ser Pro Ser Phe Ile Gln Ile Arg Ser Val
625                 630                 635                 640

Ala Lys Lys His Pro Lys Thr Trp Val His Tyr Ile Ala Ala Glu Glu
            645                 650                 655

Glu Asp Trp Asp Tyr Ala Pro Leu Val Leu Ala Pro Asp Asp Arg Ser
                660                 665                 670

Tyr Lys Ser Gln Tyr Leu Asn Asn Gly Pro Gln Arg Ile Gly Arg Lys
            675                 680                 685

Tyr Lys Lys Val Arg Phe Met Ala Tyr Thr Asp Glu Thr Phe Lys Thr
        690                 695                 700

Arg Glu Ala Ile Gln His Glu Ser Gly Ile Leu Gly Pro Leu Leu Tyr
705                 710                 715                 720

Gly Glu Val Gly Asp Thr Leu Leu Ile Ile Phe Lys Asn Gln Ala Ser
                725                 730                 735

Arg Pro Tyr Asn Ile Tyr Pro His Gly Ile Thr Asp Val Arg Pro Leu
            740                 745                 750

Tyr Ser Arg Arg Leu Pro Lys Gly Val Lys His Leu Lys Asp Phe Pro
        755                 760                 765

Ile Leu Pro Gly Glu Ile Phe Lys Tyr Lys Trp Thr Val Thr Val Glu
    770                 775                 780

Asp Gly Pro Thr Lys Ser Asp Pro Arg Cys Leu Thr Arg Tyr Tyr Ser
785                 790                 795                 800

Ser Phe Val Asn Met Glu Arg Asp Leu Ala Ser Gly Leu Ile Gly Pro
                805                 810                 815

Leu Leu Ile Cys Tyr Lys Glu Ser Val Asp Gln Arg Gly Asn Gln Ile
            820                 825                 830

Met Ser Asp Lys Arg Asn Val Ile Leu Phe Ser Val Phe Asp Glu Asn
        835                 840                 845

Arg Ser Trp Tyr Leu Thr Glu Asn Ile Gln Arg Phe Leu Pro Asn Pro
    850                 855                 860

Ala Gly Val Gln Leu Glu Asp Pro Glu Phe Gln Ala Ser Asn Ile Met
865                 870                 875                 880

His Ser Ile Asn Gly Tyr Val Phe Asp Ser Leu Gln Leu Ser Val Cys
                885                 890                 895

Leu His Glu Val Ala Tyr Trp Tyr Ile Leu Ser Ile Gly Ala Gln Thr
            900                 905                 910

Asp Phe Leu Ser Val Phe Phe Ser Gly Tyr Thr Phe Lys His Lys Met
        915                 920                 925

Val Tyr Glu Asp Thr Leu Thr Leu Phe Pro Phe Ser Gly Glu Thr Val
    930                 935                 940

Phe Met Ser Met Glu Asn Pro Gly Leu Trp Ile Leu Gly Cys His Asn
945                 950                 955                 960

Ser Asp Phe Arg Asn Arg Gly Met Thr Ala Leu Leu Lys Val Ser Ser
                965                 970                 975

Cys Asp Lys Asn Thr Gly Asp Tyr Tyr Glu Asp Ser Tyr Glu Asp Ile
            980                 985                 990

Ser Ala Tyr Leu Leu Ser Lys Asn  Asn Ala Ile Glu Pro  Arg Ser Phe
        995                 1000                 1005
```

-continued

Ser Gln Asn Gly Gly Gly Gly Ser Gly Gly Ser Gly Gly Ser
1010                1015                1020

Gly Gly Ser Gly Gly Gly Gly Asp Glu Asn Gln Ser Pro Arg
1025                1030                1035

Ser Phe Gln Lys Lys Thr Arg His Tyr Phe Ile Ala Ala Val Glu
1040                1045                1050

Arg Leu Trp Asp Tyr Gly Met Ser Ser Ser Pro His Val Leu Arg
1055                1060                1065

Asn Arg Ala Gln Ser Gly Ser Val Pro Gln Phe Lys Lys Val Val
1070                1075                1080

Phe Gln Glu Phe Thr Asp Gly Ser Phe Thr Gln Pro Leu Tyr Arg
1085                1090                1095

Gly Glu Leu Asn Glu His Leu Gly Leu Leu Gly Pro Tyr Ile Arg
1100                1105                1110

Ala Glu Val Glu Asp Asn Ile Met Val Thr Phe Arg Asn Gln Ala
1115                1120                1125

Ser Arg Pro Tyr Ser Phe Tyr Ser Ser Leu Ile Ser Tyr Glu Glu
1130                1135                1140

Asp Gln Arg Gln Gly Ala Glu Pro Arg Lys Asn Phe Val Lys Pro
1145                1150                1155

Asn Glu Thr Lys Thr Tyr Phe Trp Lys Val Gln His His Met Ala
1160                1165                1170

Pro Thr Lys Asp Glu Phe Asp Cys Lys Ala Trp Ala Tyr Phe Ser
1175                1180                1185

Asp Val Asp Leu Glu Lys Asp Val His Ser Gly Leu Ile Gly Pro
1190                1195                1200

Leu Leu Val Cys His Thr Asn Thr Leu Asn Pro Ala His Gly Arg
1205                1210                1215

Gln Val Thr Val Gln Glu Phe Ala Leu Phe Phe Thr Ile Phe Asp
1220                1225                1230

Glu Thr Lys Ser Trp Tyr Phe Thr Glu Asn Met Glu Arg Asn Cys
1235                1240                1245

Arg Ala Pro Cys Asn Ile Gln Met Glu Asp Pro Thr Phe Lys Glu
1250                1255                1260

Asn Tyr Arg Phe His Ala Ile Asn Gly Tyr Ile Met Asp Thr Leu
1265                1270                1275

Pro Gly Leu Val Met Ala Gln Asp Gln Arg Ile Arg Trp Tyr Leu
1280                1285                1290

Leu Ser Met Gly Ser Asn Glu Asn Ile His Ser Ile His Phe Ser
1295                1300                1305

Gly His Val Phe Thr Val Arg Lys Lys Glu Glu Tyr Lys Met Ala
1310                1315                1320

Leu Tyr Asn Leu Tyr Pro Gly Val Phe Glu Thr Val Glu Met Leu
1325                1330                1335

Pro Ser Lys Ala Gly Ile Trp Arg Val Glu Cys Leu Ile Gly Glu
1340                1345                1350

His Leu His Ala Gly Met Ser Thr Leu Phe Leu Val Tyr Ser Asn
1355                1360                1365

Lys Cys Gln Thr Pro Leu Gly Met Ala Ser Gly His Ile Arg Asp
1370                1375                1380

Phe Gln Ile Thr Ala Ser Gly Gln Tyr Gly Gln Trp Ala Pro Lys
1385                1390                1395

Leu Ala Arg Leu His Tyr Ser Gly Ser Ile Asn Ala Trp Ser Thr

```
                1400                1405                1410

Lys Glu Pro Phe Ser Trp Ile Lys Val Asp Leu Leu Ala Pro Met
    1415                1420                1425

Ile Ile His Gly Ile Lys Thr Gln Gly Ala Arg Gln Lys Phe Ser
    1430                1435                1440

Ser Leu Tyr Ile Ser Gln Phe Ile Ile Met Tyr Ser Leu Asp Gly
    1445                1450                1455

Lys Lys Trp Gln Thr Tyr Arg Gly Asn Ser Thr Gly Thr Leu Met
    1460                1465                1470

Val Phe Phe Gly Asn Val Asp Ser Ser Gly Ile Lys His Asn Ile
    1475                1480                1485

Phe Asn Pro Pro Ile Ile Ala Arg Tyr Ile Arg Leu His Pro Thr
    1490                1495                1500

His Tyr Ser Ile Arg Ser Thr Leu Arg Met Glu Leu Met Gly Cys
    1505                1510                1515

Asp Leu Asn Ser Cys Ser Met Pro Leu Gly Met Glu Ser Lys Ala
    1520                1525                1530

Ile Ser Asp Ala Gln Ile Thr Ala Ser Ser Tyr Phe Thr Asn Met
    1535                1540                1545

Phe Ala Thr Trp Ser Pro Ser Lys Ala Arg Leu His Leu Gln Gly
    1550                1555                1560

Arg Ser Asn Ala Trp Arg Pro Gln Val Asn Asn Pro Lys Glu Trp
    1565                1570                1575

Leu Gln Val Asp Phe Gln Lys Thr Met Lys Val Thr Gly Val Thr
    1580                1585                1590

Thr Gln Gly Val Lys Ser Leu Leu Thr Ser Met Tyr Val Lys Glu
    1595                1600                1605

Phe Leu Ile Ser Ser Ser Gln Asp Gly His Gln Trp Thr Leu Phe
    1610                1615                1620

Phe Gln Asn Gly Lys Val Lys Val Phe Gln Gly Asn Gln Asp Ser
    1625                1630                1635

Phe Thr Pro Val Val Asn Ser Leu Asp Pro Pro Leu Leu Thr Arg
    1640                1645                1650

Tyr Leu Arg Ile His Pro Gln Ser Trp Val His Gln Ile Ala Leu
    1655                1660                1665

Arg Met Glu Val Leu Gly Cys Glu Ala Gln Asp Leu Tyr
    1670                1675                1680

<210> SEQ ID NO 132
<211> LENGTH: 1661
<212> TYPE: PRT
<213> ORGANISM: Artificial Sequence
<220> FEATURE:
<223> OTHER INFORMATION: Synthetic Sequence

<400> SEQUENCE: 132

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Arg Tyr Ile
            20                  25                  30

Tyr Trp Phe Gln Gln Lys Pro Gly Lys Ala Pro Lys Leu Leu Ile Tyr
        35                  40                  45

Ala Thr Ser Phe Arg Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
```

-continued

```
                65                  70                  75                  80
Asp Phe Ala Thr Tyr Tyr Cys His Gln Arg Asn Ser Phe Pro Tyr Thr
                    85                  90                  95
Phe Gly Gln Gly Thr Lys Leu Glu Ile Lys Gly Gly Gly Gly Ser Gly
                   100                 105                 110
Gly Gly Gly Ser Gly Gly Gly Gly Ser Gly Gly Gly Gly Ser Glu Val
                   115                 120                 125
Gln Leu Val Gln Ser Gly Ala Glu Val Lys Lys Pro Gly Ala Ser Val
        130                 135                 140
Lys Val Ser Cys Lys Ala Ser Gly Tyr Thr Phe Thr Thr Tyr Ala Ile
145                 150                 155                 160
His Trp Val Arg Gln Ala Pro Gly Gln Gly Leu Glu Trp Met Gly Tyr
                   165                 170                 175
Ile Asn Pro Ser Ser Gly Tyr Thr Arg Tyr Asn Pro Lys Phe Lys Gly
                   180                 185                 190
Arg Val Thr Met Thr Arg Asp Lys Ser Thr Ser Thr Ala Tyr Met Glu
            195                 200                 205
Leu Arg Ser Leu Arg Ser Asp Asp Thr Ala Val Tyr Tyr Cys Trp Thr
        210                 215                 220
Gly Thr Arg Asp Tyr Trp Gly Gln Gly Thr Thr Val Thr Val Ser Ser
225                 230                 235                 240
Gly Gly Gly Ser Gly Gly Gly Gly Ser Gly Leu Val Pro Arg Gly Ser
                   245                 250                 255
Gly Gly Gly Ser Gly Gly Gly Gly Ser Gly Ala Thr Arg Arg Tyr Tyr
                   260                 265                 270
Leu Gly Ala Val Glu Leu Ser Trp Asp Tyr Met Gln Ser Asp Leu Gly
            275                 280                 285
Glu Leu Pro Val Asp Ala Arg Phe Pro Pro Arg Val Pro Lys Ser Phe
        290                 295                 300
Pro Phe Asn Thr Ser Val Val Tyr Lys Lys Thr Leu Phe Val Glu Phe
305                 310                 315                 320
Thr Asp His Leu Phe Asn Ile Ala Lys Pro Arg Pro Pro Trp Met Gly
                   325                 330                 335
Leu Leu Gly Pro Thr Ile Gln Ala Glu Val Tyr Asp Thr Val Val Ile
                   340                 345                 350
Thr Leu Lys Asn Met Ala Ser His Pro Val Ser Leu His Ala Val Gly
            355                 360                 365
Val Ser Tyr Trp Lys Ala Ser Glu Gly Ala Glu Tyr Asp Asp Gln Thr
        370                 375                 380
Ser Gln Arg Glu Lys Glu Asp Asp Lys Val Phe Pro Gly Gly Ser His
385                 390                 395                 400
Thr Tyr Val Trp Gln Val Leu Lys Glu Asn Gly Pro Met Ala Ser Asp
                   405                 410                 415
Pro Leu Cys Leu Thr Tyr Ser Tyr Leu Ser His Val Asp Leu Val Lys
                   420                 425                 430
Asp Leu Asn Ser Gly Leu Ile Gly Ala Leu Leu Val Cys Arg Glu Gly
            435                 440                 445
Ser Leu Ala Lys Glu Lys Thr Gln Thr Leu His Lys Phe Ile Leu Leu
        450                 455                 460
Phe Ala Val Phe Asp Glu Gly Lys Ser Trp His Ser Glu Thr Lys Asn
465                 470                 475                 480
Ser Leu Met Gln Asp Arg Asp Ala Ala Ser Ala Arg Ala Trp Pro Lys
                   485                 490                 495
```

```
Met His Thr Val Asn Gly Tyr Val Asn Arg Ser Leu Pro Gly Leu Ile
            500                 505                 510

Gly Cys His Arg Lys Ser Val Tyr Trp His Val Ile Gly Met Gly Thr
        515                 520                 525

Thr Pro Glu Val His Ser Ile Phe Leu Glu Gly His Thr Phe Leu Val
    530                 535                 540

Arg Asn His Arg Gln Ala Ser Leu Glu Ile Ser Pro Ile Thr Phe Leu
545                 550                 555                 560

Thr Ala Gln Thr Leu Leu Met Asp Leu Gly Gln Phe Leu Leu Phe Cys
                565                 570                 575

His Ile Ser Ser His Gln His Asp Gly Met Glu Ala Tyr Val Lys Val
            580                 585                 590

Asp Ser Cys Pro Glu Glu Pro Gln Leu Arg Met Lys Asn Asn Glu Glu
        595                 600                 605

Ala Glu Asp Tyr Asp Asp Leu Thr Asp Ser Glu Met Asp Val Val
    610                 615                 620

Arg Phe Asp Asp Asp Asn Ser Pro Ser Phe Ile Gln Ile Arg Ser Val
625                 630                 635                 640

Ala Lys Lys His Pro Lys Thr Trp Val His Tyr Ile Ala Ala Glu Glu
                645                 650                 655

Glu Asp Trp Asp Tyr Ala Pro Leu Val Leu Ala Pro Asp Asp Arg Ser
            660                 665                 670

Tyr Lys Ser Gln Tyr Leu Asn Asn Gly Pro Gln Arg Ile Gly Arg Lys
        675                 680                 685

Tyr Lys Lys Val Arg Phe Met Ala Tyr Thr Asp Glu Thr Phe Lys Thr
    690                 695                 700

Arg Glu Ala Ile Gln His Glu Ser Gly Ile Leu Gly Pro Leu Leu Tyr
705                 710                 715                 720

Gly Glu Val Gly Asp Thr Leu Leu Ile Ile Phe Lys Asn Gln Ala Ser
                725                 730                 735

Arg Pro Tyr Asn Ile Tyr Pro His Gly Ile Thr Asp Val Arg Pro Leu
            740                 745                 750

Tyr Ser Arg Arg Leu Pro Lys Gly Val Lys His Leu Lys Asp Phe Pro
        755                 760                 765

Ile Leu Pro Gly Glu Ile Phe Lys Tyr Lys Trp Thr Val Thr Val Glu
    770                 775                 780

Asp Gly Pro Thr Lys Ser Asp Pro Arg Cys Leu Thr Arg Tyr Tyr Ser
785                 790                 795                 800

Ser Phe Val Asn Met Glu Arg Asp Leu Ala Ser Gly Leu Ile Gly Pro
                805                 810                 815

Leu Leu Ile Cys Tyr Lys Glu Ser Val Asp Gln Arg Gly Asn Gln Ile
            820                 825                 830

Met Ser Asp Lys Arg Asn Val Ile Leu Phe Ser Val Phe Asp Glu Asn
        835                 840                 845

Arg Ser Trp Tyr Leu Thr Glu Asn Ile Gln Arg Phe Leu Pro Asn Pro
    850                 855                 860

Ala Gly Val Gln Leu Glu Asp Pro Glu Phe Gln Ala Ser Asn Ile Met
865                 870                 875                 880

His Ser Ile Asn Gly Tyr Val Phe Asp Ser Leu Gln Leu Ser Val Cys
                885                 890                 895

Leu His Glu Val Ala Tyr Trp Tyr Ile Leu Ser Ile Gly Ala Gln Thr
            900                 905                 910
```

-continued

Asp Phe Leu Ser Val Phe Phe Ser Gly Tyr Thr Phe Lys His Lys Met
915                 920                 925

Val Tyr Glu Asp Thr Leu Thr Leu Phe Pro Phe Ser Gly Glu Thr Val
930                 935                 940

Phe Met Ser Met Glu Asn Pro Gly Leu Trp Ile Leu Gly Cys His Asn
945                 950                 955                 960

Ser Asp Phe Arg Asn Arg Gly Met Thr Ala Leu Leu Lys Val Ser Ser
            965                 970                 975

Cys Asp Lys Asn Thr Gly Asp Tyr Tyr Glu Asp Ser Tyr Glu Asp Ile
            980                 985                 990

Ser Ala Tyr Leu Leu Ser Lys Asn Asn Ala Ile Glu Pro Gly Gly Gly
            995                 1000                1005

Gly Gly Gly Asp Glu Asn Gln Ser Pro Arg Ser Phe Gln Lys Lys
    1010                1015                1020

Thr Arg His Tyr Phe Ile Ala Ala Val Glu Arg Leu Trp Asp Tyr
    1025                1030                1035

Gly Met Ser Ser Ser Pro His Val Leu Arg Asn Arg Ala Gln Ser
    1040                1045                1050

Gly Ser Val Pro Gln Phe Lys Lys Val Val Phe Gln Glu Phe Thr
    1055                1060                1065

Asp Gly Ser Phe Thr Gln Pro Leu Tyr Arg Gly Glu Leu Asn Glu
    1070                1075                1080

His Leu Gly Leu Leu Gly Pro Tyr Ile Arg Ala Glu Val Glu Asp
    1085                1090                1095

Asn Ile Met Val Thr Phe Arg Asn Gln Ala Ser Arg Pro Tyr Ser
    1100                1105                1110

Phe Tyr Ser Ser Leu Ile Ser Tyr Glu Glu Asp Gln Arg Gln Gly
    1115                1120                1125

Ala Glu Pro Arg Lys Asn Phe Val Lys Pro Asn Glu Thr Lys Thr
    1130                1135                1140

Tyr Phe Trp Lys Val Gln His His Met Ala Pro Thr Lys Asp Glu
    1145                1150                1155

Phe Asp Cys Lys Ala Trp Ala Tyr Phe Ser Asp Val Asp Leu Glu
    1160                1165                1170

Lys Asp Val His Ser Gly Leu Ile Gly Pro Leu Leu Val Cys His
    1175                1180                1185

Thr Asn Thr Leu Asn Pro Ala His Gly Arg Gln Val Thr Val Gln
    1190                1195                1200

Glu Phe Ala Leu Phe Phe Thr Ile Phe Asp Glu Thr Lys Ser Trp
    1205                1210                1215

Tyr Phe Thr Glu Asn Met Glu Arg Asn Cys Arg Ala Pro Cys Asn
    1220                1225                1230

Ile Gln Met Glu Asp Pro Thr Phe Lys Glu Asn Tyr Arg Phe His
    1235                1240                1245

Ala Ile Asn Gly Tyr Ile Met Asp Thr Leu Pro Gly Leu Val Met
    1250                1255                1260

Ala Gln Asp Gln Arg Ile Arg Trp Tyr Leu Leu Ser Met Gly Ser
    1265                1270                1275

Asn Glu Asn Ile His Ser Ile His Phe Ser Gly His Val Phe Thr
    1280                1285                1290

Val Arg Lys Lys Glu Glu Tyr Lys Met Ala Leu Tyr Asn Leu Tyr
    1295                1300                1305

Pro Gly Val Phe Glu Thr Val Glu Met Leu Pro Ser Lys Ala Gly

```
                1310                1315                1320

Ile Trp Arg Val Glu Cys Leu Ile Gly Glu His Leu His Ala Gly
    1325                1330                1335

Met Ser Thr Leu Phe Leu Val Tyr Ser Asn Lys Cys Gln Thr Pro
    1340                1345                1350

Leu Gly Met Ala Ser Gly His Ile Arg Asp Phe Gln Ile Thr Ala
    1355                1360                1365

Ser Gly Gln Tyr Gly Gln Trp Ala Pro Lys Leu Ala Arg Leu His
    1370                1375                1380

Tyr Ser Gly Ser Ile Asn Ala Trp Ser Thr Lys Glu Pro Phe Ser
    1385                1390                1395

Trp Ile Lys Val Asp Leu Leu Ala Pro Met Ile Ile His Gly Ile
    1400                1405                1410

Lys Thr Gln Gly Ala Arg Gln Lys Phe Ser Ser Leu Tyr Ile Ser
    1415                1420                1425

Gln Phe Ile Ile Met Tyr Ser Leu Asp Gly Lys Lys Trp Gln Thr
    1430                1435                1440

Tyr Arg Gly Asn Ser Thr Gly Thr Leu Met Val Phe Phe Gly Asn
    1445                1450                1455

Val Asp Ser Ser Gly Ile Lys His Asn Ile Phe Asn Pro Pro Ile
    1460                1465                1470

Ile Ala Arg Tyr Ile Arg Leu His Pro Thr His Tyr Ser Ile Arg
    1475                1480                1485

Ser Thr Leu Arg Met Glu Leu Met Gly Cys Asp Leu Asn Ser Cys
    1490                1495                1500

Ser Met Pro Leu Gly Met Glu Ser Lys Ala Ile Ser Asp Ala Gln
    1505                1510                1515

Ile Thr Ala Ser Ser Tyr Phe Thr Asn Met Phe Ala Thr Trp Ser
    1520                1525                1530

Pro Ser Lys Ala Arg Leu His Leu Gln Gly Arg Ser Asn Ala Trp
    1535                1540                1545

Arg Pro Gln Val Asn Asn Pro Lys Glu Trp Leu Gln Val Asp Phe
    1550                1555                1560

Gln Lys Thr Met Lys Val Thr Gly Val Thr Thr Gln Gly Val Lys
    1565                1570                1575

Ser Leu Leu Thr Ser Met Tyr Val Lys Glu Phe Leu Ile Ser Ser
    1580                1585                1590

Ser Gln Asp Gly His Gln Trp Thr Leu Phe Phe Gln Asn Gly Lys
    1595                1600                1605

Val Lys Val Phe Gln Gly Asn Gln Asp Ser Phe Thr Pro Val Val
    1610                1615                1620

Asn Ser Leu Asp Pro Pro Leu Leu Thr Arg Tyr Leu Arg Ile His
    1625                1630                1635

Pro Gln Ser Trp Val His Gln Ile Ala Leu Arg Met Glu Val Leu
    1640                1645                1650

Gly Cys Glu Ala Gln Asp Leu Tyr
    1655                1660

<210> SEQ ID NO 133
<211> LENGTH: 1673
<212> TYPE: PRT
<213> ORGANISM: Artificial Sequence
<220> FEATURE:
<223> OTHER INFORMATION: Synthetic Sequence
```

```
<400> SEQUENCE: 133

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Arg Tyr Ile
            20                  25                  30

Tyr Trp Phe Gln Gln Lys Pro Gly Lys Ala Pro Lys Leu Leu Ile Tyr
            35                  40                  45

Ala Thr Ser Phe Arg Gln Ser Gly Val Pro Ser Arg Phe Ser Gly Ser
            50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys His Gln Arg Asn Ser Phe Pro Tyr Thr
                85                  90                  95

Phe Gly Gln Gly Thr Lys Leu Glu Ile Lys Gly Gly Gly Gly Ser Gly
            100                 105                 110

Gly Gly Gly Ser Gly Gly Gly Ser Gly Gly Gly Ser Glu Val
            115                 120                 125

Gln Leu Val Gln Ser Gly Ala Glu Val Lys Lys Pro Gly Ala Ser Val
130                 135                 140

Lys Val Ser Cys Lys Ala Ser Gly Tyr Thr Phe Thr Thr Tyr Ala Ile
145                 150                 155                 160

His Trp Val Arg Gln Ala Pro Gly Gln Gly Leu Glu Trp Met Gly Tyr
                165                 170                 175

Ile Asn Pro Ser Ser Gly Tyr Thr Arg Tyr Asn Pro Lys Phe Lys Gly
            180                 185                 190

Arg Val Thr Met Thr Arg Asp Lys Ser Thr Ser Thr Ala Tyr Met Glu
            195                 200                 205

Leu Arg Ser Leu Arg Ser Asp Asp Thr Ala Val Tyr Tyr Cys Trp Thr
210                 215                 220

Gly Thr Arg Asp Tyr Trp Gly Gln Gly Thr Thr Val Thr Val Ser Ser
225                 230                 235                 240

Gly Gly Gly Ser Gly Gly Gly Gly Ser Gly Leu Val Pro Arg Gly Ser
            245                 250                 255

Gly Gly Gly Ser Gly Gly Gly Gly Ser Gly Ala Thr Arg Arg Tyr Tyr
            260                 265                 270

Leu Gly Ala Val Glu Leu Ser Trp Asp Tyr Met Gln Ser Asp Leu Gly
            275                 280                 285

Glu Leu Pro Val Asp Ala Arg Phe Pro Pro Arg Val Pro Lys Ser Phe
290                 295                 300

Pro Phe Asn Thr Ser Val Val Tyr Lys Lys Thr Leu Phe Val Glu Phe
305                 310                 315                 320

Thr Asp His Leu Phe Asn Ile Ala Lys Pro Arg Pro Pro Trp Met Gly
                325                 330                 335

Leu Leu Gly Pro Thr Ile Gln Ala Glu Val Tyr Asp Thr Val Val Ile
            340                 345                 350

Thr Leu Lys Asn Met Ala Ser His Pro Val Ser Leu His Ala Val Gly
            355                 360                 365

Val Ser Tyr Trp Lys Ala Ser Glu Gly Ala Glu Tyr Asp Asp Gln Thr
370                 375                 380

Ser Gln Arg Glu Lys Glu Asp Lys Val Phe Pro Gly Gly Ser His
385                 390                 395                 400

Thr Tyr Val Trp Gln Val Leu Lys Glu Asn Gly Pro Met Ala Ser Asp
                405                 410                 415
```

```
Pro Leu Cys Leu Thr Tyr Ser Tyr Leu Ser His Val Asp Leu Val Lys
            420                 425                 430

Asp Leu Asn Ser Gly Leu Ile Gly Ala Leu Leu Val Cys Arg Glu Gly
            435                 440                 445

Ser Leu Ala Lys Glu Lys Thr Gln Thr Leu His Lys Phe Ile Leu Leu
450                 455                 460

Phe Ala Val Phe Asp Glu Gly Lys Ser Trp His Ser Glu Thr Lys Asn
465                 470                 475                 480

Ser Leu Met Gln Asp Arg Asp Ala Ala Ser Ala Arg Ala Trp Pro Lys
                485                 490                 495

Met His Thr Val Asn Gly Tyr Val Asn Arg Ser Leu Pro Gly Leu Ile
            500                 505                 510

Gly Cys His Arg Lys Ser Val Tyr Trp His Val Ile Gly Met Gly Thr
            515                 520                 525

Thr Pro Glu Val His Ser Ile Phe Leu Glu Gly His Thr Phe Leu Val
            530                 535                 540

Arg Asn His Arg Gln Ala Ser Leu Glu Ile Ser Pro Ile Thr Phe Leu
545                 550                 555                 560

Thr Ala Gln Thr Leu Leu Met Asp Leu Gly Gln Phe Leu Leu Phe Cys
                565                 570                 575

His Ile Ser Ser His Gln His Asp Gly Met Glu Ala Tyr Val Lys Val
            580                 585                 590

Asp Ser Cys Pro Glu Glu Pro Gln Leu Arg Met Lys Asn Asn Glu Glu
            595                 600                 605

Ala Glu Asp Tyr Asp Asp Asp Leu Thr Asp Ser Glu Met Asp Val Val
            610                 615                 620

Arg Phe Asp Asp Asp Asn Ser Pro Ser Phe Ile Gln Ile Arg Ser Val
625                 630                 635                 640

Ala Lys Lys His Pro Lys Thr Trp Val His Tyr Ile Ala Ala Glu Glu
                645                 650                 655

Glu Asp Trp Asp Tyr Ala Pro Leu Val Leu Ala Pro Asp Asp Arg Ser
            660                 665                 670

Tyr Lys Ser Gln Tyr Leu Asn Asn Gly Pro Gln Arg Ile Gly Arg Lys
            675                 680                 685

Tyr Lys Lys Val Arg Phe Met Ala Tyr Thr Asp Glu Thr Phe Lys Thr
690                 695                 700

Arg Glu Ala Ile Gln His Glu Ser Gly Ile Leu Gly Pro Leu Leu Tyr
705                 710                 715                 720

Gly Glu Val Gly Asp Thr Leu Leu Ile Ile Phe Lys Asn Gln Ala Ser
                725                 730                 735

Arg Pro Tyr Asn Ile Tyr Pro His Gly Ile Thr Asp Val Arg Pro Leu
            740                 745                 750

Tyr Ser Arg Arg Leu Pro Lys Gly Val Lys His Leu Lys Asp Phe Pro
            755                 760                 765

Ile Leu Pro Gly Glu Ile Phe Lys Tyr Lys Trp Thr Val Thr Val Glu
            770                 775                 780

Asp Gly Pro Thr Lys Ser Asp Pro Arg Cys Leu Thr Arg Tyr Tyr Ser
785                 790                 795                 800

Ser Phe Val Asn Met Glu Arg Asp Leu Ala Ser Gly Leu Ile Gly Pro
                805                 810                 815

Leu Leu Ile Cys Tyr Lys Glu Ser Val Asp Gln Arg Gly Asn Gln Ile
            820                 825                 830
```

```
Met Ser Asp Lys Arg Asn Val Ile Leu Phe Ser Val Phe Asp Glu Asn
            835                 840                 845
Arg Ser Trp Tyr Leu Thr Glu Asn Ile Gln Arg Phe Leu Pro Asn Pro
    850                 855                 860
Ala Gly Val Gln Leu Glu Asp Pro Glu Phe Gln Ala Ser Asn Ile Met
865                 870                 875                 880
His Ser Ile Asn Gly Tyr Val Phe Asp Ser Leu Gln Leu Ser Val Cys
            885                 890                 895
Leu His Glu Val Ala Tyr Trp Tyr Ile Leu Ser Ile Gly Ala Gln Thr
            900                 905                 910
Asp Phe Leu Ser Val Phe Phe Ser Gly Tyr Thr Phe Lys His Lys Met
            915                 920                 925
Val Tyr Glu Asp Thr Leu Thr Leu Phe Pro Phe Ser Gly Glu Thr Val
    930                 935                 940
Phe Met Ser Met Glu Asn Pro Gly Leu Trp Ile Leu Gly Cys His Asn
945                 950                 955                 960
Ser Asp Phe Arg Asn Arg Gly Met Thr Ala Leu Leu Lys Val Ser Ser
            965                 970                 975
Cys Asp Lys Asn Thr Gly Asp Tyr Tyr Glu Asp Ser Tyr Glu Asp Ile
            980                 985                 990
Ser Ala Tyr Leu Leu Ser Lys Asn Asn Ala Ile Glu Pro Arg Ser Phe
            995                 1000                1005
Ser Gln Asn Pro Pro Val Leu Lys Arg His Gln Arg Glu Ile Thr
    1010                1015                1020
Asp Glu Asn Gln Ser Pro Arg Ser Phe Gln Lys Lys Thr Arg His
    1025                1030                1035
Tyr Phe Ile Ala Ala Val Glu Arg Leu Trp Asp Tyr Gly Met Ser
    1040                1045                1050
Ser Ser Pro His Val Leu Arg Asn Arg Ala Gln Ser Gly Ser Val
    1055                1060                1065
Pro Gln Phe Lys Lys Val Val Phe Gln Glu Phe Thr Asp Gly Ser
    1070                1075                1080
Phe Thr Gln Pro Leu Tyr Arg Gly Glu Leu Asn Glu His Leu Gly
    1085                1090                1095
Leu Leu Gly Pro Tyr Ile Arg Ala Glu Val Glu Asp Asn Ile Met
    1100                1105                1110
Val Thr Phe Arg Asn Gln Ala Ser Arg Pro Tyr Ser Phe Tyr Ser
    1115                1120                1125
Ser Leu Ile Ser Tyr Glu Glu Asp Gln Arg Gln Gly Ala Glu Pro
    1130                1135                1140
Arg Lys Asn Phe Val Lys Pro Asn Glu Thr Lys Thr Tyr Phe Trp
    1145                1150                1155
Lys Val Gln His His Met Ala Pro Thr Lys Asp Glu Phe Asp Cys
    1160                1165                1170
Lys Ala Trp Ala Tyr Phe Ser Asp Val Asp Leu Glu Lys Asp Val
    1175                1180                1185
His Ser Gly Leu Ile Gly Pro Leu Leu Val Cys His Thr Asn Thr
    1190                1195                1200
Leu Asn Pro Ala His Gly Arg Gln Val Thr Val Gln Glu Phe Ala
    1205                1210                1215
Leu Phe Phe Thr Ile Phe Asp Glu Thr Lys Ser Trp Tyr Phe Thr
    1220                1225                1230
Glu Asn Met Glu Arg Asn Cys Arg Ala Pro Cys Asn Ile Gln Met
```

-continued

```
            1235                1240                1245
Glu Asp Pro Thr Phe Lys Glu Asn Tyr Arg Phe His Ala Ile Asn
            1250                1255                1260
Gly Tyr Ile Met Asp Thr Leu Pro Gly Leu Val Met Ala Gln Asp
            1265                1270                1275
Gln Arg Ile Arg Trp Tyr Leu Leu Ser Met Gly Ser Asn Glu Asn
            1280                1285                1290
Ile His Ser Ile His Phe Ser Gly His Val Phe Thr Val Arg Lys
            1295                1300                1305
Lys Glu Glu Tyr Lys Met Ala Leu Tyr Asn Leu Tyr Pro Gly Val
            1310                1315                1320
Phe Glu Thr Val Glu Met Leu Pro Ser Lys Ala Gly Ile Trp Arg
            1325                1330                1335
Val Glu Cys Leu Ile Gly Glu His Leu His Ala Gly Met Ser Thr
            1340                1345                1350
Leu Phe Leu Val Tyr Ser Asn Lys Cys Gln Thr Pro Leu Gly Met
            1355                1360                1365
Ala Ser Gly His Ile Arg Asp Phe Gln Ile Thr Ala Ser Gly Gln
            1370                1375                1380
Tyr Gly Gln Trp Ala Pro Lys Leu Ala Arg Leu His Tyr Ser Gly
            1385                1390                1395
Ser Ile Asn Ala Trp Ser Thr Lys Glu Pro Phe Ser Trp Ile Lys
            1400                1405                1410
Val Asp Leu Leu Ala Pro Met Ile Ile His Gly Ile Lys Thr Gln
            1415                1420                1425
Gly Ala Arg Gln Lys Phe Ser Ser Leu Tyr Ile Ser Gln Phe Ile
            1430                1435                1440
Ile Met Tyr Ser Leu Asp Gly Lys Lys Trp Gln Thr Tyr Arg Gly
            1445                1450                1455
Asn Ser Thr Gly Thr Leu Met Val Phe Phe Gly Asn Val Asp Ser
            1460                1465                1470
Ser Gly Ile Lys His Asn Ile Phe Asn Pro Pro Ile Ile Ala Arg
            1475                1480                1485
Tyr Ile Arg Leu His Pro Thr His Tyr Ser Ile Arg Ser Thr Leu
            1490                1495                1500
Arg Met Glu Leu Met Gly Cys Asp Leu Asn Ser Cys Ser Met Pro
            1505                1510                1515
Leu Gly Met Glu Ser Lys Ala Ile Ser Asp Ala Gln Ile Thr Ala
            1520                1525                1530
Ser Ser Tyr Phe Thr Asn Met Phe Ala Thr Trp Ser Pro Ser Lys
            1535                1540                1545
Ala Arg Leu His Leu Gln Gly Arg Ser Asn Ala Trp Arg Pro Gln
            1550                1555                1560
Val Asn Asn Pro Lys Glu Trp Leu Gln Val Asp Phe Gln Lys Thr
            1565                1570                1575
Met Lys Val Thr Gly Val Thr Thr Gln Gly Val Lys Ser Leu Leu
            1580                1585                1590
Thr Ser Met Tyr Val Lys Glu Phe Leu Ile Ser Ser Ser Gln Asp
            1595                1600                1605
Gly His Gln Trp Thr Leu Phe Phe Gln Asn Gly Lys Val Lys Val
            1610                1615                1620
Phe Gln Gly Asn Gln Asp Ser Phe Thr Pro Val Val Asn Ser Leu
            1625                1630                1635
```

```
Asp Pro Pro Leu Leu Thr Arg Tyr Leu Arg Ile His Pro Gln Ser
    1640            1645                1650

Trp Val His Gln Ile Ala Leu Arg Met Glu Val Leu Gly Cys Glu
    1655            1660                1665

Ala Gln Asp Leu Tyr
    1670
```

RED BLOOD CELL TARGETED FACTOR VIII AND METHOD OF USING THE SAME

FIELD

Provided herein are Factor VIII (FVIII) compounds targeted to red blood cells having an improved half-life and/or increased efficacy. Further provided are methods of treating patients suffering from a coagulation factor deficiency disorder by selectively targeting coagulation factors to their biological sites of action, such as by targeting Factor VIII (FVIII) to red blood cells. In addition, provided herein are single chain antibodies to glycophorin A on red blood cells.

BACKGROUND

The effectiveness of biological drugs is often limited by their duration of action in patients, particularly when the disease requires continuous modulation by the drug. Consequently, enhancement of pharmacokinetic properties is often more critical to the success of a therapeutic agent in the clinic than is optimization of the drug's potency. One approach to protect drugs from various mechanism of clearance so as to prolong the half-life is to add targeting domains that promote drug binding to long-lived proteins in circulation such as matrix proteins, or to the surface of cells, such as blood cells or endothelial cells. For example, localization of therapeutic peptides or proteins to blood cell surfaces has been shown to prolong their circulation half-life by preventing normal clearance mechanisms (Chen, et al., Blood 105(10):3902-3909, 2005). A wide variety of molecules may be used as the targeting domain.

In another instance, when the Kunitz-type protease inhibitor (KPI) domain of tick anticoagulant protein was linked with an anionic phospholipid, phosphatidyl-L-serine (PS) binding protein, annexin V (ANV), the fusion protein (ANV-KPI) was shown to be more active and possess higher in vivo antithrombotic activities than the non-fusion counterpart (Chen, et al., 2005). Because ANV has strong affinities for PS and phosphatidylethanolamine (PE), it is hypothesized that the fusion protein ANV-KPI can be specifically targeted to the PS/PE-rich anionic membrane-associated coagulation enzyme complexes present at sites of thrombogenesis. Similarly, Dong, et al., reported fusing the fibrin-selective *Desmodus rotundus* salivary PA al (dsPA al) to a urokinase (uPA)/anti-P-selectin antibody (HuSZ51) to produce a fusion protein that is fully functional with similar antithrombotic activities as the non-fusion counterpart in in vitro assays. Furthermore, the fusion protein HuSZ51-dsPA al was shown to bind to thrombin-activated human and dog platelets (Dong, et al., Thromb. Haemost. 92:956-965, 2004).

Other efforts have been made in targeting anticoagulants to prevent clots and to reduce mortality associated with thrombotic diseases (see, e.g., WO 94/09034). A more recent development is demonstrated by Stoll, et al., (Arterioscler. Thromb. Vasc. Biol. 27:1206-1212, 2007), in which a Factor Xa (FXa) inhibitor, tick anticoagulant peptide (TAP), was targeted to ligand-induced binding sites (LIBS) on GPIIb/IIIa, a glycoprotein abundantly expressed on the platelet surface, via an anti-LIBS single-chain antibody ($scFv_{anti-LIBS}$). The fusion protein $scFv_{anti-LIBS}$-TAP was shown to possess an effective anticoagulation activity even at low doses at which the non-targeted counterpart failed. The aforementioned targeted anticoagulants were fusion proteins designed to target specific cells. According to Stoll, et al., the targeted anticoagulant should be a small molecule with a highly potent coagulation inhibition activity that is retained while fused to an antibody. The release of the anticoagulant from the fusion proteins in its targeted sites was not discussed.

Muzykantov et al (U.S. Pat. No. 8,333,973) discloses fusion proteins of a single chain antigen-binding domain to an anti-thrombotic agent, specifically thrombomodulin. While Muzykantov et al also suggest targeting glycophorin A with the scFv, only a murine antibody to glycophorin A is disclosed. No other antibodies or scFvs were disclosed.

Additionally, others have made efforts to target other blood cells. For example, Hilden et al (US2016/0263230A1) discloses targeting of FVIIa to platelets by fusion to an monoclonal antibody or fragment thereof that binds to TREM-like transcript 1 protein (TLT-1). The antibody was attached to FVIIa either by conjugation to a glycosylation site or via direct genetic fusion to FVIIa.

The present disclosure focuses on targeting therapeutic proteins for the treatment of hematological diseases such as hemophilia. For example, current treatment of hemophilia A patients with FVIII concentrates or recombinant FVIII is limited by the high cost of these factors and their relatively short duration of action. Hemophilia A patients are currently treated by intravenous administration of FVIII on demand or as a prophylactic therapy administered several times a week. For prophylactic treatment, FVIII is administered three times a week. Unfortunately, this frequency is cost prohibitive for many patients. Because of its short half-life in man, FVIII must be administered frequently. Despite its large size of greater than 300 kD for the full-length protein, FVIII has a half-life in humans of only about 11-18 (average 14) hours (Gruppo, et al., Haemophila 9:251-260, 2003). For those who can afford the frequent dosing recommended, it is nevertheless very inconvenient to frequently intravenously inject the protein. It would be more convenient for the patients if a FVIII product could be developed that had a longer half-life and therefore required less frequent administration. Furthermore, the cost of treatment could be reduced if the half-life were increased because fewer dosages may then be required. It is therefore desirable to have more efficient forms of FVIII that can lower the effective dose or have a prolonged duration of action to significantly improve treatment options for hemophiliacs.

Also, a sustained plasma concentration of targeted FVIII may reduce the extent of adverse side effects by reducing the trough to peak levels of FVIII, thus eliminating the need to introduce super-physiological levels of protein at early time-points. Therefore, it is desirable to have forms of FVIII that have sustained duration and a longer half-life than current marketed forms. It is also desirable to maintain trough levels of FVIII above 5%, or above 10%, or ideally above 15% of normal FVIII levels because these levels will reduce or eliminate breakthrough bleeds that can occur when FVIII levels are between 1% and 5% FVIII.

An additional disadvantage to the current therapy is that about 25-30% of patients develop antibodies that inhibit FVIII activity (Saenko, et al., Haemophilia 8:1-11, 2002). Antibody development prevents the use of FVIII as a replacement therapy, forcing this group of patients to seek an even more expensive treatment with high-dose recombinant Factor VIIa (FVIIa) and immune tolerance therapy. A less immunogenic FVIII replacement product is therefore desirable.

One approach in improving the treatment for hemophiliacs involves gene therapy. Ectopically targeting FVIII to platelets by directing FVIII expression in platelets can have therapeutic effects in the treatment of hemophilia A in animal models (Shi, et al., J. Clin. Invest. 116(7):1974-1982, 2006).

It is an object to provide targeted coagulation factors that have prolonged duration of action, greater efficacy, fewer side effects, and less immunogenicity compared to the untargeted protein.

Another object is to reduce side effects associated with therapeutic protein administration by having the protein targeted to the specific site of desired action and thereby reducing the exposure of the protein to other potential biologically active sites that may result in undesired side effects.

A further object is to obtain further advantages by designing targeted therapeutic coagulation factors in which the therapeutic protein is released from the targeting domain in the immediate vicinity of its site of action in vivo. A high local concentration of the non-fusion, activated proteins may be achieved. Thus, the therapeutic efficacy of the proteins is enhanced.

SUMMARY

Provided herein are recombinant fusion proteins comprising a functional Factor VIII polypeptide, at least one binding domain that specifically binds to a membrane protein on a red blood cell.

In some embodiments, the functional Factor VIII polypeptide is a full-length Factor VIII or a B-domain deleted Factor VIII. In some embodiments, the membrane protein is glycophorin A or Band3.

In some embodiments, the binding domain is an antibody, an antibody fragment, a scFv, a peptide, a peptide mimetic, or a small molecule. In further embodiments, the binding domain is a scFv and the membrane protein is glycophorin A.

In some embodiments, the scFv comprises a heavy chain selected from the group consisting of SEQ IS NOS: 33, 35, 37, 39, 41, 43, 45, 47, 49, 51, 53, 55, 57, 59, 61, 63, 65 and 67, and/or the scFv comprises a light chain selected from the group consisting of SEQ IS NOS: 32, 34, 36, 38, 40, 42, 44, 46, 48, 50, 52, 54, 56, 58, 60, 62, 64 and 66.

In some embodiments, the scFv may be strategically located in the Factor VIII. In some embodiments, the scFv is inserted into the functional Factor VIII polypeptide in the B-domain and most of the B-domain is removed. In some embodiments, the scFv is fused at the N-terminus of the functional Factor VIII polypeptide. In other embodiments, the scFv is fused at the C-terminus of the functional Factor VIII polypeptide.

In some embodiments, the functional Factor VIII polypeptide comprises a reduced or no binding to vWF. To achieve this, in some embodiments, the functional Factor VIII polypeptide comprises a deletion of the a3 domain of the functional Factor VIII polypeptide. In some embodiments, the deletion of the a3 domain of the functional Factor VIII polypeptide comprises deletion of residues 1652 to 1682 of Factor VIII.

In some embodiments, the functional Factor VIII polypeptide comprises a composition of predominantly a 1 chain form. The 1 chain form can be generated by removing the furin proteolytic cleavage site at residue 1648 of the functional Factor VIII or by deleting residues 1645-1648 of the functional Factor VIII or by deleting residues 1637-1651 of the functional Factor VIII.

In specific embodiments, the recombinant fusion protein of claim 1, wherein the recombinant fusion protein comprises the sequence selected from the group consisting of SEQ ID NO: 113-133.

Also disclosed are pharmaceutical compositions comprising a therapeutically effective amount of the recombinant fusion protein as described above and a pharmaceutically acceptable excipient or carrier. Further disclosed are methods for treating hematological diseases comprising administering an effective amount of the recombinant fusion protein to a patient in need thereof.

While a majority of this disclosure focuses on Factor VIII, it is envisioned that such targeting domains may be used to extend the half-life of any protein where half-life extension is desired. Thus, also disclosed are recombinant fusion proteins comprising a protein wherein extension of circulating half-life would be beneficial to a patient, and at least one binding domain that specifically binds to a membrane protein on a red blood cell. In some embodiments, the membrane protein is glycophorin A or Band3. In some embodiments, the binding domain is an antibody, an antibody fragment, a scFv, a peptide, a peptide mimetic, or a small molecule. In some embodiments, the binding domain is a scFv and the membrane protein is glycophorin A.

In specific embodiments, the scFv comprises a heavy chain selected from the group consisting of SEQ IS NOS: 33, 35, 37, 39, 41, 43, 45, 47, 49, 51, 53, 55, 57, 59, 61, 63, 65 and 67, and/or comprises a light chain selected from the group consisting of SEQ IS NOS: 32, 34, 36, 38, 40, 42, 44, 46, 48, 50, 52, 54, 56, 58, 60, 62, 64 and 66.

DESCRIPTION OF THE DRAWINGS

FIG. 2: Shown is a flow diagram of the hybridoma screening cascade to identify glycophorin A antibodies.

FIG. 4: Flourescence activated cell sorting analysis of (A) parental CHO-QMCF1 cells and (B) human GPA transfected CHO-QMCF1 cells using antibodies 6C12 (TPP-3422), 13G7(TPP-3423), 7G4(TPP-3424), and 10F7(TPP-3430).

FIG. 5: Comparison of the sequences of the heavy chain variable domains of humanized variants of 6C12

FIG. 7: (A) Epitope mapping study using alanine scanning peptides for 7 affinity matured Fabs (TPP #7782, 7783, 7778, 7790, 7792, 7793, 7797). The mean binding to each peptide as a percentage of the average of the binding to GP5-1, 5-2, 5-3, 5-4, 5-5, 5-6, 5-7 and 5-8 is plotted. (B) Epitope mapping study using alanine scanning peptides for the humanized and germlined Fab TPP-5906. The mean binding to each peptide as a percentage of the average of the binding to GP5-1, 5-2, 5-3, 5-4, 5-5, 5-6, 5-7 and 5-8 is plotted.

DESCRIPTION

Figure 1:
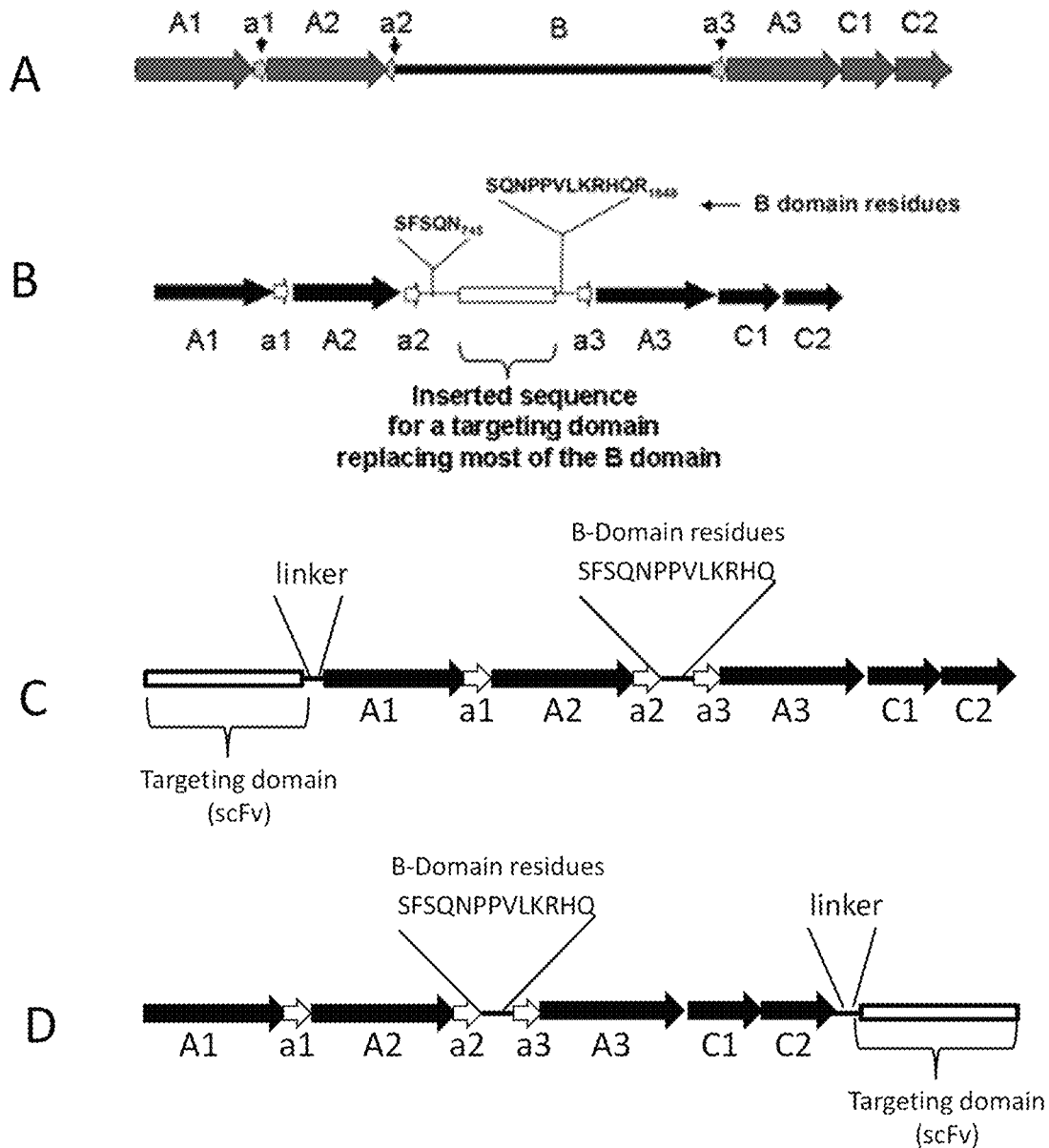
FIG. 1: Schematic drawings of (A) full-length FVIII ("Full Length FVIII, (B) B-domain deleted FVIII ("FVIII-BDD-TD") in which a targeting domain ("TD") is inserted into the B-domain and most of the B-domain is removed, (C) B-domain deleted FVIII in which a targeting domain is fused at the N-terminus of FVIII, and (D) B-domain deleted FVIII in which a targeting domain is fused at the C-terminus of FVIII.

The present disclosure is directed to targeting a coagulation factor to blood cells in order to prolong the circulating half-life and thus reduce the frequency of administration of the coagulation factor. In one embodiment, a targeted coagulation factor is provided that is specifically targeted to erythrocytes through linking the factor to at least one domain that binds to a membrane protein on the surface of erythrocytes.

Erythrocytes, also referred to as red blood cells are very abundant, composing about 50% of total blood volume with a cell density of about $5 \times 10^9$ per ml in normal human blood. In addition erythrocytes have a long lifespan in circulation of about 120 days in humans, 95 days in primates and about 30 days in mice. The abundance and long life-span make erythrocytes an attractive target cell to which to bind a coagulation factor in order to prolong it's circulating half-life. In addition erythrocytes are a common component of clots such that coagulation factors present on the surface of erythrocytes are likely to be available a sites of injury to promote stable clot formation.

The cell surface protein on the erythrocyte to which the coagulation factor is targeted should ideally be an abundant protein in order to facilitate efficient binding of the targeted coagulation factor. In addition, binding to this cell surface protein should not interfere with the function of the erythrocyte. Examples of proteins with these characteristics are glycophorin A and Band 3 (AE1). Approximately $0.5 \times 10^6$ to $1 \times 10^6$ copies of the glycophorin A protein are present on each erythrocyte. Glycophorin A (also referred to GPA in this disclosure) is a structural component of the erythrocyte membrane and also contributes to the overall negative charge of the erythrocyte surface. Similarly, Band 3 is a structural component of the erythrocyte membrane and is present at about $10^6$ copies per erythrocytes. While Band 3 is a structural component of the erythrocyte, it also functions as an anion transporter.

The domain for targeting the coagulation factor to the blood cell may be without limitation an antibody fragment, an antibody, a peptide, a receptor ligand, a carbohydrate, or a small molecule that has a high affinity to a membrane protein on the surface of the blood cell. The blood cell for example is a red blood cell or a platelet.

As used herein, "coagulation factor" refers to a protein that is involved in the coagulation cascade and has predominantly procoagulant activity. Coagulation factors are well known in the art and include without limitation coagulation factors I, II, V, VI, VII, VIII, IX, X, XI, XII, and XIII, and protein S. The coagulation factors may be concentrated from plasma or may be recombinantly produced. If recombinantly produced, the coagulation factors may have an amino acid structure that varies from the natural structure as long as sufficient procoagulant activity is maintained such that the variant is therapeutically useful. In one embodiment, the coagulation factor is a functional FVIII polypeptide, such as without limitation a FVIII concentrate from plasma or recombinantly produced FVIII, or Factor IX (FIX).

"Functional FVIII polypeptide" as used herein denotes a functional polypeptide or combination of polypeptides that are capable, in vivo or in vitro, of correcting human FVIII deficiencies, characterized, for example, by hemophilia A. FVIII has multiple degradation or processed forms in the natural state. These are proteolytically derived from a precursor, one chain protein. A functional FVIII polypeptide includes such single chain protein and also provides for these various degradation products that have the biological activity of correcting human FVIII deficiencies. Allelic variations likely exist. The functional FVIII polypeptides include all such allelic variations, glycosylated versions, modifications and fragments resulting in derivatives of FVIII so long as they contain the functional segment of human FVIII and the essential, characteristic human FVIII functional activity. Those derivatives of FVIII possessing the requisite functional activity can readily be identified by straightforward in vitro tests described herein. Furthermore, functional FVIII polypeptide is capable of catalyzing the conversion of Factor X (FX) to FXa in the presence of Factor IXa (FIXa), calcium, and phospholipid, as well as correcting the coagulation defect in plasma derived from hemophilia A affected individuals. From the published sequence of the human FVIII amino acid sequence and the published information on its functional regions, the fragments that can be derived via restriction enzyme cutting of the DNA or proteolytic or other degradation of human FVIII protein will be apparent to those skilled in the art. Specifically included within functional FVIII polypeptides without limitation is full-length human FVIII (e.g., SEQ ID NO: 1 and SEQ ID NO: 2) and B-domain deleted factor VIII (e.g., SEQ ID NO: 3 and SEQ ID NO: 4) and having the amino acid sequences as disclosed in WO 2006/053299.

The primary polypeptide chain of both full length and B-domain deleted FVIII are normally partially proteolytically cleaved during their expression to produce a mixture of molecules composed of heavy and light chains held together by a non-covalent interaction and a smaller proportion of un-cleaved single chain FVIII. A predominantly single chain FVIII can be generated by mutation of the two residues R1313 and R1648 within full length human FVIII as described previously (Pittman et al, J. Biol Chem (1994) vol 269, p 17329-17337). Mutation of residue R1313 inactivates a proteolytic cleavage site within the B-domain of FVIII while mutation of residue R1648 inactivates a proteolytic cleavage site the lies between the end of the B-domain and the start of the a3 domain. Thus it can be inferred that in the context of a B-domain deleted FVIII molecule the inactivation of the proteolytic cleavage site at R1648 will be sufficient to generate a predominantly single chain FVIII protein. The proteolytic cleavage at R1648 is thought to be catalyzed by an enzyme of the subtilisin family of proteases. The sequence RHQR (residues 1645 to 1648) within full-length human FVIII that borders residue R1648 is similar to that of the furin protease and thus has been called the furin cleavage site. Thus it is well described that inactivation of this furin cleavage site either by mutation or deletion will lead to the generation of a primarily single chain FVIII protein. A potential advantage of a single chain FVIII protein is improved stability because the heavy and light chains will be held together by a covalent bond as well as by non-covalent interactions. A predominantly single chain FVIII protein is also a more homogeneous molecule which is a preferred property of therapeutic products.

FVIII binds with high affinity (KD about 0.5 nM) to von Willebrand Factor (vWF), a protein found in the blood of humans and mammalian species. Thus, FVIII circulates in blood as a complex with vWF. The interaction with vWF reduces clearance of FVIII via the liver presumably because vWF reduces binding to the clearance receptor. The binding site for vWF within FVIII lies primarily within the acidic a3 domain, a 43 amino acid domain between the B-domain and the A3 domain (Fay, Int. J Hemat (2006) 83, 103-108). Deletion of the a3 domain was reported to prevent binding to vWF and result in a shorter half-life in mice (Tang et al 2013, Hemophilia 19, 539-545). While vWF binding to FVIII prolongs circulation half-life it is possible that vWF binding might interfere with the binding of a targeted FVIII molecule to erythrocytes by sterically masking the ability of the targeting moiety to bind to its target on the erythrocyte.

"Procoagulant activity" of FVIII refers to the activity of FVIII in the coagulation cascade. FVIII itself does not cause coagulation, but plays an essential role in the coagulation cascade. The role of FVIII in coagulation is to be activated to FVIIIa, which is a catalytic cofactor for intrinsic FX activation (Thompson, Semin. Thromb. Hemost. 29:11-22, 2003). FVIII is proteolytically activated by thrombin or FXa, which dissociates it from von Willebrand factor (vWf) and activates its procoagulant function in the cascade. In its active form, FVIIIa functions as a cofactor for the FX activation enzyme complex in the intrinsic pathway of blood coagulation, and it is decreased or nonfunctional in patients with hemophilia A.

"FIX" means coagulation factor IX, which is also known as human clotting factor IX, or plasma thromboplastin component.

As used herein, the term "targeted coagulation factor" refers to a coagulation factor that is coupled with at least one domain that specifically binds to a membrane protein on a blood cell. The targeted coagulation factor should bind potently to the blood cells, for example, with an affinity of less than 10 nM. Binding should be specific to the targeted blood cells, for example, through binding to membrane proteins selectively expressed on the targeted cell.

"Targeting domain" as used herein refers to a moiety that has a high affinity for membrane proteins on target cells. Targeting domains suitable for the present invention include, but are not limited to, antibodies, antibody fragments, such as single chain antibodies (scFv) or FAB fragments, antibody mimetics, and peptides or small molecules with high affinity for membrane proteins on the surface of the blood cells.

The coagulation factor can be coupled with the domain either chemically or by recombinant expression of a fusion protein. Chemical linkage can be achieved by linking together chemical moieties present on the coagulation factor and the targeting domain, including chemical linkages using moieties such as amino, carboxyl, sulfydryl, hydroxyl groups, and carbohydrate groups. A variety of homo- and hetero-bifunctional linkers can be used that have groups that are activated, or can be activated to link to attach these moieties. Some useful reactive groups on linker molecules include maleimides, N-hydroxy-succinamic esters and hyrazides. Many different spacers of different chemical composition and length can be used for separating these reactive groups including, for example, polyethylene glycol (PEG), aliphatic groups, alkylene groups, cycloalkylene groups, fused or linked aryl groups, peptides and/or peptidyl mimetics of one to 20 amino acids or amino acid analogs in length. For example, the domain may be linked with the coagulation factor in such a way that in vivo a functional form of the coagulation factor would be released from its targeted domain or the release occurs at or near the site of biological activity of the coagulation factor in the body.

In another method, the coagulation factor can be fused to a single chain antibody fragment or a peptide, wherein its coding sequence can be genetically linked with the FVIII coding sequence to produce a fusion protein using recombinant technology. Use of scFv may avoid cross-linking of binding sites or determinants thereby avoiding potentially harmful cell membrane modification and cell aggregation.

Accordingly, in one embodiment of the invention, a targeted coagulation factor is provided wherein the linkage attaching the coagulation factor to the targeting domain for targeting the coagulation factor to the blood cell can be cleaved or degraded thereby releasing the coagulation factor from the conjugate.

The targeted coagulation factor as described herein can be prepared by linking (fusing) the above-described scFv capable of binding a determinant expressed on the surface of a red blood cell to the coagulation factor, e.g., FVIII. Moreover, genetic engineering allows the design and synthesis of targeted coagulation factor which can be cleaved by pathophysiologically relevant enzymes that are generated at the site of disease that cannot be attained using chemical conjugation.

As noted above, linkers may also be utilized to join variable heavy and variable light chain fragments. A linker as used herein refers to a chain of as short as about 1 amino acid to as long as about 100 amino acids, or longer. In a further embodiment, the linker is 3, 4, 5, 6, 7, 8, 9, 10, 11, 12, 13, 14, 15, 16, 17, 18, 19, or 20 amino acids in length. In one embodiment, the linker is 13 amino acids in length.

Further, a cleavage sequence, such as the thrombin-sensitive cleavage sequence or other enzyme cleavage sequence, can be inserted in the linker to provide for release of the drug when the RBC to which it is targeted encounters the appropriate cleaving enzyme at the site of the pathological condition, e.g., upon active coagulation. This cleavage sequence may be located within a linker or at a terminus thereof.

In another embodiment, antibody-derived scFv with a thrombin releasing site can be cloned by an upstream primer, which anneals to the carboxy terminus and introduces the sequence including a short peptide linker with the thrombin cleavage site. In still another embodiment, the cleavage site is internal to the targeted coagulation factor itself.

The release of the coagulation factors from their conjugate form (i.e., from the targeted coagulation factor) can be achieved by linking the targeting domain to a site on the coagulation factor that is removed during its activation process, or by using a linker that degrades in a controlled manner by enzymes in the blood. For example, sugar polymers or peptides can be used that are susceptible to general blood proteases or hydrolases. A variety of such technologies is known in the art and has been used to make pro-drugs. The linker could be further engineered to be cleaved specifically at sites where the coagulation factors are most needed, such as sites of inflammation or blood coagulation triggered through trauma. For example, the linker may be susceptible to specific proteases produced only at the desired site of action, such as proteases released by the inflammation process or generated by the blood coagulation cascade. This selective release of the therapeutic protein may lower the potential for side effects and increase the efficiency of the protein at its site of action.

Targeting FVIII and FIX

Targeting FVIII and FIX to the surface of blood cells, such as platelets or red blood cells, may serve to slow the clearance of these coagulation factors by preventing mechanisms that normally eliminate these molecules from circulation. Such mechanism of protein clearance may include the interaction of the free protein in plasma with one or more specific endocytic receptors; proteolysis; secretion via kidneys; and extravasation. For FVIII, LRP1 and the asialoglycoprotein receptor (ASGPR) on liver cells are important means of factor FVIII clearance. The role of proteolysis on the duration of action of FVIII is uncertain. FVIII bound to RBCs, however, may potentially protect against proteolysis by the action of its dense cell surface layer of glycans as has been documented previously for other molecules. Since most plasma FVIII forms complexes with vWF, clearance mechanisms for vWF may also be an important route of plasma FVIII clearance. The mechanisms of vWF clearance are not well characterized. Targeting FVIII to the surface of red blood cells is of particular interest because of their long circulation time. In humans the average life span of red blood cell is about 120 days and the abundance in blood is $5\times10^9$ cells per ml. By comparison the average life span of a platelet is only 7 to 10 days in humans and their abundance is between $1.5\times10^8$ to $4\times10^8$/ml. The longer life span and higher abundance of red blood cells compared to platelets make red blood cells more attractive target cells for increasing the half-life of targeted coagulation factors.

For targeted FVIII to promote coagulation, the molecule must be capable of being processed to a functional form (FVIIIa). Additionally, it may be beneficial if the FVIII has been released from its binding site, e.g. glycophorin A. However it is also possible that activated FVIII that remained bound would also be functional in promoting coagulation via complex formation with FIXa and Factor X. In one embodiment, this is achieved by linking a glycophorin A targeting domain to FVIII in place of the B-domain of FVIII (see FIG. 1). The B-domain is removed in a pro-coagulant environment by thrombin or FXa mediated proteolysis, producing the mature FVIIIa molecule. Thus, upon activation, FVIIIa will be released from glycophorin A and be available for formation of the FX activation complex.

In other embodiments, the targeting domain can be linked to the N-terminus or C-terminus of FVIII in which case a linker sequence containing a protease cleavage site such as a thrombin cleavage site to enable the release of FVIII from the red blood cell surface in a pro-coagulant environment (See FIG. 1).

The linkage between FVIII and the targeting domain can be achieved by covalently binding the targeting domain to reactive groups on FVIII, including amino, sulfhydryl, carboxyl groups and carbonyl groups using cross-linking approaches described herein. Targeting domains can also be coupled to carbohydrate present mostly on the B-domain of the FVIII molecule. For example, mild oxidation of FVIII with periodate produces aldehydes on carbohydrate chains, which can then be reacted with amines or hyrazides, followed optionally by reduction to form more stable linkages.

Free cysteine can be selectively generated on the B-domain of recombinant FVIII through mild reduction with Tris(2-carboxyethyl)phosphine (TCEP), allowing specific linking of the B-domain with a targeting domain that reacts with a free cysteine, such as a domain containing a thiol, triflate, tresylate, aziridine, oxirane, S-pyridyl, or maleimide moiety. Furthermore, FVIII can be modified to replace an amino acid residue with cysteine to provide a specific location for attachment to a targeting domain. If a B-domain deleted FVIII is used, a variety of cysteine muteins of B-domain deleted FVIII, such as those disclosed in WO 2006/053299, can be used to link FVIII with a targeting domain through chemical binding at a surface cysteine residue. Examples of amino acid residues that may be modified to replace an amino acid residue with cysteine include, but not limited to, 81, 129, 377, 378, 468, 487, 491, 504, 556, 570, 1648, 1795, 1796, 1803, 1804, 1808, 1810, 1864, 1911, 2091, 2118, and 2284 (the amino acid residue is designated by its position in the sequence of full-length FVIII).

The coagulation factor may also be coupled to the targeting domain using recombinant technology. Host cells may be transfected with a vector comprising a fusion protein of FVIII and the targeting domain. In one embodiment, the targeting domain may be inserted in place of the B-domain of B-domain deleted FVIII. As illustrated in FIG. 1, the remaining portions of the B-domain are specified that allow for biological processing and removal of the B-domain under physiological conditions. In another embodiment the targeting domain may be inserted at the N-terminus of B-domain deleted FVIII or full length FVIII. In another embodiment the targeting domain may be inserted at the C-terminus of B-domain deleted FVIII or full length FVIII.

The host cell line may be any cell known to those skilled in the art as useful for producing a coagulation factor such as without limitation for FVIII CHO cells, HEK cells, BHK cells, and HKB11 cells (a hybrid of a human embryonic kidney cell line, HEK293 and a human Burkitt B cell lymphoma line, 2B8).

A number of domains can be linked chemically to FVIII, or recombinantly expressed with FVIII, to target FVIII to glycophorin A on the surface of red blood cells. Examples of such domains include, but are not limited to, antibodies against glycophorin A, peptide mimetics, or small molecule mimetics targeting glycophorin A. Antibodies, such as single chain antibodies (scFv) or FAB fragments targeting glycophorin A, are particularly useful as targeting domains.

It has been shown that the B-domain of FVIII can be removed without loss of FVIII function. Additionally, it has been also shown that various B-domain truncated forms of FVIII and B-domain fusions with other protein domains can yield functionally active FVIII. In one aspect, the invention involves targeting domains that can be engineered to insert into, replace, or partially replace the B-domain of FVIII without blocking the normal processing of the molecule to yield active FVIII. For example, using recombinant DNA technology, a FVIII molecule can be produced in which single chain antibody fragments are fused to the C-terminus of the B-domain of FVIII. Alternatively, scFv fragments can also be used to replace the whole or a part of the B-domain of FVIII. This can be achieved through insertion of the DNA sequence encoding the scFv fragments, in frame, after the B-domain coding sequence, or replacing some or all of the B-domain coding sequence. This strategy will preserve thrombin cleavage sites required for normal proteolyic activation of FVIII.

Use of an Antibody as the Targeting Domain

As used herein, an "antibody" refers to a whole antibody and any antigen binding fragment (i.e., "antigen-binding portion") or single chain thereof. The term includes a full-length immunoglobulin molecule (e.g., an IgG antibody) that is naturally occurring or formed by normal immunoglobulin gene fragment recombinatorial processes, or an immunologically active portion of an immunoglobulin molecule, such as an antibody fragment, that retains the specific binding activity. Regardless of structure, an antibody fragment binds with the same antigen that is recognized by the full-length antibody. For example, an anti-glycophorin A monoclonal antibody fragment binds to an epitope of glycophorin A. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are analyzed for utility in the same manner as are intact antibodies.

If an antibody is used as the targeting domain, a single chain fragment of the antibody, such as scFv or Fab fragment, can be used.

Furthermore, it is contemplated that an antigen binding fragment can be encompassed in an antibody mimetic. The term "antibody mimetic" or "mimetic" as used herein is meant a protein that exhibits binding similar to an antibody but is a smaller alternative antibody or a non-antibody protein. Such antibody mimetic can be comprised in a scaffold. The term "scaffold" refers to a polypeptide platform for the engineering of new products with tailored functions and characteristics.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

An "isolated antibody," as used herein, is intended to refer to an antibody which is substantially free of other antibodies having different antigenic specificities (e.g., an isolated antibody that binds to glycophorin A is substantially free of antibodies that bind antigens other than glycophorin A). An isolated antibody that binds to an epitope, isoform or variant of human glycophorin A may, however, have cross-reactivity to other related antigens, e.g., from other species (e.g., glycophorin A species homologs). Moreover, an isolated antibody may be substantially free of other cellular material and/or chemicals.

As used herein, "specific binding" refers to antibody binding to a predetermined antigen. Typically, the antibody binds with an affinity of at least about $10^5$ $M^{-1}$ and binds to the predetermined antigen with an affinity that is higher, for example at least two-fold greater, than its affinity for binding to an irrelevant antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, the term "high affinity" for an IgG antibody refers to a binding affinity of at least about $10^7 M^{-1}$, in some embodiments at least about $10^8 M^{-1}$, in some embodiments at least about $10^9 M^{-1}$, $10^{10} M^{-1}$, $10^{11} M^{-1}$ or greater, e.g., up to $10^{13} M^{-1}$ or greater. However, "high affinity" binding can vary for other antibody isotypes. For example, "high affinity" binding for an IgM isotype refers to a binding affinity of at least about $1.0 \times 10^7 M^{-1}$. As used herein, "isotype" refers to the antibody class (e.g., IgM or IgG1) that is encoded by heavy chain constant region genes. High affinity binding for a scFv refers to binding affinity of at least $10^9 M^{-1}$ or greater.

"Complementarity-determining region" or "CDR" refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1," "CDR2," and "CDR3," respectively. CDRs are involved in antigen-antibody binding, and the CDR3 of the heavy chain comprises a unique region often of particular importance for specific antigen-antibody binding. An antigen-binding site, therefore, may include six CDRs, comprising the CDR regions from each of a heavy and a light chain V region.

As used herein, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). It is envisioned that the antibodies of the present invention may have conservative amino acid substitutions and still retain activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, preferably about 90%, 91%, 92%, 93%, 94%, or 95%, more preferably at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. The invention includes nucleic acid sequences and polypeptide sequences having substantial homology to the specific nucleic acid sequences and amino acid sequences recited herein.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40. (further details found at http://www.invitrogen.com/site/us/en/home/LINNEA-Online-Guides/LINNEA-Communities/Vector-NTI-Community/Sequence-analysis-and-data-management-software-for-PCs/AlignX-Module-for-Vector-NTI-Advance.reg.us.html).

Another method for determining the best overall match between a query sequence (a sequence of the present invention) and a subject sequence, also referred to as a global sequence alignment, can be determined using the CLUSTALW computer program (Thompson et al., Nucleic Acids Research, 1994, 2(22): 4673-4680), which is based on the algorithm of Higgins et al., (Computer Applications in the Biosciences (CABIOS), 1992, 8(2): 189-191). In a sequence alignment the query and subject sequences are both DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty=0.1. For multiple alignments, the following CLUSTALW parameters are preferred: Gap Opening Penalty=10, Gap Extension Parameter=0.05; Gap Separation Penalty Range=8; % Identity for Alignment Delay=40.

The nucleic acids may be present in whole cells, in a cell lysate, or in a partially purified or substantially pure form. A nucleic acid is "isolated" or "rendered substantially pure" when purified away from other cellular components with which it is normally associated in the natural environment. To isolate a nucleic acid, standard techniques such as the following may be used: alkaline/SDS treatment, CsCl banding, column chromatography, agarose gel electrophoresis and others well known in the art.

A goal of the antibody generation campaign was to identify antibodies that bound to cell surface proteins on red blood cells from humans that also cross reacted with other mammalian species, e.g. monkeys. Antibodies that cross react to humans and monkey are essential to enable testing in the monkey before proceeding to human testing. In addition antibodies that bind only to red blood cells and not to other cells types such as peripheral blood mononuclear cells and endothelial cells is essential to avoid off target effects. Furthermore, antibodies that specifically bind to glycophorin A (GPA) are highly desirable because GPA is red blood cell specific, very abundant on the red blood cell surface (0.5 to $1 \times 10^6$ copies per cell) and because knock out of GPA in mice as well as humans who naturally lack GPA have no pathology. Thus antibodies that bind to GPA are unlikely to have undesirable side effects. Although it is known that antibodies against GPA can cause lysis of red blood cells (hemolysis) this requires complement activation which requires large numbers of antibodies to be bound to a given red blood cell. At therapeutic doses of a red blood cell targeted Factor VIII molecule the number of copies per cell is estimated to be less than 100 and thus not sufficient to activate the complement system. Another potentially suitable target on red blood cells is Band3, a transmembrane protein that is also red blood cell specific and very abundant on the red blood cell surface. Therefore candidate antibodies were screened for binding to GPA or Band3.

Two approaches were used to generate antibodies against human red blood cell surface proteins that cross react to monkey red blood cell surface proteins. In one method mice were immunized with intact red blood cells. In a second approach phage display libraries of human antibodies were panned against intact red blood cells. The use of intact red blood cells ensures that the cell surface proteins to which antibodies may be generated are in their native physiologic conformation. This is especially important for cell surface proteins that contain membrane spanning regions and are typically hard to express recombinantly in their native conformation. Details of specific embodiments are provided in the Examples below.

Pharmaceutical Compositions and Uses

The invention also concerns pharmaceutical compositions comprising therapeutically effective amounts of the targeted coagulation factors of the invention and a pharmaceutically acceptable excipient or carrier. "Pharmaceutically acceptable excipient or carrier" is a substance that may be added to the active ingredient to help formulate or stabilize the preparation and causes no significant adverse toxicological effects to the patient. Examples of such excipients or carriers are well known to those skilled in the art and include water, sugars such as maltose or sucrose, albumin, salts, etc. Other excipients or carriers are described, for example, in Remington's Pharmaceutical Sciences (Mack Publishing Co., Easton, Pa., 20$^{th}$ edition, 2000). Such compositions will contain an effective amount of the targeted coagulation factors together with a suitable amount of excipients or carriers to prepare pharmaceutically acceptable compositions suitable for effective administration to a patient in need thereof.

For example, the conjugate may be parenterally administered to subjects suffering from hemophilia A at a dosage that may vary with the severity of the bleeding episode.

In one embodiment, the present invention concerns a method for treating hematological diseases comprising administering an therapeutically effective amount of the aforementioned targeted coagulation factor to a patient in need thereof.

As used herein, "therapeutically effective amount" means an amount of a targeted coagulation factor that is need to provide a desired level of the targeted factor (or corresponding unconjugated factor released from the targeted form) in the bloodstream or in the target tissue. The precise amount will depend upon numerous factors, including, but not limited to the components and physical characteristics of the therapeutic composition, frequency of dosing, intended patient population, individual patient considerations, and the like, and can readily be determined by one skilled in the art.

As used herein, "patient" refers to human or animal individuals receiving medical care and/or treatment.

The polypeptides, materials, compositions, and methods described herein are intended to be representative examples of the invention, and it will be understood that the scope of the invention is not limited by the scope of the examples. Those skilled in the art will recognize that the invention may be practiced with variations on the disclosed polypeptides, materials, compositions and methods, and such variations are regarded as within the ambit of the invention.

The following examples are presented to illustrate the invention described herein, but should not be construed as limiting the scope of the invention in any way.

EXAMPLES

In order that this invention may be better understood, the following examples are set forth. These examples are for the purpose of illustration only, and are not to be construed as limiting the scope of the invention in any manner. All publications mentioned herein are incorporated by reference in their entirety.

Example 1: Anti-GPA Antibody Generation: Mouse Hybridomas

Antibodies against cell surface proteins of human and monkey red blood cells (RBC) were generated by immunization of mice with human red blood cells followed by a boost immunization with monkey red blood cells. Hybridomas were generated from the spleen cells of these mice and these hybriomas were screened first by fluorescence activated cell sorting (FACS) against isolated human and monkey (Cynomolgus monkey and Rhesus monkey) red blood cells (RBC) and then by ELISA against purified human glycophorin A protein (GPA). Isolated RBC were prepared from whole blood from normal human, cynomolgus monkey, and beagle dog, were anticoagulant with sodium heparin (Bioreclamation). 2-3 mL of whole blood was loaded gently on the top of 3 mL Ficoll Plus (Sigma Aldrich) then centrifuged at 500 g for 20 min at room temperature (RT). The RBC pellets were washed 3 times with 10 mL of PBS, and centrifuge 400 g for 10 min at RT. RBC pellets were re-suspended in PBS at the same total volume as the original blood volume to achieve the same RBC cell density as in whole blood and stored at 4° C. Purified human glycophorin A protein was obtained from Sigma Aldrich and coated on ELISA plates at 2 ug/ml. Binding of antibodies to human GPA was detected using appropriate secondary antibodies using methods well known in the art.

Clones that bound to both human and monkey RBC and were positive for GPA binding by ELISA were selected. Antibody clones that bound to human peripheral blood mononuclear cells (PBMC) and human endothelial cells were excluded. A summary of the hybridoma screening cascade is shown in FIG. 2.

Twelve clones were identified as positive for binding to human and monkey red blood cells by FACS and to human GPA by ELISA as shown in Table 1 below. Only background binding was observed on human umbilical vein endothelial cells (HUVEC) and very low binding was seen on dog red blood cells. Hybridoma supernatants were used as a source of the IgG form of the antibodies. Clones 10B7 and 8G8 were excluded from further analysis due to inability to generate VH sequences from these clones.

TABLE 1

| Clone ID | FACS signal (relative flourescence units) | | | | hGPA EC50 (nM) | Subtype H/L | comments from sequencing | FACS to PBMC and HUVEC (specificity) |
| --- | --- | --- | --- | --- | --- | --- | --- | --- |
| | hu RBC | Cyno RBC | dog RBC | HUVEC | | | | |
| 6C12B8/H8 | 3101 | 292 | 1.18 | 0.51 | 0.791 | IgG1/k | 1 HC, 1 LC | negative |
| 13G7G1/C3 | 2879 | 294 | 1.14 | 0.51 | 0.402 | IgG1/k | 1 HC, 1 LC | negative |
| 1B3H1/C9 | 2646 | 271 | 1.1 | 0.45 | 0.297 | IgG1/k | 1 HC, 2 VLs | negative |
| 1E4A2/F8 | 2564 | 272 | 1 | 0.45 | 0.221 | IgG1/k | 1 HC, 1 LC | negative |
| 10F1B10/F3 | 2857 | 280 | 1.04 | 0.49 | 0.192 | IgG1/k | 1 HC, 1 LC | negative |
| 8F9E9/F11 | 2863 | 284 | 1.05 | 0.45 | 0.159 | IgG1/k | 1 HC, 1 LC | negative |
| 1H5B4/H12 | 1.05 | 0.93 | NT | NT | 0.403 | IgG1/k | 1 HC, 1 LC | negative |
| 12C6A6/A5 | 2840 | 7 | 0.96 | 0.46 | 0.266 | IgG1/k | 1 HC, 1 LC | negative |
| 7G4E9/A8 | 2833 | 8 | 0.98 | NT | 0.071 | IgG1/k | 1 HC, 1 LC | Positive |
| 6F1F12/H4 | 2523 | 257 | 1.02 | 0.44 | 0.618 | IgG1/k | 1 HC, 1 LC | negative |

Figure 3:
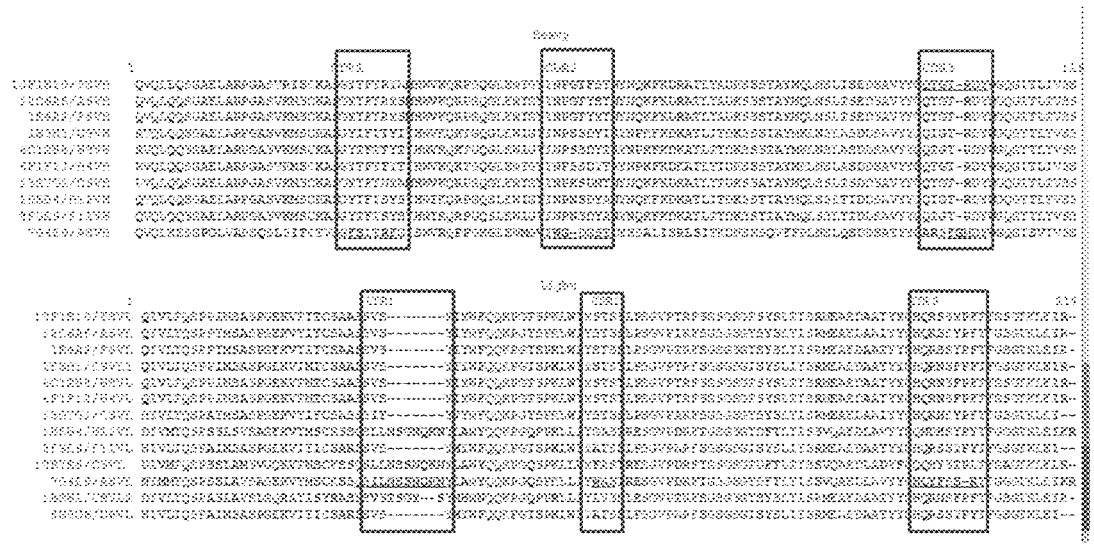
FIG. 3: Alignment of the variable domain sequences of the 10 monoclonal antibodies selected for RBC binding and GPA binding. The heavy chain sequences are shown in the top half of the figure, the light chain in the bottom half. The CDR regions are boxed.
Figure 6:
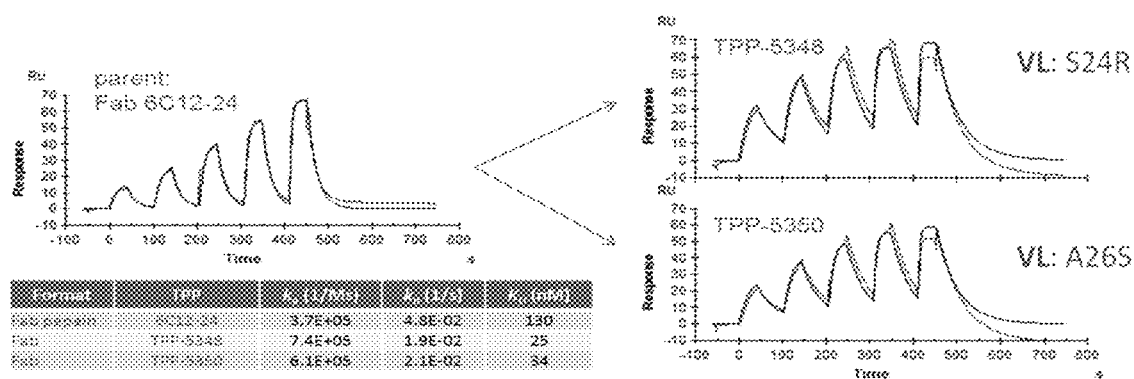
FIG. 6: Kinetic analysis of humanized 6C12 antibody binding to human red blood cell membranes using surface plasmon resonance

The alignment of the sequences of the antibody variable regions from the 10 hybridoma clones that bound to both human and monkey red blood cells demonstrated that 9 out of the 10 antibodies contained unique but closely related complementarity determining regions (CDR), see FIG. 3. Since the CDR sequences are the primary determinant of the antigen recognition specificity of antibodies this suggested that these 9 antibodies are likely to recognize the same or a very similar epitope within GPA. These 9 antibodies will be referred to as the "6C12" cluster. The sequence of the remaining antibody called 7G4E9/A8 exhibited significant sequence differences within the CDR domains compared to the other 9 antibodies indicating 7G4E9/A8 likely recognizes a different epitope on GPA, consistent with the observation that this antibody only bound to human and not to monkey RBC.

Nine of the 10 antibodies were recombinantly expressed in mammalian cells as a single chain Fv format fused to a mouse Fc fragment at the C terminus of the protein to improve expression and stability of the protein. The antibody clone identifier (ID) was shortened to the first identifier, for example "6C12B8/H8" was shortened to "6C12". These scFv-Fc proteins were assessed for binding to human, Rhesus, Cynomolgus and Dog red blood cells by FACS as shown in Table 2. The results indicated that all but two of the antibodies from the "6C12 cluster" bound similarly to Human, and Rhesus RBC and to RBC isolated from 2 out of 3 individual Cynomolgus monkeys. Clones 1B3 and 1H5 had no binding to RBC which may relate to the quality of these protein preparations. The 7G4 antibody in the scFv-Fc format bound to human but not to monkey or dog RBC.

TABLE 2

| | FACS signal (Flourescent units) using scFv-Fc format | | | | | |
|---|---|---|---|---|---|---|
| Clone ID | Human RBC | Rhesus RBC | Cyno #1 RBC | Cyno #2 RBC | Cyno #3 RBC | Dog RBC |
| 6C12 | 2042 | 1451 | 2 | 876 | 602 | 1 |
| 13G7 | 2764 | 1858 | 2 | 981 | 632 | 1 |
| 1B3 | 1 | 1 | 1 | 1 | 1 | 1 |
| 1E4 | 1720 | 969 | 1 | 453 | 487 | 1 |
| 10F1 | 2975 | 2067 | 2 | 842 | 647 | 1 |
| 8F9 | 2342 | 1769 | 2 | 761 | 582 | 1 |
| 1H5 | 1 | 1 | 1 | 1 | 1 | 1 |
| 12C6 | 2899 | 1862 | 2 | 956 | 580 | 1 |
| 7G4 | 1407 | 1 | 1 | 1 | 1 | 1 |

Shown in Table 3 is a summary of the sequences of the CDR regions of 7 of the antibodies that were positive in FACS using the scFv-Fc format. Differences to the sequences of the CDRs of 13G7 antibody are shown (an asterisk [*] indicates an identical residue at that position; and a dash [-] indicates a missing residue).

Based on these data, two antibodies from the 6C12 cluster were selected, namely 13G7 and 6C12, together with 7G4 (the human GPA specific antibody) for more detailed analysis. The IgG forms of these 3 antibodies were purified to homogeneity then tested in ELISA against different preparations of human GPA. The "Sigma GPA" is a crude preparation of human GPA extracted from human red blood cells and is therefore representative of the highly glycosylated form of the native protein. The kinetics of binding to the recombinantly expressed ectodomain of human GPA was determined using surface plasmon resonance. The ectodomain is composed of the 72 amino acids that comprise the extracellular region of GPA:

(SEQ ID NO: 5)
LSTTEVAMHTSTSSSVTKSYISSQTNDTHKRDTYAATPRAHEVSEISV
RTVYPPEEETGERVQLAHHFSEPE.

The lack of binding of the 7G4 IgG antibody to the de-sialylated human GPA (asialo-GPA) and to recombinant GPA (which was poorly glycosylated, data not shown) suggests that the epitope for this antibody contains a glycan component (Table 4). In contrast, the binding of 6C12 and 13G7 antibodies was not dependent on the sialylation status of the human GPA.

An ELISA was run against different preparations of human GPA, see Table 4. EC 50 values were determined from a dilution curve of the antibody. Sigma GPA is partially purified GPA extracted from human red blood cells and purchased from Sigma Chemical Company (cat #G5017), asialo hGPA is human GPA that was desialylated and ECD is the recombinantly expressed ectodomain which is the extracellular portion of GPA.

TABLE 4

| | ELISA EC50 (nM) with purified IgG | | |
|---|---|---|---|
| | Sigma hGPA | Asialo hGPA | recombinant hGPA ECD |
| 6C12 | 0.64 | 0.69 | 0.59 |
| 13G7 | 1.45 | 1.24 | 1.43 |
| 7G4 | 0.33 | no binding | no binding |

Surface plasmon resonance was performed to determine the kinetics of binding of the IgG forms of three antibodies to recombinant human GPA ectodomain as shown in Table 5.

TABLE 3

| | Heavy Chain differences to 13G7 | | | Light Chain differences to 13G7 | | |
|---|---|---|---|---|---|---|
| Ab | CDR1 | CDR2 | CDR3 | CDR1 | CDR2 | CDR3 |
| 13G7 | GYTFTNYA | INPKSDNT | QTGTRDY | SSITY | STS | HQRNSYPFT |
| 6C12 | *****T*T | *SY* | Identical | **VS* | Identical | ***F* |
| 10F1 | ***R | ***GTFS* | Identical | **VS* | Identical | *S*** |
| 12C6 | *****R*S | ***GTYS* | Identical | **VS* | Identical | *S*** |
| 1E4 | *****R*S | ***GTYY* | Identical | **VS* | Identical | *S*** |
| 8F9 | *****S*S | *NYA | Identical | **VS* | A | *S***Y* |
| 7G4 | *FSL*RFG | *WG-DGS* | ARSFGM** | Q**LNSSNQKN* | WA* | **YF*S-R* |

TABLE 5

| Antibody | ka (M$^{-1}$s$^{-1}$) | kd (s$^{-1}$) | KD (nM) | t½ (min) |
|---|---|---|---|---|
| 6C12 | 7.11E+05 | 0.002121 | 2.98 | 5.4 |
| 7G4 | 7.77E+04 | 4.60E−04 | 5.92 | 25.1 |
| 13G7 | 7.64E+04 | 4.05E−04 | 5.3 | 28.5 |

To further confirm that antibodies 6C12 and 13G7 bind specifically to GPA, Chinese hamster ovary (CHO) cells (QMCF1 cells) were transfected with an expression plasmid encoding human GPA. While the 6C12 and 13G7 antibodies failed to bind to the non-transfected parental QMCF1 cells, both antibodies bound well to the QMCF1 cells transfected with the human GPA expression plasmid (FIG. 4). The expression of human GPA on the surface was confirmed by the binding of anti-GPA tool antibody 10F7.

Based on these data, the 6C12 antibody sequence was selected for sequence humanization and affinity optimization. However, it should be recognized that the 6C12 antibody is representative of all of the nine antibodies identified in the 6C12 cluster since these antibodies all have closely related CDR sequences and similar binding to red blood cells.

Provided in SEQ ID NOs: 6-14 are the sequences of the murine hybridoma derived antibodies as scFv-Fc formats. The domain structure of these sequences is (from N to C terminus): Signal peptide, light chain variable domain, artificial linker (GGGGSGGGGSGGGGS, SEQ ID NO: 15), heavy chain variable domain, 230 amino acid Fc fragment domain. The artificial linker sequence between VH and VL domains is underlined. Bold text shows the heavy chain variable domain (located at the N-terminal side of the linker) and the light chain variable domain (located at the C-terminal side of the linker). The C-terminal 230 amino acids is the common antibody Fc domain that was added to each antibody to improve expression and stability.

Example 3: Humanization and Germlining of Select Antibodies

In order to humanize the anti-GPA antibody 6C12 the mouse framework regions are replaced by human framework regions. While the variable regions remain unchanged the framework sequences can affect the ability of the antibody to bind to its epitope. Thus it is important to test a number of different human framework sequences for both the heavy and light chains. Humanization of antibody 6C12 was performed by generating a number of variants containing different pairs of heavy chain (columns) and light chain (rows) framework sequences as outlined in Table 6 and 7. A total of 23 variants were generated using 8 different heavy chain framework sequences and 3 different light chain framework sequences.

TABLE 6

Sequences of Light chains (Vk) and
heavy chains (VH) of humanized 6C12 antibodies
One Vk and one VH chain was combined
in the combinations shown in Table 10 to
generate 23 different humanized IgG forms of 6C12

| Antibody | Seq ID | Sequence |
|---|---|---|
| Hu6C12Vk.1 | 16 | DIQLTQSPSFLSASVGDRVTITCSAASSVS YIYWYQQKPGKAPKLLIYSTSTLPSGVPSR FSGSGSGTEFTLTISSLQPEDFATYYCHQR NSFPFTFGQGTKLEIK |
| Hu6C12Vk.1a | 17 | DIQLTQSPSFLSASVGDRVTITCSAASSVS YIYWYQQKPGKAPKLLIYSTSTLPSGVPSR FSGSGSGTEYTLTISSLQPEDFATYYCHQR NSFPFTFGQGTKLEIK |
| Hu6C12Vk.1b | 18 | DIQLTQSPSFLSASVGDRVTITCSAASSVS YIYWFQQKPGKAPKLLIYSTSTLPSGVPSR FSGSGSGTEYTLTISSLQPEDFATYYCHQR NSFPFTFGQGTKLEIK |
| Hu6C12 VH.1 | 19 | EVQLVQSGAEVKKPGASVKVSCKASGYTFT TYTIHWVRQAPGQGLEWMGYINPSSDYTRY NPKFKDRVTMTTDTSTSTAYMELRSLRSDD TAVYYCARGTRDYWGQGTTVTVSS |
| Hu6C12 VH.1a | 20 | EVQLVQSGAEVKKPGASVKVSCKASGYTFT TYTIHWVRQAPGQGLEWMGYINPSSDYTRY NPKFKDRVTMTTDTSTSTAYMELRSLRSDD TAVYYCQRGTRDYWGQGTTVTVSS |
| Hu6C12 VH.1c | 21 | EVQLVQSGAEVKKPGASVKVSCKASGYTFT TYTIHWVRQAPGQGLEWMGYINPSSDYTRY NPKFKDRVTMTTDTSTSTAYMELRSLRSDD TAVYYCQTGTRDYWGQGTTVTVSS |
| Hu6C12 VH.1d | 22 | EVQLVQSGAEVKKPGASVKVSCKASGYTFT TYTIHWVRQAPGQGLEWMGYINPSSDYTRY NPKFKDRVTLTTDTSTSTAYMELRSLRSDD TAVYYCQRGTRDYWGQGTIVTVSS |
| Hu6C12 VH.1e | 23 | EVQLVQSGAEVKKPGASVKVSCKASGYTFT TYTIHWVRQAPGQGLEWMGYINPSSDYTRY NPKFKDRVTLTTDTSTSTAYMELRSLRSDD TAVYYCATGTRDYWGQGTIVTVSS |
| Hu6C12 VH.1f | 24 | EVQLVQSGAEVKKPGASVKVSCKASGYTFT TYTIHWVRQAPGQGLEWMGYINPSSDYTRY NPKFKDRVTLTTDTSTSTAYMELRSLRSDD TAVYYCQTGTRDYWGQGTIVTVSS |
| Hu6C12 VH.1g | 25 | EVQLVQSGAEVKKPGASVKVSCKASGYTFT TYTIHWVRQAPGQGLEWIGYINPSSDYTRY NPKFKDRVTLTTDKSTSTAYMELRSLRSDD TAVYYCQTGTRDYWGQGTTVTVSS |

TABLE 7

|  | Hu6C12 VH.1 | Hu6C12 VH.1a | Hu6C12 VH.1b | Hu6C12 VH.1c | Hu6C12 VH.1d | Hu6C12 VH.1e | Hu6C12 VH.1f | Hu6C12 VH.1g |
|---|---|---|---|---|---|---|---|---|
| Hu6C12Vk.1 |  | Hu6C12-1 | Hu6C12-2 | Hu6C12-3 | Hu6C12-4 | Hu6C12-5 | Hu6C12-6 | Hu6C12-7 |
| Hu6C12Vk.1a | Hu6C12-9 | Hu6C12-10 | Hu6C12-11 | Hu6C12-12 | Hu6C12-13 | Hu6C12-14 | Hu6C12-15 | Hu6C12-16 |
| Hu6C12Vk.1b | Hu6C12-17 | Hu6C12-18 | Hu6C12-19 | Hu6C12-20 | Hu6C12-21 | Hu6C12-22 | Hu6C12-23 | Hu6C12-24 |

The antibodies in the above table were expressed in the IgG format and their binding to human glycophorin A was tested using an ELISA assay and the results are in Table 8.

TABLE 8

| Antibody variant | EC50 (nM) |
|---|---|
| 6C12 parental | 0.326 |
| Hu 6C12-1 | Low or no binding observed |
| Hu 6C12-2 | 8.649 |
| Hu 6C12-3 | 2.167 |
| Hu 6C12-4 | Low or no binding observed |
| Hu 6C12-5 | 8.450 |
| Hu 6C12-6 | 3.457 |
| Hu 6C12-7 | 1.784 |
| Hu 6C12-9 | Low or no binding observed |
| Hu 6C12-10 | Low or no binding observed |
| Hu 6C12-11 | Low or no binding observed |
| Hu 6C12-12 | 10.439 |
| Hu 6C12-13 | Low or no binding observed |
| Hu 6C12-14 | Low or no binding observed |
| Hu 6C12-15 | 9.685 |
| Hu 6C12-16 | 4.805 |
| Hu 6C12-17 | Low or no binding observed |
| Hu 6C12-18 | Low or no binding observed |
| Hu 6C12-19 | 0.876 |
| Hu 6C12-20 | 0.393 |
| Hu 6C12-21 | 34.530 |
| Hu 6C12-22 | 0.886 |
| Hu 6C12-23 | 0.374 |
| Hu 6C12-24 | 0.282 |

The binding of the humanized variants to intact red blood cells (RBC) from humans (Hu01 to 03; 3 individuals), Rhesus monkey (Rh01 to 03; 3 individuals) and Cynomolgus monkey (Cy01 to 02; 2 individuals) was measured by fluorescence activated cell sorting (FACS). The results, shown in Table 9, indicate that some variants (−3, −7, −19, −20, −22, −23, −24) retained binding to both human and monkey RBC. Some variants (−3, −5, −6, −11, −12, −14, −15, −16) had reduced binding to human RBC. Some variants (−1, −4, −9, −10, −13, −17, −18, −21) lost all binding to human RBC. There was a good correlation between the GPA ELISA results and the binding to human RBC. In particular, variants 19, 20, 22, 23, 24 maintained the highest levels of binding to both human and monkey RBC and so were selected as possible therapeutic candidates. Humanized variants 20, 23 and 24 were preferred due to the differences to germline sequences. The light chain sequence of Hu6C12-20, Hu6C12-23 and Hu6C12-24 are identical. The heavy chain sequences of Hu6C12-20, Hu6C12-23 and Hu6C12-24 differ from each other by only 1 to 3 amino acids. The humanized antibodies that retained binding to human GPA and human RBC contained combinations of 3 different light chains (VK.1, VK.1a and VK.1b) and six different heavy chains (VH.1b, VH.1c, VH.1d, VH.1e, VH.1f, VH.1g), the sequences of which are included in Appendix A. The most promising candidates Hu6C12-20, Hu6C12-23 and Hu6C12-24 are composed of the same light chain VK.1b combined with the heavy chains VH.1c, VH.1f and VH.1g respectively. In particular Hu6C12-24 is preferred based on the lowest number of amino acid differences from human germline sequences.

TABLE 9

Binding of humanized 6C12 variants to red blood cells measured by fluorescence activated cell sorting (FACS). Values are fluorescence intensnity

| Antibody | RBC Samples | | | | | | | |
|---|---|---|---|---|---|---|---|---|
|  | Hu01 | Hu02 | Hu03 | Rh01 | Rh02 | Rh03 | Cy01 | Cy02 |
| 6C12 Parental | 3515 | 2540 | 2678 | 3781 | 3406 | 3181 | 2572 | 2566 |
| Hu 6C12-1 | 3 | 3 | 2 | 1194 | 1117 | 1135 | 742 | 801 |
| Hu 6C12-2 | 897 | 603 | 716 | 1526 | 1396 | 1380 | 962 | 1033 |
| Hu 6C12-3 | 1073 | 739 | 862 | 1727 | 1599 | 1604 | 1115 | 1203 |
| Hu 6C12-4 | 3 | 3 | 2 | 1074 | 1319 | 1335 | 884 | 989 |
| Hu 6C12-5 | 921 | 625 | 758 | 1658 | 1553 | 1556 | 1071 | 1135 |
| Hu 6C12-6 | 909 | 634 | 786 | 1638 | 1523 | 1542 | 1063 | 1100 |
| Hu 6C12-7 | 1233 | 945 | 1099 | 2055 | 1941 | 1924 | 1365 | 1432 |
| Hu 6C12-9 | 3 | 3 | 2 | 1055 | 1059 | 1048 | 680 | 756 |
| Hu 6C12-10 | 3 | 3 | 2 | 1413 | 1311 | 1306 | 872 | 973 |
| Hu 6C12-11 | 548 | 315 | 387 | 1531 | 1435 | 1424 | 960 | 1022 |
| Hu 6C12-12 | 646 | 393 | 484 | 1480 | 1396 | 1409 | 959 | 1028 |
| Hu 6C12-13 | 3 | 3 | 2 | 1371 | 1276 | 1271 | 824 | 937 |
| Hu 6C12-14 | 514 | 298 | 384 | 1481 | 1482 | 1476 | 978 | 1083 |
| Hu 6C12-15 | 590 | 375 | 482 | 1520 | 1480 | 1492 | 1007 | 1074 |
| Hu 6C12-16 | 895 | 637 | 786 | 2005 | 1856 | 1872 | 1271 | 1358 |
| Hu 6C12-17 | 3 | 3 | 2 | 144 | 151 | 151 | 104 | 127 |
| Hu 6C12-18 | 3 | 3 | 2 | 1134 | 1091 | 1064 | 741 | 876 |
| Hu 6C12-19 | 1633 | 1272 | 1444 | 1620 | 1512 | 1522 | 1042 | 1245 |
| Hu 6C12-20 | 1672 | 1298 | 1464 | 1673 | 1620 | 1549 | 1071 | 1253 |
| Hu 6C12-21 | 3 | 3 | 2 | 1466 | 1329 | 1342 | 908 | 1119 |
| Hu 6C12-22 | 1572 | 1171 | 1331 | 1529 | 1489 | 1452 | 991 | 1173 |
| Hu 6C12-23 | 1682 | 1301 | 1458 | 1714 | 1682 | 1702 | 1142 | 1322 |
| Hu 6C12-24 | 2250 | 1852 | 2098 | 2332 | 2541 | 2370 | 1665 | 1769 |
| Hu igG isotype | 3 | 3 | 2 | 2 | 2 | 2 | 2 | 3 |

Figure 5:
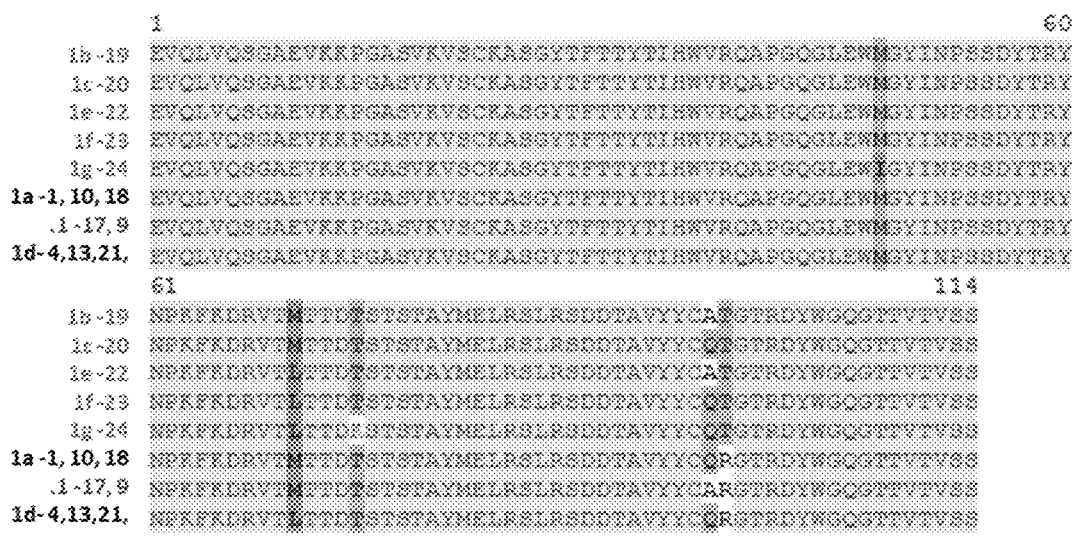

Comparison of the sequences of the heavy chain variable domains of humanized variants of 6C12 (FIG. 5) demonstrates that changing residue T98 to R was responsible for loss of binding to human GPA. Thus residue T98 is implicated as being critical for the binding to GPA. Variant Hu6C12-17 also had poor binding to monkey GPA suggesting that residue 97 plays a role in binding to monkey GPA and Q rather than A is preferred in this position for improved binding.

Generation of germlined variants of Hu6C12-24 and testing of the binding to GPA was performed. Germlining is a process in which residues that differ from human germline sequences are changed back to the germline residue. This is performed to further reduce the risk of immunogenicity but can also provide information about which residues are critical for binding of the antibody to its target. Comparison of the sequence of the variable domains of Hu6C12-24 with sequences of human germline identified amino acids that differ from germline.

For the heavy chain variable domain 22 germline deviations were identified (7 in framework regions, 15 in CDR regions). For the light chain variable domain 16 germline deviations were identified (2 in framework regions, 14 in CDR regions). Each residue that deviated from germline was individually changed to the germline residue and the protein was expressed as a Fab format in E. coli. GPA is a transmembrane protein and therefore the correct physiologic structure of GPA may only be present when the protein is present within a cell membrane. In order to evaluate binding of antibodies to GPA in the native context of the red blood cell membrane we made use of isolated red blood cell membranes, also called red blood cells ghosts. These membranes are prepared by first isolating red blood cells from citrated whole blood. Citrated whole blood is layered on to Ficol and centrifuged at low speed for 20 minutes to pellet the red blood cells. The supernatant containing plasma and other blood cells is discarded and the red blood cell pellet is subsequently washed 3 times in 10 cell volumes of phosphate buffered saline (PBS). A 10 ml pellet of purified red blood cells is resuspended in 30 ml of cold low osmorality 20 mM phosphate buffer (pH7.4) and incubated for 30 mins to break open the RBC. After Centrifugation at 10,000 rpm for 30 min at 5° C. the hemoglobin containing supernatant is discarded. To the membrane pellet another 30 ml of 20 mM phosphate buffer is added and the sample centrifuged again at 10,000 rpm for 30 min at 5° C. to pellet the membrane fraction. This wash and centrifugation step is repeated another 4 times. The red blood cell membranes are then resuspended in 20 mL of PBS to achieve an equivalent of approximately 2.5E9 cells/mL and stored frozen at -20° C. Binding of antibodies to RBC ghost can be measured by ELISA in which the RBC ghost suspension ($5 \times 10^6$ in 100 ul PBS) was added to each well of flat bottom 96-well ELISA microtiter plates (2HB, Immunolon) and the plates incubated overnight at 4° C. The plates were blocked with Starting blocking buffer (Thermo Fisher) for 2 hours at room temperature (RT). Antibodies or other test molecules were added to each well and incubated for 1.5 hours at RT. After 4 washes 100 ul of an appropriate detection antibody was added to each well and incubated for 1 hour at RT. After 4 washes the detection antibody was measured using appropriate detection reagents.

The germlined variants were assayed for binding to GPA protein and to RBC ghost membranes by ELISA and the results are summarized in Table 10. Binding and expression is relative to that of the hu6C12-24 parental antibody. The Rel Expn column indicates the expression level of the Fab protein relative to that of the parental Fab TPP-4935. The hRBC column is binding to human RBC membranes. The natGPA and recGPA columns are binding to native human GPA protein and recombinant human GPA ectodomain protein respectively.

TABLE 10

Effect of single amino acid germline reversions upon binding to human GPA or human RBC ghost membranes by ELISA. (VL; variable light chain, VH; variable heavy chain.)

| ID | Variant | Rel Expn | Binding by ELISA | | |
|---|---|---|---|---|---|
| | | | hRBC | natGPA | recGPA |
| TPP-4935 | Parental | 1.00 | 0.99 | 1.00 | 0.99 |
| TPP-5316 | VH: (E1Q) | 1.02 | 1.16 | 1.33 | 1.29 |
| TPP-5317 | VH: (T31S) | 0.99 | 0.68 | 1.36 | 1.34 |
| TPP-5318 | VH: (T33Y) | 0.97 | 0.40 | 0.21 | 0.15 |
| TPP-5319 | VH: (I34M) | 1.00 | 0.85 | 0.99 | 1.08 |
| TPP-5320 | VH: (I48M) | 1.00 | 0.99 | 1.24 | 1.35 |
| TPP-5321 | VH: (Y50I) | 1.03 | 0.33 | 0.06 | 0.06 |
| TPP-5322 | VH: (S55G) | 1.05 | 0.82 | 0.86 | 0.91 |
| TPP-5323 | VH: (D56G) | 1.05 | 1.72 | 1.49 | 1.64 |
| TPP-5324 | VH: (Y57S) | 1.01 | 0.41 | 0.53 | 0.34 |
| TPP-5325 | VH: (R59S) | 0.98 | 0.22 | 0.07 | 0.06 |
| TPP-5326 | VH: (N61A) | 0.98 | 0.45 | 0.56 | 0.53 |

TABLE 10-continued

Effect of single amino acid germline reversions upon binding to human GPA or human RBC ghost membranes by ELISA. (VL; variable light chain, VH; variable heavy chain.)

| ID | Variant | Rel Expn | Binding by ELISA | | |
|---|---|---|---|---|---|
| | | | hRBC | natGPA | recGPA |
| TPP-5327 | VH: (P62Q) | 0.99 | 0.74 | 0.98 | 0.99 |
| TPP-5328 | VH: (K65Q) | 0.96 | 0.61 | 0.89 | 0.91 |
| TPP-5329 | VH: (D66G) | 0.99 | 1.00 | 1.02 | 1.12 |
| TPP-5330 | VH: (L70M) | 1.02 | 0.91 | 1.20 | 1.29 |
| TPP-5331 | VH: (T72R) | 1.01 | 0.96 | 1.11 | 1.07 |
| TPP-5332 | VH: (K74T) | 0.98 | 0.58 | 0.83 | 0.87 |
| TPP-5333 | VH: (R84S) | 0.99 | 0.59 | 0.92 | 0.97 |
| TPP-5334 | VH: (D89E) | 0.97 | 0.72 | 0.80 | 0.89 |
| TPP-5335 | VH: (Q97A) | 0.97 | 0.65 | 0.77 | 0.83 |
| TPP-5336 | VH: (T98R) | 0.97 | 0.23 | 0.06 | 0.06 |
| TPP-5340 | VL: (S24R) | 1.00 | 0.90 | 1.17 | 1.23 |
| TPP-5341 | VL: (A26S) | 0.98 | 0.82 | 1.03 | 1.19 |
| TPP-5342 | VL: (S27Q) | 0.97 | 0.75 | 0.91 | 0.95 |
| TPP-5343 | VL: (S28G) | 0.98 | 0.71 | 0.95 | 0.97 |
| TPP-5344 | VL: (V29I) | 0.98 | 0.60 | 0.84 | 0.77 |
| TPP-5345 | VL: (I32L) | 0.99 | 0.43 | 0.60 | 0.48 |
| TPP-5346 | VL: (Y33A) | 1.05 | 0.42 | 0.04 | 0.03 |
| TPP-5347 | VL: (F35Y) | 1.04 | 0.43 | 0.52 | 0.35 |
| TPP-5348 | VL: (S49A) | 0.99 | 1.76 | 1.62 | 1.50 |
| TPP-5349 | VL: (T50A) | 0.96 | 0.27 | 0.12 | 0.09 |
| TPP-5350 | VL: (P54Q) | 0.97 | 1.64 | 1.45 | 1.70 |
| TPP-5351 | VL: (Y70F) | 0.94 | 0.71 | 0.71 | 0.78 |
| TPP-5352 | VL: (H88Q) | 1.00 | 0.34 | 0.36 | 0.26 |
| TPP-5353 | VL: (R90L) | 0.91 | 0.20 | 0.04 | 0.04 |
| TPP-5354 | VL: (F93Y) | 0.96 | 0.35 | 0.33 | 0.17 |
| TPP-5355 | VL: (F95Y) | 0.97 | 1.18 | 1.16 | 1.35 |
| TPP-5357 | VL: (S24R)# | 1.02 | 0.37 | 0.23 | 0.23 | on the backbone of insertion of serine at position 30 to convert CDR loop 1to 11 amino acids These results demonstrate that for many of the non-germline residues the reversion to germline had a negative effect on binding to GPA protein and/or red blood cells. In particular amino acid changes in the heavy chain of T33Y, Y50I, R59S, and T98R significantly reduced binding demonstrating that these residues are important for recognition of the epitope. In particular amino acid changes in the light chain of Y33A, T50A, H88Q, R90L, F93Y significantly reduced binding demonstrating that these residues are also important for recognition of the epitope. However, 6 residues in the heavy chain (E1Q, I48M, D56G, D66G, L70M, T72R) and 5 residues in the light chain (S24R, A26S, S49A, P54Q, F95Y) were identified that either had no effect on binding or increased binding. Residues D56G, S49A and P54Q significantly increased the binding to GPA and to RBC membranes.

It was noted that the CDR-L1 loop has an untypical length of 10 amino acids and that repair of this loop length by insertion of a serine at position 30 abrogated binding to GPA by about 70 to 80% indicating the importance the atypical CDR-L1 loop configuration.

Critical residues where more than 80% of the binding to GPA was inhibited when mutated to germline were identified in all CDRs. A predominant role of CDR-L3 was revealed by the mutations H88Q, R90L and F93Y within CDR-L3 that dramatically reduced the binding to GPA. These data also confirm the finding from the humanization that the untypical heavy chain CDR3 residue T98 is critical for binding.

Combining individual germline reversions that have no effect on binding or improve binding within a single protein was also examined. The results of these combinations is shown in Table 11 (Rel Expn: relative expression level of the Fab protein; Hu-nat GPA: native human GPA protein; Hurec GPA; recombinant human GPA ectodomain protein; hRBC: human RBC membranes; Cyno_rec GPA: Cynomolgus monkey recombinant GPA ectodoamin; Cyno RBC: Cynomolgus monkey RBC membranes. Proteins or membranes were coated on plates and binding of antibodies was determined by ELISA. Binding is reported as relative to the parental antibody. Blank cells indicate that binding was not tested).

TABLE 11

Combinations of germline reversions of Hu6C12-24 and the effect of binding to GPA and RBC.

| | | | Binding in ELISA relative to parental Fab | | | | |
|---|---|---|---|---|---|---|---|
| ID | Variant | Rel Expn | Hu_nat GPA | Hu_rec GPA | hRBC | Cyno_rec GPA | Cyno RBC |
| TPP-4935 | parent Fab | 1.0 | 1.0 | 1.0 | 1.0 | 1.0 | |
| TPP-5674 | VH: (I48M, L70M) | 1.4 | 1.4 | 1.5 | 0.7 | 1.1 | |
| TPP-5675 | VH: (I48M, L70M, T72R) | 1.1 | 0.8 | 1.1 | 0.7 | 1.0 | |
| TPP-5676 | VH: (I48M, D66G) | 1.1 | 1.3 | 1.5 | 0.7 | 1.1 | |
| TPP-5677 | VH: (I48M, D66G, L70M) | 1.1 | 1.8 | 1.8 | 0.8 | 1.2 | |
| TPP-5678 | VH: (I48M, D66G, L70M, T72R) | 1.1 | 1.2 | 1.1 | 0.8 | 1.2 | |
| TPP-5695 | VH: (L70M, T72R) | 1.1 | 0.9 | 1.0 | 0.9 | 1.1 | |
| TPP-5696 | VH: (D66G, L70M) | 1.0 | 1.3 | 1.2 | 1.0 | 1.2 | |
| TPP-5697 | VH: (D66G, L70M, T72R) | 1.0 | 1.2 | 1.3 | 1.1 | 1.2 | |
| TPP-5698 | VL: (S24R, A26S) | 1.3 | 1.6 | 1.7 | 0.6 | 1.0 | |
| TPP-5699 | VL: (S49A, P54Q) | 1.2 | 3.8 | 3.2 | 3.1 | 0.8 | |
| TPP-5700 | VL: (S24R, A26S, F95Y) | 1.3 | 2.5 | 2.4 | 2.5 | 1.2 | |
| TPP-5701 | VL: (S49A, P54Q, F95Y) | 1.1 | 4.6 | 3.9 | 4.7 | 1.0 | |
| TPP-5702 | VL: (S24R, A26S, S49A, P54Q, F95Y) | 1.2 | 5.2 | 4.3 | 10.2 | 1.1 | 1.1 |
| TPP-5703 | VL: (N91S) | 1.1 | 2.1 | 1.1 | 0.7 | 0.9 | |
| TPP-5704 | VL: (N91D) | 1.1 | 1.0 | 1.1 | 0.9 | 1.0 | |
| TPP-5835 | VL: (S24R, A26S, S49A, P54Q, F95Y); VH: (I48M, L70M) | 1.3 | 5.2 | 4.3 | 10.3 | 1.1 | 1.4 |
| TPP-5836 | VL: (S24R, A26S, S49A, P54Q, F95Y); VH: (I48M, L70M, T72R) | 1.2 | 5.1 | 4.1 | 4.7 | 1.0 | |
| TPP-5837 | VL: (S24R, A26S, S49A, P54Q, F95Y); VH: (I48M, D66G) | 1.2 | 5.2 | 4.5 | 9.1 | 1.1 | |
| TPP-5838 | VL: (S24R, A26S, S49A, P54Q, F95Y); VH: (I48M, D66G, L70M) | 1.4 | 5.6 | 4.7 | 9.3 | 1.1 | |
| TPP-5839 | VL: (S24R, A26S, S49A, P54Q, F95Y); VH: (I48M, D66G, L70M, T72R) | 1.2 | 5.8 | 4.7 | 5.8 | 1.2 | 2.3 |
| TPP-5840 | VL: (S24R, A26S, S49A, P54Q, F95Y); VH: (L70M, T72R) | 1.0 | 5.3 | 4.2 | 6.0 | 1.0 | |
| TPP-5841 | VL: (S24R, A26S, S49A, P54Q, F95Y); VH: (D66G, L70M) | 1.3 | 5.8 | 4.7 | 11.9 | 1.2 | 2.1 |
| TPP-5842 | VL: (S24R, A26S, S49A, P54Q, F95Y); VH: (D66G, L70M, T72R) | 1.1 | 5.9 | 4.7 | 7.0 | 1.1 | |
| TPP-5906 | VL: (S24R, A26S, S49A, P54Q, F95Y); VH: (I48M, D56G, D66G, L70M, T72R) | 0.9 | 12.9 | 7.2 | 93.5 | 1.4 | 2.5 |
| TPP-5907 | VL: (S24R, A26S, S49A, P54Q, F95Y); VH: (I48M, S54G, D56G, D66G, L70M, T72R) | 1.0 | 12.3 | 6.9 | 90.1 | 1.4 | 1.9 |
| TPP-5373 | VL: (F36Y, Y71F) | 1.0 | 0.1 | 0.1 | 0.3 | | |
| TPP-5356 | VL: (F35Y, Y70F) | 1.0 | 0.7 | 0.6 | 0.7 | | |
| TPP-5337 | VH: (Q97A, T98R) | 1.0 | 0.1 | 0.1 | 0.3 | | |
| TPP-5338 | VH: (E1Q, I48M, L70M, T72R, K74T, R84S, D89E) | 1.0 | 0.5 | 0.4 | 0.5 | | |
| TPP-5339 | VH: (E1Q, I48M, L70M, T72R, K74T, R84S, D89E, Q97A, T98R) | 1.0 | 0.0 | 0.0 | 0.3 | | |
| TPP-5374 | VLdelS31 | 1.0 | 0.1 | 0.2 | 0.3 | | |

In particular when 10 or 11 of the germline reversions were included in to a single protein as in TPP-5906 and TPP-5907 the binding to human GPA protein was increased 7-fold to 13-fold and the binding to human RBC membranes was increased 90-fold. Binding to Cyno GPA protein and Cyno RBC membranes was also increased for these variants by about 1.5 to 2.5-fold. These data demonstrate that mutations VL: (S24R, A26S, S49A, P54O, F95Y); VH: (I48M, D56G, D66G, L70M, T72R) or VL: (S24R, A26S, S49A, P54O, F95Y); VH: (I48M, S54G, D56G, D66G, L70M, T72R) could improve the binding to human and cyno monkey GPA and red blood cells while reducing the sequence differences to human germline. Sequences of the humanized 6C12 parental Fab antibody and the final germlined 6C12 Fab antibodies is shown in Table 12.

TABLE 12

Sequences of humanized 6C12 parental Fab antibody and final germlined 6C12 Fab antibody

| Antibody | Seq ID | Sequence |
|---|---|---|
| TPP-4935 Heavy chain | 26 | EVQLVQSGAEVKKPGASVKVSCKASGYTFTT<br>YTIHWVRQAPGQGLEWIGYINPSSDYTRYNP<br>KFKDRVTLTTDKSTSTAYMELRSLRSDDTAV<br>YYCQTGTRDYWGQGTTVTVSSASTKGPSVFP<br>LAPSSKSTSGGTAALGCLVKDYFPEPVTVSW<br>NSGALTSGVHTFPAVLQSSGLYSLSSVVTVP<br>SSSLGTQTYICNVNHKPSNTKVDKKVEPKSC<br>AAGS |
| TPP-4935 Light chain | 27 | DIQLTQSPSFLSASVGDRVTITCSAASSVSY<br>IYWFQQKPGKAPKLLIYSTSTLPSGVPSRFS<br>GSGSGTEYTLTISSLQPEDFATYYCHQRNSF<br>PFTFGQGTKLEIKRTVAAPSVFIFPPSDEQL<br>KSGTASVVCLLNNFYPREAKVQWKVDNALQS<br>GNSQESVTEQDSKDSTYSLSSTLTLSKADYE<br>KHKVYACEVTHQGLSSPVTKSFNRGEC |
| TPP-5906 Heavy Chain | 28 | EVQLVQSGAEVKKPGASVKVSCKASGYTFTT<br>YTIHWVRQAPGQGLEWMGYINPSSGYTRYNP<br>KFKGRVTMTRDKSTSTAYMELRSLRSDDTAV<br>YYCQTGTRDYWGQGTTVTVSSASTKGPSVFP<br>LAPSSKSTSGGTAALGCLVKDYFPEPVTVSW<br>NSGALTSGVHTFPAVLQSSGLYSLSSVVTVP<br>SSSLGTQTYICNVNHKPSNTKVDKKVEPKSC<br>AAGS |
| TPP-5906 Light Chain | 29 | DIQLTQSPSFLSASVGDRVTITCRASSSVSY<br>IYWFQQKPGKAPKLLIYATSTLQSGVPSRFS<br>GSGSGTEYTLTISSLQPEDFATYYCHQRNSF<br>PYTFGQGTKLEIKRTVAAPSVFIFPPSDEQL<br>KSGTASVVCLLNNFYPREAKVQWKVDNALQS<br>GNSQESVTEQDSKDSTYSLSSTLTLSKADYE<br>KHKLYACEVTHQGLSSPVTKSFNRGEC |
| TPP-5907 Heavy Chain | 30 | EVQLVQSGAEVKKPGASVKVSCKASGYTFTT<br>YTIHWVRQAPGQGLEWMGYINPGSGYTRYNP<br>KFKGRVTMTRDKSTSTAYMELRSLRSDDTAV<br>YYCQTGTRDYWGQGTTVTVSSASTKGPSVFP<br>LAPSSKSTSGGTAALGCLVKDYFPEPVTVSW<br>NSGALTSGVHTFPAVLQSSGLYSLSSVVTVP<br>SSSLGTQTYICNVNHKPSNTKVDKKVEPKSC<br>AAGS |
| TPP-5907 Light Chain | 31 | DIQLTQSPSFLSASVGDRVTITCRASSSVSY<br>IYWFQQKPGKAPKLLIYATSTLQSGVPSRFS<br>GSGSGTEYTLTISSLQPEDFATYYCHQRNSF<br>PYTFGQGTKLEIKRTVAAPSVFIFPPSDEQL<br>KSGTASVVCLLNNFYPREAKVQWKVDNALQS<br>GNSQESVTEQDSKDSTYSLSSTLTLSKADYE<br>KHKLYACEVTHQGLSSPVTKSFNRGEC |

Kinetic analysis of the antibody binding to human red blood cell membranes was also performed using surface plasmon resonance (SPR) using a Biacore instrument. In this assay membranes prepared from human red blood cells were attached to a L1 sensor matrix and antibodies were flowed over the RBC membranes. Data from single cycle kinetics as shown in FIG. 6 demonstrated that the affinity (KD) was improved from 130 nM for the parental 6C12 antibody to 25 nM or 34 nM by the single amino acid changes S24R or A26S in the light chain, respectively.

Additional SPR analysis of the different germlined variants of hu6C12-24 as shown in Table 13 confirmed the results seen by ELISA assay. In particular TPP-5906 and TPP-5907 exhibited affinities for human RBC membranes of 0.9 and 0.8 nM which is improved by about 200-fold compared to the parental antibody. Thus the Hu6C12 antibody variants TPP5906 and TPP-5907 represent attractive lead candidates for binding to GPA on human red blood cells.

TABLE 13

Summary of kinetic parameters for different germlined variants of Hu6C12-24. Binding data are from Fab formats of the antibody 1:1 fit w/ 5 conc.

| TPP | $k_a$ (1/Ms) | $k_d$ (1/s) | $K_D$ (nM) |
|---|---|---|---|
| TPP-4935 (Parental) | 1.9E+05* | 3.1E−02* | 167* |
| TPP-5907 | 4.9E+06 | 4.0E−03 | 0.8 |
| TPP-5906 | 4.0E+06* | 3.4E−03* | 0.9* |
| TPP-5842 | 1.5E+06 | 5.9E−03 | 3.9 |
| TPP-5841 | 1.3E+06 | 4.3E−03 | 3.3 |
| TPP-5840 | 1.1E+06 | 4.6E−03 | 4.1 |
| TPP-5839 | 2.1E+06 | 3.5E−03 | 1.6 |
| TPP-5838 | 1.3E+06 | 4.0E−03 | 3.1 |
| TPP-5836 | 1.2E+06 | 4.2E−02 | 3.6 |
| TPP-5702 | 6.5E+05 | 1.1E−01 | 170 |
| TPP-5678 | 1.1E−06 | 4.1E−02 | 37 |
| TPP-5675 | 4.2E+05 | 3.6E−02 | 87 |

*slight deviation possible due to non-adapted concentrations during experiment

Example 4: Affinity Maturation of Selected Antibodies

Surface plasmon resonance (SPR) analysis of the humanized and germlined 6C12 antibody TPP-5906 binding to human RBC membranes indicated that this antibody had a relatively fast on rate (Ka=4 E+06) but a fast off rate (Kd=3.4 E−03). Thus despite having an affinity (KD) of around 0.9 nM the estimated time for 50% dissociation from the RBC membranes was only a few minutes. A FVIII fusion protein containing this parental antibody inserted in place of the B-domain was able to bind to intact human red blood cells, but only about 60% binding was observed after about 1 hour in a plasma matrix. Therefore an antibody with a slower off rate would be beneficial at increasing the binding of FVIII-antibody fusions to red blood cells. To improve the off rate of the 6C12 antibody an affinity maturation process was used. The starting point for affinity maturation was the humanized 6C12-24 antibody that recognizes human GPA and cross reacts to monkey GPA. A CDR focused library containing amino acid substitutions at all positions within the CDR regions was generated. This library was screened for changes in binding to both human and Cyno monkey RBC membranes and recombinant glycophorin A protein. This enabled the identification of positions within the CDRs that either improved binding, reduced binding or had no effect when substituted with a specific amino acid. Based on these results 11 positions within the CDRs were selected which when altered to the specified amino acid resulted in improved binding. The improved binding for these positions was confirmed using FACS analysis of human and Cyno monkey RBC. A combinatorial library was then created on the backbone of the humanized and germlined 6C12 antibody variant TPP-5906 where each of these 11 positions was varied from the parental residue resulting in a theoretical complexity of 2048 different CDR sequences. In total this library contained approximately 700 unique antibodies. This library was screened using ELISA assay for binding to human and Cyno monkey RBC membranes and recombinant glycophorin A protein. Based on these results a set of 24 antibodies with the most improved binding to human and Cyno RBC membranes and recombinant GPA proteins was identified. Table 14 provides the sequences for these 24 antibodies.

TABLE 14

Sequences affinity matured variants of humanized and germlined 6C12 scFv antibodies

| Antibody | Chain | Seq ID | Sequence |
|---|---|---|---|
| TPP-7776 | VL | 32 | DIQLTQSPSFLSASVGDRVTITCRASSSVRYIYWFQQKPGKAPKLLIYATSTLRSGVPSRFSGSGSGTEYTLTISSLQPEDFATYYCHQRNSFPYTFGQGTKLEIK |
| | VH | 33 | EVQLVQSGAEVKKPGASVKVSCKASGYTFTTYAIHWVRQAPGQGLEWMGYINPSSGYTRYNPKFKGRVTMTRDKSTSTAYMELRSLRSDDTAVYYCQTGTRDYWGQGTTVTVSS |
| TPP-7777 | VL | 34 | DIQLTQSPSFLSASVGDRVTITCRASSSVSYIYWFQQKPGKAPKLLIYATSTRQSGVPSRFSGSGSGTEYTLTISSLQPEDFATYYCHQRNSFPYTFGQGTKLEIK |
| | VH | 35 | EVQLVQSGAEVKKPGASVKVSCKASGYTFTTYTIHWVRQAPGQGLEWMGYINPSSGWTRYNPKFKGRVTMTRDKSTSTAYMELRSLRSDDTAVYYCWTGRRDYWGQGTTVTVSS |
| TPP-7778 | VL | 36 | DIQLTQSPSFLSASVGDRVTITCRASSSVRYIYWFQQKPGKAPKLLIYATSTLQSGVPSRFSGSGSGTEYTLTISSLQPEDFATYYCHQRNSFPYTFGQGTKLEIK |
| | VH | 37 | EVQLVQSGAEVKKPGASVKVSCKASGYTFTTYAIHWVRQAPGQGLEWMGYINPSSGYTRYNPKFKHRVTMTRDKSTSTAYMELRSLRSDDTAVYYCQTGTRDYWGQGTTVTVSS |
| TPP-7779 | VL | 38 | DIQLTQSPSFLSASVGDRVTITCRASSSVRYIYWFQQKPGKAPKLLIYATSTRQSGVPSRFSGSGSGTEYTLTISSLQPEDFATYYCHQRNSFPYTFGQGTKLEIK |
| | VH | 39 | EVQLVQSGAEVKKPGASVKVSCKASGYTFTRYAIHWVRQAPGQGLEWMGYINPSSGYTRYNPKFKHRVTMTRDKSTSTAYMELRSLRSDDTAVYYCWTGTRDYWGQGTTVTVSS |
| TPP-7781 | VL | 40 | DIQLTQSPSFLSASVGDRVTITCRASSSVRYIYWFQQKPGKAPKLLIYATSTLQSGVPSRFSGSGSGTEYTLTISSLQPEDFATYYCHQRNSFPYTFGQGTKLEIK |
| | VH | 41 | EVQLVQSGAEVKKPGASVKVSCKASGYTFTTYTIHWVRQAPGQGLEWMGYINPKSGWTRYNPKFKGRVTMTRDKSTSTAYMELRSLRSDDTAVYYCQTGTRDYWGQGTTVTVSS |
| TPP-7782 | VL | 42 | DIQLTQSPSFLSASVGDRVTITCRASSSVRYIYWFQQKPGKAPKLLIYATSFRQSGVPSRFSGSGSGTEYTLTISSLQPEDFATYYCHQRNSFPYTFGQGTKLEIK |
| | VH | 43 | EVQLVQSGAEVKKPGASVKVSCKASGYTFTTYTIHWVRQAPGQGLEWMGYINPSSGYTRYNPKFKGRVTMTRDKSTSTAYMELRSLRSDDTAVYYCQTGTRDYWGQGTTVTVSS |
| TPP-7783 | VL | 44 | DIQLTQSPSFLSASVGDRVTITCRASSSVRYIYWFQQKPGKAPKLLIYATSFRRSGVPSRFSGSGSGTEYTLTISSLQPEDFATYYCHQRNSFPYTFGQGTKLEIK |
| | VH | 45 | EVQLVQSGAEVKKPGASVKVSCKASGYTFTTYAIHWVRQAPGQGLEWMGYINPSSGYTRYNPKFKHRVTMTRDKSTSTAYMELRSLRSDDTAVYYCWTGTRDYWGQGTTVTVSS |
| TPP-7787 | VL | 46 | DIQLTQSPSFLSASVGDRVTITCRASSSVSYIYWFQQKPGKAPKLLIYATSTRQSGVPSRFSGSGSGTEYTLTISSLQPEDFATYYCHQRNSFPYTFGQGTKLEIK |
| | VH | 47 | EVQLVQSGAEVKKPGASVKVSCKASGYTFTTYAIHWVRQAPGQGLEWMGYINPSSGYTRYNPKFKGRVTMTRDKSTSTAYMELRSLRSDDTAVYYCWTGTRDYWGQGTTVTVSS |
| TPP-7788 | VL | 48 | DIQLTQSPSFLSASVGDRVTITCRASSSVSYIYWFQQKPGKAPKLLIYATSFRQSGVPSRFSGSGSGTEYTLTISSLQPEDFATYYCHQRNSFPYTFGQGTKLEIK |
| | VH | 49 | EVQLVQSGAEVKKPGASVKVSCKASGYTFTTYTIHWVRQAPGQGLEWMGYINPKSGWTRYNPKFKGRVTMTRDKSTSTAYMELRSLRSDDTAVYYCQTGTRDYWGQGTTVTVSS |

TABLE 14-continued

Sequences affinity matured variants of humanized
and germlined 6C12 scFv antibodies

| Antibody | Chain | Seq ID | Sequence |
|---|---|---|---|
| TPP-7789 | VL | 50 | DIQLTQSPSFLSASVGDRVTITCRASSSVRYIYWFQQKPGKAPKLLI YATSTLQSGVPSRFSGSGSGTEYTLTISSLQPEDFATYYCHQRNSFP YTFGQGTKLEIK |
|  | VH | 51 | EVQLVQSGAEVKKPGASVKVSCKASGYTFTTYTIHWVRQAPGQGLEW MGYINPSSGYTRYNPKFKHRVTMTRDKSTSTAYMELRSLRSDDTAVY YCWTGTRDYWGQGTTVTVSS |
| TPP-7790 | VL | 52 | DIQLTQSPSFLSASVGDRVTITCRASSSVRYIYWFQQKPGKAPKLLI YATSFLQSGVPSRFSGSGSGTEYTLTISSLQPEDFATYYCHQRNSFP YTFGQGTKLEIK |
|  | VH | 53 | EVQLVQSGAEVKKPGASVKVSCKASGYTFTTYAIHWVRQAPGQGLEW MGYINPSSGYTRYNPKFKHRVTMTRDKSTSTAYMELRSLRSDDTAVY YCWTGTRDYWGQGTTVTVSS |
| TPP-7791 | VL | 54 | DIQLTQSPSFLSASVGDRVTITCRASSSVRYIYWFQQKPGKAPKLLI YATSTLRSGVPSRFSGSGSGTEYTLTISSLQPEDFATYYCHQRNSFP YTFGQGTKLEIK |
|  | VH | 55 | EVQLVQSGAEVKKPGASVKVSCKASGYTFTTYAIHWVRQAPGQGLEW MGYINPSSGYTRYNPKFKHRVTMTRDKSTSTAYMELRSLRSDDTAVY YCWTGTRDYWGQGTTVTVSS |
| TPP-7792 | VL | 56 | DIQLTQSPSFLSASVGDRVTITCRASSSVRYIYWFQQKPGKAPKLLI YATSFRQSGVPSRFSGSGSGTEYTLTISSLQPEDFATYYCHQRNSFP YTFGQGTKLEIK |
|  | VH | 57 | EVQLVQSGAEVKKPGASVKVSCKASGYTFTTYAIHWVRQAPGQGLEW MGYINPSSGYTRYNPKFKGRVTMTRDKSTSTAYMELRSLRSDDTAVY YCWTGTRDYWGQGTTVTVSS |
| TPP-7793 | VL | 58 | DIQLTQSPSFLSASVGDRVTITCRASSSVSYIYWFQQKPGKAPKLLI YATSTLQSGVPSRFSGSGSGTEYTLTISSLQPEDFATYYCHQRNSFP YTFGQGTKLEIK |
|  | VH | 59 | EVQLVQSGAEVKKPGASVKVSCKASGYTFTRYTIHWVRQAPGQGLEW MGYINPSSGYTRYNPKFKGRVTMTRDKSTSTAYMELRSLRSDDTAVY YCWTGTRDYWGQGTTVTVSS |
| TPP-7794 | VL | 60 | DIQLTQSPSFLSASVGDRVTITCRASSSVRYIYWFQQKPGKAPKLLI YATSFRQSGVPSRFSGSGSGTEYTLTISSLQPEDFATYYCHQRNSFP YTFGQGTKLEIK |
|  | VH | 61 | EVQLVQSGAEVKKPGASVKVSCKASGYTFTTYAIHWVRQAPGQGLEW MGYINPSSGYTRYNPKFKHRVTMTRDKSTSTAYMELRSLRSDDTAVY YCWTGTRDYWGQGTTVTVSS |
| TPP-7795 | VL | 62 | DIQLTQSPSFLSASVGDRVTITCRASSSVSYIYWFQQKPGKAPKLLI YATSFLQSGVPSRFSGSGSGTEYTLTISSLQPEDFATYYCHQRNSFP YTFGQGTKLEIK |
|  | VH | 63 | EVQLVQSGAEVKKPGASVKVSCKASGYTFTTYTIHWVRQAPGQGLEW MGYINPKSGWTRYNPKFKGRVTMTRDKSTSTAYMELRSLRSDDTAVY YCQTGTRDYWGQGTTVTVSS |
| TPP-7796 | VL | 64 | DIQLTQSPSFLSASVGDRVTITCRASSSVSYIYWFQQKPGKAPKLLI YATSTLQSGVPSRFSGSGSGTEYTLTISSLQPEDFATYYCHQRNSFP YTFGQGTKLEIK |
|  | VH | 65 | EVQLVQSGAEVKKPGASVKVSCKASGYTFTTYTIHWVRQAPGQGLEW MGYINPKSGWTRYNPKFKGRVTMTRDKSTSTAYMELRSLRSDDTAVY YCQTGTRDYWGQGTTVTVSS |
| TPP-7797 | VL | 66 | DIQLTQSPSFLSASVGDRVTITCRASSSVRYIYWFQQKPGKAPKLLI YATSFRQSGVPSRFSGSGSGTEYTLTISSLQPEDFATYYCHQRNSFP YTFGQGTKLEIK |
|  | VH | 67 | EVQLVQSGAEVKKPGASVKVSCKASGYTFTTYTIHWVRQAPGQGLEW MGYINPSSGYTRYNPKFKGRVTMTRDKSTSTAYMELRSLRSDDTAVY YCWTGRRDYWGQGTTVTVSS |

The binding kinetics of the affinity matured Fab antibodies was also measured. The top 24 affinity matured antibodies identified from the high throughput screen of the library of approximately 700 unique variants of the humanized and germlined 6C12 antibody were evaluated for their binding to human RBC membranes using surface plasma resonance in a Biacore instrument. Fifteen of the Fabs generated interpretable data, another 4 had slow off rates but kinetic values could not be assigned, and another 6 did not give interpretable data. TPP-5906 is the parental humanized and germlined antibody before affinity maturation. The results are summarized in Table 15 as the on rate (Ka), off rate (kd), affinity (KD) and estimated time to 50% dissociation (T1/2).

TABLE 15

Kinetics of binding of top 24 selected affinity matured
variants of antibody 6C12 to human RBC membranes

| Antibody ID | ka (1/Ms) | kd (1/s) | KD (M) | Estimated T½ (min)# |
|---|---|---|---|---|
| TPP-7776 | 1.17E+07* | 9.70E−04 | 8.29E−11 | 12 |
| TPP-7777 | 7.44E+06 | 3.71E−04 | 4.99E−11 | 31 |
| TPP-7778 | 1.00E+08* | 1.10E−03 | 1.10E−11 | 10 |
| TPP-7779 | not able to evaluate due to very low off-rate | | | |
| TPP-7781 | 1.89E+07* | 5.47E−04 | 2.89E−11 | 21 |
| TPP-7782 | 1.40E+07* | 4.13E−04 | 2.95E−11 | 28 |
| TPP-7783 | 2.67E+05 | 2.42E−07* | 9.04E−13* | 47521* |
| TPP-7787 | 6.25E+06 | 1.39E−04 | 2.22E−11 | 83 |
| TPP-7788 | 3.03E+06 | 4.13E−04 | 1.36E−10 | 28 |
| TPP-7789 | 1.61E+07* | 1.28E−04 | 7.99E−12 | 90 |
| TPP-7790 | 8.58E+06 | 1.34E−08* | 1.56E−15* | 858209* |
| TPP-7791 | not able to evaluate due to very low off-rate | | | |
| TPP-7792 | not able to evaluate due to very low off-rate | | | |
| TPP-7793 | 2.05E+07* | 5.04E−04 | 2.46E−11 | 23 |
| TPP-7794 | 2.22E+07* | 8.66E−09* | 3.89E−16* | 1327945* |
| TPP-7795 | not able to evaluate due to very low off-rate | | | |
| TPP-7796 | 2.15E+07* | 2.38E−03 | 1.11E−10 | 5 |
| TPP-7797 | 6.49E+07* | 1.64E−05* | 2.53E−13* | 701* |
| TPP-5906 | 7.14E+06 | 5.04E−03 | 7.07E−10 | 2 |

T½ = 0.69/Kd (sec)
*Ka values > 7e6 and Kd values < 2e−5 and KD values less than 1e−11 are not accurate due to Biacore instrument limitations The binding of affinity matured Fab antibodies to intact human RBC was also measured. Human RBC were isolated from fresh anti-coagulated normal human blood by centrifugation through a ficol gradient and washing in PBS buffer. RBC diluted to 1/10th of normal hematocrit were incubated with purified Fab antibodies at a final concentration of 7 ug/ml for 1 hour at room temperature on a rotating shaker after which a sample was taken and the RBC were pelleted by centrifugation and the supernatant was collected. The remaining RBC suspension was diluted 200-fold in PBS buffer and incubated for a total of 2 hours at room temperature on a rotating shaker and samples were removed at 0, 5 min, 20 min, 1 h and 2 h and the RBC pelleted and the supernatant collected. The amount of Fab in the supernatants was then measured using an ELISA assay and the results used to calculate the percentage of the input Fab that was bound to the RBC. Following dilution it is expected that antibodies with a faster off-rate and/or overall lower affinity will dissociate from the RBC and reach a new equilibrium binding. The percentage that remains bound after 200-fold dilution of the RBC suspension is an indication of the overall strength of the binding to human RBC. The results are summarized in Table 16 below. It can be seen that compared to the parental antibody (TPP-5906) the affinity matured antibodies exhibited significantly improved binding as indicated by the observation that binding is retained following 200-fold dilution. By contrast the parental antibody dissociated rapidly from the RBC such that <5% remained bound after 20 minutes. In general there was a good correlation between the binding to intact RBC and the affinity (KD) measured by SPR. For example TPP-7792, 7797, 7793, 7794, 7790 and 7783 which exhibited the strongest binding to intact RBC also had the highest affinities. From these results TPP-7796 was eliminated as a potential candidate. The remaining 10 antibodies ("the top 10 set") were reformatted as single chain antibodies (scFv) with a C-terminal 6xHIS tag and expressed in mammalian HEK-293 cells and purified by affinity chromatography on NiNTA columns.

TABLE 16

Binding of selected affinity matured 6C12 antibodies to intact human RBC.
(The time points 0, 5, 20, 60 amd 120 indicate the percentage of the input antibody that remains bound at different times following 200-fold dilution of the RBC suspension)

| Antibody ID | Percentage of input antibody bound to Human RBC at each time point | | | | | |
|---|---|---|---|---|---|---|
| | Pre-dilution | 0 | 5 min | 20 min | 60 min | 120 min |
| TPP-7792 | 98 | 97 | 97 | 96 | 97 | 96 |
| TPP-7797 | 97 | 96 | 95 | 94 | 94 | 92 |
| TPP-7793 | 98 | 96 | 92 | 86 | 85 | 86 |
| TPP-7794 | 93 | 92 | 91 | 90 | 90 | 90 |
| TPP-7790 | 91 | 88 | 89 | 88 | 87 | 88 |
| TPP-7783 | 90 | 87 | 86 | 86 | 84 | 85 |
| TPP-7782 | 99 | 95 | 83 | 76 | 79 | 77 |
| TPP-7778 | 95 | 84 | 76 | 66 | 66 | 64 |
| TPP-7795 | 95 | 86 | 74 | 63 | 63 | 63 |
| TPP-7781 | 97 | 93 | 69 | 61 | 64 | 59 |
| TPP-7796 | 96 | 82 | 48 | 12 | 15 | 13 |
| TPP-5906 # | 93 | 82 | 28 | 4 | 8 | 8 |

TPP-5906 is the parental 6C12 antibody before affinity maturation

The binding of affinity matured Fab antibodies to intact Cynomolgus monkey RBC was measured. Cynomolgus monkey RBC were isolated from fresh anti-coagulated blood by centrifugation through a ficol gradient and washing in PBS buffer. RBC diluted to 1/10th of normal hematocrit were incubated with the Fab at a final concentration of 7 ug/ml for 1 hour at room temperature on a rotating shaker after which a sample was taken and the RBC were pelleted by centrifugation and the supernatant was collected. The remaining RBC suspension was diluted 200-fold in PBS buffer and incubated for a total of 2 hours at room temperature on a rotating shaker and samples were removed at 0, 5 min, 20 min, 1 h and 2 h and the RBC pelleted and the supernatant collected. Following dilution it is expected that antibodies with a faster off-rate and/or overall lower affinity will dissociate and reach a new equilibrium binding. The amount of Fab in the supernatants was then measured using an ELISA assay and the results used to calculate the percentage of the input Fab that was bound to the RBC. The results are summarized in Table 17. It can be seen that the affinity matured antibodies exhibited strong binding to Cynomolgus RBC as indicated by the observation that binding is retained following 200-fold dilution. In particular antibodies TPP-7792 and TPP-7790 remained 89% and 85% bound at 2 hours after 200-fold dilution. The other antibodies exhibited less tight binding to Cynomolgus monkey RBC as indicated by their reduced binding after dilution. Based on these results antibodies TPP-7792 and TPP-7790 were selected as antibody candidates that exhibit the tightest binding to both human and Cynomolgus monkey RBC. An antibody with tight binding to Cynomolgus monkey RBC is desirable to enable testing of drug candidates in Cynomolgus monkeys.

TABLE 17

Binding of selected affinity matured 6C12 antibodies to intact Cynomolgus monkey RBC.
(The time points 0, 5, 20, 60 amd 120 indicate the percentage of the input antibody that remains bound at different times following 200-fold dilution of the RBC suspension)

| Antibody ID | Percentage of input antibody bound to Cyno RBC at each time point | | | | | |
|---|---|---|---|---|---|---|
| | Pre-dilution | 0 | 5 min | 20 min | 60 min | 120 min |
| TPP-7792 | 92 | 96 | 94 | 93 | 92 | 89 |
| TPP-7797 | 79 | 81 | 66 | 59 | 56 | 50 |
| TPP-7793 | 72 | 58 | 58 | 51 | 51 | 46 |
| TPP-7794 | 73 | 67 | 66 | 65 | 67 | 57 |
| TPP-7790 | 94 | 87 | 90 | 90 | 87 | 85 |
| TPP-7783 | 72 | 60 | 62 | 62 | 64 | 56 |
| TPP-7782 | 94 | 88 | 68 | 59 | 57 | 52 |
| TPP-7778 | 81 | 56 | 54 | 48 | 36 | 27 |
| TPP-7795 | 73 | | 51 | 39 | 29 | 22 |
| TPP-7781 | 86 | 40 | 34 | 32 | 24 | 19 |
| TPP-7796 | 68 | 56 | 43 | 21 | 7 | 0 |
| TPP-5906 | NT | NT | NT | NT | NT | NT |

NT: not tested

Example 5: Binding of Affinity Matured scFv Antibodies to Intact Human RBC

Human RBC were isolated from fresh anti-coagulated normal human blood by centrifugation through a ficol gradient and washing in PBS buffer. RBC diluted to 1/10th of normal hematocrit were incubated with the set of "Top 10" purified scFv antibodies at a final concentration of 7 ug/ml for 1 hour at room temperature on a rotating shaker after which a sample was taken and the RBC were pelleted by centrifugation and the supernatant was collected. The remaining RBC suspension was diluted 200-fold in PBS buffer and incubated for a total of 2 hours at room temperature on a rotating shaker and samples were removed at 0, 5 min, 20 min, 1 h and 2 h and the RBC pelleted and the supernatant collected. The amount of scFv antibody in the supernatants was then measured using an ELISA assay and the results used to calculate the percentage of the input scFv that was bound to the RBC. Following dilution it is expected that scFv antibodies with a faster off-rate and/or overall lower affinity will dissociate from the RBC and reach a new equilibrium binding. The percentage that remains bound after dilution is an indication of the overall strength of the binding to human RBC. The results are summarized in Table 18. The parental scFv (TPP-5906) exhibited poor binding to human RBC after dilution. Although all of the parental scFv was bound to RBC after the initial incubation with RBC at 1/10th normal hematocrit (when the effective concentration of the target protein is high), only 16% remained at 5 minutes after 200-fold dilution and all of the scFv had dissociated from the RBC after 20 minutes. By comparison all of the top 10 affinity matured scFv exhibited significantly improved binding to human RBC. All 10 of the affinity matured scFv retained 76% or more binding at 2 hours after dilution. Some of the scFv, for example TPP-7792, 7797, 7783, 7781 retained >90% binding at 2 hours.

TABLE 18

Binding of selected affinity matured scFv 6C12 scFv formated antibodies to intact human RBC
(The time points 0, 5, 20, 60 amd 120 indicate the percentage of the input antibody that remains bound at different times following 200-fold dilution of the RBC suspension)

| Antibody ID | Percentage of input scFv antibody bound to RBC at each time point | | | | | |
|---|---|---|---|---|---|---|
| | Pre-dilution | 0 | 5 min | 20 min | 60 min | 120 min |
| TPP-7792 | 100 | 100 | 99 | 98 | 95 | 92 |
| TPP-7797 | 98 | 98 | 98 | 98 | 99 | 97 |
| TPP-7793 | 92 | 92 | 92 | 84 | 81 | 79 |
| TPP-7794 | 85 | 85 | 85 | 85 | 85 | 85 |
| TPP-7790 | 99 | 99 | 99 | 99 | 94 | 87 |
| TPP-7783 | 94 | 94 | 94 | 94 | 94 | 94 |
| TPP-7782 | 92 | 92 | 91 | 87 | 89 | 85 |
| TPP-7778 | 98 | 97 | 88 | 81 | 79 | 76 |
| TPP-7795 | 100 | 100 | 85 | 82 | 84 | 80 |
| TPP-7781 | 97 | 97 | 94 | 93 | 93 | 92 |
| TPP-5906 | 100 | 90 | 16 | 0 | 3 | 0 |

Example 6: Epitope Mapping of the Affinity Matured Fab Antibodies

Initial peptide mapping studies were performed in which a series of overlapping 20 residue peptides derived from the human GPA extracellular domain were bound to plates and then incubated with the antibody (data not shown). These experiments identified a 20 amino acid peptide (called GP5) containing residues 42 to 61 the human glycophorin A extracellular domain that was bound by the 6C12 IgG antibody. In order to determine if the affinity matured antibodies bound to the same peptide and further map the specific amino acids in the peptide required for binding a series of overlapping 8 amino acid long peptides were synthesized covering the sequence of the GP5 peptide as shown in Table 19.

TABLE 19

Sequences of peptides covering regions of the human GPA ectodomain used in epitope mapping studies

| Name | Sequence |
|---|---|
| GP5 | EVSEISVRTVYPPEEETGER (SEQ ID NO. 68) |
| GP7 | SVRTVYPP (SEQ ID NO. 69) |
| GP8 | VRTVYPPE (SEQ ID NO. 70) |
| GP9 | RTVYPPEE (SEQ ID NO. 71) |
| GP10 | TVYPPEEE (SEQ ID NO. 72) |
| GP11 | VYPPEEET (SEQ ID NO. 73) |
| GP12 | YPPEEETG (SEQ ID NO. 74) |
| GP13 | PPEEETGE (SEQ ID NO. 75) |
| GP14 | PEEETGER (SEQ ID NO. 76) |
| GP15 | EEETGERV (SEQ ID NO. 77) |
| GP16 | EETGERVQ (SEQ ID NO. 78) |

These peptides were attached to the surface of a streptavidin coated plate via a biotin moiety that was present at the N-terminus of each peptide. Two concentrations of two of the affinity matured Fabs (TPP-7792 and TPP-7790) together with the parental humanized and germlined 6C12 Fab (TPP-5906) were incubated on the peptide coated plate and after a series of washing steps with PBS/0.05% tween the amount of antibody bound was detected using a secondary antibody against the 6×HIS tag present on the Fabs. The results are summarized Table 20. The affinity matured antibodies TPP-7792 and TPP-7790 bound to the 21 amino acid peptide GP5 that contains the epitope for the parental antibody 6C12. The affinity matured antibodies also bound to the 8 mer GP8 peptide, but only weakly to the neighboring peptide GP9, and did not bind to any of the other 8 amino acid overlapping peptides. The binding to the 8 amino acid GP8 peptide appeared to be weaker than to the 20 amino acid GP5 peptide as evidenced by the weaker signal at the lower antibody concentration. The parental antibody failed to bind to any of the 8 amino acid peptides likely because of the lower affinity of this antibody. These results indicate that the core epitope recognized by the affinity matured antibodies lies within the 8 amino acid sequence of peptide GP8, that being VRTVYPPE. Peptide GP7 (SVRTVYPP) was not recognized by the affinity matured antibodies indicating that the Glutamic acid (E) at the C-terminus of GP8 is essential for binding. Similarly peptide GP9 (RTVYPPEE) was recognized only weakly by the affinity matured antibodies indicating that the valine (V) at the C-terminus of the GP8 peptide is important for binding.

TABLE 20

Binding of germlined and affinity matured Fab formats of the 6C12 antibody to peptides covering different regions of the human GPA ectodomain.

| Peptide | Binding Signal in ELISA (Relative light units) | | | | |
|---|---|---|---|---|---|
| | TPP-5906 0.5 ug/ml | TPP-5906 0.05 ug/ml | TPP-7792 0.5 ug/ml | TPP-7792 0.05 ug/ml | TPP-7790 0.5 ug/ml | TPP-7790 0.05 ug/ml |
| GP7 | 0 | −1 | 1 | 0 | 1 | 0 |
| GP8 | 1 | −1 | 5134 | 291 | 3366 | 83 |
| GP9 | 1 | −1 | 534 | 18 | 169 | 7 |
| GP10 | 0 | 0 | 71 | 14 | 38 | 7 |
| GP11 | 0 | −1 | 2 | 0 | 1 | 0 |
| GP12 | −1 | −1 | 0 | −1 | 0 | −1 |
| GP13 | −1 | −1 | 0 | −1 | −1 | 0 |
| GP14 | −1 | −1 | 0 | −1 | 0 | −1 |
| GP15 | −1 | −1 | 0 | −1 | 0 | −1 |
| GP16 | −1 | 0 | 0 | −1 | 0 | −1 |
| GP5 | 6685 | 1998 | 7228 | 3505 | 6986 | 2883 |
| PBS | 0 | 0 | 0 | 1 | 0 | 0 |

To further define the epitope of the affinity matured antibodies a series of peptides containing the sequence corresponding to the 20 amino acid GP5 peptide were synthesized in which each peptide contained 1 residue that was substituted with alanine (A) as shown in Table 21.

TABLE 21

Sequences of alanine scanning peptides used for epitope mapping studies

| Peptide Name | Sequence |
|---|---|
| GP5-1 | AVSEISVRTVYPPEEETGER (SEQ ID NO. 79) |
| GP5-2 | EASEISVRTVYPPEEETGER (SEQ ID NO. 80) |
| GP5-3 | EVAEISVRTVYPPEEETGER (SEQ ID NO. 81) |

TABLE 21-continued

Sequences of alanine scanning peptides used for epitope mapping studies

| Peptide Name | Sequence |
|---|---|
| GP5-4 | EVSAISVRTVYPPEEETGER (SEQ ID NO. 82) |
| GP5-5 | EVSEASVRTVYPPEEETGER (SEQ ID NO. 83) |
| GP5-6 | EVSEIAVRTVYPPEEETGER (SEQ ID NO. 84) |
| GP5-7 | EVSEISARTVYPPEEETGER (SEQ ID NO. 85) |
| GP5-8 | EVSEISVATVYPPEEETGER (SEQ ID NO. 86) |
| GP5-9 | EVSEISVRAVYPPEEETGER (SEQ ID NO. 87) |
| GP5-10 | EVSEISVRTAYPPEEETGER (SEQ ID NO. 88) |
| GP5-11 | EVSEIS<u>VRTVAPP</u>EEETGER (SEQ ID NO. 89) |
| GP5-12 | EVSEISVRTVYAPEEETGER (SEQ ID NO. 90) |
| GP5-13 | EVSEISVRTVYPAEEETGER (SEQ ID NO. 91) |
| GP5-14 | EVSEISVRTVYPPAEETGER (SEQ ID NO. 92) |
| GP5-15 | EVSEISVRTVYPPEAETGER (SEQ ID NO. 93) |
| GP5-16 | EVSEISVRTVYPPEEATGER (SEQ ID NO. 94) |
| GP5-17 | EVSEISVRTVYPPEEEAGER (SEQ ID NO. 95) |
| GP5-18 | EVSEISVRTVYPPEEETAER (SEQ ID NO. 96) |
| GP5-19 | EVSEISVRTVYPPEEETGAR (SEQ ID NO. 97) |
| GP5-20 | EVSEISVRTVYPPEEETGEA (SEQ ID NO. 98) |

These alanine scanning peptides which also contained biotin at the N-terminus were attached to streptavidin plates and then incubated with affinity matured Fab antibodies TPP-7790 and TPP-7792 or the parental Fab TPP-5906. After extensive washing with PBS/0.05% tween buffer the bound antibody was detected using a secondary antibody against the 6×HIS tag present on the Fab and the results are summarized in Table 22.

TABLE 22

Binding of germlined and affinity matured Fab formats of the 6C12 antibody to alanine scanning peptides derived from residues 42 to 61 of the human GPA ectodomain.

| Peptide | TPP-7790 0.5 ug/ml | TPP7792 0.5 ug/ml | TPP-5906 1 ug/ml |
|---|---|---|---|
| 5-1 | 6211 | 6798 | 5312 |
| 5-2 | 6359 | 6695 | 6166 |
| 5-3 | 6685 | 7370 | 6164 |
| 5-4 | 6537 | 6626 | 4841 |
| 5-5 | 6269 | 7397 | 6785 |
| 5-6 | 6523 | 6665 | 6366 |
| 5-7 | 6700 | 6691 | 7185 |
| 5-8 | 6791 | 6696 | 7363 |
| 5-9 | 6814 | 7272 | 7278 |
| 5-10 | 5912 | 6214 | 337 |
| 5-11 | 1 | 2 | −1 |
| 5-12 | 6447 | 6792 | 282 |
| 5-13 | 6566 | 6955 | 1999 |
| 5-14 | 1277 | 2671 | 9 |
| 5-15 | 6715 | 7251 | 366 |
| 5-16 | 6538 | 6677 | 3389 |
| 5-17 | 6869 | 7414 | 6251 |
| 5-18 | 6397 | 7151 | 6289 |

TABLE 22-continued

Binding of germlined and affinity matured Fab formats of
the 6C12 antibody to alanine scanning peptides derived
from residues 42 to 61 of the human GPA ectodomain.

| Peptide | TPP-7790 0.5 ug/ml | TPP7792 0.5 ug/ml | TPP-5906 1 ug/ml |
|---|---|---|---|
| 5-19 | 6472 | 6978 | 4584 |
| 5-20 | 6441 | 7169 | 6847 |
| PBS | −1 | 1 | −2 |

The same epitope mapping study on the 20 alanine scanning peptides was performed for a total of 7 affinity matured Fabs (TPP #7782, 7783, 7778, 7790, 7792, 7793, 7797). A similar trend in binding was seen. The binding to peptides GP5-1, 5-2, 5-3, 5-4, 5-5, 5-6, 5-7 and 5-8 was similarly strong indicating that substitution of the first 8 residues for alanine had no effect upon binding. In order to visualize the average binding of all 7 affinity matured Fabs to the different peptides the mean binding to each peptide as a percentage of the average of the binding to GP5-1, 5-2, 5-3, 5-4, 5-5, 5-6, 5-7 and 5-8 was calculated and is plotted in the graph as shown in FIG. 7A. For comparison the same analysis was performed for the parental antibody TPP-5906 as shown in FIG. 7B.

The alanine substitution present in the peptides GP5-11 (EVSEISVRTVAPPEEETGER) and GP5-14 (EVSEISVRTVYPPAEETGER) reduced binding of the affinity matured Fabs by 100% and 90% respectively while the alanine substitution present in GP5-10 (EVSEISVRTAYPPEEETGER) reduced binding by about 20%. Therefore residues at positions 11 (Tyrosine) and 14 (glutamic acid), as defined by counting from the N-terminus of GP5, are essential for binding to the affinity matured Fabs. The residue at position 10 (valine) plays a minor role. These results are consistent with the observation described above in which the peptide scanning analysis defined the core epitope as an 8 amino acid sequence present in GP8 (VRTVYPPE) which span from residues 8 to 14 of GP5 and thus contains residues 11 and 14 that were defined as critical by the alanine scanning.

The pattern of binding of the paternal 6C12 Fab antibody to the alanine scanning peptides was different to that seen for the affinity matured Fabs. The binding of the parental Fab was sensitive to alanine substitution at an additional 5 positions. Binding was reduced by >95% by alanine substitution at positions 10, 11, 12, 14, and 15 and was reduced by 70% and 50% by substitution at residues 13 and 16. This defines the epitope for the parental antibody as spanning residues 10 to 16 which corresponds to the 7 amino acid sequence VYPPEEE in which residues valine, tyrosine, proline and glutamic acid (underlined) are critical. While overlapping with the "core" sequence recognized by the affinity matured Fabs (VRTVYPPE) the parental Fab appears to require the additional residues EE at positions 15 and 16. The finding that substitution of additional residues interferes with binding of the parental antibody is likely related to the lower affinity of this antibody such that binding can be prevented more readily.

In summary the core epitope of the affinity matured antibodies is the sequence VRTVYPPE within which the tyrosine (Y) and the glutamic acid (E) are essential and thus are likely critical contact points for the antibody.

Habib et al (Analytical Biochemistry 2013, vol 438 p 82-89) to mapped the epitope of the anti-GPA nanobody IH4 and the results are summarized in Table 23 in comparison to the epitope mapping data for the affinity matured 6C12 Fabs on the same GPA peptide sequences. While the IH4 nanobody bound well to the GP9, GP11 and GP12 peptides, the 6C12 Fabs did not bind to any of these peptides. The strongest binding of the IH4 nanobody was to the GP11 peptide that was not bound by 6C12. The peptide mapping data for the affinity matured 6C12 Fabs indicate that they require the sequence VRTV that is present at the N-terminus of GP8 and this VRTV sequence is not present in GP11 peptide that was the strongest binder for IH4. Therefore the epitopes for 6C12 Fabs and the IH4 Nanobody are distinct.

TABLE 23

Comparison of the epitope recognized by the affinity matured 6C12 antibodies and the nanobody IH4. Peptides GP7, GP8, GP9, GP11, GP12, and GP13 were used in Habib et al (Analytical Biochemistry 2013, vol 438 p82-89) to map the epitope of the anti-GPA nanobody IH4 and these results are summarized in the table and compared to the binding data for the affinity matured 6C12 Fabs to the same peptides

| Name | Sequence | Residues of mature human GPA | Binding of affinity matured 6C12 Fabs | Binding to IH4 Nanobody # |
|---|---|---|---|---|
| GP7 | SVRTVYPP (SEQ ID NO: 99) | 40 to 47 | None | None |
| GP8 | VRTVYPPE (SEQ ID NO: 100) | 41 to 48 | Strong | Strong |
| GP9 | RTVYPPEE (SEQ ID NO: 101) | 42 to 49 | Weak | Stronger |
| GP10 | TVYPPEEE (SEQ ID NO: 102) | 43 to 50 | None | Not tested |
| GP11 | VYPPEEET (SEQ ID NO: 103) | 44 to 51 | None | Strongest |
| GP12 | YPPEEETG (SEQ ID NO: 104) | 45 to 52 | None | Strongest |
| GP13 | PPEEETGE (SEQ ID NO: 105) | 46 to 53 | None | None |

From Habib et al (Analytical Biochemistry 2013, vol 438 p82-89)

Example 7: Generation of Factor VIII-scFv Fusion Constructs and Expression in HK8-11 Cells DNA encoding various fusions between B-domain deleted human FVIII and different scFV antibodies were constructed using standard molecular biology techniques which are well known in the art. A combination of synthetically synthesized DNA fragments, PCR, and restriction enzyme based cloning techniques was used. The native human FVIII signal peptide was used in all constructs, for example in constructs in which the scFv was fused at the N-terminus of FVIII, the scFv was inserted between the native FVIII signal peptide and the start of the mature FVIII protein. The resulting cDNA sequences encoding human FVIII-scFv fusion proteins were transferred to the mammalian expression vector pSS207 (pSS207 is described in Mei et. al, 2006 Molecular Biotechnology, 34:165-178). The mammalian cell line HKB11 was stably transfected with the expression vectors, and clones were selected that express the corresponding FVIII-scFv fusion proteins by measuring FVIII chromogenic activity in the cell culture supernatant. To produce FVIII scFv fusion proteins, stably transfected HKB11 cells were cultured at a 10 liter scale using Wave fermenters and condition media containing the secreted FVIII protein was harvested, concentrated between 3 and 5-fold then frozen at −80° C.

Example 8: Purification of Factor VIII-scFv Fusion Proteins

FVIII-scFv fusion proteins were purified using methods well known in the art. Fractions containing the peak of FVIII activity were pooled, sucrose was added at final concentration of 1% and protein concentration measured by soloVPE. Aliquots were flash frozen and stored at −80° C. Purity of purified FVIII fusion proteins was assessed by SDS PAGE, and analytical SEC. FVIII activity was assessed using the two stage Coatest FVIII chromogenic assay.

Example 9: Generation of Hemophilia a Mice Expressing Human Glycophorin a on their Red Blood Cells The most widely used animal model to evaluate FVIII based therapeutics is the Hemoiphilia A mouse in which the mouse FVIII gene was disrupted resulting in the complete absence of mouse FVIII protein. These mice exhibit a hemophilic phenotype as typified by inability to form clots and rapid death after tail injury. Because the anti-GPA antibodies described herein do not bind to mouse GPA we created a transgenic mouse expressing the human GPA protein. To do this a bacterial artificial chromosome (BAC) containing the human glycophorin A gene genomic sequence and surrounding regulatory regions selected from among BAC ID's RP11-5005 (size of 176 Kb with the human GYPA gene in the middle of the BAC). After removal of the cloning vector portion the BAC was used for pro-nuclei of fertilized oocytes from C57BL/6 mice. Founder mice that carried the BAC inserted in to their genome were identified by PCR analysis with primer pairs homologous to the 5' end of the BAC, the 3' end of the BAC and to exon 5 of the glycophorin A gene. Only mice that were positive for all 3 sets of PCR primers were selected. The founder mice were screened for expression of human GPA on the surface of their red blood cells by FACS analysis using the antibody BRIC256 that binds to human GPA. The Ter119 antibody that recognizes mouse GPA was used as a control. One founder animal was identified that expressed human GPA on its RBC at levels similar to that measured on normal human RBC. This animal was bred with non-transgenic C57BL/6 mice to generate F1 animals which were screened for the presence of the transgene by PCR. PCR positive F1 mice were screened for expression of human GPA on their RBC by FACS. Several F1 mice with human GPA expression were identified and one animal (M9) with human GPA levels of between 15 and 30% of that on normal human RBC (depending on whether the BRIC256 antibody or the 6C12 antibody was used for FACS analysis) was selected.

Figure 8:
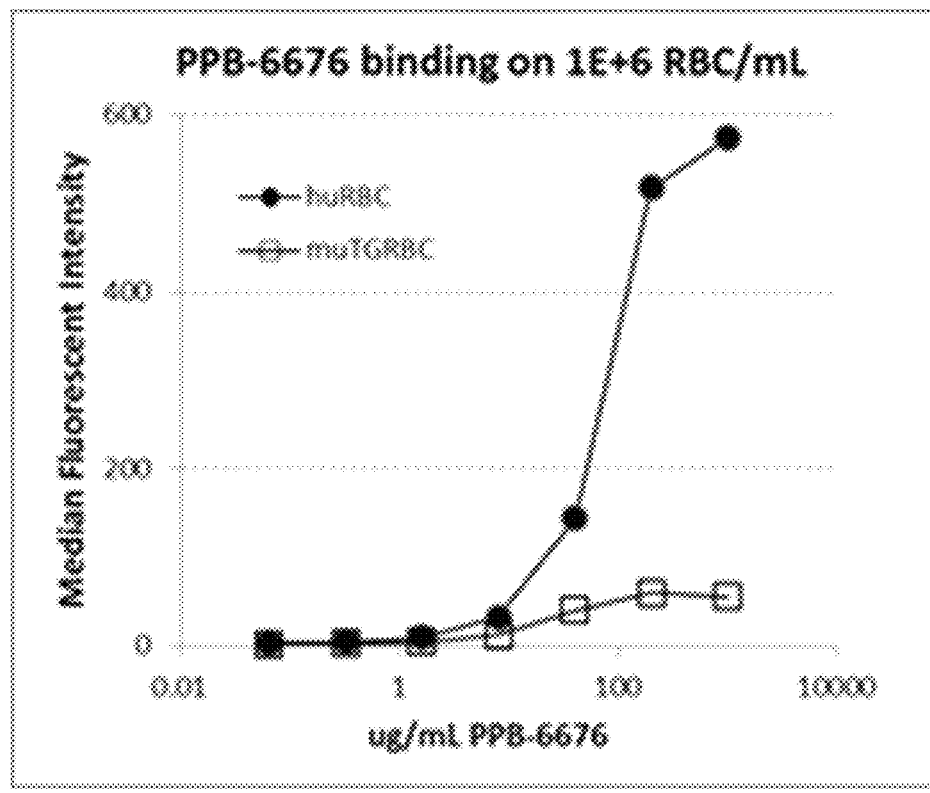
FIG. 8: FACS measurement of human GPA levels on huGPA/HemA transgenic mice RBC and human RBC.

The M9 F1 mouse was then bred to the Hemophilia A mouse strain (also in C57BL/6 background) to generate Hemophilia A mice expressing human GPA on their RBC. Mice homozygous for the human glycophorin A transgene could not be generated and this was presumed to be because the presence of the transgene was homozygous lethal. This is likely to have been caused by integration of the BAC in to an essential gene, but the precise cause was not investigated. The hemizygous huGPA/HemA mice were evaluated for the expression of human GPA on the surface of their RBC by FACS using the 7792 anti-GPA scFV (PPB-6676) and compared to the signal on normal human RBC (FIG. 8). After correction for the smaller size of mouse RBC compared to human RBC, the level of human GPA on the huGPA/HemA mice was calculated as 5% of than on human RBC. While the level of human GPA on the huGPA/HemA mouse RBC is low this still equates to approximately $2.5 \times 10^4$ to $5 \times 10^4$ copies per RBC and was sufficient to enable binding of RBC targeted FVIII molecules in vitro and in vivo.

Example 10: Design of FVIII-scFv Fusion Proteins with Optimal Properties

An ideal FVIII-scFv fusion protein will have the properties of rapid and tight binding to red blood cells while maintaining sufficient coagulation activity. While some of these properties can be evaluated in vitro it is also appreciated that given the complexity of the coagulation system and the natural clearance mechanisms for FVIII, evaluation in vivo will also be needed. A number of design variables were considered when designing FVIII-scFv fusions. These included (i) the specific anti-GPA scFv to be selected from among the affinity matured scFv described in example 4; (ii) the location within FVIII at which the scFv is fused to FVIII; (iii) the length and composition of the polypeptide linker to fuse the scFv to FVIII; (iv) the vWF binding capability of the molecule as determined by the presence or absence of the a3 domain; and (v) the chain composition of the fusion protein as defined by the presence or absence of the furin cleavage site. The first step in the design of FVIII-scFv fusion proteins with optimal properties was to define the specific scFv antibody that provides the longest duration of action in vivo. It was envisaged that differences in the binding kinetics between different affinity matured variants might result in different RBC binding characteristics when the scFv is fused to FVIII.

Based upon a combination of the binding kinetics on isolated human RBC membranes and the binding to intact Human and Cyno RBC, the scFv variants of antibody 6C12 called 7790, 7792 and 7793 were selected for fusion to FVIII. These scFv variants were also selected based on their degree of net positive charge. The parent scFv, 6C12, is net positively charged, and all of the affinity-matured scFv variants are even more net positively charged. GPA is net negatively charged. However, in order to minimize the risk of non-specific binding to undesired, negatively charged moieties, such as proteins other than GPA, cells other than RBCs, or to avoid intramolecular association with negatively charged regions of FVIII, scFv variants with minimally increased net positive charge were selected.

Variants 7790 and 7792 were among the best binders to intact Human and Cyno RBC and 7790 had amongst the lowest KD values of the different scFv variants. The binding kinetics of the scFv variant 7792 to human RBC membranes was not quantifiable but was observed to have low off rates that were too slow to be quantified by the Biacore instrument. The scFv 7793 exhibited a faster on rate than the 7790 variant but also a faster off-rate such that the overall affinity was less (KD 2.46 E−11 as compared to an estimated KD of 1.56 E−15 for 7790). In addition the 7793 variant exhibited lower binding strength to intact human RBC but similar binding strength to intact Cyno RBC. Thus 7790 and 7792 were selected as examples of scFv with very tight binding including slow off-rates whereas 7793 was selected to evaluate if an scFv with a faster off-rate but a faster on-rate might be more beneficial in targeting FVIII to RBC in vivo. All 3 scFv were fused to B-domain deleted FVIII in place of the B-domain. The order of the VH and VL domains within the fusion protein was established as N-terminus-VL-linker-VH-C-terminus. This order of the heavy and light chains appeared to enable more effective purification of the FVIII-scFv fusion due to reduced levels of aggregation (data not shown).

In order to maintain correct folding of the VH and VL regions in the context of a scFv it has been well established in the art that a linker of not less than 15 amino acids composed of GGGGS repeats is required (Huston et al 1988, PNAS vol 85, 5879; Huston et al, Methods in Enzymology 1991, vol 203 p 46-88). The use of linkers composed of glycine and serine residues is well established in the art due to the structural flexibility of such sequences and the low risk of immunogenicity in patients established with protein drugs containing such linkers. The use of the repeating motif GGGGS is well known in the art as described in Huston et al, Methods in Enzymology 1991, vol 203 p 46-88. It is also well appreciated in the art that longer linkers for example of 20 amino acids or more may be beneficial in the case of certain scFv molecules to provide improved folding and stability (for example see Albrecht et al, J. of Immunological Methods 2006, vol 310 p 100-116). Preliminary experiments with FVIII fusions to the scFv format of antibody 6C12 that incorporated a 15 amino acid linker (GGGGSGGGGSGGGGS, SEQ ID NO: 106) between the VH and VL regions and the chain order VH-VL suggested that the protein exhibited unexpectedly high levels of aggregation during purification that was not seen previously using a similar FVIII fusion to a scFv derived from the mouse GPA specific antibody Ter119. When a longer 20 amino acid linker (GGGGSGGGGSGGGGSGGGGS, SEQ ID NO: 107) was used and the order of the heavy and light chains of the scFv was changed to VL-VH the level of protein aggregation was significantly reduced and the yields of purified FVIII-scFv fusion protein was increased. Based on these observations all subsequent FVIII-scFv fusion proteins incorporated the scFv with the domain order VL-VH (N-term to C-term) with the VL and VH domains separated by the 20 amino acid linker with the sequence; GGGGSGGGGSGGGGSGGGGS.

When fusing an RBC targeting moiety such as an scFv to a normal 2 chain form of FVIII-BDD in place of the B-domain, the scFv could be placed either on the N-terminal side of the furin site or on the C-terminal side of the furin site resulting in a mature 2 chain protein in which the scFv is fused either on the C-terminus of heavy chain (composed of A1-A2 domains of FVIII) or on the N-terminus of the light chain (composed of A3-C1-C2 domains of FVIII), respectively. In both cases the fusion protein can be designed to include to native FVIII thrombin sites such that the FVIII will be released from the scFv in the presence of thrombin or other related proteases of the coagulation system such as Factor Xa (FXa) or Factor XIa (FXIa). Such a fusion protein design provides for the release of an essentially normal FVIIIa molecule from the RBC surface upon activation of the coagulation cascade at the site of an injury. While not proven experimentally it is envisioned that the release of FVIIIa from the RBC bound scFv would provide for normal control of bleeding. However it is also possible that activated FVIII that remained bound to RBC would also be functional in promoting coagulation via complex formation with FIXa and Factor X. When fusing a RBC targeting moiety such as an scFv at the N-terminus or the C-terminus of either full length FVIII or B-domain deleted FVIII a linker sequence may be included between the targeting moiety and the FVIII. It is well appreciated in the art that linkers can be beneficial when fusing two different proteins or protein domains because they provide for structural flexibility to ensure correct folding, steric accessibility and function of the two proteins or protein domains. Typical linkers used in the art of protein engineering consist of flexible sequences of between 4 and 20 amino acids. Linkers are typically made up of combinations of glycine and serine residues as described in Huston et al, Methods in Enzymology 1991, vol 203 p 46-88. In order to enable the release of a FVIII-scFv fusion from the surface of RBC upon activation of coagulation a cleavage site for the proteases thrombin and/or FXa and/or FXIa can be included. Thrombin, FXa and FXIa are all generated during the activation of the coagulation cascade and thus are good candidates as proteases to enable the release of an RBC targeted FVIII protein. The sequences of the cleavage sites for thrombin, FXa and FXIa are well known in the art and the use of these protease cleavage sites within fusion proteins has been described (Jenny et al 2003, Protein Expression and Purification vol 31, p 1-11). Thrombin and FXa are serine proteases that cleave on the C-terminal side of a basic amino acid residue, typically arginine (R) referred to as the P1' residue. Cleavage sites for thrombin and FXa and FXIa can be derived from proteins known to be cleaved by these enzymes, including FVIII itself. Alternatively a consensus cleavage site that is derived by comparing the cleavage sites within different proteins can be derived. Additionally, the substrate specificity of proteases has been studies in vitro to further define the recognition sequences (Backes et al 2000, Nature Biotechnology vol 18, p 187-193, Gallwitz et al 2012, PLoS ONE 7(2):e31756.doi:10.1371/journal.pone.0031756)

A commonly used thrombin cleavage site is LVPRGS (SEQ ID NO: 108) in which the R residue is the P1' residue. The sequence IEGR taken from prothrombin has been commonly used as the cleavage site for FXa. It is well known in the art that various different sequences can function as cleavage sites for thrombin or FXa or FXIa. In theory any sequence that functions as a cleavage site for these proteases could be used. These cleavage sites are preferentially incorporated within a flexible glycine serine linker having at least 4 but up to 15 or more glycine or serine residues either side of the protease recognition sequence. The protease site may be located in the middle of the flexible linker, for example the sequence GGGSGGGSG LVPRGSGGGSGGGGSG (SEQ ID NO: 109) which consists of 10 and 10 amino acid glycine serine flexible linker either site of the thrombin recognition sequence LVPRGS. Alternatively more than one protease sites may be located at the N-terminus of the linker for example the sequence G GEGRTATGGGSGLVPRGSGGGSGGGGSG (SEQ ID NO: 110) which consists of a FXa site (GEGRTAT, SEQ ID NO: 111) followed by a 5 residue flexible linker, a thrombin recognition sequence (LVPRGS) followed by a 10 residue flexible linker. Alternatively the protease site may be located at the C-terminal end of a flexible linker for example in the sequence GGGGSGGGGSGGLVPRGSGGGG (SEQ ID NO: 112) which contains a 12 residue flexible linker at the N-terminus followed by a thrombin recognition sequence and a short 4 residue flexible linker at the C-terminus. Depending on the location of the protease site within the linker and relative to the flanking protein domains in the fusion protein, different linker sequences will be left on the flanking sequences after cleavage. In the case of fusions of a scFv at the N-terminus of FVIII the linker GGGSGGGGSGLVPRGSGGGSGGGGSG will leave the sequence GSGGGSGGGGSG attached at the N-terminus of FVIII. In the case of fusions of a scFv at the C-terminus of FVIII the linker GGGSGGGGSGLVPRGSGGGSGGGGSG will leave the sequence GGGSGGGGSGLVP attached at the C-terminus of FVIII. Many different linker sequences could theoretically provide for correct folding of the fusion protein and efficient cleavage by the selected protease.

Using standard molecular biology techniques a series of FVIII-scFv fusion gene expression cassettes were constructed that encode proteins with the features as listed in Table 24. The proteins encoded by these constructs were expressed in HKB11 cells and purified.

Using standard molecular biology techniques a series of FVIII-scFv fusion gene expression cassettes were constructed that encode proteins with the features as listed in Table 24. The proteins encoded by these constructs were expressed in HKB11 cells and purified.

Example 11: In Vitro Partition Assay of RBC Targeted FVIII Molecules in Whole Blood Whole blood was drawn from huGPA/Hem A mice in to anticoagulant with 4% sodium citrate (Sigma, St Louis, Mo.). B-domain deleted FVIII (BDD) and FVIII-scFv fusion molecules were spiked into anticoagulated fresh whole blood from human GPA/Hem A mice at 1 IU/mL, and incubated at room temperature for 2-3 hours with gentle rotation. Plasma was prepared from an aliquot of blood by centrifugation at 1000 g for 3 min after incubation for 0, 5, 15, 30, 45, 60, 120, 180 min and the FVIII activity remaining in the plasma was determined using the chromogenic assay. By subtracting the amount of FVIII activity in the plasma from the amount of FVIII activity spiked in, the amount of the FVIII-scFv fusion bound to RBC was calculated.

To evaluate partition to cynomolgus monkey or human red blood cells, whole blood was draw from Cynomolgus monkey or normal human volunteers in to anticoagulant with 4% sodium citrate (Sigma, St Louis, Mo.). The red blood cells were purified by layering the whole blood on to ficoll followed by low speed centrifugation. The supernatant containing plasma, platelets and white blood cells was discarded and the red blood cell pellet was resuspended in 10 pellet volumes of PBS (50 mM Phosphate buffer, pH7.4, 150 mM NaCl). The red blood cells were then pelleted by slow speed centrifugation and the red blood cells re-suspended in

TABLE 24

Summary of FVIII-scFv fusion proteins with different characteristics

| Protein ID (TPP) | SEQ ID NO. | scFv antibody | Fusion site in FVIII | a3 domain status | Furin site present/% 1 chain | XSpecific activity (IU/mg) |
|---|---|---|---|---|---|---|
| 6195 | 113 | so6C12 | B-domain | Y1680F | Y/20% | 4600 |
| 8277 | 114 | so6C12 | B-domain | a3Δ | N/89% | 4500 |
| 8743 | 115 | 7792 | B-domain | a3Δ | Y/2% | 4580 |
| 8820 | 116 | 7790 | B-domain | a3Δ | Y/0.2% | 5320 |
| 8744 | 117 | 7793 | B-domain | a3Δ | Y/6% | 6174 |
| 8741 | 118 | 7792 | B-domain | WT | Y/7.5% | 6453 |
| 8798 | 119 | 7792 | N-terminus | WT | Y/22% | 4100 |
| 9049 | 120 | 7792 | C-terminus | WT | Y/22% | 5600 |
| 9049X | 121 | 7792 | C-terminus | a3Δ | N/ND | ND |
| 9049Y | 122 | 7792 | C-terminus | a3Δ | Y/ND | ND |
| 9711 | 123 | 7792 | B-domain | a3Δ | N/90% | 9549 |
| 9161 | 124 | 7792 | B-domain | a3Δ | Y/22% | 4361 |
| 9423 | 125 | 7792 | N-terminus (F2196K) | a3Δ | N/62% | 4971 |
| 9424 | 126 | 7792 | N-terminus | a3Δ | N/65% | 6493 |
| 9900 | 127 | 7792 | N and C | a3Δ | N/50% | 3001 |
| 9901 | 128 | 7792 | B and C | a3Δ | N/90% | 4872 |
| 9976 | 129 | 7792 | 2x in B | a3Δ | N/75% | 2695 |
| 9977 | 130 | 7792 | N and B | a3Δ | N/ND | ND |
| 10297 | 131 | 7792 | N-terminus | a3Δ | N; variant 1/ND | ND |
| 10298 | 132 | 7792 | N-terminus | a3Δ | N; variant 2/ND | ND |
| 10299 | 133 | 7792 | N-terminus | a3Δ | Y/ND | ND |
| 7867 | | FVIII-BDD-F2196K | | WT | Y/19.5% | 10836 |

ND: Not determined 10 volumes of PBS. This washing step was repeated 4 more times and the red blood cells finally resuspended in a volume of plasma from Hemophilia patients with less than 1% of normal levels of FVIII (GeorgeKing Bio-Medical, Overland Park, Kans.) to generate a total volume equal to the initial blood volume such that the RBC density was equal to that of normal whole blood. BDD and RBC targeted FVIII molecules were then spiked into RBC suspension in HemA plasma at 1 IU/mL, and incubated at room temperature for 2-3 hours with gentle rotation. After incubation for 0, 5, 15, 30, 45, 60, 120, 180 min a sample of the suspension was removed and centrifuged to pellet the RBC and the plasma was collected and frozen. An additional control was performed in which BDD or RBC targeted FVIII molecules were added at 1 IU/ml into the same human hemophilia A plasma and incubated for 5 minutes and 180 mins. These samples were used to determine the input FVIII activity in the presence of plasma which was used to calculate the percentage of the molecule that was bound to RBC. All plasma samples were then assayed together for FVIII activity using the Coatest SP assay (DiaPharma, Columbus, Ohio). The assay was performed following the manufacturer's instructions in a 96-well plate format. Briefly, 50 uL of WHO8 calibrator, plasma sample diluted 100-fold with 1× Coatest buffer and 50 uL of a mixture of activated FIX/FX/ phospholipid were added to each well, followed by 25 uL of 25 mM $CaCl_2$ and 50 uL of chromogenic substrate S-2765/I-2581. The plate was incubated at 37° C. for 10 minutes with shaking between each reagent addition. After the final addition of chromogenic substrate, the kinetics of FXa generated reflecting FVIII activity (Vmax, mIU/min) in each well were read at 405 nm at 37° C. for 10 min with 30 sec interval. The amount of FVIII activity in the plasma reflects the amount of unbound FVIII. The FVIII activity of the same molecule spiked in to Hemophilia A plasma alone (no RBC) and incubated for 5 minutes was normalized to 100%.

The data (see Table 25) demonstrated that the amount of BDD present in the plasma did not change significantly over time, indicating that BDD did not bind to RBC, as expected. However, increased binding of the scFv-FVIII fusion proteins over time was observed indicating that the anti-GPA scFv was mediating the binding of the scFv-FVIII fusions to the human RBC (Table 26). TPP-8798 in particular showed very fast association with human RBC when the experiment was performed in vWF deficient plasma. TPP-8798 consists of the 7792 scFv fused to the N-terminus of FVIII-BDD that contains the a3 domain and is primarily a 2 chain molecule. The observation that TPP-8798 exhibits no binding to human RBC in the presence of human Hem A plasma that contains vWF provides evidence that vWF interferes with binding of scFv-FVIII fusions to RBC. TPP-8741 and TPP-8798 differ only in the site at which the 7792 scFv is fused to FVIII with TPP-8741 having the scFv fused in place of the B-domain and TPP-8798 having the scFv fused at the N-terminus of FVIII. While both TPP-8741 and TPP-8798 achieved similar levels of RBC binding after 120 minutes, TPP-8798 bound to the RBC more rapidly with 76% bound after 1 minute compared to 35% for the B-domain fusion TPP-8741. These data demonstrated that a FVIII molecule in which the scFv is fused at the N-terminus of FVIII results in a molecule with more rapid binding to RBC, a characteristic that is preferred as it should enable more complete binding to RBC in vivo, especially in a situation where vWF or other plasma proteins may interfere with the binding to RBC. The protein TPP-9423 which consists of the 7792 scFv fused at the N-terminus of FVIII-BDD containing a deletion of the a3 domain and the furin site also exhibited rapid and complete binding to human RBC. TPP-9049 in which the 7792 scFv is fused at the C-terminus of FVIII-BDD containing the a3 domain and the furin site also exhibited slower binding to RBC than the corresponding N-terminal fusion with the same scFv (TPP-8798) suggesting that the C-terminus of FVIII is a less favorable location for fusion to a RBC targeting scFv.

TABLE 25

Examples of binding of FVIII-scFv fusion proteins to human RBC in vitro in vWF deficient and HemA plasma. The percentage of input scFv-FVIII fusion protein that was bound to human RBC at different time points is shown. For experiment s run in human Hemophilia A plasma only the 120 minute time point was collected

| | Percentage bound to human RBC over time | | | | | | |
|---|---|---|---|---|---|---|---|
| | vWF deficient plasma | | | | | | HemA Plasma |
| Protein ID | Time of incubation (Minutes) | | | | | | |
| (TPP) | 1 | 5 | 15 | 30 | 60 | 120 | 120 |
| 8743 | 45.9 | 69.5 | 78.0 | 79.4 | 78.8 | 79.6 | 76.4 |
| 8820 | NT | NT | NT | NT | NT | NT | NT |
| 8744 | NT | NT | NT | NT | NT | NT | NT |
| 8741 | 35.1 | 67.9 | 88.3 | 92.4 | 93.3 | 93.0 | 52.8 |
| 8798 | 76.5 | 92.5 | 95.2 | 95.7 | 95.8 | 95.7 | 0 |
| 9049 | 24.6 | 48.5 | 64.8 | 72.5 | 77.8 | 80.3 | NT |
| 9711 | 76.2 | 85.3 | 87.0 | 87.0 | 88.7 | 86.3 | NT |
| 9161 | 51.4 | 78.4 | 82.9 | 85.9 | 86.2 | 84.2 | NT |
| 9161 | 56.9 | 81.1 | 86.4 | 87.6 | 88.7 | 88.9 | NT |
| 9423 | 44.1 | 87.4 | 89.9 | 91.2 | 80.3 | 92.3 | NT |
| 9423 | 69.8 | 90.6 | 92.1 | 92.9 | 94.0 | 94.8 | NT |
| 9424 | NT | NT | NT | NT | NT | NT | 95.6 |
| 9900 | NT | NT | NT | NT | NT | NT | 71.8 |
| 9901 | 26.0 | 44.9 | 53.8 | 57.3 | 64.3 | 72.7 | 86.7 |
| 9976 | NT | NT | NT | NT | NT | NT | 95.2 |

Partitioning to human RBC in human hemophilia A plasma, which most closely mimics the situation in humans, is shown in Table 26. TPP-8741 that consists of the 7792 scFv fused in place of the B-domain in FVIII-BDD containing the a3 domain and furin site exhibited slow and incomplete binding to human RBC, reaching only 52% bound after 120 minutes. The slow binding of TPP-8741 is due to the presence of vWF in the Hemophilia A plasma. TPP-9424 that consists of the 7792 scFv fused at the N-terminus of FVIII-BDD containing a deletion of the a3 domain and the furin site exhibited very rapid and complete binding to human RBC in the presence of human hemophilia A plasma with 76% bound within 1 minute and reaching saturation binding of about 95% by 15 minutes. Interestingly, scFv-FVIII fusions containing 2 copies of the 7792 scFv exhibited slower binding to human RBC in hemophilia A plasma than did TPP-9424 that contains a single copy of the scFv. It might have been expected that including 2 copies of the scFv in one scFv-FVIII fusion might have increased the affinity for GPA via an avidity effect given that each scFv contains only a single antigen binding site. Surprisingly these data indicate that scFv-FVIII fusions containing 2 copies of the GPA targeting scFv exhibited slower binding than scFv-FVIII fusion containing one copy of the same scFv at the N-terminus. Among the three scFv-FVIII fusions containing 2 copies of the 7792 scFv, TPP-9976 that contains 2 tandem copies of the scFv in place of the B-domain of FVIII exhibited the fastest and most complete binding to human RBC. Interestingly, among FVIII-scFv containing two copies of the scFv, TPP-9976 also exhibited the longest persistence in vivo in the huGPA/HemA mice.

TABLE 26

Examples of binding of FVIII-scFv fusion proteins to human RBC in vitro in human Hemophilia A plasma. The percentage of input scFv-FVIII fusion protein that was bound to human RBC at different time points is shown. Percentage bound to human RBC in HemA plasma

| Protein ID (TPP) | Time of Incubation (Minutes) | | | | | |
|---|---|---|---|---|---|---|
|  | 1 | 5 | 15 | 30 | 60 | 120 |
| BDD-FVIII | 0 | 2 | 4 | 0 | 2 | 0 |
| 8741 | 0.0 | 13.8 | 16.3 | 20.5 | 37.1 | 52.8 |
| 9424 | 76.5 | 90.5 | 94.4 | 94.5 | 95.2 | 95.6 |
| 9900 | 19.3 | 34.4 | 52.0 | 57.7 | 66.9 | 71.8 |
| 9901 | 31.4 | 53.8 | 71.5 | 78.9 | 84.1 | 86.7 |
| 9976 | 55.2 | 74.3 | 86.6 | 90.4 | 93.5 | 95.2 |

Specific scFv-FVIII fusion proteins also bound to RBC from Cynomolgus (Cyno) monkey in human HemA plasma as shown in Table 27. The fastest and most complete binding was observed for TPP-9424 indicating that this molecule was a good candidate for evaluation in the Cyno monkey. TPP-9711, TPP-9161 and TPP-9976 also exhibited good binding to Cyno RBC. It was apparent that scFv-Fusions that contained the a3 domain such as TPP-8741 and TPP-8798 and thus were capable of binding vWF with high affinity exhibited little or no binding to Cyno RBC in human Hem A plasma that contains vWF. These same proteins (TPP-8741 and TPP-8798) did bind to Cyno RBC in vWF deficient plasma (Table 28) achieving 70 to 80% bound after 30 minutes.

TABLE 27

Examples of binding of FVIII-scFv fusion proteins to Cynomolgus monkey RBC in vitro in human Hemophilia A plasma. The percentage of input scFv-FVIII fusion protein that was bound to Cyno RBC after incubation for different times in Human Hemophilia A plasma is shown

| Protein ID (TPP) | PPB # | % Bound to Cyno RBC at different times in Hemophilia A plasma Time of incubation (Minutes) | | | | | |
|---|---|---|---|---|---|---|---|
|  |  | 1 | 5 | 15 | 30 | 60 | 120 |
| 8743 | 6723 | 17.43 | 53.03 | 65.69 | 73.03 | 78.5 | 79.02 |
| 8820 | 6778 | NT | NT | NT | NT | NT | NT |
| 8744 | 6950 | NT | NT | NT | NT | NT | NT |
| 8741 | 6559 | 0.0 | −19.3 | −12.5 | −1.9 | −9.8 | −1.9 |
| 8798 | 6705 | 0.0 | −21.9 | −7.8 | −8.7 | −19.1 | 2.9 |
| 9049 | 6733 | 28.1 | 48.2 | 62.1 | 67.5 | 72.2 | 73.8 |
| 9711 | 7816 | 40.6 | 63.0 | 72.1 | 74.2 | 80.2 | 81.8 |
| 9161 | 7644 | 35.0 | 52.8 | 58.2 | 67.9 | 73.2 | 71.0 |
| 9423 | 7677 | NT | NT | NT | NT | NT | 62.8 |
| 9424 | 7888 | 62.9 | 83.0 | 87.2 | 87.8 | 89.0 | 89.1 |
| 9900 | 7960 | 30.9 | 38.2 | 40.6 | 43.2 | 52.9 | 55.1 |
| 9901 | 7855 | 26.4 | 46.0 | 54.0 | 58.0 | 68.0 | 71.0 |
| 9976 | 7998 | 53.4 | 65.7 | 75.6 | 78.1 | 84.5 | 86.8 |
| Protein ID |  |  |  |  |  |  |  |

TABLE 28

Examples of binding of FVIII-scFv fusion proteins to Cynomolgus monkey RBC in vitro in human vWF deficient plasma. The percentage of input scFv-FVIII fusion protein that was bound to Cyno RBC after incubation for different times in Human vWF deficient plasma is shown

| Protein ID (TPP) | % bound to Cyno RBC in wWF deficient plasma Time of Incubation (Minutes) | | | | | |
|---|---|---|---|---|---|---|
|  | 1 | 5 | 15 | 30 | 60 | 120 |
| 8741 | 28.1 | 45.0 | 58.5 | 69.3 | 76.9 | 79.3 |
| 8798 | 28.1 | 63.9 | 79.5 | 83.4 | 84.7 | 84.5 |
| 9161 | 0.0 | 45.0 | 62.8 | 71.4 | 76.7 | 77.8 |

It can also be appreciated that the binding of a given scFv-FVIII fusion protein to human RBC was faster and more complete than to Cyno RBC in the same human HemA plasma matrix. This is likely due to a lower affinity of the anti-GPA scFv for Cyno GPA compared to human GPA. This is expected given that the sequence of GPA in the region of the epitope for the 6C12 antibody (monkey; GRTHYPPEE and human; VRTVYPPEE) are not identical.

Example 12: Kinetics of Binding of FVIII-scFv Fusion Proteins to Glycophorin a Peptide GP5

The binding kinetics of FVIII-scFv fusions to glycophorin A may be evaluated using surface plasmon resonance (SPR), a technique well known in the art. Attempts to perform SPR analysis of FVIII-scFv fusion proteins binding to membrane preparations from human RBC were not successful for technical reasons. However, binding data could be obtained by using a peptide that was identified in Example 6 to contain the epitope for the anti-GPA antibody 6C12 used in the FVIII-scFv fusions. The peptide GP5 (EVSEASVRTVYPPEEETGER) was attached to the probe of the OCTET instrument (ForteBio/Pall Corp) which was dipped in to a solution of the purified FVII-scFv fusion protein and the binding kinetics were measured by the instrument and fitted to a 1:1 binding model. The results are summarized in Table 29 for selected FVIII-scFv fusion proteins. The results demonstrate that the affinities to the GPA peptide ranged from 13.3 to 1.3 nM with off-rates ranging from 2.7 E−3 to 6.6 E−4 and on-rates ranging from 3.5 E+5 to 1.27 E+6. The true affinity to an intact, correctly folded GPA protein in the RBC membrane is expected to be higher than the values obtained for binding to a 20 residue peptide. This was supported by the observation that the affinity of binding of the affinity matured anti-GPA 6C12 antibodies to RBC membranes was higher than for the GP5 peptide by about 10-fold

TABLE 29

Binding kinetics of FVIII-scFv fusions to glycophorin A peptide GP5 as measured by surface plasmon resonance in the Octet instrument

| Sample ID | TPP# | KD (nM) | kon (1/Ms) | kdis (1/s) | R^2 |
|---|---|---|---|---|---|
| BDD-N scFv | 8798 | 4.0 | 8.23E+05 | 3.29E−03 | 0.98 |
| BDD-C scFv | 9049 | 2.4 | 1.27E+06 | 3.05E−03 | 0.98 |
| BDD-Bdom scFv | 8741 | 13.3 | 3.51E+05 | 4.65E−03 | 0.97 |
| BDD 7792 A3 del | 8743 | 4.89 | 5.25E+05 | 2.70E−03 | 0.98 |
| BDD-Bdom 7793 α3del | 8744 | 7.35 | 6.52E+05 | 4.80E−03 | 0.97 |
| BDD-N-7792 a3 del | 9423 | 1.27 | 5.2E+05 | 6.6E−04 | 0.99 |

Example 13: In Vitro ROTEM Whole Blood Clotting Assay

Figure 9:
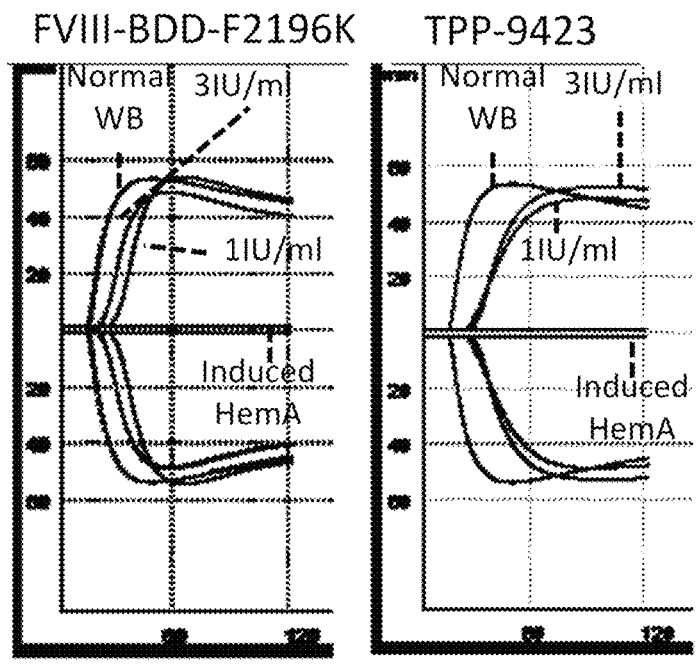
FIG. 9: Whole blood clotting ex vivo measured by thromboelastography in the ROTEM instrument. The X-axis is time in seconds and the Y axis is amplitude which is proportional to the firmness of the clot.

The majority of optimized FVIII-scFv fusion molecules will bind quickly to RBC after injection into the circulation such that low levels of FVIII activity remains in plasma. Therefore, traditional plasma based chromogenic and aPTT assays are not appropriate for monitoring RBC targeted FVIII levels. Therefore the ROTEM® whole blood clotting assay was used to assess the FVIII activity after spiking of RBC targeted FVIII molecules into HemA whole blood. To perform the assay, citrated whole blood from huGPA/HemA mice drawn via vena cava was mixed with equal IU of RBC targeted FVIII or rFVIII-BDD (based on the Coatest® chromogenic assay) at room temperature. Samples were decalcified by dispensing 300 μL treated blood with an automated pipette into ROTEM® cups with 20 μL Star-tem® (200 mM $CaCl_2$, Munich, Germany) without exogenous activator (NATEM). Clotting was initiated immediately after the last pipetting, and blood clot formation was continuously monitored for 2 hours at 37° C. ROTEM® analysis parameters include clotting time (CT), clot formation time (CFT), and α-angle. The same assay was performed in normal human whole blood by using the anti-FVIII neutralizing monoclonal antibody BO2C11 to neutralize the endogenous human FVIII. After addition of 100 ug/ml of BO2C11 to normal human whole blood and analysis by ROTEM, no clot formation was observed ("Induced HemA" in FIG. 9). After addition of both BO2C11 and either I IU/ml or 3 IU/ml of the FVIII-BDD-F2196K protein and pre-incubation for 20 minutes prior to re-calcification, clotting was restored to levels similar to that in human whole blood without added BO2C11 9 (FIG. 9). The addition of the FVIII-scFv fusion protein TPP-9423 which contains the F2196K amino acid change provided a similar restoration of clotting in ROTEM as was seen for FVIII-BDD-F2196K. In this assay format it is expected that 80 to 90% of the added TPP-9423 will have bound to the RBC within the 20 minute incubation period prior to the initiation of clot formation by re-calcification. Thus the clotting activity observed for TPP-9423 in this assay format is derived primarily from TPP-9423 bound to RBC and thus indicates that RBC bound TPP-9423 exhibits clotting activity similar to FVIII-BDD-F2196K that remains free in the plasma.

Example 14: Measuring In Vivo Pharmacodynamics of RBC Targeted FVIII in huGPA/HemA Mice Using Ex Vivo ROTEM Assay The pharmacodynamics of RBC targeted FVIII proteins were assessed in huGPA/HemA mice. As a comparator we used Eloctate which is a marketed FVIII based drug in which human FVIII is genetically fused to a human Fc domain in order to prolong the circulating half-life of the protein. Eloctate has a 2-fold longer T1/2 in mice than un-modified FVIII and protects HemA mice from bleeding for about twice as long as un-modified FVIII protein (Dumont et al, Blood 29, p 3024-3030, 2012). RBC targeted FVIII molecules or Eloctate were administered into HuGPA/HemA mice by tail vein injection at 200 IU/kg. At different times after injection ranging from 2 h to 16 days, 400 uL of whole blood were drawn via vena cava from 4 mice with 25G syringe filled with 40 uL of 4% sodium citrate. Clotting time was measured by ROTEM by immediately transferring 300 uL of the whole blood and 20 uL of Star-tem® (0.2 mol/l $CaCl_2$) to the cuvette of the ROTEM® delta machine. The median clotting time of the 4 mice per time point was calculated. To correlate clotting time to the level of FVIII activity, different amounts of un-modified FVIII ranging from 0.6% to 60% FVIII activity (based on units from chromogenic assay and assuming I IU/ml of plasma equals 100% FVIII) were added to anti-coagulated whole blood from the huGPA/HemA mice and clotting time measured by ROTEM. These results indicated that 0.6% FVIII was equivalent to clotting time of about 1450 sec, 2% FVIII was equivalent to clotting time of about 1150 sec, 6% FVIII was equivalent to clotting time of about 800 sec, 60% FVIII was equivalent to clotting time of about 750 sec. Un-treated whole blood from the huGPA/HemA mice that contains no FVIII had a clot time in ROTEM of 2250 seconds or longer

Figure 10:
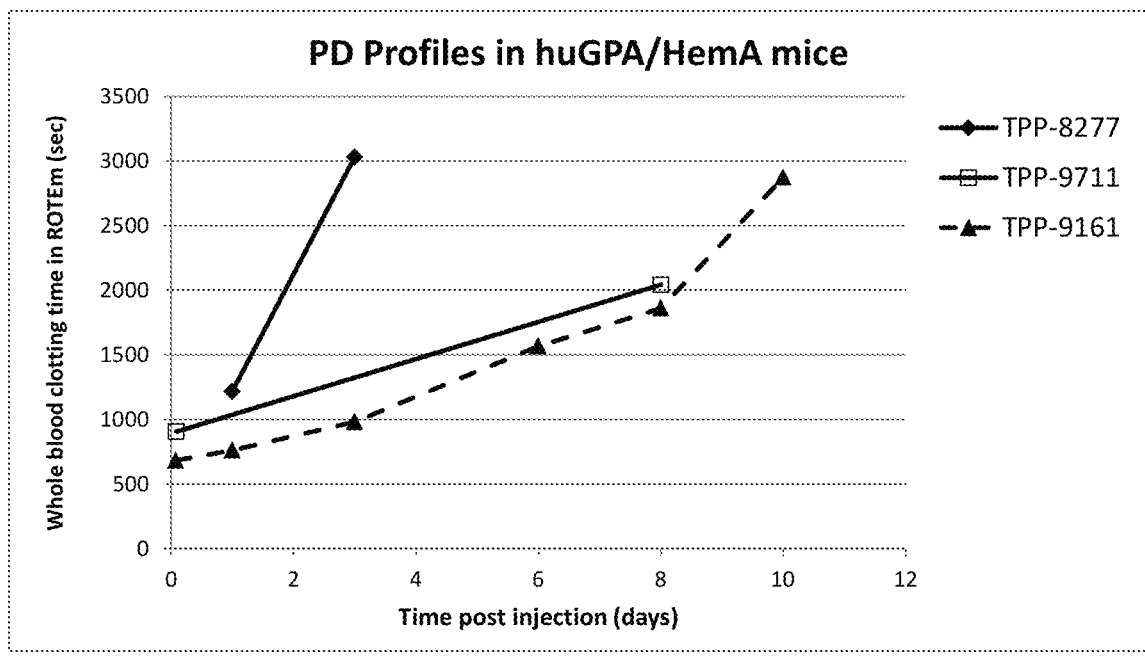
FIG. 10: Shown are PD profiles of TPP-8277, TPP-9711, and TPP-9161 in huGPA/HemA mice.

Example 15: Affinity Maturation of the scFv Antibody Prolongs the Pharmacodynamics of a scFV-FVIII Fusion In Vivo To confirm that affinity maturation of the anti-GPA targeting antibody 6C12 translates to improved duration of action when fused to FVII, the molecules TPP-8277 and TPP-9711 were produced. Both TPP-8277 and TPP-9711 contain a variant of the 6C12 scFv inserted in place of the B-domain of FVIII from which the a3 domain and the furin site were deleted. TPP-8277 contains the humanized and germlined version of the 6C12 scFv (antibody TPP-5906) while TPP-9711 contains the affinity matured scFv variant 7792. An additional comparator molecule is TPP-9161 that contains the affinity matured 7792 scFv fused to FVIII in place of the B-domain and a deletion of the a3 domain but is a predominantly 2 chain molecule. At different time points after injection in to the huGPA/HemA mice the whole blood clotting time was measured by ROTEM as described in example 14 and the results are shown in FIG. 10. The FVIII fused to the humanized and germlined 6C12 scFv had detectable FVIII activity in circulation at 24 h post dosing as indicated by a clotting time of around 1200 seconds. However, by 3 days post injection of TPP-8277 the clotting time had returned to the hemophilic range indicating that FVIII fused to the humanized and germlined 6C12 scFv was rapidly cleared from circulation. In contrast, TPP-9711 and 9161 that both contain the affinity matured scFv 7792 exhibited a prolonged PD profile with clotting times returning to the hemophilic range only after 8 to 10 days. From this it can be concluded that the affinity maturation of the 6C12 antibody which improved the KD, and in particular reduced the off-rate was essential to achieve a long persistence in circulation when fused to FVIII.

Figure 11:
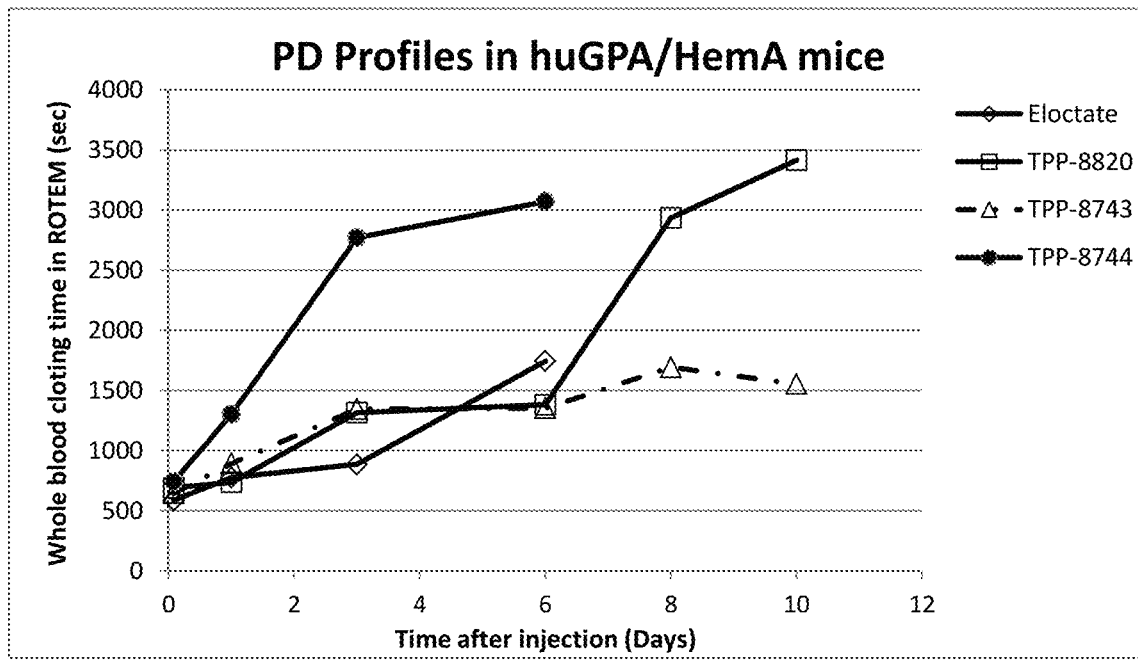
FIG. 11: Shown are PD profiles of TPP 8820, 8743 and 8744 compared to Eloctate in huGPA/HemA mice.

Example 16: Selection of the scFv Antibody with Maximal Prolongation of Pharmacodynamics in Vivo To identify the specific variant of the affinity matured 6C12 scFv antibody that when fused to FVIII provided the longest persistence in the circulation of mice, the fusion proteins TPP-8820, 8743 and 8744 that contain the 7790, 7792 and 7793 scFv variants, respectively fused in place of the B-domain of FVIII from which the a3 domain was deleted were injected into huGPA/HemA mice and their pharmacodynamics (PD) profiles were measured using ex vivo ROTEM as the read out and compared to that of Eloctate. As shown in FIG. 11, TPP-8743 (7792 scFv-FVIII fusion) exhibited the longest PD effect with clotting times remaining at or below 1500 seconds for the duration of the study (10 days). TPP-8820 (scFv 7790) had a similar profile to TPP-8743 until day 6 but by day 8 the clot times had increased in to the hemophilic range (above 2250 seconds).

TPP-8744 (scFv 7793) exhibited a very short persistence in circulation with clotting times returning to the hemophilic range by day 3. The rapid clearance of TPP-8744 is similar to that of un-modified FVIII (data not shown). In conclusion, these in vivo data demonstrate that the specific scFv variant 7792 present in TPP-8743 provided the longest persistence when fused in place of the B-domain of FVIII. The duration of action of TPP-8743 in mice was also superior to that of the FVIII-Fc fusion (Eloctate).

Figure 12:
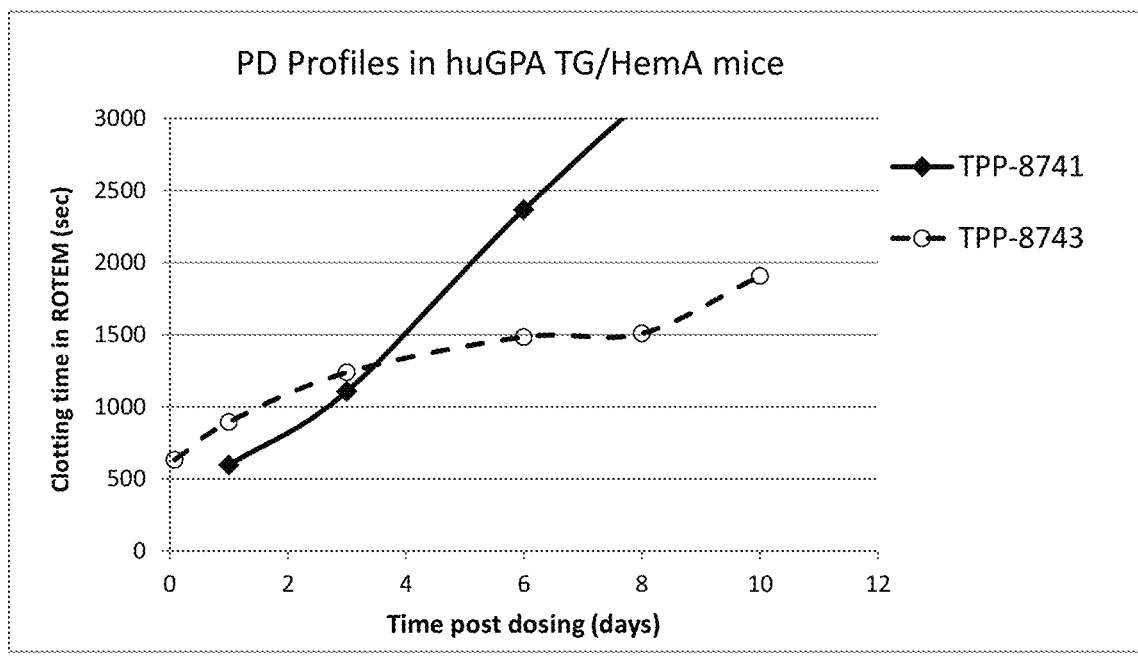
FIG. 12: Shown are PD profiles of TPP 8741 and 8743 in huGPA/HemA mice.

Example 17: Evaluation of the Effect of Von Willebrand Factor (vWF) Binding to FVIII Upon the Duration of the Pharmacodynamics Profile of RBC Targeted FVIII Molecules While it is known that binding of vWF to FVIII prolongs the circulation time of un-modified FVIII, it is possible that vWF may interfere with the ability of a RBC targeted FVIII molecule to bind to RBC. vWF is a large multimeric protein which might stearically interfere with the ability of an anti-GPA scFv fused to FVIII to bind to RBC. In order to determine if vWF binding to a RBC targeted FVIII has a positive or negative impact on the circulation time in vivo we compared molecules TPP-8741 and TPP-8743 both of which are composed of the 7792 scFv fused in place of the B-domain of FVIII. While TPP-8741 contains the complete FVIII sequences found in FVIII-BDD, TPP-8743 contains a deletion of residues 1652 to 1682 that comprise the a3 domain of FVIII that is known to contain the major vWF binding region of FVIII. FIG. 12 shows that TPP-8743 has a longer duration of action in huGPA/HemA mice than TPP-8741, demonstrating that deleting the a3 domain enables the scFv-FVIII fusion protein to persist longer in circulation. This data suggests that vWF binding to the scFv-FVIII fusion may interfere with binding to the RBC. This conclusion was supported by in vitro RBC partition studies that demonstrated increased RBC binding of scFv-FVIII fusion proteins in which the a3 domain was deleted.

Figure 13:
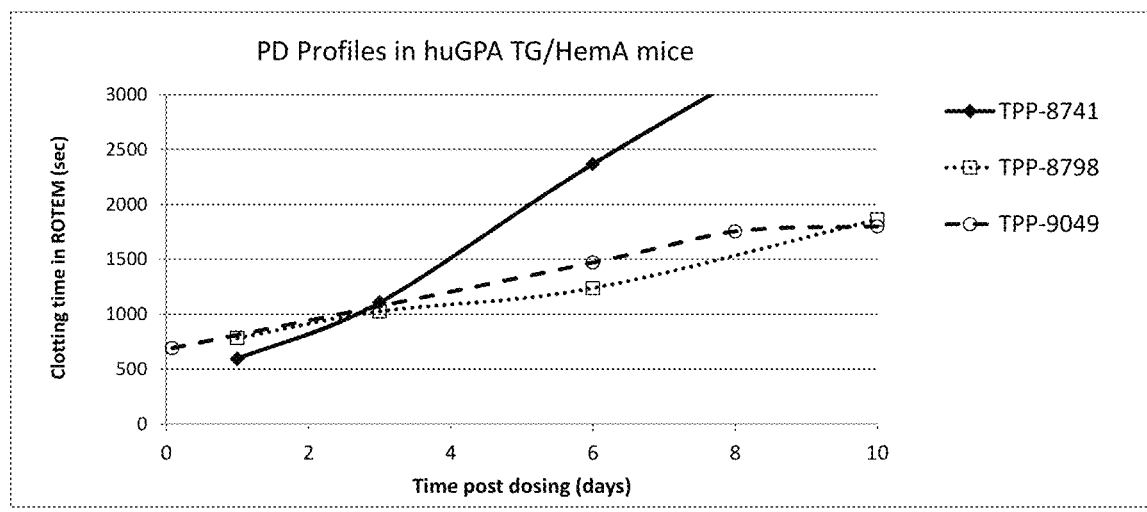
FIG. 13: Shown are PD profiles of TPP-8741, TPP-8798, and TPP-9049 in huGPA/HemA mice.

Example 18: Evaluation of the Location within FVIII of Fusion to the Anti-GPA scFv Upon the Duration of the Pharmacodynamics Profile in Mice It can be appreciated that the location within FVIII at which the anti-GPA scFv is placed might impact the kinetics of binding to RBC. The location of the scFv within FVIII might impact the ability of the scFv to access and bind to its epitope on GPA in the correct conformation. Other factors such as the local net charge of the protein in the region of the scFv might also impact the ability of the scFv-FVIII fusion to interact with GPA on the highly negatively charged surface of an RBC. The molecules TPP-8741, 8798, and 9049 are composed of the optimal scFv 7792 fused to FVIII-BDD either in place of the B-domain (TPP-8741) or at the N-terminus of FVIII (TPP-8798) or at the C-terminus of FVIII (TPP-9049). For fusion at the N-terminus and the C-terminus a linker containing a consensus thrombin cleavage site (GGGSGGGGSGLVPRGSGGGSGGGGSG) was placed between the scFv and FVIII to enable removal of FVIII from the RBC surface upon local activation of the coagulation system. All three of these molecules contain the a3 domain and are thus capable of binding to vWF. FIG. 13 shows the PD profiles of TPP-8741, TPP-8798, and TPP-9049 in the huGPA/HemA mice. TPP-8741 where the scFv is in the B-domain had the shortest duration of action, returning to the hemophilic range by day 6. TPP-9049 in which the scFv is fused at the C-terminus of FVIII had an intermediate duration of action. TPP-8798 in which the scFv is fused at the N-terminus of FVIII exhibited a significantly longer duration of action than TPP-8741 and was slightly improved over TPP-9049. These data demonstrate that fusing the scFv to the N-terminus of FVIII provided a significantly longer duration of action in vivo than fusion in place of the B-domain. Fusion of the scFv at the C-terminus of FVIII provided a similarly extended duration of action as did fusion at the N-terminus of FVIII. These results demonstrate that the N-terminus and the C-terminus of FVIII are preferred sites for fusion to an scFv designed to target FVIII to RBC in order to extend their persistence in the circulation. Fusion at the N-terminus provided a small improvement over fusion at the C-terminus.

Figure 14:
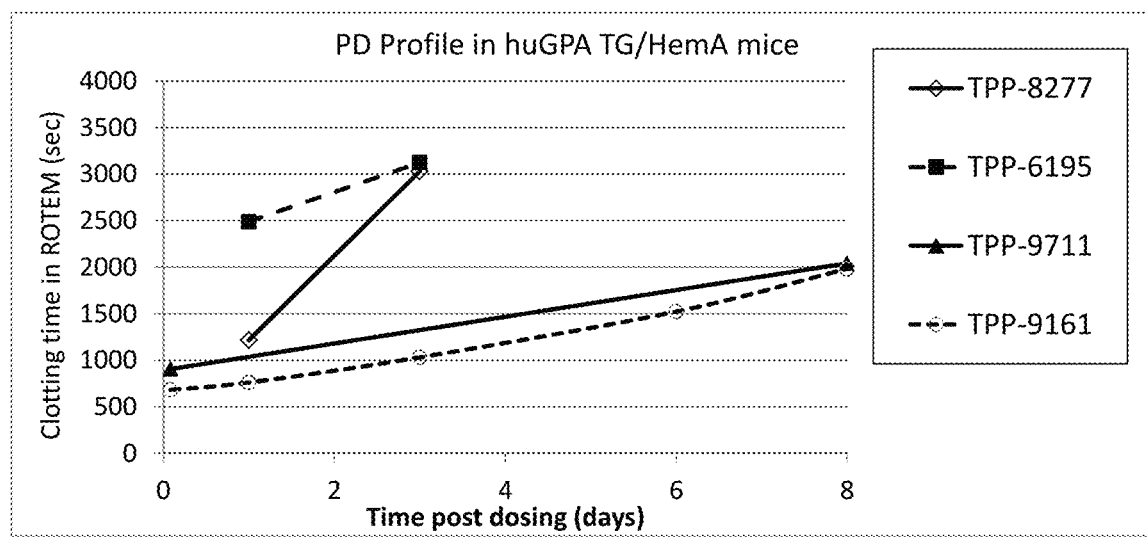
FIG. 14: Shown are PD profiles of TPP-9161, TPP-9711, TPP-8277 and TPP-6195 in huGPA/HemA mice.

Example 19: Comparison of 1 Chain and 2 Chain Forms of scFv-FVIII Fusion Proteins While endogenous FVIII proteins exist primarily as a 2 chain molecule derived from the proteolytic cleavage of the primary polypeptide at the furin site at residue 1648, a 1 chain FVIII molecule might be more stable in vivo. A 1 chain molecule might also be more homogenous and thus be less complex to manufacture. To generate predominantly 1 chain forms of scFv-FVIII fusion proteins we deleted the furin site (RHQR) located between residues and 1645 and 1648. Molecule TPP-9161 is composed on the 7792 scFv fused to FVIII in place of the B-domain in which the a3 domain was deleted but the furin site remains intact. Molecule TPP-9711 is identical to TPP-9161 except that the sequence SQNPPVLKRHQREIT from residues 1637 to 1651 that contains the furin site (RHQR) have been deleted. The scFv-FVIII fusions TPP-6195 and TPP-8277 both contain the humanized and germlined 6C12 scFv (so6C12) in place of the B-domain and both are deficient in vWF binding via deletion of the a3 domain in the case of TPP-8277 or by mutation of the residue Y1680 to F in the case of TPP-6195. Mutation of Y1680 to F is known to significantly reduce vWF binding (Leyte et al 1991, J. Biol Chem. Vol 266, p 740-746). While TPP-6195 contains the furin site and is primarily a 2 chain molecule, TPP-8277 lacks the furin site and is composed of about 90% 1 chain molecule. FIG. 14 shows the PD profile of TPP-9161, TPP-9711, TPP-6195 and TPP-8277 in the huGPA/HemA mice. In the case of the FVIII fusion with the affinity matured scFv 7792, the PD profile was similar for the 1 molecule that was predominantly 1 chain (TPP-9711) and the the molecule that was predominantly 2 chain (TPP-9161) with the 2 chain form having a slight advantage in absolute clotting activity. As expected the FVIII fusions to the humanized and germlined 6C12 scFv that has lower affinity to GPA than the affinity matured scFv exhibited short persistence in circulation. The molecule that was primarily 1 chain (TPP-8277) exhibited much better clotting activity at 24 h as compared to the molecule composed of primarily 2 chains (TPP-6195). By 3 days after dosing the clotting activity provided by both TPP-8277 and 6195 had returned to the hemophilic range. TPP-8277 contains the a3 domain deletion that is expected to result in a more complete blockade of vWF binding than the Y1680F mutation present in TPP-6195. Given that vWF binding reduces RBC binding the more complete blockade of vWF binding afforded by the a3 domaian deletion in TPP-8277 could have resulted in superior RBC binding and to the observed superior clotting activity as compared to TPP-6195 that only contains the Y160F mutation. Overall these data suggest that a 1 chain form of a scFv-FVIII fusion does not have a significantly improved PD profile in mice.

However, scFv-FVIII fusion composed of primarily 1 chain FVIII does not have a significantly inferior PD profile in mice and would represent an more homogenous product and thus could be preferred from a manufacturing perspective Example 20: Combination of the Optimal scFv, Fusion Site and vWF Binding Status in One scFv-FVIII Fusion Examples 15 to 19 demonstrated that the longest persistence in the huGPA/HemA mice was provided by (i) the 7792 affinity matured anti GPA scFv; (ii) fusion of the scFv at the N-terminus of FVIII; (iii) deletion of the a3 domain of FVIII to prevent or reduce vWF binding to FVIII. In addition a single chain form of the scFv-FVIII fusion protein may be preferred due to greater protein homogeneity and does not negatively impact the PD profile as compared to a predominantly 2 chain form of the protein.

Therefore the molecule TPP-9424 was constructed that is composed of the 7792 scFv fused at the N-terminus of a B domain deleted FVIII that also has the a3 domain deleted and the furin site deleted. A variant of this molecule called TPP-9423 was also generated that is identical to TPP-9424 except that it contains a point mutation F2196K within the FVIII portion of the protein. The F2196K mutation makes the FVIII resistant to neutralization by the anti-FVIII antibody BO2C11. This mutation was introduced specifically for the purpose of enabling the clotting activity of the molecule to be detected in the blood of normal animals such as non-human primates that contain normal levels of endogenous FVIII. Neutralization of the endogenous FVIII by addition of the BO2C11 antibody will render the blood hemophilic and thus enable the clotting activity of an introduced FVIII-F2196K variant protein to be measured.

Figure 15:
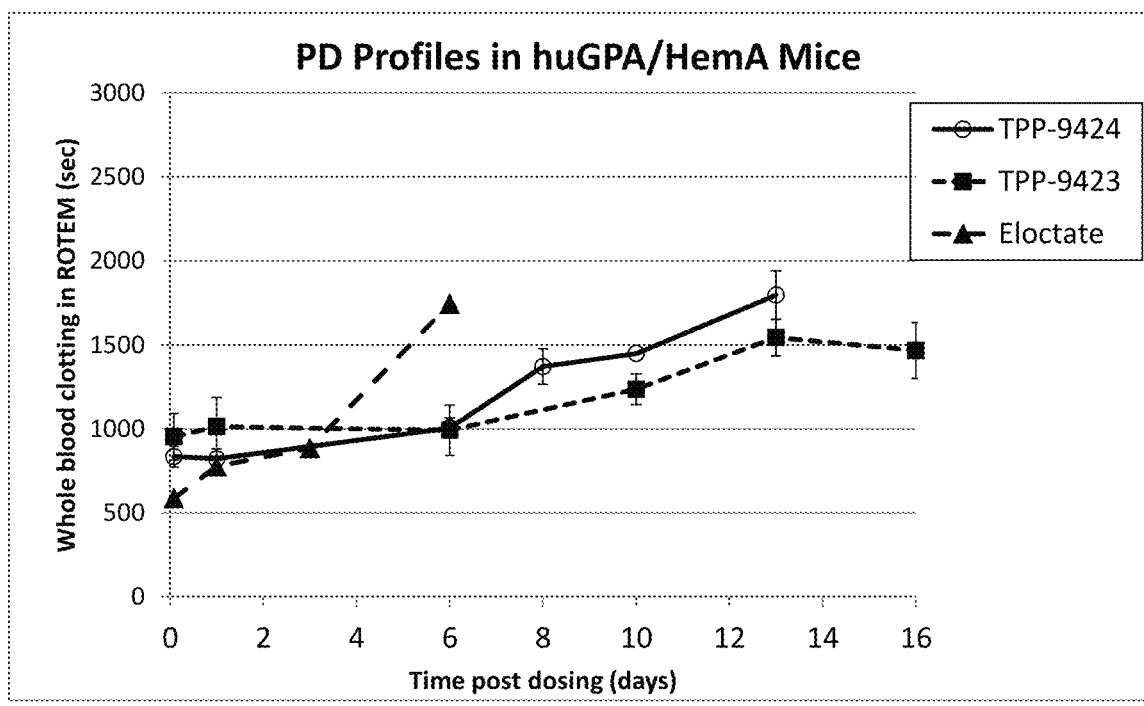
FIG. 15: Shown are PD profiles of TPP-9424 and TPP-9423 in huGPA/HemA mice.

The PD profiles of TPP-9424 and TPP-9423 were evaluated in the huGPA/HemA mice and the results are shown in FIG. 15. Starting at day 10 post injection some mice had developed antibodies against human FVIII which is expected given than human FVIII is a foreign protein in mice. Mice within a group which exhibited clotting times significantly longer than those of mice within the same group were assumed to have cleared the injected FVIII-scFv fusion protein as a result of these anti-FVIII antibodies and were excluded from analysis. The results (FIG. 15) demonstrate that both TPP-9423 and TP-9424 exhibit a long persistence in the circulation of the huGPA/HemA mice with ex vivo clotting times remaining in the non-hemophilic range until day 16, the last day of the study.

Figure 16:
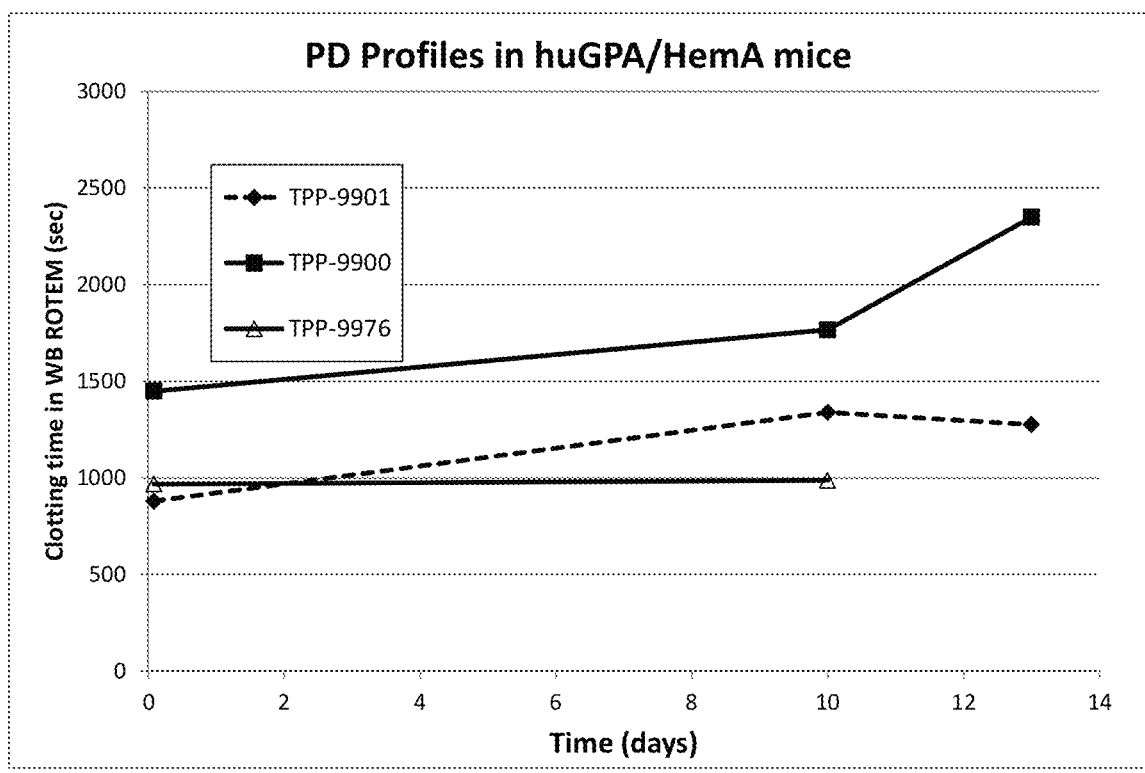
FIG. 16: Shown are PD profiles of TPP-9900, 9901, and 9976 in huGPA/HemA mice

Example 21: PD Profiles of scFv-FVIII Fusions Containing 2 Copies of the Anti-GPA scFv in huGPA/HemA Mice A scFv form of an antibody contains a single antigen binding domain composed of the VL and VH domains and thus is monomeric in terms of the binding to the epitope. Full length antibody formats such as IgG contain two antigen binding domains and as such the apparent binding strength to a surface bound epitope can be increased via an avidity effect in which both binding domains engage adjacent epitopes simulataneously. Thus it was envisaged that a scFv-FVIII fusion protein containing 2 copies of the anti-GPA scFv might have increased binding strength to GPA on the surface of RBC. Such increased binding strength would be expected to be beneficial in terms of increasing the speed of binding to RBC and prolonging the time that the scFv-FVIII fusion protein remains bound to the RBC surface. An avidity effect could be particularly important in reducing the off rate from the RBC surface which should translate to a longer persistence in circulation, the main goal of this invention. Therefore scFv-FVIII fusion proteins were constructed in which 2 copies of the 7792 scFv were fused to FVIII-BDD containing the deletion of the a3 domain and the furin site. The fusion sites in these molecules were; (i) TPP-9900; N-terminus and C-terminus, (ii) TPP-9901; B-domain and C-terminus, (iii) TPP-9976; 2 tandem scFv in place of the B-domain, and (iv) TPP-9977; N-terminus and B-domain. The proteins TPP-9900, 9901, and 9976 were purified and their PD profiles in huGPA/HemA mice were determined as shown in FIG. 16. Some of the mice dosed with TPP-9976 and TPP-9900 appeared to have developed antibodies against the dosed molecules at day 10 and day 13 as evidenced by clot times in the hemophilic range. Nevertheless the data showed that TPP 9976 and TPP-9901 exhibited a long duration of action. The PD profile of TPP-9900 was inferior to that of TPP-9976 and TPP-9901 indicating that the bivalent fusion containing the the scFv at the N and C termini was not as favorable as the bivalent fusion containing the scFv at the C-terminus and in place of the B-domain or the bivalent fusion containing two tandem copies of the scFv in place of the B-domain. Comparison to the mouse PD data for TPP-9423 in which a single copy of the 7792 scFv was fused to FVIII at the N-terminus indicates that scFv-FVIII fusions containing 2 copies of the 7792 scFv did not provide a further improvement in the duration of action in mice.

Figure 17:
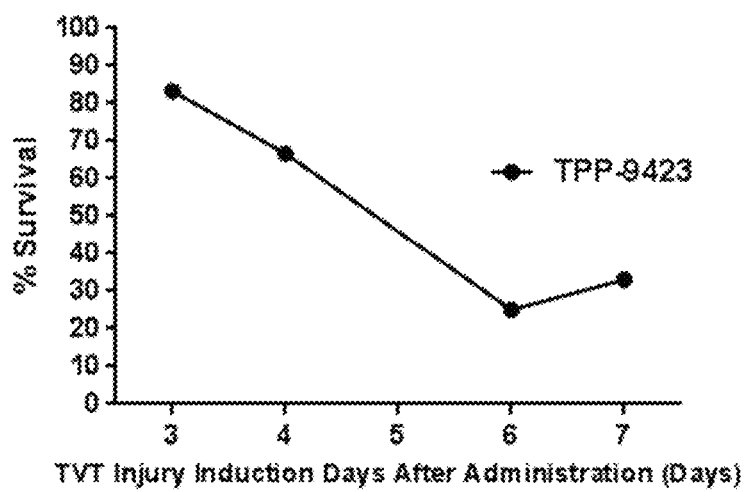
FIG. 17: Efficacy of TPP-9423 in huGPA/HemA mice as measured by survival at 24 h after tail vein transection. Mice were injected with 200 IU/kg of TPP-9423.

Example 22: Evaluation the Efficacy of scFv-FVIII Fusion Proteins in HuGPA/HemA Tail Vein Transection Mouse Bleeding Model Eight (8) week old male mice were randomized into different treatment groups by their body weight. Mice were dosed by tail vein injection at different times prior to the tail vein transection. Before the tail vein transection, mice were anesthetized (IP) with a cocktail containing 70 µg/kg of ketamine and 0.7 mg/kg of medetomidine. The tail was marked at the location where the diameter is about 2.7 mm. The anesthetic effect of medetomidine was reversed with 0.7 mg/kg of atipamezole by IP injection. The tail vein was transected with a scalpel blade where it was the marked. The tail was then submerged into 37° C. saline tube for 3 minutes to rinse away the blood from the cut. The mouse was then returned to a clean cage with white paper bedding placed on top of a 4×8 inch heating pad. The observation for morbidity was made hourly for the next 9 hours followed by a final observation at 24 hr post transection. The survival rate at 24 h after the TVT injury was plotted in FIG. 17. These results demonstrate that TPP-9423 provided protection against bleeding at 3, 4, 6 and 7 days after a single injection of the protein. The level of protection against bleeding as measured by survival is consistent with the PD profile of this molecule in the same mice which showed (FIG. 15) clotting activity equivalent to FVIII levels between 6% and 2% on days 3 to 7.

Example 23: Measurement of TPP-9423 in Cynomolgus Monkeys

Figure 18:
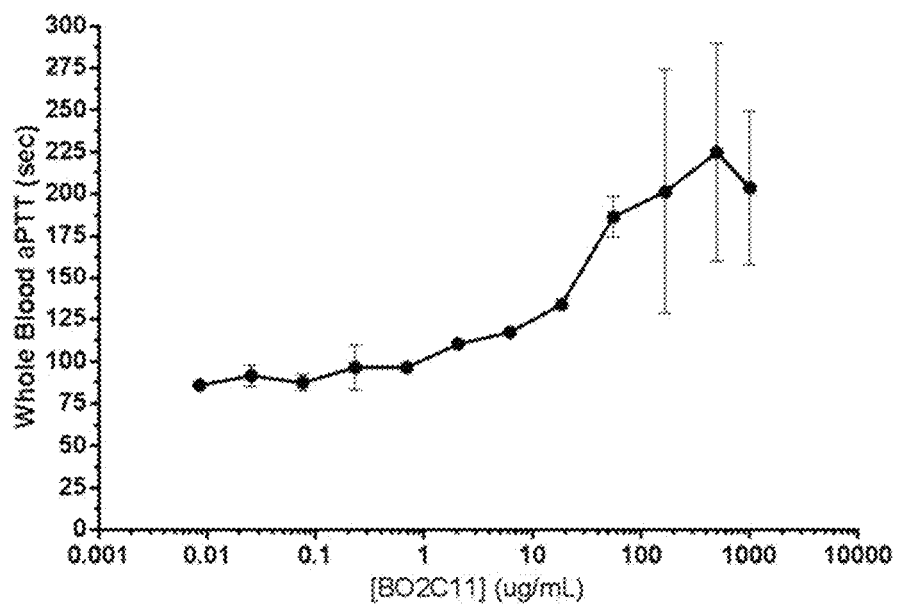
FIG. 18: Titration of BO2C11 mAB in inhibition of clotting time in Cynomalgus monkey whole blood using Hemochron aPTT assay.

A non-human primate such as the Cynomolgus (Cyno) monkey represents a species more closely related to humans and as such is more likely to be predictive of patient responses to a FVIII molecule. In order to evaluate the persistence of scFV-FVIII fusion proteins in the Cyno monkey, one amino acid change, F2196K, was made in the FVIII portion of the protein. This single amino acid change blocks the neutralization of FVIII activity by the monoclonal antibody (mAb) BO2C11 while not impacting the coagulation activity of FVIII itself (Lin et al 2015, PLOS ONE, 10(1) e01 16577. doi:10.1371). The BO2C11 mAB is also able to neutralize monkey FVIII. To confirm that the effect of the F2196K mutation was translatable to scFv-FVIII fusions the protein TPP-9423 was tested in a whole blood clotting assay using the Hemochron Signature Elite instrument (Accriva Diagnostics). Whole blood was collected from Cyno monkey into 3.2% citrate at a 9:1 ratio (blood to citrate) and stored at 4° C. up to 48 h until needed. Anti-coagulated Cyno whole blood was incubated with BO2C11 mAB at different concentrations or left untreated then added to the Hemochron cuvette and clotting time was measured using the aPTT program setting. In the absence of BO2C11 the Cyno whole blood clotted rapidly with a clot time of about 80 seconds as would be expected given that the blood was taken from a normal Cyno with normal coagulation system including normal FVIII levels (FIG. 18). As expected, when the neutralizing anti-FVIII mAB BO2C11 was spiked in to the anti-coagulated Cyno whole blood at increasing concentrations the clotting time increased until a plateau was reached at about 180 seconds (FIG. 18). Based on these results a BO2C11 concentration of 100 ug/ml was selected as sufficient to fully neutralize the endogenous monkey FVIII and this concentration was used in all subsequent assays.

Figure 19:
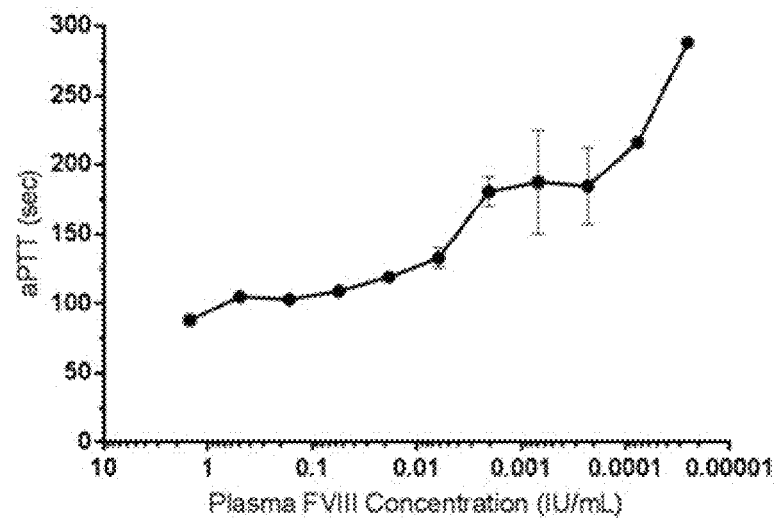
FIG. 19: Dose response of TPP-9161 in Cynomalgus monkey whole blood clotting assay (aPTT measured in Hemochron) in the presence of BO2C11 mAB.

To evaluate the resistance of TPP-9161 (7792 scFv fused in place of the B-domain of FVIII-BDD with a3 domain deleted and F2196K) to inhibition by BO2C11, anti-coagulated Cyno whole blood was mixed with 100 ug/ml of BO2C11 and increasing concentrations of TPP-9161. The clotting time was then measured in the Hemochron device. There was a linear dose response to TPP-9161 (FIG. 19) with 1 IU/ml of TPP-9161 which is equivalent to 100% of normal FVIII returning the clotting time to that of Cyno whole blood in the absence of BO2C11. These data indicate that TPP-9161 is resistant to BO2C11. By extrapolation, the FVIII activity of any FVIII containing protein in which residue 2196F was changed to K will be measurable in this ex-vivo assay. Moreover, this assay format enables the quantitation of the FVIII activity of TPP-9161 or any other FVIII based protein containing F2196K in whole blood from Cyno monkeys.

Example 24: Pharmacodyamic Profile of TPP-9423 in Cynomolgus Monkey

Figure 20:
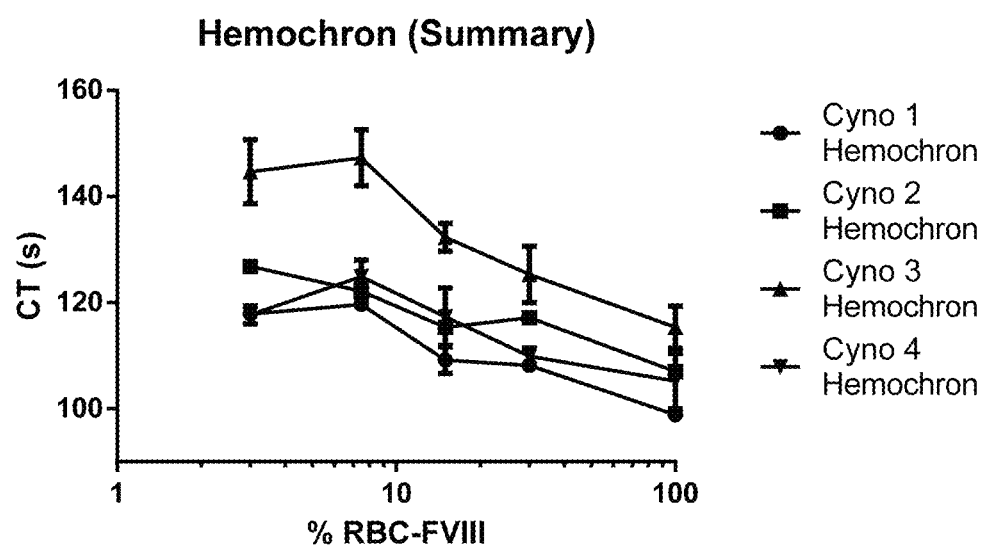
FIG. 20: Ex vivo whole blood clotting dose response curves for TPP-9423 in the four Cynomalgus monkeys used for the PD study.

Prior to dosing, a dose response curve for TPP-9423 (7792 scFv fused at the N-terminus of FVIII-BDD with a3 domain and furin sites deleted and F2196K) was generated in whole blood drawn from the four adult male Cyno monkeys used in the PD study using the same Hemochron assay. The assay was run in triplicate samples from two separate blood draws and the means from the 2 blood draws are plotted in FIG. 20. All four animals exhibited a linear dose response covering the range between 7.5% FVIII and 100% FVIII (FIG. 20). Because the dose response curves were different in each animal, the individual curves were used to estimate the equivalent FVIII level present in each animal in the PD study.

Figure 21:
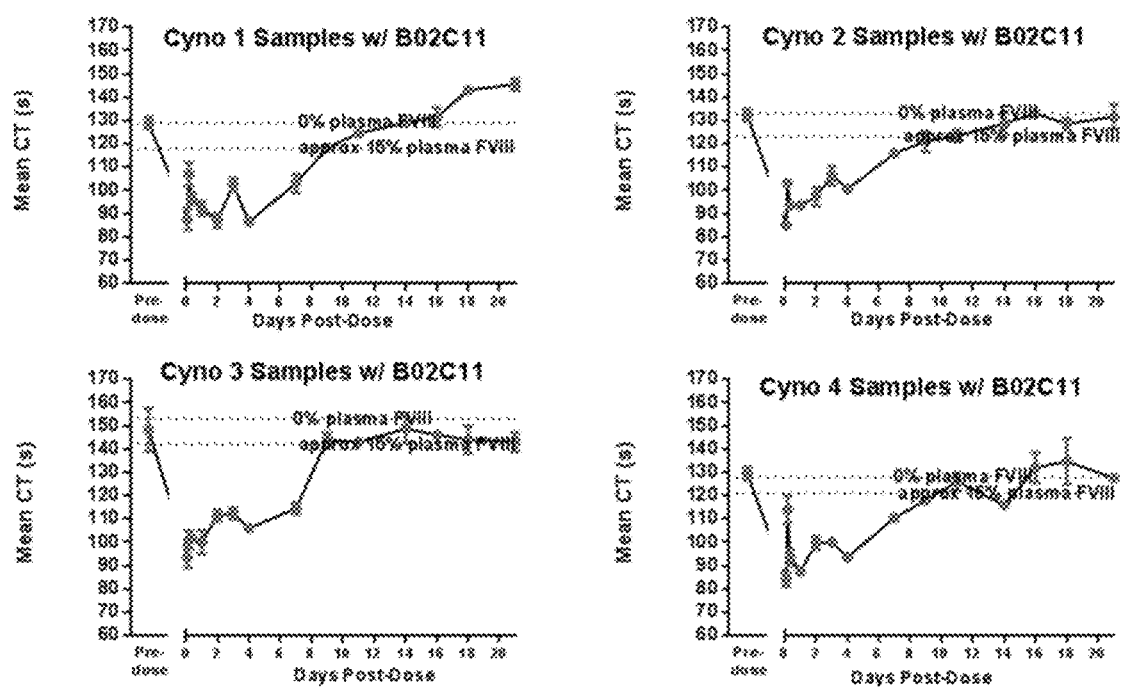
FIG. 21: Pharmacodynamic profiles of TPP-9423 in 4 Cynomalgus monkeys as measured by ex vivo whole blood clotting time with Hemochron in the presence of BO2C11 mAB.

The same four Cyno monkeys used to generate the dose response curves to TPP-9423 were dosed with TPP-9423 at 200 IU/kg (units based on chromogenic assay) and whole blood samples were drawn in to 3.2% citrate (1:9 ratio of citrate to blood) at different time points. After adding 100 ug/ml of BO2C11 to neutralize the endogenous monkey FVIII the clotting time of the whole blood was measured in the Hemochron using the aPTT program. Duplicate or triplicate assays were performed on each blood sample and the mean value was calculated. The results are summarized in FIG. 21. Prior to dosing (pre-dose) the clotting time was in the range of 130 to 150 seconds as expected because the monkey FVIII had been neutralized by BO2C11. After dosing the clotting times dropped in all 4 animals to between 80 and 90 seconds which translates to FVIII activity of more than 100% based on the ex vivo dose response curves. Thus TPP-9423 exhibited a clear pharmacodynamic effect in all four Cyno monkeys. Over time after dosing the clotting times in all four animals gradually increased. Of particular interest is the duration that the clotting time remains at a level equivalent to about 15% FVIII because it is well appreciated that FVIII levels of 10% to 15% protect hemophilia A patients from all bleeding events. Based on the ex vivo dose response curves in FIG. 21 it was possible to establish the clot times for each animal that represent a FVIII activity level of about 15% of normal levels. The 15% FVIII level is indicated as a dotted line in FIG. 21. Based on these criteria the FVIII levels remained at 15% or above until day 11 in Cyno 2 and until day 9 to 10 in Cyno 1, 3 and 4. By comparison, at the same dose of 200 IU/kg a un-modified recombinant full length FVIII protein was predicted, based on experimental pharmacokinetic data in Cyno monkeys, to maintain FVIII activity at 15% or above for only 1 day. Thus TPP-9423 exhibits about a 10-fold longer persistence in the circulation of Cyno monkeys than an un-modified recombinant FVIII. Modeling of a 200 IU/kg dose of FVIII-Fc fusion in Cyno monkey based upon published pharmacokinetic predicted that the FVIII-Fc fusion protein would maintain FVIII levels at or above 15% until day 3 after dosing. Thus TPP-9423 maintained FVIII levels at or above 15% for about 3-fold longer than FVIII-Fc. It is well known in the art that human FVIII is immunogenic in monkeys as evidenced by anti-human FVIII antibody formation (Canadian PRODUCT MONOGRAPH, Xyntha® Solofuse™ (BDD-FVIII)™, Wyeth LLC Pfizer Canada Inc., Licensee, Date of Approval: Jul. 10, 2013 and FDA (CBER Home Page) Sep. 26, 2007 Pharmacology/Toxicology Review Memorandum, Sep. 26, 2007). Antibody formation is typically seen within the first 2 weeks after dosing of human FVIII and as early as 7 days. In the Cyno PD study of TPP-9423, animals 1, 3, and 4 developed binding anti-drug antibodies (ADA) that were detectable by day 12 while no ADA were measurable in animal 2. In addition, ex vivo spike in of TPP-9423 into aliquots of the whole blood from the PD study followed by measurement of clotting time in the hemochron (in the presence of BO2C11) demonstrated that neutralizing ADA were appearing in animals 1, 3, and 4 as early as day 10 (data not shown) but not in animal 2. Therefore, the development of antibodies against human FVIII may have negatively impacted the duration of the PD effect in animals 1, 3 and 4. Thus the time at 15% FVIII or above of 11 days in animal #2 that did not develop ADA is likely a more relevant value while the 9-10 days at or above 15% in animals 1, 3 and 4 may have been reduced due to ADA formation.

Example 25: Additional Variants of TPP-9424 Designed to be Comprised of Predominantly a 1 Chain Molecule While TPP-9424/9423 exhibited desirable pharmacodynamics in both the huGPA/HemA mouse and in the Cyno monkey, this protein as expressed and purified from HKB11 cells is composed of a mixture of about 65% 1 chain molecule and 35% 2 chain molecule. While the percentage of 1 chain molecule is higher than is typically seen for a un-modified FVIII molecule, a characteristic attributable to the deletion of the furin site in TPP-9424/9423, it might be desirable for manufacturing purposes to further increase the percentage of the 1 chain form of the molecule to >70%, or >80%, or >90%, or >95%, or >98% or 100%. The normal cleavage of FVIII at the furin site (RHQR) that generates the heavy and light chains of FVIII is believed to be catalyzed by the protease Furin (also called PACE) or a similar protease. This cleavage occurs during the post-translational modification of FVIII in the golgi-ER system. Post-translational modifications are often cell type dependent and thus it is possible that the percentage of the 1 chain form of the scFv-FVIII fusion will vary dependent upon the cell type used for expression and even between stable clones generated in the same cell type. Thus it is possible that by using BHK21 or CHO cells, which are typically used in the manufacture of FVIII based drugs, that the percentage of 1 chain scFV-FVIII fusion will be altered from what was obtained in HKB11 cells used to produce the scFv-FVIII fusion proteins described herein.

The mechanism by which TPP-9424 and TPP-9423 are cleaved to generate the heavy and light chain despite the deletion of the furin site has not been fully elucidated. Analysis of the N-terminal sequences present in TPP-9423 identified both the expected N-terminus of the 1 chain form of the protein and the N-terminus of a second species with the sequence SFSQNDE (residues 741 to 747 in full length FVIII), indicating that the cleavage site was between residue R740 and S741 in the sequence EPRSF (residues 738 to 742 of full length FVIII). Residue R740 is the naturally occurring thrombin sites between the A2 domain and the B domain in full length FVIII. Because serine proteases such as Furin and Thrombin cleave proteins at related sequences it is possible that in the absence of the normal furin cleavage site that furin is instead cutting at the R740 thrombin site which lies within 10 amino acids of where the furin site would have been within TPP-9423 and TPP-9424.

We have also observed that when the scFv is fused in place of the B-domain in the context of a FVIII protein from which the furin site was deleted, the molecule was produced as a greater than 90% 1 chain molecule, for example as in TPP-9711. This suggests that the presence of additional amino acid sequences between the R740 thrombin site and the where the furin site would normally be found in FVIII prevents furin from cleaving efficiently at R740.

Based on these observations two additional scFv-FVIII fusion molecules were designed in order to reduce cleavage by furin. The designs incorporate deletions of the R740 thrombin site and insertion of flexible, non-immunogenic linkers in place of the B-domain. While specific sequence designs are provide as examples it should be appreciated that alternative sequence designs that incorporate deletion of part or all of the R740 thrombin recognition sequence (IEPRSF) and/or different linker sequences that may be longer or shorter or incorporate amino acids other than G or S may serve the same purpose and are hereby included. The molecules TPP-10297 and TPP-10298 were designed. TPP-10297 contains a 20 residue flexible linker (bold text) between the heavy and light chains of FVIII resulting in the sequence: . . . SKNNAIEP RSFSQNGGGGGSGGSGGSGGSGGGGGDENQSPR . . . which spans residues 732 to 1689 of full length FVIII. TPP-10298 contains a deletion of the R740 thrombin site and a 6 residue flexible glycine linker (bold text) such that the sequence between the heavy and light chains of FVIII is: . . . SKNNAIEPGGGGGGDENQSPR . . . which spans residues 732 to 1689 of full length FVIII.

Both TPP-10297 and TPP-10298 would be expressed in HKB11 or another suitable mammalian cell type and the expressed scFv-FVIII fusion proteins purified and the chain composition of the proteins would be evaluated by SDS-PAGE analysis. In the event that either of these proteins was predominantly a 1 chain molecule, for example >70% or >80% or >90% or >95% or >98% 1 chain then the PD profile of these proteins would be evaluated in the huGPA/HemA mice as described in the earlier examples. Incorporation of the F2196K amino acid change in to TPP-10297 and TPP-10298 would enable their PD profiles to be evaluated in Cyno monkey.

Example 26: Additional Variants of TPP-9424 Designed to be Comprised of Predominantly a 2 Chain Molecule While a predominantly 1 chain form of the scFv-FVIII fusion proteins such as TPP-9423 and 9424 described herein have extended durations of action in animals models, it is also appreciated that a predominantly 2 chain form is expected to also have a long duration of action in vivo. Example 19 demonstrates that the 1 chain form of one of the scFv-FVIII fusions did not provided a significant improvement in the duration of action in the huGPA/HemA mice. While a 2 chain form of the scFv-FVIII fusion protein might be less desirable for manufacturing due to potentially greater heterogeneity it is also appreciated that existing un-modified recombinant FVIII drugs are composed of mostly 2 chain FVIII with a variable amount of one chain FVIII, typically in the range of 5 to 20%. Two chain forms of all of the optimized scFv-FVIII fusion proteins described herein are expected to have desirable pharmacologic properties, in particular a significantly longer circulation time as compared to current marketed FVIII based drugs, and thus are explicitly included.

TPP-10299 represents an example of a variant of TPP-9424 in which the native FVIII furin site is retained in its normal location within the FVIII portion of the protein. This molecule contains the 7792 scFv fused at the N-terminus of FVIII-BDD via the same thrombin cleavable linker. In addition the a3 domain has been deleted to prevent or reduce vWF binding. At the junction between the heavy and light chains of FVIII (where the B-domain and a3 domain have been removed) the sequence is: . . . SKNNAIEPRSFSQNPPVLKRHQREITDENQSPR . . . (furin site underlined) which spans residues 732 to 1689 of full length FVIII.

TPP-10299 would be expressed in HKB11 or another suitable mammalian cell type and the expressed scFv-FVIII fusion proteins purified and the chain composition of the proteins would be evaluated by SDS-PAGE analysis. In the event that the protein was predominantly a 2 chain molecule, for example >70% or >80% or >90% or >95% or >98% 2 chain then the PD profile would be evaluated in the huGPA/HemA mice as described in the earlier examples. Incorporation of the F2196K amino acid change in to TPP-10299 would enable the PD profile to be evaluated in Cyno monkey.

Example 26: Additional Sequences Provided below are additional sequences:

| Seq ID | Protein ID | Sequences of murine hybridoma derived antibodies in the format of a scFv-Fc Sequence regions are: Signal peptide, light chain variable domain, artificial linker (GGGGSGGGGSGGGGS), heavy chain variable domain, 230 amino acid Fc fragment domain. The artificial linker sequence between VH and VL domains is underlined. Bold text shows the heavy chain variable domain (located at the N-terminal side of the linker) and the light chain variable domain (located at the C-terminal side of the linker). The C-terminal 230 amino acids represents the common antibody Fc domain that was added to each antibody to improve expression and stability. |
|---|---|---|
| 6 | 6C12B8/H8 | MEWSWVFLFFLSVTTGVHSRVQLQQSGAELARPGASVKMSCKASGYTFTTYTIHWVKQKT GQGLEWIGYINPSSDYTRYNPKFKDKATLTTDKSSSTAYMKLNSLASDDSAVYYCQTGTR DYWGQGTTLTVSS<u>GGGGSGGGGSGGGGS</u>QIVLTQSPPIMSASPGEKVTMTCSAASSVSYI YWFQQKPGTSPKLWIYSTSTLPSGVPTRFSGSGSGTSYSLTISRMEAEDAATYYCHQRNS FPFTFGSGTKLEIRGGGGAGGGGCKPCICTVPEVSSVFIFPPKPKDVLTITLTPKVTCVV VDISKDDPEVQFSWFVDDVEVHTAQTQPREEQFNSTFRSVSELPIMHQDWLNGKEFKCRV NSAAFPAPIEKTISKTKGRPKAPQVYTIPPPKEQMAKDKVSLTCMITDFFPEDITVEWQW NGQPAENYKNTQPIMDTDGSYFVYSKLNVQKSNWEAGNTFTCSVLHEGLHNHHTEKSLSH SPGK |
| 7 | 13G7G1/C3 | MEWSWVFLFFLSVTTGVHSRVQLQQSGAELARPGASVKMSCKASGYTFTNYAMHWVKQRP GQGLEWIGYINPKSDNTNYNQKFKDKATLTTDKSSATAYMQLSSLTSDDSAVYYCQTGTR DYWGQGTTLTVSS<u>GGGGSGGGGSGGGGS</u>HIVLTQSPAIMSASPGEKVTIFCSASSSITYV YWFQQKPGTSPKLWIYSTSSLPSGVPARFSGSGSGTSYSLTISRMEAEDAATYYCHQRNS YPFTFGSGTKLEIKGGGGAGGGGCKPCICTVPEVSSVFIFPPKPKDVLTITLTPKVTCVV VDISKDDPEVQFSWFVDDVEVHTAQTQPREEQFNSTFRSVSELPIMHQDWLNGKEFKCRV NSAAFPAPIEKTISKTKGRPKAPQVYTIPPPKEQMAKDKVSLTCMITDFFPEDITVEWQW NGQPAENYKNTQPIMDTDGSYFVYSKLNVQKSNWEAGNTFTCSVLHEGLHNHHTEKSLSH SPGK |
| 8 | 1B3H1/C9 | MEWSWVFLFFLSVTTGVHSRVQLQQSGAELARPGASVKMSCKASGYTFTTYTIHWVKQKT GQGLEWIGYINPSSDYTRYNPKFKDKATLTTDKSSSTAYMKLNSLASDDSAVYYCQTGTR DYWGQGTTLTVSS<u>GGGGSGGGGSGGGGS</u>DIVLTQSPASLAVSLGQRATISYRASKSVSTS GYSYMHWNQQKPGQPPRLLIYLVSNLESGVPTRFSGSGSGTSYSLTISRMEAEDAATYYC HQRNSFPFTFGSGTKLEIRGGGGAGGGGCKPCICTVPEVSSVFIFPPKPKDVLTITLTPK VTCVVVDISKDDPEVQFSWFVDDVEVHTAQTQPREEQFNSTFRSVSELPIMHQDWLNGKE FKCRVNSAAFPAPIEKTISKTKGRPKAPQVYTIPPPKEQMAKDKVSLTCMITDFFPEDIT VEWQWNGQPAENYKNTQPIMDTDGSYFVYSKLNVQKSNWEAGNTFTCSVLHEGLHNHHTE KSLSHSPGK |
| 9 | 1E4A2/F8 | MEWSWVFLFFLSVTTGVHSQVQLQQSGAELARPGASVKMSCKASGYTFTRYSMHWVKQRP GQGLEWIGYINPGTYYTNYNQKFKDRATLTADKSSSTAYMQLNSLTSEDSAVYYCQTGTR DYWGQGTTLTVSS<u>GGGGSGGGGSGGGGS</u>QIVLTQSPPIMSASPGEKVTITCSAASSVSYI YWFQQKPGTSPKLWIYSTSSLPSGVPTRFSGSGSGTSYSLTISRMEAEDAATYYCHQRSS YPFTFGSGTKLEIRGGGGAGGGGCKPCICTVPEVSSVFIFPPKPKDVLTITLTPKVTCVV VDISKDDPEVQFSWFVDDVEVHTAQTQPREEQFNSTFRSVSELPIMHQDWLNGKEFKCRV NSAAFPAPIEKTISKTKGRPKAPQVYTIPPPKEQMAKDKVSLTCMITDFFPEDITVEWQW NGQPAENYKNTQPIMDTDGSYFVYSKLNVQKSNWEAGNTFTCSVLHEGLHNHHTEKSLSH SPGK |
| 10 | 10F1B10/F3 | MEWSWVFLFFLSVTTGVHSQVQLLQSGAELARPGASVRISCKASGYTFTRYAMHWVKQRP GQGLEWIGYINPGTFSTNYNQKFKDRATLTADKSSSTAYMQLNSLTSEDSAVYYCQTGTR DYWGQGTTLTVSS<u>GGGGSGGGGSGGGGS</u>QIVLTQSPPIMSASPGEKVTITCSAASSVSYI YWFQQKPGTSPKLWIYSTSSLPSGVPTRFSGSGSGTSYSLTISRMEAEDAATYYCHQRSS YPFTFGSGTKLEIRGGGGAGGGGCKPCICTVPEVSSVFIFPPKPKDVLTITLTPKVTCVV VDISKDDPEVQFSWFVDDVEVHTAQTQPREEQFNSTFRSVSELPIMHQDWLNGKEFKCRV NSAAFPAPIEKTISKTKGRPKAPQVYTIPPPKEQMAKDKVSLTCMITDFFPEDITVEWQW NGQPAENYKNTQPIMDTDGSYFVYSKLNVQKSNWEAGNTFTCSVLHEGLHNHHTEKSLSH SPGK |
| 11 | 8F9E9/F11 | MEWSWVFLFFLSVTTGVHSQVQLQQSGAELARPGASVKMSCKASGYTFTSYSIHWIKQRP GQSLEWIGYINPNSDYANYNQKFKDKATLTTDKSSTTAYMQLSSLTTDDSAVYYCQTGTR DYWGQGTTLTVSS<u>GGGGSGGGGSGGGGS</u>HIVLTQSPAIMSASPGEKVTIICSARSSVSYM YWFQQKPGTSPKLWIYATSSLPSGVPARFSGSGSGTSYSLTISRMEAEDAATYYCHQRSS YPYTFGSGTKLEIKGGGGAGGGGCKPCICTVPEVSSVFIFPPKPKDVLTITLTPKVTCVV VDISKDDPEVQFSWFVDDVEVHTAQTQPREEQFNSTFRSVSELPIMHQDWLNGKEFKCRV NSAAFPAPIEKTISKTKGRPKAPQVYTIPPPKEQMAKDKVSLTCMITDFFPEDITVEWQW NGQPAENYKNTQPIMDTDGSYFVYSKLNVQKSNWEAGNTFTCSVLHEGLHNHHTEKSLSH SPGK |
| 12 | 1H5B4/H12 | MEWSWVFLFFLSVTTGVHSQVQLQQSGAELARPGASVKMSCKASGYTFTSYSIHWIKQRP GQSLEWIGYINPNSDYANYNQKFKDKATLTTDKSSTTAYMQLSSLTTDDSAVYYCQTGTR DYWGQGTTLTVSS<u>GGGGSGGGGSGGGGS</u>DIVMTQSPSSLSVSAGEKVTMSCKSSQSLLNS |

-continued

| Seq ID | Protein ID | Sequences of murine hybridoma derived antibodies in the format of a scFv-Fc<br>Sequence regions are: Signal peptide, light chain variable domain, artificial linker (GGGGSGGGGSGGGGS), heavy chain variable domain, 230 amino acid Fc fragment domain. The artificial linker sequence between VH and VL domains is underlined. Bold text shows the heavy chain variable domain (located at the N-terminal side of the linker) and the light chain variable domain (located at the C-terminal side of the linker). The C-terminal 230 amino acids represents the common antibody Fc domain that was added to each antibody to improve expression and stability. |
|---|---|---|
| | | GNQKNYLAWYQQKPGQPPKLLIYGASTRESGVPDRFTGSGSGTDFTLTISSVQAEDLAVY YCQNDHSYPYTFGGGTKLEIKGGGGAGGGGCKPCICTVPEVSSVFIFPPKPKDVLTITLT PKVTCVVVDISKDDPEVQFSWFVDDVEVHTAQTQPREEQFNSTFRSVSELPIMHQDWLNG KEFKCRVNSAAFPAPIEKTISKTKGRPKAPQVYTIPPPKEQMAKDKVSLTCMITDFFPED ITVEWQWNGQPAENYKNTQPIMDTDGSYFVYSKLNVQKSNWEAGNTFTCSVLHEGLHNHH TEKSLSHSPGK |
| 13 | 12C6A6/A5 | MEWSWVFLFFLSVTTGVHSQVQLQQSGAELARPGASVKMSCKASGYTFTRYSMHWVKQRP GQGLEWIGYINPGTYSTNYNQKFKDRATLTADKSSSTAYMQLNSLTSEDSAVYYCQTGTR DYWGQGTTLTVSSGGGGSGGGGSGGGGSQIVLTQSPPIMSASPGEKVTITCSAASSVSYI YWFQQKPGTSPKLWIYSTSSLPSGVPTRFSGSGSGTSYSLTISRMEAEDAATYYCHQRSS YPFTFGSGTKLEIRGGGGAGGGGCKPCICTVPEVSSVFIFPPKPKDVLTITLTPKVTCVV VDISKDDPEVQFSWFVDDVEVHTAQTQPREEQFNSTFRSVSELPIMHQDWLNGKEFKCRV NSAAFPAPIEKTISKTKGRPKAPQVYTIPPPKEQMAKDKVSLTCMITDFFPEDITVEWQW NGQPAENYKNTQPIMDTDGSYFVYSKLNVQKSNWEAGNTFTCSVLHEGLHNHHTEKSLSH SPGK |
| 14 | 7G4E9/A8 | MEWSWVFLFFLSVTTGVHSQVQLKESGPGLVAPSQSLSITCTVSGFSLTRFGISWVRQPP GKGLEWMGVIWGDGSTDYHSALISRLSITKDNSKSQVFFRLNSLQSDDSATYYCARSFGM DYWGQGTSVTVSSGGGGSGGGGSGGGGSNIMMTQSPSSLAVSAGEKVTMSCKSSQSILNS SNQKNYLAWYQQKPGQSPKLLIYWASTRESGVPDRFTGSGSGTDFTLTISSVQAEDLAVY YCHQYFSSRTFGGGTKLEIKGGGGAGGGGCKPCICTVPEVSSVFIFPPKPKDVLTITLTP KVTCVVVDISKDDPEVQFSWFVDDVEVHTAQTQPREEQFNSTFRSVSELPIMHQDWLNGK EFKCRVNSAAFPAPIEKTISKTKGRPKAPQVYTIPPPKEQMAKDKVSLTCMITDFFPEDI TVEWQWNGQPAENYKNTQPIMDTDGSYFVYSKLNVQKSNWEAGNTFTCSVLHEGLHNHHT EKSLSHSPGK |

| SEQ ID | Protein ID (TPP #) | scFv-FVIII protein sequences referred to in table 24<br>Amino acid sequence of mature protein (signal peptide removed) |
|---|---|---|
| 113 | 6195 | ATRRYYLGAVELSWDYMQSDLGELPVDARFPPRVPKSFPFNTSVVYKKTLFVEFTDHLFN IAKPRPPWMGLLGPTIQAEVYDTVVITLKNMASHPVSLHAVGVSYWKASEGAEYDDQTSQ REKEDDKVFPGGSHTYVWQVLKENGPMASDPLCLTYSYLSHVDLVKDLNSGLIGALLVCR EGSLAKEKTQTLHKFILLLFAVFDEGKSWHSETKNSLMQDRDAASARAWPKMHTVNGYVNR SLPGLIGCHRKSVYWHVIGMGTTPEVHSIFLEGHTFLVRNHRQASLEISPITFLTAQTLL MDLGQFLLFCHISSHQHDGMEAYVKVDSCPEEPQLRMKNNEEAEDYDDDLTDSEMDVVRF DDDNSPSFIQIRSVAKKHPKTWVHYIAAEEEDWDYAPLVLAPDDRSYKSQYLNNGPQRIG RKYKKVRFMAYTDETFKTREAIQHESGILGPLLYGEVGDTLLIIFKNQASRPYNIYPHGI TDVRPLYSRRLPKGVKHLKDFPILPGEIFKYKWTVTVEDGPTKSDPRCLTRYYSSFVNME RDLASGLIGPLLICYKESVDQRGNQIMSDKRNVILFSVFDENRSWYLTENIQRFLPNPAG VQLEDPEFQASNIMHSINGYVFDSLQLSVCLHEVAYWYILSIGAQTDFLSVFFSGYTFKH KMVYEDTLTLFPFSGETVFMSMENPGLWILGCHNSDFRNRGMTALLKVSSCDKNTGDYYE DSYEDISAYLLSKNNAIEPRSFSQNGGGGSTGGTGGSGGGTGSGGGGTGGSGGTDIQLT QSPSFLSASVGDRVTITCRASSSVSYIYWFQQKPGKAPKLLIYATSTLQSGVPSRFSGSG SGTEYTLTISSLQPEDFATYYCHQRNSFPYTFGQGTKLEIKGGGGSGGGGSGGGGSGGGG SEVQLVQSGAEVKKPGASVKVSCKASGYTFTTYTIHWVRQAPGQGLEWMGYINPSSGYTR YNPKFKGRVTMTRDKSTSTAYMELRSLRSDDTAVYYCQTGTRDYWGQGTTVTVSSGGGGS QNPPVLKRHQREITRTTLQSDQEEIDYDDTISVEMKKEDFDIFDEDENQSPRSFQKKTRH YFIAAVERLWDYGMSSSPHVLRNRAQSGSVPQFKKVVFQEFTDGSFTQPLYRGELNEHLG LLGPYIRAEVEDNIMVTFRNQASRPYSFYSSLISYEEDQRQGAEPRKNFVKPNETKTYFW KVQHHMAPTKDEFDCKAWAYFSDVDLEKDVHSGLIGPLLVCHTNTLNPAHGRQVTVQEFA LFFTIFDETKSWYFTENMERNCRAPCNIQMEDPTFKENYRFHAINGYIMDTLPGLVMAQD QRIRWYLLSMGSNENIHSIHFSGHVFTVRKKEEYKMALYNLYPGVFETVEMLPSKAGIWR VECLIGEHLHAGMSTLFLVYSNKCQTPLGMASGHIRDFQITASGQYGQWAPKLARLHYSG SINAWSTKEPFSWIKVDLLAPMIIHGIKTQGARQKFSSLYISQFIIMYSLDGKKWQTYRG NSTGTLMVFFGNVDSSGIKHNIFNPPIIARYIRLHPTHYSIRSTLRMELMGCDLNSCSMP LGMESKAISDAQITASSYFTNMFATWSPSKARLHLQGRSNAWRPQVNNPKEWLQVDFQKT MKVTGVTTQGVKSLLTSMYVKEFLISSSQDGHQWTLFFQNGKVKVFQGNQDSFTPVVNSL DPPLLTRYLRIHPQSWVHQIALRMEVLGCEAQDLY |
| 114 | 8277 | ATRRYYLGAVELSWDYMQSDLGELPVDARFPPRVPKSFPFNTSVVYKKTLFVEFTDHLFN IAKPRPPWMGLLGPTIQAEVYDTVVITLKNMASHPVSLHAVGVSYWKASEGAEYDDQTSQ |

| SEQ ID | Protein ID (TPP #) | scFv-FVIII protein sequences referred to in table 24<br>Amino acid sequence of mature protein (signal peptide removed) |
|---|---|---|
| | | REKEDDKVFPGGSHTYVWQVLKENGPMASDPLCLTYSYLSHVDLVKDLNSGLIGALLVCR<br>EGSLAKEKTQTLHKFILLLFAVFDEGKSWHSETKNSLMQDRDAASARAWPKMHTVNGYVNR<br>SLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEFQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNGGGGSTGGTGGSSGGGTGSGGGGTGGSGGTDIQLT<br>QSPSFLSASVGDRVTITCRASSSVSYIYWFQQKPGKAPKLLIYATSTLQSGVPSRFSGSG<br>SGTEYTLTISSLQPEDFATYYCHQRNSFPYTFGQGTKLEIKGGGGSGGGGSGGGGSGGGG<br>SEVQLVQSGAEVKKPGASVKVSCKASGYTFTTYTIHWVRQAPGQGLEWMGYINPSSGYTR<br>YNPKFKGRVTMTRDKSTSTAYMELRSLRSDDTAVYYCQTGTRDYWGQGTTVTVSSGGGGS<br>GGGGSGGGGSDENQSPRSFQKKTRHYFIAAVERLWDYGMSSSPHVLRNRAQSGSVPQFKK<br>VVFQEFTDGSFTQPLYRGELNEHLGLLGPYIRAEVEDNIMVTFRNQASRPYSFYSSLISY<br>EEDQRQGAEPRKNFVKPNETKTYFWKVQHHMAPTKDEFDCKAWAYFSDVDLEKDVHSGLI<br>GPLLVCHTNTLNPAHGRQVTVQEFALFFTIFDETKSWYFTENMERNCRAPCNIQMEDPTF<br>KENYRFHAINGYIMDTLPGLVMAQDQRIRWYLLSMGSNENIHSIHFSGHVFTVRKKEEYK<br>MALYNLYPGVFETVEMLPSKAGIWRVECLIGEHLHAGMSTLFLVYSNKCQTPLGMASGHI<br>RDFQITASGQYGQWAPKLARLHYSGSINAWSTKEPFSWIKVDLLAPMIIHGIKTQGARQK<br>FSSLYISQFIIMYSLDGKKWQTYRGNSTGTLMVFFGNVDSSGIKHNIFNPPIIARYIRLH<br>PTHYSIRSTLRMELMGCDLNSCSMPLGMESKAISDAQITASSYFTNMFATWSPSKARLHL<br>QGRSNAWRPQVNNPKEWLQVDFQKTMKVTGVTTQGVKSLLTSMYVKEFLISSSQDGHQWT<br>LFFQNGKVKVFQGNQDSFTPVVNSLDPPLLTRYLRIHPQSWVHQIALRMEVLGCEAQDLY |
| 115 | 8743 | ATRRYYLGAVELSWDYMQSDLGELPVDARFPPRVPKSFPFNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLLFAVFDEGKSWHSETKNSLMQDRDAASARAWPKMHTVNGYVNR<br>SLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEFQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNGGGGSTGGTGGSSGGGTGSGGGGTGGSGGTDIQLT<br>QSPSFLSASVGDRVTITCRASSSVRYIYWFQQKPGKAPKLLIYATSFRQSGVPSRFSGSG<br>SGTEYTLTISSLQPEDFATYYCHQRNSFPYTFGQGTKLEIKGGGGSGGGGSGGGGSGGGG<br>SEVQLVQSGAEVKKPGASVKVSCKASGYTFTTYAIHWVRQAPGQGLEWMGYINPSSGYTR<br>YNPKFKGRVTMTRDKSTSTAYMELRSLRSDDTAVYYCWTGTRDYWGQGTTVTVSSGGGGS<br>QNPPVLKRHQREITDENQSPRSFQKKTRHYFIAAVERLWDYGMSSSPHVLRNRAQSGSVP<br>QFKKVVFQEFTDGSFTQPLYRGELNEHLGLLGPYIRAEVEDNIMVTFRNQASRPYSFYSS<br>LISYEEDQRQGAEPRKNFVKPNETKTYFWKVQHHMAPTKDEFDCKAWAYFSDVDLEKDVH<br>SGLIGPLLVCHTNTLNPAHGRQVTVQEFALFFTIFDETKSWYFTENMERNCRAPCNIQME<br>DPTFKENYRFHAINGYIMDTLPGLVMAQDQRIRWYLLSMGSNENIHSIHFSGHVFTVRKK<br>EEYKMALYNLYPGVFETVEMLPSKAGIWRVECLIGEHLHAGMSTLFLVYSNKCQTPLGMA<br>SGHIRDFQITASGQYGQWAPKLARLHYSGSINAWSTKEPFSWIKVDLLAPMIIHGIKTQG<br>ARQKFSSLYISQFIIMYSLDGKKWQTYRGNSTGTLMVFFGNVDSSGIKHNIFNPPIIARY<br>IRLHPTHYSIRSTLRMELMGCDLNSCSMPLGMESKAISDAQITASSYFTNMFATWSPSKA<br>RLHLQGRSNAWRPQVNNPKEWLQVDFQKTMKVTGVTTQGVKSLLTSMYVKEFLISSSQDG<br>HQWTLFFQNGKVKVFQGNQDSFTPVVNSLDPPLLTRYLRIHPQSWVHQIALRMEVLGCEA<br>QDLY |
| 116 | 8820 | ATRRYYLGAVELSWDYMQSDLGELPVDARFPPRVPKSFPFNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLLFAVFDEGKSWHSETKNSLMQDRDAASARAWPKMHTVNGYVNR<br>SLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEFQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNGGGGSTGGTGGSSGGGTGSGGGGTGGSGGTDIQLT<br>QSPSFLSASVGDRVTITCRASSSVRYIYWFQQKPGKAPKLLIYATSFLQSGVPSRFSGSG<br>SGTEYTLTISSLQPEDFATYYCHQRNSFPYTFGQGTKLEIKGGGGSGGGGSGGGGSGGGG<br>SEVQLVQSGAEVKKPGASVKVSCKASGYTFTTYAIHWVRQAPGQGLEWMGYINPSSGYTR<br>YNPKFKHRVTMTRDKSTSTAYMELRSLRSDDTAVYYCWTGTRDYWGQGTTVTVSSGGGGS<br>QNPPVLKRHQREITDENQSPRSFQKKTRHYFIAAVERLWDYGMSSSPHVLRNRAQSGSVP |

| SEQ ID | Protein ID (TPP #) | scFv-FVIII protein sequences referred to in table 24<br>Amino acid sequence of mature protein (signal peptide removed) |
|---|---|---|
| | | QFKKVVFQEFTDGSFTQPLYRGELNEHLGLLGPYIRAEVEDNIMVTFRNQASRPYSFYSS<br>LISYEEDQRQGAEPRKNFVKPNETKTYFWKVQHHMAPTKDEFDCKAWAYFSDVDLEKDVH<br>SGLIGPLLVCHTNTLNPAHGRQVTVQEFALFFTIFDETKSWYFTENMERNCRAPCNIQME<br>DPTFKENYRFHAINGYIMDTLPGLVMAQDQRIRWYLLSMGSNENIHSIHFSGHVFTVRKK<br>EEYKMALYNLYPGVFETVEMLPSKAGIWRVECLIGEHLHAGMSTLFLVYSNKCQTPLGMA<br>SGHIRDFQITASGQYGQWAPKLARLHYSGSINAWSTKEPFSWIKVDLLAPMIIHGIKTQG<br>ARQKFSSLYISQFIIMYSLDGKKWQTYRGNSTGTLMVFFGNVDSSGIKHNIFNPPIIARY<br>IRLHPTHYSIRSTLRMELMGCDLNSCSMPLGMESKAISDAQITASSYFTNMFATWSPSKA<br>RLHLQGRSNAWRPQVNNPKEWLQVDFQKTMKVTGVTTQGVKSLLTSMYVKEFLISSSQDG<br>HQWTLFFQNGKVKVFQGNQDSFTPVVNSLDPPLLTRYLRIHPQSWVHQIALRMEVLGCEA<br>QDLY |
| 117 | 8744 | ATRRYYLGAVELSWDYMQSDLGELPVDARFPPRVPKSFPPNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLLFAVFDEGKSWHSETKNSLMQDRDAASARAWPKMHTVNGYVNR<br>SLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEFQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNGGGGSTGGTGGSSGGGTGSGGGGTGGSGGTDIQLT<br>QSPSFLSASVGDRVTITCRASSSVSYIYWFQQKPGKAPKLLIYATSTLQSGVPSRFSGSG<br>SGTEYTLTISSLQPEDFATYYCHQRNSFPYTFGQGTKLEIKGGGGSGGGGSGGGGSGGGG<br>SEVQLVQSGAEVKKPGASVKVSCKASGYTFTRYTIHWVRQAPGQGLEWMGYINPSSGYTR<br>YNPKFKGRVTMTRDKSTSTAYMELRSLRSDDTAVYYCWTGTRDYWGQGTTVTVSSGGGGS<br>QNPPVLKRHQREITDENQSPRSFQKKTRHYFIAAVERLWDYGMSSSPHVLRNRAQSGSVP<br>QFKKVVFQEFTDGSFTQPLYRGELNEHLGLLGPYIRAEVEDNIMVTFRNQASRPYSFYSS<br>LISYEEDQRQGAEPRKNFVKPNETKTYFWKVQHHMAPTKDEFDCKAWAYFSDVDLEKDVH<br>SGLIGPLLVCHTNTLNPAHGRQVTVQEFALFFTIFDETKSWYFTENMERNCRAPCNIQME<br>DPTFKENYRFHAINGYIMDTLPGLVMAQDQRIRWYLLSMGSNENIHSIHFSGHVFTVRKK<br>EEYKMALYNLYPGVFETVEMLPSKAGIWRVECLIGEHLHAGMSTLFLVYSNKCQTPLGMA<br>SGHIRDFQITASGQYGQWAPKLARLHYSGSINAWSTKEPFSWIKVDLLAPMIIHGIKTQG<br>ARQKFSSLYISQFIIMYSLDGKKWQTYRGNSTGTLMVFFGNVDSSGIKHNIFNPPIIARY<br>IRLHPTHYSIRSTLRMELMGCDLNSCSMPLGMESKAISDAQITASSYFTNMFATWSPSKA<br>RLHLQGRSNAWRPQVNNPKEWLQVDFQKTMKVTGVTTQGVKSLLTSMYVKEFLISSSQDG<br>HQWTLFFQNGKVKVFQGNQDSFTPVVNSLDPPLLTRYLRIHPQSWVHQIALRMEVLGCEA<br>QDLY |
| 118 | 8741 | ATRRYYLGAVELSWDYMQSDLGELPVDARFPPRVPKSFPPNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLLFAVFDEGKSWHSETKNSLMQDRDAASARAWPKMHTVNGYVNR<br>SLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEFQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNGGGGSTGGTGGSSGGGTGSGGGGTGGSGGTDIQLT<br>QSPSFLSASVGDRVTITCRASSSVRYIYWFQQKPGKAPKLLIYATSFRQSGVPSRFSGSG<br>SGTEYTLTISSLQPEDFATYYCHQRNSFPYTFGQGTKLEIKGGGGSGGGGSGGGGSGGGG<br>SEVQLVQSGAEVKKPGASVKVSCKASGYTFTTYAIHWVRQAPGQGLEWMGYINPSSGYTR<br>YNPKFKGRVTMTRDKSTSTAYMELRSLRSDDTAVYYCWTGTRDYWGQGTTVTVSSGGGGS<br>QNPPVLKRHQREITRTTLQSDQEEIDYDDTISVEMKKEDFDIYDEDENQSPRSFQKKTRH<br>YFIAAVERLWDYGMSSSPHVLRNRAQSGSVPQFKKVVFQEFTDGSFTQPLYRGELNEHLG<br>LLGPYIRAEVEDNIMVTFRNQASRPYSFYSSLISYEEDQRQGAEPRKNFVKPNETKTYFW<br>KVQHHMAPTKDEFDCKAWAYFSDVDLEKDVHSGLIGPLLVCHTNTLNPAHGRQVTVQEFA<br>LFFTIFDETKSWYFTENMERNCRAPCNIQMEDPTFKENYRFHAINGYIMDTLPGLVMAQD<br>QRIRWYLLSMGSNENIHSIHFSGHVFTVRKKEEYKMALYNLYPGVFETVEMLPSKAGIWR<br>VECLIGEHLHAGMSTLFLVYSNKCQTPLGMASGHIRDFQITASGQYGQWAPKLARLHYSG<br>SINAWSTKEPFSWIKVDLLAPMIIHGIKTQGARQKFSSLYISQFIIMYSLDGKKWQTYRG<br>NSTGTLMVFFGNVDSSGIKHNIFNPPIIARYIRLHPTHYSIRSTLRMELMGCDLNSCSMP<br>LGMESKAISDAQITASSYFTNMFATWSPSKARLHLQGRSNAWRPQVNNPKEWLQVDFQKT<br>MKVTGVTTQGVKSLLTSMYVKEFLISSSQDGHQWTLFFQNGKVKVFQGNQDSFTPVVNSL<br>DPPLLTRYLRIHPQSWVHQIALRMEVLGCEAQDLY |
| 119 | 8798 | DIQLTQSPSFLSASVGDRVTITCRASSSVRYIYWFQQKPGKAPKLLIYATSFRQSGVPSR<br>FSGSGSGTEYTLTISSLQPEDFATYYCHQRNSFPYTFGQGTKLEIKGGGGSGGGGSGGGG<br>SGGGGSEVQLVQSGAEVKKPGASVKVSCKASGYTFTTYAIHWVRQAPGQGLEWMGYINPS |

-continued

| SEQ ID | Protein ID (TPP #) | scFv-FVIII protein sequences referred to in table 24<br>Amino acid sequence of mature protein (signal peptide removed) |
|---|---|---|
| | | SGYTRYNPKFKGRVTMTRDKSTSTAYMELRSLRSDDTAVYYCWTGTRDYWGQGTTVTVSS<br>GGGSGGGGSGLVPRGSGGGSGGGGSGATRRYYLGAVELSWDYMQSDLGELPVDARFPPRV<br>PKSFPFNTSVVYKKTLFVEFTDHLFNIAKPRPPWMGLLGPTIQAEVYDTVVITLKNMASH<br>PVSLHAVGVSYWKASEGAEYDDQTSQREKEDDKVFPGGSHTYVWQVLKENGPMASDPLCL<br>TYSYLSHVDLVKDLNSGLIGALLVCREGSLAKEKTQTLHKFILLFAVFDEGKSWHSETKN<br>SLMQDRDAASARAWPKMHTVNGYVNRSLPGLIGCHRKSVYWHVIGMTTPEVHSIFLEGH<br>TFLVRNHRQASLEISPITFLTAQTLLMDLGQFLLFCHISSHQHDGMEAYVKVDSCPEEPQ<br>LRMKNNEEAEDYDDDLTDSEMDVVRFDDDNSPSFIQIRSVAKKHPKTWVHYIAAEEEDWD<br>YAPLVLAPDDRSYKSQYLNNGPQRIGRKYKKVRFMAYTDETFKTREAIQHESGILGPLLY<br>GEVGDTLLIIFKNQASRPYNIYPHGITDVRPLYSRRLPKGVKHLKDFPILPGEIFKYKWT<br>VTVEDGPTKSDPRCLTRYYSSFVNMERDLASGLIGPLLICYKESVDQRGNQIMSDKRNVI<br>LFSVFDENRSWYLTENIQRFLPNPAGVQLEDPEFQASNIMHSINGYVFDSLQLSVCLHEV<br>AYWYILSIGAQTDFLSVFFSGYTFKHKMVYEDTLTLFPPSGETVFMSMENPGLWILGCHN<br>SDFRNRGMTALLKVSSCDKNTGDYYEDSYEDISAYLLSKNNAIEPRSFSQNPPVLKRHQR<br>EITRTTLQSDQEEIDYDDTISVEMKKEDFDIYDEDENQSPRSFQKKTRHYFIAAVERLWD<br>YGMSSSPHVLRNRAQSGSVPQFKKVVFQEFTDGSFTQPLYRGELNEHLGLLGPYIRAEVE<br>DNIMVTFRNQASRPYSFYSSLISYEEDQRQGAEPRKNFVKPNETKTYFWKVQHHMAPTKD<br>EFDCKAWAYFSDVDLEKDVHSGLIGPLLVCHTNTLNPAHGRQVTVQEFALFFTIFDETKS<br>WYFTENMERNCRAPCNIQMEDPTFKENYRFHAINGYIMDTLPGLVMAQDQRIRWYLLSMG<br>SNENIHSIHFSGHVFTVRKKEEYKMALYNLYPGVFETVEMLPSKAGIWRVECLIGEHLHA<br>GMSTLFLVYSNKCQTPLGMASGHIRDFQITASGQYGQWAPKLARLHYSGSINAWSTKEPF<br>SWIKVDLLAPMIIHGIKTQGARQKFSSLYISQFIIMYSLDGKKWQTYRGNSTGTLMVFFG<br>NVDSSGIKHNIFNPPIIARYIRLHPTHYSIRSTLRMELMGCDLNSCSMPLGMESKAISDA<br>QITASSYFTNMFATWSPSKARLHLQGRSNAWRPQVNNPKEWLQVDFQKTMKVTGVTTQGV<br>KSLLTSMYVKEFLISSSQDGHQWTLFFQNGKVKVFQGNQDSFTPVVNSLDPPLLTRYLRI<br>HPQSWVHQIALRMEVLGCEAQDLY |
| 120 | 9049 | ATRRYYLGAVELSWDYMQSDLGELPVDARFPPRVPKSFPFNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLFAVFDEGKSWHSETKNSLMQDRDAASARAWPKMHTVNGYVNR<br>SLPGLIGCHRKSVYWHVIGMTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEFQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNPPVLKRHQREITRTTLQSDQEEIDYDDTISVEMKK<br>EDFDIYDEDENQSPRSFQKKTRHYFIAAVERLWDYGMSSSPHVLRNRAQSGSVPQFKKVV<br>FQEFTDGSFTQPLYRGELNEHLGLLGPYIRAEVEDNIMVTFRNQASRPYSFYSSLISYEE<br>DQRQGAEPRKNFVKPNETKTYFWKVQHHMAPTKDEFDCKAWAYFSDVDLEKDVHSGLIGP<br>LLVCHTNTLNPAHGRQVTVQEFALFFTIFDETKSWYFTENMERNCRAPCNIQMEDPTFKE<br>NYRFHAINGYIMDTLPGLVMAQDQRIRWYLLSMGSNENIHSIHFSGHVFTVRKKEEYKMA<br>LYNLYPGVFETVEMLPSKAGIWRVECLIGEHLHAGMSTLFLVYSNKCQTPLGMASGHIRD<br>FQITASGQYGQWAPKLARLHYSGSINAWSTKEPFSWIKVDLLAPMIIHGIKTQGARQKFS<br>SLYISQFIIMYSLDGKKWQTYRGNSTGTLMVFFGNVDSSGIKHNIFNPPIIARYIRLHPT<br>HYSIRSTLRMELMGCDLNSCSMPLGMESKAISDAQITASSYFTNMFATWSPSKARLHLQG<br>RSNAWRPQVNNPKEWLQVDFQKTMKVTGVTTQGVKSLLTSMYVKEFLISSSQDGHQWTLF<br>FQNGKVKVFQGNQDSFTPVVNSLDPPLLTRYLRIHPQSWVHQIALRMEVLGCEAQDLYGG<br>GSGGGGSGLVPRGSGGGSGGGGSGDIQLTQSPSFLSASVGDRVTITCRASSSVRYIYWFQ<br>QKPGKAPKLLIYATSFRQSGVPSRFSGSGSGTEYTLTISSLQPEDFATYYCHQRNSFPYT<br>FGQGTKLEIKGGGGSGGGGSGGGGSGGGGSEVQLVQSGAEVKKPGASVKVSCKASGYTFT<br>TYAIHWVRQAPGQGLEWMGYINPSSGYTRYNPKFKGRVTMTRDKSTSTAYMELRSLRSDD<br>TAVYYCWTGTRDYWGQGTTVTVSS |
| 121 | 9049X | ATRRYYLGAVELSWDYMQSDLGELPVDARFPPRVPKSFPFNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLFAVFDEGKSWHSETKNSLMQDRDAASARAWPKMHTVNGYVNR<br>SLPGLIGCHRKSVYWHVIGMTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEFQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNDENQSPRSFQKKTRHYFIAAVERLWDYGMSSSPHV<br>LRNRAQSGSVPQFKKVVFQEFTDGSFTQPLYRGELNEHLGLLGPYIRAEVEDNIMVTFRN<br>QASRPYSFYSSLISYEEDQRQGAEPRKNFVKPNETKTYFWKVQHHMAPTKDEFDCKAWAY<br>FSDVDLEKDVHSGLIGPLLVCHTNTLNPAHGRQVTVQEFALFFTIFDETKSWYFTENMER<br>NCRAPCNIQMEDPTFKENYRFHAINGYIMDTLPGLVMAQDQRIRWYLLSMGSNENIHSIH<br>FSGHVFTVRKKEEYKMALYNLYPGVFETVEMLPSKAGIWRVECLIGEHLHAGMSTLFLVY |

| SEQ ID | Protein ID (TPP #) | scFv-FVIII protein sequences referred to in table 24<br>Amino acid sequence of mature protein (signal peptide removed) |
|---|---|---|
| | | SNKCQTPLGMASGHIRDFQITASGQYGQWAPKLARLHYSGSINAWSTKEPFSWIKVDLLA<br>PMIIHGIKTQGARQKFSSLYISQFIIMYSLDGKKWQTYRGNSTGTLMVFFGNVDSSGIKH<br>NIFNPPIIARYIRLHPTHYSIRSTLRMELMGCDLNSCSMPLGMESKAISDAQITASSYFT<br>NMFATWSPSKARLHLQGRSNAWRPQVNNPKEWLQVDFQKTMKVTGVTTQGVKSLLTSMYV<br>KEFLISSSQDGHQWTLFFQNGKVKVFQGNQDSFTPVVNSLDPPLLTRYLRIHPQSWVHQI<br>ALRMEVLGCEAQDLYGGGSGGGGSGLVPRGSGGGSGGGGSGDIQLTQSPSFLSASVGDRV<br>TITCRASSSVRYIYWFQQKPGKAPKLLIYATSFRQSGVPSRFSGSGSGTEYTLTISSLQP<br>EDFATYYCHQRNSFPYTFGQGTKLEIKGGGGSGGGGSGGGGSGGGGSEVQLVQSGAEVKK<br>PGASVKVSCKASGYTFTTYAIHWVRQAPGQGLEWMGYINPSSGYTRYNPKFKGRVTMTRD<br>KSTSTAYMELRSLRSDDTAVYYCWTGTRDYWGQGTTVTVSS |
| 122 | 9049Y | ATRRYYLGAVELSWDYMQSDLGELPVDARFPPRVPKSFPFNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLFAVFDEGKSWHSETKNSLMQDRDAASARAWPKMHTVNGYVNR<br>SLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEPQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNPPVLKRHQREITDENQSPRSFQKKTRHYFIAAVER<br>LWDYGMSSSPHVLRNRAQSGSVPQFKKVVFQEFTDGSFTQPLYRGELNEHLGLLGPYIRA<br>EVEDNIMVTFRNQASRPYSFYSSLISYEEDQRQGAEPRKNFVKPNETKTYFWKVQHHMAP<br>TKDEFDCKAWAYFSDVDLEKDVHSGLIGPLLVCHTNTLNPAHGRQVTVQEFALFFTIFDE<br>TKSWYFTENMERNCRAPCNIQMEDPTFKENYRFHAINGYIMDTLPGLVMAQDQRIRWYLL<br>SMGSNENIHSIHFSGHVFTVRKKEEYKMALYNLYPGVFETVEMLPSKAGIWRVECLIGEH<br>LHAGMSTLFLVYSNKCQTPLGMASGHIRDFQITASGQYGQWAPKLARLHYSGSINAWSTK<br>EPFSWIKVDLLAPMIIHGIKTQGARQKFSSLYISQFIIMYSLDGKKWQTYRGNSTGTLMV<br>FFGNVDSSGIKHNIFNPPIIARYIRLHPTHYSIRSTLRMELMGCDLNSCSMPLGMESKAI<br>SDAQITASSYFTNMFATWSPSKARLHLQGRSNAWRPQVNNPKEWLQVDFQKTMKVTGVTT<br>QGVKSLLTSMYVKEFLISSSQDGHQWTLFFQNGKVKVFQGNQDSFTPVVNSLDPPLLTRY<br>LRIHPQSWVHQIALRMEVLGCEAQDLYGGGSGGGGSGLVPRGSGGGSGGGGSGDIQLTQS<br>PSFLSASVGDRVTITCRASSSVRYIYWFQQKPGKAPKLLIYATSFRQSGVPSRFSGSGSG<br>TEYTLTISSLQPEDFATYYCHQRNSFPYTFGQGTKLEIKGGGGSGGGGSGGGGSGGGGSE<br>VQLVQSGAEVKKPGASVKVSCKASGYTFTTYAIHWVRQAPGQGLEWMGYINPSSGYTRYN<br>PKFKGRVTMTRDKSTSTAYMELRSLRSDDTAVYYCWTGTRDYWGQGTTVTVSS |
| 123 | 9711 | ATRRYYLGAVELSWDYMQSDLGELPVDARFPPRVPKSFPFNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLFAVFDEGKSWHSETKNSLMQDRDAASARAWPKMHTVNGYVNR<br>SLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEPQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNGGGGSTGGTGGSSGGGTGSGGGGTGGSGGTDIQLT<br>QSPSFLSASVGDRVTITCRASSSVRYIYWFQQKPGKAPKLLIYATSFRQSGVPSRFSGSG<br>SGTEYTLTISSLQPEDFATYYCHQRNSFPYTFGQGTKLEIKGGGGSGGGGSGGGGSGGGG<br>SEVQLVQSGAEVKKPGASVKVSCKASGYTFTTYAIHWVRQAPGQGLEWMGYINPSSGYTR<br>YNPKFKGRVTMTRDKSTSTAYMELRSLRSDDTAVYYCWTGTRDYWGQGTTVTVSSGGGGD<br>ENQSPRSFQKKTRHYFIAAVERLWDYGMSSSPHVLRNRAQSGSVPQFKKVVFQEFTDGSF<br>TQPLYRGELNEHLGLLGPYIRAEVEDNIMVTFRNQASRPYSFYSSLISYEEDQRQGAEPR<br>KNFVKPNETKTYFWKVQHHMAPTKDEFDCKAWAYFSDVDLEKDVHSGLIGPLLVCHTNTL<br>NPAHGRQVTVQEFALFFTIFDETKSWYFTENMERNCRAPCNIQMEDPTFKENYRFHAING<br>YIMDTLPGLVMAQDQRIRWYLLSMGSNENIHSIHFSGHVFTVRKKEEYKMALYNLYPGVF<br>ETVEMLPSKAGIWRVECLIGEHLHAGMSTLFLVYSNKCQTPLGMASGHIRDFQITASGQY<br>GQWAPKLARLHYSGSINAWSTKEPFSWIKVDLLAPMIIHGIKTQGARQKFSSLYISQFII<br>MYSLDGKKWQTYRGNSTGTLMVFFGNVDSSGIKHNIFNPPIIARYIRLHPTHYSIRSTLR<br>MELMGCDLNSCSMPLGMESKAISDAQITASSYFTNMFATWSPSKARLHLQGRSNAWRPQV<br>NNPKEWLQVDFQKTMKVTGVTTQGVKSLLTSMYVKEFLISSSQDGHQWTLFFQNGKVKVF<br>QGNQDSFTPVVNSLDPPLLTRYLRIHPQSWVHQIALRMEVLGCEAQDLY |
| 124 | 9161 | ATRRYYLGAVELSWDYMQSDLGELPVDARFPPRVPKSFPFNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLFAVFDEGKSWHSETKNSLMQDRDAASARAWPKMHTVNGYVNR<br>SLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF |

| SEQ ID | Protein ID (TPP #) | scFv-FVIII protein sequences referred to in table 24<br>Amino acid sequence of mature protein (signal peptide removed) |
|---|---|---|
| | | DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEFQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNGGGGSTGGTGGSSGGGTGSGGGGTGGSGGTDIQLT<br>QSPSFLSASVGDRVTITCRASSSVRYIYWFQQKPGKAPKLLIYATSFRQSGVPSRFSGSG<br>SGTEYTLTISSLQPEDFATYYCHQRNSFPYTFGQGTKLEIKGGGGSGGGGSGGGGSGGGG<br>SEVQLVQSGAEVKKPGASVKVSCKASGYTFTTYAIHWVRQAPGQGLEWMGYINPSSGYTR<br>YNPKFKGRVTMTRDKSTSTAYMELRSLRSDDTAVYYCWTGTRDYWGQGTTVTVSSGGGGS<br>QNPPVLKRHQREITDENQSPRSFQKKTRHYFIAAVERLWDYGMSSSPHVLRNRAQSGSVP<br>QFKKVVFQEFTDGSFTQPLYRGELNEHLGLLGPYIRAEVEDNIMVTFRNQASRPYSFYSS<br>LISYEEDQRQGAEPRKNFVKPNETKTYFWKVQHHMAPTKDEFDCKAWAYFSDVDLEKDVH<br>SGLIGPLLVCHTNTLNPAHGRQVTVQEFALFFTIFDETKSWYFTENMERNCRAPCNIQME<br>DPTFKENYRFHAINGYIMDTLPGLVMAQDQRIRWYLLSMGSNENIHSIHFSGHVFTVRKK<br>EEYKMALYNLYPGVFETVEMLPSKAGIWRVECLIGEHLHAGMSTLFLVYSNKCQTPLGMA<br>SGHIRDFQITASGQYGQWAPKLARLHYSGSINAWSTKEPFSWIKVDLLAPMIIHGIKTQG<br>ARQKFSSLYISQFIIMYSLDGKKWQTYRGNSTGTLMVFFGNVDSSGIKHNIFNPPIIARY<br>IRLHPTHYSIRSTLRMELMGCDLNSCSMPLGMESKAISDAQITASSYFTNMFATWSPSKA<br>RLHLQGRSNAWRPQVNNPKEWLQVDFQKTMKVTGVTTQGVKSLLTSMYVKEFLISSSQDG<br>HQWTLFFQNGKVKVFQGNQDSFTPVVNSLDPPLLTRYLRIHPQSWVHQIALRMEVLGCEA<br>QDLY |
| 125 | 9423<br>(F2196K) | DIQLTQSPSFLSASVGDRVTITCRASSSVRYIYWFQQKPGKAPKLLIYATSFRQSGVPSR<br>FSGSGSGTEYTLTISSLQPEDFATYYCHQRNSFPYTFGQGTKLEIKGGGGSGGGGSGGGG<br>SGGGGSEVQLVQSGAEVKKPGASVKVSCKASGYTFTTYAIHWVRQAPGQGLEWMGYINPS<br>SGYTRYNPKFKGRVTMTRDKSTSTAYMELRSLRSDDTAVYYCWTGTRDYWGQGTTVTVSS<br>GGGSGGGGSGLVPRGSGGGSGGGGSGATRRYYLGAVELSWDYMQSDLGELPVDARFPPRV<br>PKSFPFNTSVVYKKTLFVEFTDHLFNIAKPRPPWMGLLGPTIQAEVYDTVVITLKNMASH<br>PVSLHAVGVSYWKASEGAEYDDQTSQREKEDDKVFPGGSHTYVWQVLKENGPMASDPLCL<br>TYSYLSHVDLVKDLNSGLIGALLVCREGSLAKEKTQTLHKFILLLFAVFDEGKSWHSETKN<br>SLMQDRDAASARAWPKMHTVNGYVNRSLPGLIGCHRKSVYWHVIGMGTTPEVHSIFLEGH<br>TFLVRNHRQASLEISPITFLTAQTLLMDLGQFLLFCHISSHQHDGMEAYVKVDSCPEEPQ<br>LRMKNNEEAEDYDDDLTDSEMDVVRFDDDNSPSFIQIRSVAKKHPKTWVHYIAAEEEDWD<br>YAPLVLAPDDRSYKSQYLNNGPQRIGRKYKKVRFMAYTDETFKTREAIQHESGILGPLLY<br>GEVGDTLLIIFKNQASRPYNIYPHGITDVRPLYSRRLPKGVKHLKDFPILPGEIFKYKWT<br>VTVEDGPTKSDPRCLTRYYSSFVNMERDLASGLIGPLLICYKESVDQRGNQIMSDKRNVI<br>LFSVFDENRSWYLTENIQRFLPNPAGVQLEDPEFQASNIMHSINGYVFDSLQLSVCLHEV<br>AYWYILSIGAQTDFLSVFFSGYTFKHKMVYEDTLTLFPPSGETVFMSMENPGLWILGCHN<br>SDFRNRGMTALLKVSSCDKNTGDYYEDSYEDISAYLLSKNNAIEPRSFSQNDENQSPRSF<br>QKKTRHYFIAAVERLWDYGMSSSPHVLRNRAQSGSVPQFKKVVFQEFTDGSFTQPLYRGE<br>LNEHLGLLGPYIRAEVEDNIMVTFRNQASRPYSFYSSLISYEEDQRQGAEPRKNFVKPNE<br>TKTYFWKVQHHMAPTKDEFDCKAWAYFSDVDLEKDVHSGLIGPLLVCHTNTLNPAHGRQV<br>TVQEFALFFTIFDETKSWYFTENMERNCRAPCNIQMEDPTFKENYRFHAINGYIMDTLPG<br>LVMAQDQRIRWYLLSMGSNENIHSIHFSGHVFTVRKKEEYKMALYNLYPGVFETVEMLPS<br>KAGIWRVECLIGEHLHAGMSTLFLVYSNKCQTPLGMASGHIRDFQITASGQYGQWAPKLA<br>RLHYSGSINAWSTKEPFSWIKVDLLAPMIIHGIKTQGARQKFSSLYISQFIIMYSLDGKK<br>WQTYRGNSTGTLMVFFGNVDSSGIKHNIFNPPIIARYIRLHPTHYSIRSTLRMELMGCDL<br>NSCSMPLGMESKAISDAQITASSYKTNMFATWSPSKARLHLQGRSNAWRPQVNNPKEWLQ<br>VDFQKTMKVTGVTTQGVKSLLTSMYVKEFLISSSQDGHQWTLFFQNGKVKVFQGNQDSFT<br>PVVNSLDPPLLTRYLRIHPQSWVHQIALRMEVLGCEAQDLY |
| 126 | 9424 | DIQLTQSPSFLSASVGDRVTITCRASSSVRYIYWFQQKPGKAPKLLIYATSFRQSGVPSR<br>FSGSGSGTEYTLTISSLQPEDFATYYCHQRNSFPYTFGQGTKLEIKGGGGSGGGGSGGGG<br>SGGGGSEVQLVQSGAEVKKPGASVKVSCKASGYTFTTYAIHWVRQAPGQGLEWMGYINPS<br>SGYTRYNPKFKGRVTMTRDKSTSTAYMELRSLRSDDTAVYYCWTGTRDYWGQGTTVTVSS<br>GGGSGGGGSGLVPRGSGGGSGGGGSGATRRYYLGAVELSWDYMQSDLGELPVDARFPPRV<br>PKSFPFNTSVVYKKTLFVEFTDHLFNIAKPRPPWMGLLGPTIQAEVYDTVVITLKNMASH<br>PVSLHAVGVSYWKASEGAEYDDQTSQREKEDDKVFPGGSHTYVWQVLKENGPMASDPLCL<br>TYSYLSHVDLVKDLNSGLIGALLVCREGSLAKEKTQTLHKFILLLFAVFDEGKSWHSETKN<br>SLMQDRDAASARAWPKMHTVNGYVNRSLPGLIGCHRKSVYWHVIGMGTTPEVHSIFLEGH<br>TFLVRNHRQASLEISPITFLTAQTLLMDLGQFLLFCHISSHQHDGMEAYVKVDSCPEEPQ<br>LRMKNNEEAEDYDDDLTDSEMDVVRFDDDNSPSFIQIRSVAKKHPKTWVHYIAAEEEDWD<br>YAPLVLAPDDRSYKSQYLNNGPQRIGRKYKKVRFMAYTDETFKTREAIQHESGILGPLLY<br>GEVGDTLLIIFKNQASRPYNIYPHGITDVRPLYSRRLPKGVKHLKDFPILPGEIFKYKWT<br>VTVEDGPTKSDPRCLTRYYSSFVNMERDLASGLIGPLLICYKESVDQRGNQIMSDKRNVI<br>LFSVFDENRSWYLTENIQRFLPNPAGVQLEDPEFQASNIMHSINGYVFDSLQLSVCLHEV<br>AYWYILSIGAQTDFLSVFFSGYTFKHKMVYEDTLTLFPPSGETVFMSMENPGLWILGCHN<br>SDFRNRGMTALLKVSSCDKNTGDYYEDSYEDISAYLLSKNNAIEPRSFSQNDENQSPRSF<br>QKKTRHYFIAAVERLWDYGMSSSPHVLRNRAQSGSVPQFKKVVFQEFTDGSFTQPLYRGE<br>LNEHLGLLGPYIRAEVEDNIMVTFRNQASRPYSFYSSLISYEEDQRQGAEPRKNFVKPNE<br>TKTYFWKVQHHMAPTKDEFDCKAWAYFSDVDLEKDVHSGLIGPLLVCHTNTLNPAHGRQV<br>TVQEFALFFTIFDETKSWYFTENMERNCRAPCNIQMEDPTFKENYRFHAINGYIMDTLPG<br>LVMAQDQRIRWYLLSMGSNENIHSIHFSGHVFTVRKKEEYKMALYNLYPGVFETVEMLPS |

| SEQ ID | Protein ID (TPP #) | scFv-FVIII protein sequences referred to in table 24<br>Amino acid sequence of mature protein (signal peptide removed) |
|---|---|---|
| | | KAGIWRVECLIGEHLHAGMSTLFLVYSNKCQTPLGMASGHIRDFQITASGQYGQWAPKLA<br>RLHYSGSINAWSTKEPFSWIKVDLLAPMIIHGIKTQGARQKFSSLYISQFIIMYSLDGKK<br>WQTYRGNSTGTLMVFFGNVDSSGIKHNIFNPPIIARYIRLHPTHYSIRSTLRMELMGCDL<br>NSCSMPLGMESKAISDAQITASSYFTNMFATWSPSKARLHLQGRSNAWRPQVNNPKEWLQ<br>VDFQKTMKVTGVTTQGVKSLLTSMYVKEFLISSSQDGHQWTLFFQNGKVKVFQGNQDSFT<br>PVVNSLDPPLLTRYLRIHPQSWVHQIALRMEVLGCEAQDLY |
| 127 | 9900 | DIQLTQSPSFLSASVGDRVTITCRASSSVRYIYWFQQKPGKAPKLLIYATSFRQSGVPSR<br>FSGSGSGTEYTLTISSLQPEDFATYYCHQRNSFPYTFGQGTKLEIKGGGGSGGGGSGGGG<br>SGGGGSEVQLVQSGAEVKKPGASVKVSCKASGYTFTTYAIHWVRQAPGQGLEWMGYINPS<br>SGYTRYNPKFKGRVTMTRDKSTSTAYMELRSLRSDDTAVYYCWTGTRDYWGQGTTVTVSS<br>GGGSGGGGSGLVPRGSGGGSGGGGSGATRRYYLGAVELSWDYMQSDLGELPVDARFPPRV<br>PKSFPFNTSVVYKKTLFVEFTDHLFNIAKPRPPWMGLLGPTIQAEVYDTVVITLKNMASH<br>PVSLHAVGVSYWKASEGAEYDDQTSQREKEDDKVFPGGSHTYVWQVLKENGPMASDPLCL<br>TYSYLSHVDLVKDLNSGLIGALLVCREGSLAKEKTQTLHKFILLFAVFDEGKSWHSETKN<br>SLMQDRDAASARAWPKMHTVNGYVNRSLPGLIGCHRKSVYWHVIGMGTTPEVHSIFLEGH<br>TFLVRNHRQASLEISPITFLTAQTLLMDLGQFLLFCHISSHQHDGMEAYVKVDSCPEEPQ<br>LRMKNNEEAEDYDDDLTDSEMDVVRFDDDNSPSFIQIRSVAKKHPKTWVHYIAAEEEDWD<br>YAPLVLAPDDRSYKSQYLNNGPQRIGRKYKKVRFMAYTDETFKTREAIQHESGILGPLLY<br>GEVGDTLLIIFKNQASRPYNIYPHGITDVRPLYSRRLPKGVKHLKDFPILPGEIFKYKWT<br>VTVEDGPTKSDPRCLTRYYSSFVNMERDLASGLIGPLLICYKESVDQRGNQIMSDKRNVI<br>LFSVFDENRSWYLTENIQRFLPNPAGVQLEDPEFQASNIMHSINGYVFDSLQLSVCLHEV<br>AYWYILSIGAQTDFLSVFFSGYTFKHKMVYEDTLTLFPFSGETVFMSMENPGLWILGCHN<br>SDFRNRGMTALLKVSSCDKNTGDYYEDSYEDISAYLLSKNNAIEPRSFSQNDENQSPRSF<br>QKKTRHYFIAAVERLWDYGMSSSPHVLRNRAQSGSVPQFKKVVFQEFTDGSFTQPLYRGE<br>LNEHLGLLGPYIRAEVEDNIMVTFRNQASRPYSFYSSLISYEEDQRQGAEPRKNFVKPNE<br>TKTYFWKVQHHMAPTKDEFDCKAWAYFSDVDLEKDVHSGLIGPLLVCHTNTLNPAHGRQV<br>TVQEFALFFTIFDETKSWYFTENMERNCRAPCNIQMEDPTFKENYRFHAINGYIMDTLPG<br>LVMAQDQRIRWYLLSMGSNENIHSIHFSGHVFTVRKKEEYKMALYNLYPGVFETVEMLPS<br>KAGIWRVECLIGEHLHAGMSTLFLVYSNKCQTPLGMASGHIRDFQITASGQYGQWAPKLA<br>RLHYSGSINAWSTKEPFSWIKVDLLAPMIIHGIKTQGARQKFSSLYISQFIIMYSLDGKK<br>WQTYRGNSTGTLMVFFGNVDSSGIKHNIFNPPIIARYIRLHPTHYSIRSTLRMELMGCDL<br>NSCSMPLGMESKAISDAQITASSYFTNMFATWSPSKARLHLQGRSNAWRPQVNNPKEWLQ<br>VDFQKTMKVTGVTTQGVKSLLTSMYVKEFLISSSQDGHQWTLFFQNGKVKVFQGNQDSFT<br>PVVNSLDPPLLTRYLRIHPQSWVHQIALRMEVLGCEAQDLYGGGSGGGGSGLVPRGSGGG<br>SGGGGSGDIQLTQSPSFLSASVGDRVTITCRASSSVRYIYWFQQKPGKAPKLLIYATSFR<br>QSGVPSRFSGSGSGTEYTLTISSLQPEDFATYYCHQRNSFPYTFGQGTKLEIKGGGGSGG<br>GGSGGGGSGGGGSEVQLVQSGAEVKKPGASVKVSCKASGYTFTTYAIHWVRQAPGQGLEW<br>MGYINPSSGYTRYNPKFKGRVTMTRDKSTSTAYMELRSLRSDDTAVYYCWTGTRDYWGQG<br>TTVTVSS |
| 128 | 9901 | ATRRYYLGAVELSWDYMQSDLGELPVDARFPPRVPKSFPFNTSVVYKKTLFVEFTDHLFN<br>IAKPRPPWMGLLGPTIQAEVYDTVVITLKNMASHPVSLHAVGVSYWKASEGAEYDDQTSQ<br>REKEDDKVFPGGSHTYVWQVLKENGPMASDPLCLTYSYLSHVDLVKDLNSGLIGALLVCR<br>EGSLAKEKTQTLHKFILLFAVFDEGKSWHSETKNSLMQDRDAASARAWPKMHTVNGYVNR<br>SLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIG<br>RKYKKVRFMAYTDETFKTREAIQHESGILGPLLYGEVGDTLLIIFKNQASRPYNIYPHGI<br>TDVRPLYSRRLPKGVKHLKDFPILPGEIFKYKWTVTVEDGPTKSDPRCLTRYYSSFVNME<br>RDLASGLIGPLLICYKESVDQRGNQIMSDKRNVILFSVFDENRSWYLTENIQRFLPNPAG<br>VQLEDPEFQASNIMHSINGYVFDSLQLSVCLHEVAYWYILSIGAQTDFLSVFFSGYTFKH<br>KMVYEDTLTLFPFSGETVFMSMENPGLWILGCHNSDFRNRGMTALLKVSSCDKNTGDYYE<br>DSYEDISAYLLSKNNAIEPRSFSQNGGGSTGGTGGSGGGTGSGGGGTGGSGGTDIQLT<br>QSPSFLSASVGDRVTITCRASSSVRYIYWFQQKPGKAPKLLIYATSFRQSGVPSRFSGSG<br>SGTEYTLTISSLQPEDFATYYCHQRNSFPYTFGQGTKLEIKGGGGSGGGGSGGGGSGGGG<br>SEVQLVQSGAEVKKPGASVKVSCKASGYTFTTYAIHWVRQAPGQGLEWMGYINPSSGYTR<br>YNPKFKGRVTMTRDKSTSTAYMELRSLRSDDTAVYYCWTGTRDYWGQGTTVTVSSGGGGD<br>ENQSPRSFQKKTRHYFIAAVERLWDYGMSSSPHVLRNRAQSGSVPQFKKVVFQEFTDGSF<br>TQPLYRGELNEHLGLLGPYIRAEVEDNIMVTFRNQASRPYSFYSSLISYEEDQRQGAEPR<br>KNFVKPNETKTYFWKVQHHMAPTKDEFDCKAWAYFSDVDLEKDVHSGLIGPLLVCHTNTL<br>NPAHGRQVTVQEFALFFTIFDETKSWYFTENMERNCRAPCNIQMEDPTFKENYRFHAING<br>YIMDTLPGLVMAQDQRIRWYLLSMGSNENIHSIHFSGHVFTVRKKEEYKMALYNLYPGVF<br>ETVEMLPSKAGIWRVECLIGEHLHAGMSTLFLVYSNKCQTPLGMASGHIRDFQITASGQY<br>GQWAPKLARLHYSGSINAWSTKEPFSWIKVDLLAPMIIHGIKTQGARQKFSSLYISQFII<br>MYSLDGKKWQTYRGNSTGTLMVFFGNVDSSGIKHNIFNPPIIARYIRLHPTHYSIRSTLR<br>MELMGCDLNSCSMPLGMESKAISDAQITASSYFTNMFATWSPSKARLHLQGRSNAWRPQV<br>NNPKEWLQVDFQKTMKVTGVTTQGVKSLLTSMYVKEFLISSSQDGHQWTLFFQNGKVKVF<br>QGNQDSFTPVVNSLDPPLLTRYLRIHPQSWVHQIALRMEVLGCEAQDLYGGGSGGGGSGL<br>VPRGSGGGSGGGGSGDIQLTQSPSFLSASVGDRVTITCRASSSVRYIYWFQQKPGKAPKL<br>LIYATSFRQSGVPSRFSGSGSGTEYTLTISSLQPEDFATYYCHQRNSFPYTFGQGTKLEI<br>KGGGGSGGGGSGGGGSGGGGSEVQLVQSGAEVKKPGASVKVSCKASGYTFTTYAIHWVRQ<br>APGQGLEWMGYINPSSGYTRYNPKFKGRVTMTRDKSTSTAYMELRSLRSDDTAVYYCWTG<br>TRDYWGQGTTVTVSS |

| SEQ ID | Protein ID (TPP #) | scFv-FVIII protein sequences referred to in table 24 Amino acid sequence of mature protein (signal peptide removed) |
|---|---|---|
| 129 | 9976 | ATRRYYLGAVELSWDYMQSDLGELPVDARFPPRVPKSFPFNTSVVYKKTLFVEFTDHLFN IAKPRPPWMGLLGPTIQAEVYDTVVITLKNMASHPVSLHAVGVSYWKASEGAEYDDQTSQ REKEDDKVFPGGSHTYVWQVLKENGPMASDPLCLTYSYLSHVDLVKDLNSGLIGALLVCR EGSLAKEKTQTLHKFILLFAVFDEGKSWHSETKNSLMQDRDAASARAWPKMHTVNGYVNR SLPGLIGCHRKSVYWHVIGMGTTPEVHSIFLEGHTFLVRNHRQASLEISPITFLTAQTLL MDLGQFLLFCHISSHQHDGMEAYVKVDSCPEEPQLRMKNNEEAEDYDDDLTDSEMDVVRF DDDNSPSFIQIRSVAKKHPKTWVHYIAAEEEDWDYAPLVLAPDDRSYKSQYLNNGPQRIG RKYKKVRFMAYTDETFKTREAIQHESGILGPLLYGEVGDTLLIIFKNQASRPYNIYPHGI TDVRPLYSRRLPKGVKHLKDFPILPGEIFKYKWTVTVEDGPTKSDPRCLTRYYSSFVNME RDLASGLIGPLLICYKESVDQRGNQIMSDKRNVILFSVFDENRSWYLTENIQRFLPNPAG VQLEDPEFQASNIMHSINGYVFDSLQLSVCLHEVAYWYILSIGAQTDFLSVFFSGYTFKH KMVYEDTLTLFPFSGETVFMSMENPGLWILGCHNSDFRNRGMTALLKVSSCDKNTGDYYE DSYEDISAYLLSKNNAIEPRSFSQNGGGGSTGGTGGSSGGGTGSGGGGTGGSGGTDIQLT QSPSFLSASVGDRVTITCRASSSVRYIYWFQQKPGKAPKLLIYATSFRQSGVPSRFSGSG SGTEYTLTISSLQPEDFATYYCHQRNSFPYTFGQGTKLEIKGGGGSGGGGSGGGGSGGGG SEVQLVQSGAEVKKPGASVKVSCKASGYTFTTYAIHWVRQAPGQGLEWMGYINPSSGYTR YNPKFKGRVTMTRDKSTSTAYMELRSLSDDTAVYYCWTGTRDYWGQGTTVTVSSGGGGGD IQLTQSPSFLSASVGDRVTITCRASSSVRYIYWFQQKPGKAPKLLIYATSFRQSGVPSRF SGSGSGTEYTLTISSLQPEDFATYYCHQRNSFPYTFGQGTKLEIKGGGGSGGGGSGGGGS GGGGSEVQLVQSGAEVKKPGASVKVSCKASGYTFTTYAIHWVRQAPGQGLEWMGYINPSS GYTRYNPKFKGRVTMTRDKSTSTAYMELRSLSDDTAVYYCWTGTRDYWGQGTTVTVSSG GGGDENQSPRSFQKKTRHYFIAAVERLWDYGMSSSPHVLRNRAQSGSVPQFKKVVFQEFT DGSFTQPLYRGELNEHLGLLGPYIRAEVEDNIMVTFRNQASRPYSFYSSLISYEEDQRQG AEPRKNFVKPNETKTYFWKVQHHMAPTKDEFDCKAWAYFSDVDLEKDVHSGLIGPLLVCH TNTLNPAHGRQVTVQEFALFFTIFDETKSWYFTENMERNCRAPCNIQMEDPTFKENYRFH AINGYIMDTLPGLVMAQDQRIRWYLLSMGSNENIHSIHFSGHVFTVRKKEEYKMALYNLY PGVFETVEMLPSKAGIWRVECLIGEHLHAGMSTLFLVYSNKCQTPLGMASGHIRDFQITA SGQYGQWAPKLARLHYSGSINAWSTKEPFSWIKVDLLAPMIIHGIKTQGARQKFSSLYIS QFIIMYSLDGKKWQTYRGNSTGTLMVFFGNVDSSGIKHNIFNPPIIARYIRLHPTHYSIR STLRMELMGCDLNSCSMPLGMESKAISDAQITASSYFTNMFATWSPSKARLHLQGRSNAW RPQVNNPKEWLQVDFQKTMKVTGVTTQGVKSLLTSMYVKEFLISSSQDGHQWTLFFQNGK VKVFQGNQDSFTPVVNSLDPPLLTRYLRIHPQSWVHQIALRMEVLGCEAQDLY |
| 130 | 9977 | DIQLTQSPSFLSASVGDRVTITCRASSSVRYIYWFQQKPGKAPKLLIYATSFRQSGVPSR FSGSGSGTEYTLTISSLQPEDFATYYCHQRNSFPYTFGQGTKLEIKGGGGSGGGGSGGGG SGGGGSEVQLVQSGAEVKKPGASVKVSCKASGYTFTTYAIHWVRQAPGQGLEWMGYINPS SGYTRYNPKFKGRVTMTRDKSTSTAYMELRSLSDDTAVYYCWTGTRDYWGQGTTVTVSS GGGGSGGGGSGSGLVPRGSGGGSGGGGSGATRRYYLGAVELSWDYMQSDLGELPVDARFPPRV PKSFPFNTSVVYKKTLFVEFTDHLFNIAKPRPPWMGLLGPTIQAEVYDTVVITLKNMASH PVSLHAVGVSYWKASEGAEYDDQTSQREKEDDKVFPGGSHTYVWQVLKENGPMASDPLCL TYSYLSHVDLVKDLNSGLIGALLVCREGSLAKEKTQTLHKFILLFAVFDEGKSWHSETKN SLMQDRDAASARAWPKMHTVNGYVNRSLPGLIGCHRKSVYWHVIGMGTTPEVHSIFLEGH TFLVRNHRQASLEISPITFLTAQTLLMDLGQFLLFCHISSHQHDGMEAYVKVDSCPEEPQ LRMKNNEEAEDYDDDLTDSEMDVVRFDDDNSPSFIQIRSVAKKHPKTWVHYIAAEEEDWD YAPLVLAPDDRSYKSQYLNNGPQRIGRKYKKVRFMAYTDETFKTREAIQHESGILGPLLY GEVGDTLLIIFKNQASRPYNIYPHGITDVRPLYSRRLPKGVKHLKDFPILPGEIFKYKWT VTVEDGPTKSDPRCLTRYYSSFVNMERDLASGLIGPLLICYKESVDQRGNQIMSDKRNVI LFSVFDENRSWYLTENIQRFLPNPAGVQLEDPEFQASNIMHSINGYVFDSLQLSVCLHEV AYWYILSIGAQTDFLSVFFSGYTFKHKMVYEDTLTLFPFSGETVFMSMENPGLWILGCHN SDFRNRGMTALLKVSSCDKNTGDYYEDSYEDISAYLLSKNNAIEPRSFSQNGGGGSTGGT GGSSGGGTGSGGGGTGGSGGTDIQLTQSPSFLSASVGDRVTITCRASSSVRYIYWFQQKP GKAPKLLIYATSFRQSGVPSRFSGSGSGTEYTLTISSLQPEDFATYYCHQRNSFPYTFGQ GTKLEIKGGGGSGGGGSGGGGSGGGGSEVQLVQSGAEVKKPGASVKVSCKASGYTFTTYA IHWVRQAPGQGLEWMGYINPSSGYTRYNPKFKGRVTMTRDKSTSTAYMELRSLSDDTAV YYCWTGTRDYWGQGTTVTVSSGGGGDENQSPRSFQKKTRHYFIAAVERLWDYGMSSSPHV LRNRAQSGSVPQFKKVVFQEFTDGSFTQPLYRGELNEHLGLLGPYIRAEVEDNIMVTFRN QASRPYSFYSSLISYEEDQRQGAEPRKNFVKPNETKTYFWKVQHHMAPTKDEFDCKAWAY FSDVDLEKDVHSGLIGPLLVCHTNTLNPAHGRQVTVQEFALFFTIFDETKSWYFTENMER NCRAPCNIQMEDPTFKENYRFHAINGYIMDTLPGLVMAQDQRIRWYLLSMGSNENIHSIH FSGHVFTVRKKEEYKMALYNLYPGVFETVEMLPSKAGIWRVECLIGEHLHAGMSTLFLVY SNKCQTPLGMASGHIRDFQITASGQYGQWAPKLARLHYSGSINAWSTKEPFSWIKVDLLA PMIIHGIKTQGARQKFSSLYISQFIIMYSLDGKKWQTYRGNSTGTLMVFFGNVDSSGIKH NIFNPPIIARYIRLHPTHYSIRSTLRMELMGCDLNSCSMPLGMESKAISDAQITASSYFT NMFATWSPSKARLHLQGRSNAWRPQVNNPKEWLQVDFQKTMKVTGVTTQGVKSLLTSMYV KEFLISSSQDGHQWTLFFQNGKVKVFQGNQDSFTPVVNSLDPPLLTRYLRIHPQSWVHQI ALRMEVLGCEAQDLY |
| 131 | 10297 | DIQLTQSPSFLSASVGDRVTITCRASSSVRYIYWFQQKPGKAPKLLIYATSFRQSGVPSR FSGSGSGTEYTLTISSLQPEDFATYYCHQRNSFPYTFGQGTKLEIKGGGGSGGGGSGGGG SGGGGSEVQLVQSGAEVKKPGASVKVSCKASGYTFTTYAIHWVRQAPGQGLEWMGYINPS SGYTRYNPKFKGRVTMTRDKSTSTAYMELRSLSDDTAVYYCWTGTRDYWGQGTTVTVSS GGGGSGGGGSGSGLVPRGSGGGSGGGGSGATRRYYLGAVELSWDYMQSDLGELPVDARFPPRV PKSFPFNTSVVYKKTLFVEFTDHLFNIAKPRPPWMGLLGPTIQAEVYDTVVITLKNMASH PVSLHAVGVSYWKASEGAEYDDQTSQREKEDDKVFPGGSHTYVWQVLKENGPMASDPLCL TYSYLSHVDLVKDLNSGLIGALLVCREGSLAKEKTQTLHKFILLFAVFDEGKSWHSETKN |

| SEQ ID | Protein ID (TPP #) | scFv-FVIII protein sequences referred to in table 24<br>Amino acid sequence of mature protein (signal peptide removed) |
|---|---|---|
| | | SLMQDRDAASARAWPKMHTVNGYVNRSLPGLIGCHRKSVYWHVIGMTTPEVHSIFLEGH<br>TFLVRNHRQASLEISPITFLTAQTLLMDLGQFLLFCHISSHQHDGMEAYVKVDSCPEEPQ<br>LRMKNNEEAEDYDDDLTDSEMDVVRFDDDNSPSFIQIRSVAKKHPKTWVHYIAAEEEDWD<br>YAPLVLAPDDRSYKSQYLNNGPQRIGRKYKKVRFMAYTDETFKTREAIQHESGILGPLLY<br>GEVGDTLLIIFKNQASRPYNIYPHGITDVRPLYSRRLPKGVKHLKDFPILPGEIFKYKWT<br>VTVEDGPTKSDPRCLTRYYSSFVNMERDLASGLIGPLLICYKESVDQRGNQIMSDKRNVI<br>LFSVFDENRSWYLTENIQRFLPNPAGVQLEDPEFQASNIMHSINGYVFDSLQLSVCLHEV<br>AYWYILSIGAQTDFLSVFFSGYTFKHKMVYEDTLTLFPPSGETVFMSMENPGLWILGCHN<br>SDFRNRGMTALLKVSSCDKNTGDYYEDSYEDISAYLLSKNNAIEPRSFSQNGGGGSGGGS<br>GGSGGSGGGGGDENQSPRSFQKKTRHYFIAAVERLWDYGMSSSPHVLRNRAQSGSVPQFK<br>KVVFQEFTDGSFTQPLYRGELNEHLGLLGPYIRAEVEDNIMVTFRNQASRPYSFYSSLIS<br>YEEDQRQGAEPRKNFVKPNETKTYFWKVQHHMAPTKDEFDCKAWAYFSDVDLEKDVHSGL<br>IGPLLVCHTNTLNPAHGRQVTVQEFALFFTIFDETKSWYFTENMERNCRAPCNIQMEDPT<br>FKENYRFHAINGYIMDTLPGLVMAQDQRIRWYLLSMGSNENIHSIHFSGHVFTVRKKEEY<br>KMALYNLYPGVFETVEMLPSKAGIWRVECLIGEHLHAGMSTLFLVYSNKCQTPLGMASGH<br>IRDFQITASGQYGQWAPKLARLHYSGSINAWSTKEPFSWIKVDLLAPMIIHGIKTQGARQ<br>KFSSLYISQFIIMYSLDGKKWQTYRGNSTGTLMVFFGNVDSSGIKHNIFNPPIIARYIRL<br>HPTHYSIRSTLRMELMGCDLNSCSMPLGMESKAISDAQITASSYFTNMFATWSPSKARLH<br>LQGRSNAWRPQVNNPKEWLQVDFQKTMKVTGVTTQGVKSLLTSMYVKEFLISSSQDGHQW<br>TLFFQNGKVKVFQGNQDSFTPVVNSLDPPLLTRYLRIHPQSWVHQIALRMEVLGCEAQDL<br>Y |
| 132 | 10298 | DIQLTQSPSFLSASVGDRVTITCRASSSVRYIYWFQQKPGKAPKLLIYATSFRQSGVPSR<br>FSGSGSGTEYTLTISSLQPEDFATYYCHQRNSFPYTFGQGTKLEIKGGGGSGGGGSGGGG<br>SGGGGSEVQLVQSGAEVKKPGASVKVSCKASGYTFTTYAIHWVRQAPGQGLEWMGYINPS<br>SGYTRYNPKFKGRVTMTRDKSTSTAYMELRSLRSDDTAVYYCWTGTRDYWGQGTTVTVSS<br>GGGSGGGGSGLVPRGSGGGSGGGGSGATRRYYLGAVELSWDYMQSDLGELPVDARFPPRV<br>PKSFPFNTSVVYKKTLFVEFTDHLFNIAKPRPPWMGLLGPTIQAEVYDTVVITLKNMASH<br>PVSLHAVGVSYWKASEGAEYDDQTSQREKEDDKVFPGGSHTYVWQVLKENGPMASDPLCL<br>TYSYLSHVDLVKDLNSGLIGALLVCREGSLAKEKTQTLHKFILLFAVFDEGKSWHSETKN<br>SLMQDRDAASARAWPKMHTVNGYVNRSLPGLIGCHRKSVYWHVIGMTTPEVHSIFLEGH<br>TFLVRNHRQASLEISPITFLTAQTLLMDLGQFLLFCHISSHQHDGMEAYVKVDSCPEEPQ<br>LRMKNNEEAEDYDDDLTDSEMDVVRFDDDNSPSFIQIRSVAKKHPKTWVHYIAAEEEDWD<br>YAPLVLAPDDRSYKSQYLNNGPQRIGRKYKKVRFMAYTDETFKTREAIQHESGILGPLLY<br>GEVGDTLLIIFKNQASRPYNIYPHGITDVRPLYSRRLPKGVKHLKDFPILPGEIFKYKWT<br>VTVEDGPTKSDPRCLTRYYSSFVNMERDLASGLIGPLLICYKESVDQRGNQIMSDKRNVI<br>LFSVFDENRSWYLTENIQRFLPNPAGVQLEDPEFQASNIMHSINGYVFDSLQLSVCLHEV<br>AYWYILSIGAQTDFLSVFFSGYTFKHKMVYEDTLTLFPPSGETVFMSMENPGLWILGCHN<br>SDFRNRGMTALLKVSSCDKNTGDYYEDSYEDISAYLLSKNNAIEPGGGGGGDENQSPRSF<br>QKKTRHYFIAAVERLWDYGMSSSPHVLRNRAQSGSVPQFKKVVFQEFTDGSFTQPLYRGE<br>LNEHLGLLGPYIRAEVEDNIMVTFRNQASRPYSFYSSLISYEEDQRQGAEPRKNFVKPNE<br>TKTYFWKVQHHMAPTKDEFDCKAWAYFSDVDLEKDVHSGLIGPLLVCHTNTLNPAHGRQV<br>TVQEFALFFTIFDETKSWYFTENMERNCRAPCNIQMEDPTFKENYRFHAINGYIMDTLPG<br>LVMAQDQRIRWYLLSMGSNENIHSIHFSGHVFTVRKKEEYKMALYNLYPGVFETVEMLPS<br>KAGIWRVECLIGEHLHAGMSTLFLVYSNKCQTPLGMASGHIRDFQITASGQYGQWAPKLA<br>RLHYSGSINAWSTKEPFSWIKVDLLAPMIIHGIKTQGARQKFSSLYISQFIIMYSLDGKK<br>WQTYRGNSTGTLMVFFGNVDSSGIKHNIFNPPIIARYIRLHPTHYSIRSTLRMELMGCDL<br>NSCSMPLGMESKAISDAQITASSYFTNMFATWSPSKARLHLQGRSNAWRPQVNNPKEWLQ<br>VDFQKTMKVTGVTTQGVKSLLTSMYVKEFLISSSQDGHQWTLFFQNGKVKVFQGNQDSFT<br>PVVNSLDPPLLTRYLRIHPQSWVHQIALRMEVLGCEAQDLY |
| 133 | 10299 | DIQLTQSPSFLSASVGDRVTITCRASSSVRYIYWFQQKPGKAPKLLIYATSFRQSGVPSR<br>FSGSGSGTEYTLTISSLQPEDFATYYCHQRNSFPYTFGQGTKLEIKGGGGSGGGGSGGGG<br>SGGGGSEVQLVQSGAEVKKPGASVKVSCKASGYTFTTYAIHWVRQAPGQGLEWMGYINPS<br>SGYTRYNPKFKGRVTMTRDKSTSTAYMELRSLRSDDTAVYYCWTGTRDYWGQGTTVTVSS<br>GGGSGGGGSGLVPRGSGGGSGGGGSGATRRYYLGAVELSWDYMQSDLGELPVDARFPPRV<br>PKSFPFNTSVVYKKTLFVEFTDHLFNIAKPRPPWMGLLGPTIQAEVYDTVVITLKNMASH<br>PVSLHAVGVSYWKASEGAEYDDQTSQREKEDDKVFPGGSHTYVWQVLKENGPMASDPLCL<br>TYSYLSHVDLVKDLNSGLIGALLVCREGSLAKEKTQTLHKFILLFAVFDEGKSWHSETKN<br>SLMQDRDAASARAWPKMHTVNGYVNRSLPGLIGCHRKSVYWHVIGMTTPEVHSIFLEGH<br>TFLVRNHRQASLEISPITFLTAQTLLMDLGQFLLFCHISSHQHDGMEAYVKVDSCPEEPQ<br>LRMKNNEEAEDYDDDLTDSEMDVVRFDDDNSPSFIQIRSVAKKHPKTWVHYIAAEEEDWD<br>YAPLVLAPDDRSYKSQYLNNGPQRIGRKYKKVRFMAYTDETFKTREAIQHESGILGPLLY<br>GEVGDTLLIIFKNQASRPYNIYPHGITDVRPLYSRRLPKGVKHLKDFPILPGEIFKYKWT<br>VTVEDGPTKSDPRCLTRYYSSFVNMERDLASGLIGPLLICYKESVDQRGNQIMSDKRNVI<br>LFSVFDENRSWYLTENIQRFLPNPAGVQLEDPEFQASNIMHSINGYVFDSLQLSVCLHEV<br>AYWYILSIGAQTDFLSVFFSGYTFKHKMVYEDTLTLFPPSGETVFMSMENPGLWILGCHN<br>SDFRNRGMTALLKVSSCDKNTGDYYEDSYEDISAYLLSKNNAIEPRSFSQNPPVLKRHQR<br>EITDENQSPRSFQKKTRHYFIAAVERLWDYGMSSSPHVLRNRAQSGSVPQFKKVVFQEFT<br>DGSFTQPLYRGELNEHLGLLGPYIRAEVEDNIMVTFRNQASRPYSFYSSLISYEEDQRQG<br>AEPRKNFVKPNETKTYFWKVQHHMAPTKDEFDCKAWAYFSDVDLEKDVHSGLIGPLLVCH<br>TNTLNPAHGRQVTVQEFALFFTIFDETKSWYFTENMERNCRAPCNIQMEDPTFKENYRFH<br>AINGYIMDTLPGLVMAQDQRIRWYLLSMGSNENIHSIHFSGHVFTVRKKEEYKMALYNLY<br>PGVFETVEMLPSKAGIWRVECLIGEHLHAGMSTLFLVYSNKCQTPLGMASGHIRDFQITA<br>SGQYGQWAPKLARLHYSGSINAWSTKEPFSWIKVDLLAPMIIHGIKTQGARQKFSSLYIS |

| SEQ ID | Protein ID (TPP #) | scFv-FVIII protein sequences referred to in table 24<br>Amino acid sequence of mature protein (signal peptide removed) |
|---|---|---|
| | | QFIIMYSLDGKKWQTYRGNSTGTLMVFFGNVDSSGIKHNIFNPPIIARYIRLHPTHYSIR<br>STLRMELMGCDLNSCSMPLGMESKAISDAQITASSYFTNMFATWSPSKARLHLQGRSNAW<br>RPQVNNPKEWLQVDFQKTMKVTGVTTQGVKSLLTSMYVKEFLISSSQDGHQWTLFFQNGK<br>VKVFQGNQDSFTPVVNSLDPPLLTRYLRIHPQSWVHQIALRMEVLGCEAQDLY |

While the present invention has been described with reference to the specific embodiments and examples, it should be understood that various modifications and changes may be made and equivalents may be substituted without departing from the true spirit and scope of the invention. The specification and examples are, accordingly, to be regarded in an illustrative rather then a restrictive sense. Furthermore, all articles, patent applications and patents referred to herein are incorporated herein by reference in their entireties.

The invention claimed is:

1. A recombinant fusion protein comprising a protein wherein extension of circulating half-life would be beneficial to a patient, and at least one binding domain that specifically binds to a membrane protein on a red blood cell, wherein the binding domain is a scFv and the membrane protein is glycophorin A, wherein the scFv comprises a heavy chain selected from the group consisting of SEQ IS NOs: 33, 35, 37, 39, 41, 43, 45, 47, 49, 51, 53, 55, 57, 59, 61, 63, 65 and 67, and a light chain is selected from the group consisting of SEQ IS NOs: 32, 34, 36, 38, 40, 42, 44, 46, 48, 50, 52, 54, 56, 58, 60, 62, 64 and 66.

* * * * *